(12) United States Patent
McLaughlin et al.

(10) Patent No.: US 11,697,825 B2
(45) Date of Patent: Jul. 11, 2023

(54) COMPOSITIONS AND METHODS FOR THE PRODUCTION OF SCAAV

(71) Applicant: VOYAGER THERAPEUTICS, INC., Cambridge, MA (US)

(72) Inventors: James McLaughlin, Cambridge, MA (US); Robert Kotin, Boston, MA (US)

(73) Assignee: Voyager Therapeutics, Inc., Cambridge, MA (US)

( * ) Notice: Subject to any disclaimer, the term of this patent is extended or adjusted under 35 U.S.C. 154(b) by 581 days.

(21) Appl. No.: 15/535,389

(22) PCT Filed: Dec. 11, 2015

(86) PCT No.: PCT/US2015/065218
§ 371 (c)(1),
(2) Date: Jun. 12, 2017

(87) PCT Pub. No.: WO2016/094783
PCT Pub. Date: Jun. 16, 2016

(65) Prior Publication Data
US 2017/0362608 A1  Dec. 21, 2017

Related U.S. Application Data

(60) Provisional application No. 62/091,062, filed on Dec. 12, 2014.

(51) Int. Cl.
| | |
|---|---|
| *C12N 15/864* | (2006.01) |
| *C12N 15/35* | (2006.01) |
| *C12N 7/00* | (2006.01) |
| *C07K 14/015* | (2006.01) |
| *C12N 15/09* | (2006.01) |
| *C12N 15/861* | (2006.01) |
| *C07K 14/005* | (2006.01) |
| *C12N 15/86* | (2006.01) |
| *C12N 7/02* | (2006.01) |

(52) U.S. Cl.
CPC .......... *C12N 15/861* (2013.01); *C07K 14/005* (2013.01); *C12N 7/00* (2013.01); *C12N 7/02* (2013.01); *C12N 15/86* (2013.01); *C12N 15/864* (2013.01); *C12N 2710/14144* (2013.01); *C12N 2750/14122* (2013.01); *C12N 2750/14143* (2013.01); *C12N 2750/14151* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis |
| 4,301,144 A | 11/1981 | Iwashita |
| 4,496,689 A | 1/1985 | Mitra |
| 4,640,835 A | 2/1987 | Shimizu |
| 4,670,417 A | 6/1987 | Iwasaki |
| 4,791,192 A | 12/1988 | Nakagawa |
| 5,064,764 A | 11/1991 | Besnainon |
| 5,474,935 A | 12/1995 | Chatterjee |
| 5,587,308 A | 12/1996 | Carter |
| 5,652,224 A | 7/1997 | Wilson |
| 5,658,785 A | 8/1997 | Johnson |
| 5,688,676 A | 11/1997 | Zhou |
| 5,691,176 A | 11/1997 | Lebkowski |
| 5,693,531 A | 12/1997 | Chiorini |
| 5,741,683 A | 4/1998 | Zhou |
| 5,756,283 A | 5/1998 | Wilson |
| 5,856,152 A | 1/1999 | Wilson |
| 5,858,351 A | 1/1999 | Podsakoff |
| 5,858,775 A | 1/1999 | Johnson |
| 5,866,552 A | 2/1999 | Wilson |
| 5,866,696 A | 2/1999 | Carter |
| 5,871,982 A | 2/1999 | Wilson |
| 5,952,221 A | 9/1999 | Kurtzman |
| 5,962,313 A | 10/1999 | Podsakoff |
| 5,989,540 A | 11/1999 | Carter |
| 6,083,716 A | 7/2000 | Wilson |
| 6,143,548 A | 11/2000 | ORiordan |
| 6,143,567 A | 11/2000 | Van Agthoven |
| 6,146,874 A | 11/2000 | Zolotukhin |
| 6,156,303 A | 12/2000 | Russell |
| 6,174,527 B1 | 1/2001 | Wilson |
| 6,180,613 B1 | 1/2001 | Kaplitt |
| 6,194,191 B1 | 2/2001 | Zhang |
| 6,200,560 B1 | 3/2001 | Couto |
| 6,204,059 B1 | 3/2001 | Samulski |
| 6,211,163 B1 | 4/2001 | Podsakoff |

(Continued)

FOREIGN PATENT DOCUMENTS

| | | |
|---|---|---|
| EP | 1015619 | 7/2000 |
| EP | 1046711 | 10/2000 |

(Continued)

OTHER PUBLICATIONS

Snyder, RO, Im, DS, Ni, T, Xiao, X, Samulski, RJ and Muzyczka, N. Features of the adeno-associated virus origin involved in substrate recognition by the viral Rep protein. Journal of Virology, Oct. 1993, p. 6096-6104.*

Young and Samulski, Adeno-associated virus (AAV) site-specific recombination does not require a Repdependent origin of replication within the AAV terminal repeat, PNAS, 2001, 13525-13530.*

Schmidt et al., Cloning and Characterization of a Bovine Adeno-Associated Virus, Journal of Virology, Jun. 2004, p. 6509-6516.*

(Continued)

*Primary Examiner* — Maria Marvich

(74) *Attorney, Agent, or Firm* — Nelson Mullins Riley & Scarborough LLP; Jane E. Remillard, Esq.; Christopher L. Frank

(57) ABSTRACT

The present invention is directed to viral vectors and methods of their production and use.

42 Claims, 22 Drawing Sheets

Specification includes a Sequence Listing.

(56) References Cited

U.S. PATENT DOCUMENTS

| | | |
|---|---|---|
| 6,251,677 B1 | 6/2001 | Wilson |
| 6,258,595 B1 | 7/2001 | Gao |
| 6,261,551 B1 | 7/2001 | Wilson |
| 6,265,389 B1 | 7/2001 | Burke |
| 6,270,996 B1 | 8/2001 | Wilson |
| 6,274,354 B1 | 8/2001 | Wilson |
| 6,281,010 B1 | 8/2001 | Gao |
| 6,325,998 B1 | 12/2001 | Podsakoff |
| 6,335,011 B1 | 1/2002 | Podsakoff |
| 6,365,394 B1 | 4/2002 | Gao |
| 6,387,368 B1 | 5/2002 | Wilson |
| 6,399,385 B1 | 6/2002 | Croyle |
| 6,410,300 B1 | 6/2002 | Samulski |
| 6,416,992 B1 | 7/2002 | Mejza |
| 6,428,988 B1 | 8/2002 | Wilson |
| 6,436,392 B1 | 8/2002 | Engelhardt |
| 6,436,394 B1 | 8/2002 | Henderson |
| 6,468,524 B1 | 10/2002 | Chiorini |
| 6,468,771 B1 | 10/2002 | Einerhand |
| 6,475,769 B1 | 11/2002 | Wilson |
| 6,482,634 B1 | 11/2002 | Wilson |
| 6,485,966 B2 | 11/2002 | Gao |
| 6,503,888 B1 | 1/2003 | Kaplitt |
| 6,509,150 B1 | 1/2003 | Salvetti |
| 6,521,426 B1 | 2/2003 | Ciliberto |
| 6,555,525 B2 | 4/2003 | Burke |
| 6,566,118 B1 | 5/2003 | Atkinson |
| 6,582,692 B1 | 6/2003 | Podsakoff |
| 6,593,123 B1 | 7/2003 | Wright |
| 6,610,290 B2 | 8/2003 | Podsakoff |
| 6,610,836 B1 | 8/2003 | Breton et al. |
| 6,642,051 B1 | 11/2003 | Lynch |
| 6,660,514 B1 | 12/2003 | Zolotukhin |
| 6,660,521 B2 | 12/2003 | Brough |
| 6,670,176 B1 | 12/2003 | Samulski |
| 6,676,935 B2 | 1/2004 | Henderson |
| 6,699,706 B1 | 3/2004 | Brooks |
| 6,710,036 B2 | 3/2004 | Kurtzman |
| 6,723,551 B2 | 4/2004 | Kotin |
| 6,726,907 B1 | 4/2004 | Zhang |
| 6,753,419 B1 | 6/2004 | Toniatti |
| 6,759,237 B1 | 7/2004 | Wilson |
| 6,846,665 B1 | 1/2005 | Horer |
| 6,855,314 B1 | 2/2005 | Chiorini |
| 6,887,463 B2 | 5/2005 | Wilson |
| 6,897,045 B2 | 5/2005 | Engelhardt |
| 6,936,466 B2 | 8/2005 | Feldhaus |
| 6,943,019 B2 | 9/2005 | Wilson |
| 6,953,690 B1 | 10/2005 | Gao |
| 6,984,517 B1 | 1/2006 | Chiorini |
| 6,995,006 B2 | 2/2006 | Atkinson |
| 7,015,026 B2 | 3/2006 | ORiordan |
| 7,022,519 B2 | 4/2006 | Gao |
| 7,048,920 B2 | 5/2006 | Yu |
| 7,056,502 B2 | 6/2006 | Hildinger |
| 7,070,998 B2 | 7/2006 | Johnson |
| 7,091,030 B2 | 8/2006 | Setiawan |
| 7,094,604 B2 | 8/2006 | Snyder |
| 7,105,345 B2 | 9/2006 | Wilson |
| 7,112,321 B2 | 9/2006 | Wang |
| 7,125,705 B2 | 10/2006 | Colosi |
| 7,125,706 B2 | 10/2006 | Zhang |
| 7,169,612 B2 | 1/2007 | Kostenis |
| 7,186,552 B2 | 3/2007 | Wilson |
| 7,198,951 B2 | 4/2007 | Gao |
| 7,223,585 B2 | 5/2007 | Coffey |
| 7,235,393 B2 | 6/2007 | Gao |
| 7,238,526 B2 | 7/2007 | Wilson |
| 7,241,447 B1 | 7/2007 | Engelhardt |
| 7,247,472 B2 | 7/2007 | Wilson |
| 7,271,002 B2 | 9/2007 | Kotin |
| 7,282,199 B2 | 10/2007 | Gao |
| 7,291,498 B2 | 11/2007 | Roy |
| 7,300,797 B2 | 11/2007 | Van Agthoven |
| 7,306,794 B2 | 12/2007 | Wilson |
| 7,319,002 B2 | 1/2008 | Wilson |
| 7,326,555 B2 | 2/2008 | Konz |
| 7,344,872 B2 | 3/2008 | Gao |
| 7,419,817 B2 | 9/2008 | Chiorini |
| 7,419,956 B2 | 9/2008 | Ohtaki |
| 7,445,930 B2 | 11/2008 | Zhang |
| 7,479,554 B2 | 1/2009 | Chiorini |
| 7,491,508 B2 | 2/2009 | Roy |
| 7,510,872 B2 | 3/2009 | Clark |
| 7,510,875 B2 | 3/2009 | Zhang |
| 7,579,181 B2 | 8/2009 | ORiordan |
| 7,588,757 B2 | 9/2009 | Ozawa et al. |
| 7,625,570 B1 | 12/2009 | Schaffer |
| 7,638,120 B2 | 12/2009 | Liu |
| 7,662,627 B2 | 2/2010 | Johnson |
| 7,704,492 B2 | 4/2010 | Podsakoff |
| 7,704,721 B2 | 4/2010 | Wright |
| 7,732,129 B1 | 6/2010 | Zhang |
| 7,790,449 B2 | 9/2010 | Gao |
| 7,803,622 B2 | 9/2010 | Engelhardt |
| 7,838,277 B2 | 11/2010 | Gao |
| 7,888,096 B2 | 2/2011 | Wu |
| 7,901,921 B2 | 3/2011 | Coffey |
| 7,906,111 B2 | 3/2011 | Wilson |
| 7,968,333 B2 | 6/2011 | Yu |
| 8,105,574 B2 | 1/2012 | Wilson |
| 8,110,351 B2 | 2/2012 | Bosnes |
| 8,137,948 B2 | 3/2012 | Qu |
| 8,163,543 B2 | 4/2012 | Urabe |
| 8,231,880 B2 | 7/2012 | Roy |
| 8,236,495 B2 | 8/2012 | Nochumson |
| 8,241,622 B2 | 8/2012 | Englehardt |
| 8,273,344 B2 | 9/2012 | Wang |
| 8,283,151 B2 | 10/2012 | Schmidt |
| 8,318,480 B2 | 11/2012 | Gao |
| 8,318,687 B2 | 11/2012 | Tabira |
| 8,394,386 B2 | 3/2013 | Wilson |
| 8,409,842 B2 | 4/2013 | Clark |
| 8,470,310 B2 | 6/2013 | Roy |
| 8,476,418 B2 | 7/2013 | Mueller |
| 8,512,981 B2 | 8/2013 | Hermens |
| 8,524,219 B2 | 9/2013 | Roy |
| 8,524,446 B2 | 9/2013 | Gao |
| 8,603,459 B2 | 12/2013 | Wilson |
| 8,614,101 B2 | 12/2013 | VanDine |
| 8,637,255 B2 | 1/2014 | Wilson |
| 8,642,314 B2 | 2/2014 | Bakker |
| 8,685,734 B2 | 4/2014 | Coffey |
| 8,697,417 B2 | 4/2014 | Bakker |
| 8,697,665 B2 | 4/2014 | Rom |
| 8,834,863 B2 | 9/2014 | Roy |
| 8,846,030 B2 | 9/2014 | Engelhardt |
| 8,846,389 B2 | 9/2014 | Chiorini |
| 8,906,387 B2 | 12/2014 | Kay |
| 8,906,675 B2 | 12/2014 | Gao |
| 8,927,514 B2 | 1/2015 | Chatterjee |
| 8,962,330 B2 | 2/2015 | Gao |
| 8,962,332 B2 | 2/2015 | Gao |
| 8,999,678 B2 | 4/2015 | Vandenberghe |
| 9,051,542 B2 | 6/2015 | Wright |
| 9,056,892 B2 | 6/2015 | Pun |
| 9,080,183 B2 | 7/2015 | Klein |
| 9,089,667 B2 | 7/2015 | Bankiewicz |
| 9,102,943 B2 | 8/2015 | Shinmura |
| 9,115,373 B2 | 8/2015 | Hermens |
| 9,163,260 B2 | 10/2015 | Wilson |
| 9,217,155 B2 | 12/2015 | Gao |
| 9,217,159 B2 | 12/2015 | Roy |
| 9,228,174 B2 | 1/2016 | Noordman |
| 9,233,174 B2 | 1/2016 | Chen |
| 9,238,800 B2 | 1/2016 | Bossis |
| 9,260,724 B2 | 2/2016 | Bakker |
| 9,439,979 B2 | 9/2016 | Chiorini |
| 9,441,206 B2 | 9/2016 | Grieger |
| 9,441,244 B2 | 9/2016 | Schaffer |
| 9,446,105 B2 | 9/2016 | Powell |
| 9,447,433 B2 | 9/2016 | Hirsch |
| 9,457,103 B2 | 10/2016 | Schaffer |
| 9,458,517 B2 | 10/2016 | Schaffer |

(56) References Cited

U.S. PATENT DOCUMENTS

| | | |
|---|---|---|
| 9,464,119 B2 | 10/2016 | Sonntag |
| 9,475,845 B2 | 10/2016 | Asokan |
| 9,493,788 B2 | 11/2016 | Gao |
| 9,499,629 B2 | 11/2016 | June |
| 9,506,083 B2 | 11/2016 | Arbetman |
| 9,518,123 B2 | 12/2016 | June |
| 9,528,126 B2 | 12/2016 | Qu |
| 9,540,445 B2 | 1/2017 | June |
| 9,540,659 B2 | 1/2017 | Davidson |
| 9,546,112 B2 | 1/2017 | Voit |
| 9,546,369 B2 | 1/2017 | Gao |
| 9,567,376 B2 | 2/2017 | Cronin |
| 9,567,607 B2 | 2/2017 | Wilson |
| 9,573,988 B2 | 2/2017 | Brogdon |
| 9,580,691 B2 | 2/2017 | Bakker |
| 9,585,971 B2 | 3/2017 | Deverman |
| 9,587,020 B2 | 3/2017 | Wu |
| 9,587,250 B2 | 3/2017 | Gao |
| 9,587,282 B2 | 3/2017 | Schaffer |
| 9,593,346 B2 | 3/2017 | Roy |
| 9,596,835 B2 | 3/2017 | Gao |
| 9,597,363 B2 | 3/2017 | Roy |
| 9,598,468 B2 | 3/2017 | Weigel-Van Aken |
| 9,598,489 B2 | 3/2017 | Powell |
| 9,598,703 B2 | 3/2017 | Garcia |
| 9,611,302 B2 | 4/2017 | Srivastava |
| 9,617,561 B2 | 4/2017 | Roy |
| 9,623,120 B2 | 4/2017 | Chatterjee |
| 9,624,274 B2 | 4/2017 | Lux |
| 9,636,370 B2 | 5/2017 | McCown |
| 9,657,105 B2 | 5/2017 | Forman |
| 9,670,507 B2 | 6/2017 | Xiao |
| 9,677,088 B2 | 6/2017 | Nakai |
| 9,677,089 B2 | 6/2017 | Gao |
| 9,682,193 B2 | 6/2017 | Anand |
| 9,695,220 B2 | 7/2017 | Vandenberghe |
| 9,701,984 B2 | 7/2017 | Gao |
| 9,708,627 B2 | 7/2017 | Mermens |
| 9,719,070 B2 | 8/2017 | Vandenberghe |
| 9,719,106 B2 | 8/2017 | Wilson |
| 9,725,485 B2 | 8/2017 | Srivastava |
| 9,732,345 B2 | 8/2017 | Martin |
| 9,737,618 B2 | 8/2017 | Wilson |
| 9,745,590 B2 | 8/2017 | Kay |
| 9,775,918 B2 | 10/2017 | Zhong |
| 9,777,291 B2 | 10/2017 | Chatterjee |
| 9,783,824 B2 | 10/2017 | Kay |
| 9,783,825 B2 | 10/2017 | Chatterjee |
| 9,790,472 B2 | 10/2017 | Gao |
| 9,803,218 B2 | 10/2017 | Chatterjee |
| 2001/0006955 A1 | 7/2001 | Wilson |
| 2001/0049144 A1 | 12/2001 | Rivera |
| 2002/0019050 A1 | 2/2002 | Gao |
| 2002/0037867 A1 | 3/2002 | Wilson |
| 2002/0081721 A1 | 6/2002 | Allen |
| 2002/0090717 A1 | 7/2002 | Gao |
| 2002/0102714 A1 | 8/2002 | Wilson |
| 2002/0131961 A1 | 9/2002 | Wilson |
| 2003/0013189 A1 | 1/2003 | Wilson |
| 2003/0032613 A1 | 2/2003 | Gao |
| 2003/0092161 A1 | 5/2003 | Gao |
| 2003/0100115 A1 | 5/2003 | Raj |
| 2003/0119191 A1 | 6/2003 | Gao |
| 2003/0138772 A1 | 7/2003 | Gao |
| 2004/0043490 A1 | 3/2004 | Shimada |
| 2004/0057931 A1 | 3/2004 | Wilson |
| 2004/0136963 A1 | 7/2004 | Wilson |
| 2004/0171807 A1 | 9/2004 | Gao |
| 2005/0261218 A1 | 11/2005 | Esau |
| 2006/0003451 A1 | 1/2006 | Gao |
| 2006/0204479 A1 | 9/2006 | Wilson |
| 2007/0004042 A1 | 1/2007 | Gao |
| 2007/0072282 A1* | 3/2007 | Chiorini ............ A61K 48/0075 435/235.1 |
| 2008/0008684 A1 | 1/2008 | Wilson |
| 2008/0050343 A1 | 2/2008 | Wilson |
| 2008/0050345 A1 | 2/2008 | Wilson |
| 2008/0075737 A1 | 3/2008 | Gao |
| 2008/0153156 A1* | 6/2008 | Gray ................. A61K 48/0066 435/320.1 |
| 2008/0226600 A1 | 9/2008 | Engelhardt et al. |
| 2009/0215871 A1 | 8/2009 | Wilson |
| 2009/0275107 A1 | 11/2009 | Lock |
| 2009/0317417 A1 | 12/2009 | Vandenberghe |
| 2010/0247490 A1 | 9/2010 | Roy |
| 2010/0278791 A1 | 11/2010 | Wilson |
| 2011/0136227 A1 | 6/2011 | Bakker |
| 2011/0171262 A1 | 7/2011 | Bakker |
| 2011/0223135 A1 | 9/2011 | Roy |
| 2011/0229971 A1 | 9/2011 | Knop |
| 2012/0046349 A1 | 2/2012 | Bell |
| 2012/0058102 A1 | 3/2012 | Wilson |
| 2012/0093853 A1 | 4/2012 | Wilson |
| 2012/0137379 A1 | 5/2012 | Gao |
| 2012/0258046 A1 | 10/2012 | Mutzke |
| 2013/0023033 A1 | 1/2013 | Wilson |
| 2013/0045186 A1 | 2/2013 | Gao |
| 2013/0101558 A1 | 4/2013 | Gao |
| 2013/0109742 A1* | 5/2013 | Hewitt ................. C07K 14/005 514/44 R |
| 2013/0195801 A1 | 8/2013 | Gao |
| 2013/0296532 A1 | 11/2013 | Mermens |
| 2013/0323226 A1 | 12/2013 | Wilson |
| 2013/0323302 A1 | 12/2013 | Constable |
| 2014/0031418 A1 | 1/2014 | Wilson |
| 2014/0044680 A1 | 2/2014 | Roy |
| 2014/0065105 A1 | 3/2014 | Wilson |
| 2014/0087361 A1 | 3/2014 | Dobbelaer |
| 2014/0099666 A1 | 4/2014 | Rossomando |
| 2014/0107186 A1 | 4/2014 | Garcia |
| 2014/0271550 A1 | 9/2014 | Rabinowitz et al. |
| 2014/0336245 A1 | 11/2014 | Mingozzi |
| 2014/0341852 A1 | 11/2014 | Srivastava |
| 2014/0342434 A1 | 11/2014 | Hermens |
| 2015/0005369 A1 | 1/2015 | Muzyczka |
| 2015/0023924 A1 | 1/2015 | High |
| 2015/0065562 A1 | 3/2015 | Yazicioglu |
| 2015/0118287 A1 | 4/2015 | Hammond |
| 2015/0139952 A1 | 5/2015 | Webster |
| 2015/0159173 A1 | 6/2015 | Vandenberghe |
| 2015/0197771 A1 | 7/2015 | Bethune |
| 2015/0238610 A1 | 8/2015 | Sista |
| 2015/0307898 A2 | 10/2015 | Hermens |
| 2015/0315610 A1 | 11/2015 | Nishie |
| 2015/0374803 A1 | 12/2015 | Wolfe |
| 2016/0032319 A1 | 2/2016 | Wright |
| 2016/0074474 A1* | 3/2016 | Passini ................ A61K 9/0085 514/44 R |
| 2016/0108373 A1 | 4/2016 | Bennett |
| 2016/0153992 A1 | 6/2016 | Buening |
| 2016/0271192 A1 | 9/2016 | Roy |
| 2016/0273058 A1 | 9/2016 | Akashika |
| 2016/0289275 A1 | 10/2016 | Chiorini |
| 2016/0296694 A1 | 10/2016 | Bankiewicz |
| 2016/0297884 A1 | 10/2016 | Kuo |
| 2016/0303230 A1 | 10/2016 | Ahmed |
| 2016/0311917 A1 | 10/2016 | Beatty |
| 2016/0331897 A1 | 11/2016 | Anand |
| 2016/0333372 A1 | 11/2016 | Srivastava |
| 2016/0333373 A1 | 11/2016 | Farley |
| 2016/0333375 A1 | 11/2016 | Chen |
| 2016/0340393 A1 | 11/2016 | Schaffer |
| 2016/0340406 A1 | 11/2016 | Zhao |
| 2016/0340692 A1 | 11/2016 | Wang |
| 2016/0361439 A1 | 12/2016 | Agbandje-Mckenna |
| 2016/0369298 A1 | 12/2016 | Marsic |
| 2016/0369299 A1 | 12/2016 | Boye |
| 2016/0375151 A1 | 12/2016 | Schaffer |
| 2016/0376323 A1 | 12/2016 | Schaffer |
| 2016/0376608 A1 | 12/2016 | Chou |
| 2017/0000904 A1 | 1/2017 | Wilson |
| 2017/0007669 A1 | 1/2017 | Sarkar |
| 2017/0007720 A1 | 1/2017 | Boye |
| 2017/0028082 A1 | 2/2017 | Wilson |

(56) References Cited

U.S. PATENT DOCUMENTS

| | | |
|---|---|---|
| 2017/0044504 A1 | 2/2017 | Schaffer |
| 2017/0049819 A1 | 2/2017 | Friedman |
| 2017/0051252 A1 | 2/2017 | Morgan |
| 2017/0051308 A1 | 2/2017 | Morgan |
| 2017/0067028 A1 | 3/2017 | Ballon |
| 2017/0071972 A1 | 3/2017 | Buj Bello |
| 2017/0073703 A1 | 3/2017 | Chatterjee |
| 2017/0088858 A1 | 3/2017 | Gao |
| 2017/0096646 A1 | 4/2017 | Roy |
| 2017/0105927 A1 | 4/2017 | Thorne |
| 2017/0112946 A1 | 4/2017 | Ikeda |
| 2017/0121419 A1 | 5/2017 | Wang |
| 2017/0121734 A1 | 5/2017 | Cairns |
| 2017/0128594 A1 | 5/2017 | Wright |
| 2017/0130208 A1 | 5/2017 | Potter |
| 2017/0130228 A1 | 5/2017 | Dominguez-Villar |
| 2017/0130245 A1 | 5/2017 | Kotin |
| 2017/0137515 A1 | 5/2017 | Chang |
| 2017/0145440 A1 | 5/2017 | Hermens |
| 2017/0151283 A1 | 6/2017 | Powell |
| 2017/0151348 A1 | 6/2017 | Kaspar |
| 2017/0151416 A1 | 6/2017 | Kutikov |
| 2017/0152525 A1 | 6/2017 | Hermens |
| 2017/0157267 A1 | 6/2017 | Kay |
| 2017/0159026 A1 | 6/2017 | Kay |
| 2017/0159027 A1 | 6/2017 | Wilson |
| 2017/0159072 A9 | 6/2017 | Arbeit |
| 2017/0165377 A1 | 6/2017 | Gao |
| 2017/0166871 A1 | 6/2017 | Nishie |
| 2017/0166925 A1 | 6/2017 | Gao |
| 2017/0166926 A1 | 6/2017 | Deverman |
| 2017/0166927 A1 | 6/2017 | Gao |
| 2017/0183636 A1 | 6/2017 | Roy |
| 2017/0191039 A1 | 7/2017 | Gao |
| 2017/0191079 A1 | 7/2017 | Vandenberghe |
| 2017/0198304 A1 | 7/2017 | Wilson |
| 2017/0204144 A1 | 7/2017 | Deverman |
| 2017/0211092 A1 | 7/2017 | Chatterjee |
| 2017/0211093 A1 | 7/2017 | Chatterjee |
| 2017/0211094 A1 | 7/2017 | Chatterjee |
| 2017/0211095 A1 | 7/2017 | Chatterjee |
| 2017/0216458 A1 | 8/2017 | Kaspar |
| 2017/0218379 A1 | 8/2017 | Lewis |
| 2017/0218395 A1 | 8/2017 | Byrne |
| 2017/0226160 A1 | 8/2017 | Sonntag |
| 2017/0232072 A1 | 8/2017 | Ikeda |
| 2017/0232117 A1 | 8/2017 | Arbetman |
| 2017/0240885 A1 | 8/2017 | Deverman |
| 2017/0240921 A1 | 8/2017 | Gao |
| 2017/0246322 A1 | 8/2017 | Mendell |
| 2017/0247664 A1 | 8/2017 | Wright |
| 2017/0258996 A1 | 9/2017 | Anand |
| 2017/0260545 A1 | 9/2017 | Qu |
| 2017/0274024 A1 | 9/2017 | McCown |
| 2017/0275337 A1 | 9/2017 | Srivastava |
| 2017/0292132 A1 | 10/2017 | Wilson |
| 2017/0298323 A1 | 10/2017 | Vandenberghe |
| 2017/0304464 A1 | 10/2017 | Kugler |
| 2017/0306354 A1 | 10/2017 | Gao |
| 2017/0306355 A1 | 10/2017 | Davidson |
| 2017/0321290 A1 | 11/2017 | Lubelski |

FOREIGN PATENT DOCUMENTS

| | | |
|---|---|---|
| EP | 1078096 | 2/2001 |
| EP | 1164195 | 12/2001 |
| EP | 1183380 | 3/2002 |
| EP | 1218035 | 7/2002 |
| EP | 1240345 | 9/2002 |
| EP | 1279740 | 1/2003 |
| EP | 1453547 | 9/2004 |
| EP | 1696036 | 8/2006 |
| EP | 1847614 A1 | 10/2007 |
| EP | 1849872 | 10/2007 |
| EP | 1857552 | 11/2007 |
| EP | 1944043 | 7/2008 |
| EP | 2007795 | 12/2008 |
| EP | 2198016 | 6/2010 |
| EP | 2220241 | 8/2010 |
| EP | 2220242 | 8/2010 |
| EP | 2250256 | 11/2010 |
| EP | 2292779 | 3/2011 |
| EP | 2292780 B1 | 3/2011 |
| EP | 2301582 B1 | 3/2011 |
| EP | 2325298 A2 | 5/2011 |
| EP | 2359866 | 8/2011 |
| EP | 2383346 | 11/2011 |
| EP | 2524037 | 11/2012 |
| EP | 2660325 | 11/2013 |
| EP | 2699270 | 2/2014 |
| EP | 2814958 | 12/2014 |
| EP | 2871239 A9 | 6/2015 |
| EP | 2879719 | 6/2015 |
| EP | 2933336 | 10/2015 |
| EP | 2943567 | 11/2015 |
| EP | 3058959 | 8/2016 |
| EP | 2176283 | 11/2016 |
| EP | 3067417 A3 | 11/2016 |
| EP | 3108000 | 12/2016 |
| EP | 3117005 A1 | 1/2017 |
| EP | 2737071 B1 | 3/2017 |
| EP | 3134431 | 3/2017 |
| EP | 2531604 B1 | 4/2017 |
| EP | 3168298 | 5/2017 |
| EP | 3209311 | 8/2017 |
| EP | 2311967 | 9/2017 |
| EP | 3215602 | 9/2017 |
| EP | 3221453 | 9/2017 |
| EP | 3221456 | 9/2017 |
| EP | 3224376 | 10/2017 |
| EP | 3230441 | 10/2017 |
| EP | 3235827 | 10/2017 |
| WO | 1993009239 | 5/1993 |
| WO | 1995034670 | 12/1995 |
| WO | 1996017947 A1 | 6/1996 |
| WO | 1996023810 | 8/1996 |
| WO | 1996030540 | 10/1996 |
| WO | 1998010088 | 3/1998 |
| WO | 1999027110 | 6/1999 |
| WO | 1999043360 | 9/1999 |
| WO | 1999058700 | 11/1999 |
| WO | 1999061595 | 12/1999 |
| WO | 1999060146 | 5/2000 |
| WO | 2000024916 | 5/2000 |
| WO | 2000066780 | 11/2000 |
| WO | 2000075353 | 12/2000 |
| WO | 2001014539 | 3/2001 |
| WO | 2001023001 | 4/2001 |
| WO | 2001025465 | 4/2001 |
| WO | 2001032711 | 5/2001 |
| WO | 2001036623 | 5/2001 |
| WO | 2001042444 | 6/2001 |
| WO | 2001068888 | 9/2001 |
| WO | 2001/092551 A2 | 12/2001 |
| WO | 2001092551 A2 | 12/2001 |
| WO | 2001096587 | 12/2001 |
| WO | 2002012525 | 2/2002 |
| WO | 2002014487 | 2/2002 |
| WO | 2002020748 | 3/2002 |
| WO | 2002070719 | 9/2002 |
| WO | 2002071843 | 9/2002 |
| WO | 2003010320 | 2/2003 |
| WO | 2003024502 | 3/2003 |
| WO | 2003042397 | 5/2003 |
| WO | 2003087382 | 10/2003 |
| WO | 2003087383 | 10/2003 |
| WO | 2004044003 | 5/2004 |
| WO | 2004083441 | 9/2004 |
| WO | 2004108922 | 12/2004 |
| WO | 2004111248 | 12/2004 |
| WO | 2005005610 | 1/2005 |
| WO | 2005012537 | 2/2005 |
| WO | 2005111220 | 11/2005 |
| WO | 2006102072 | 9/2006 |

(56) References Cited

FOREIGN PATENT DOCUMENTS

| | | |
|---|---|---|
| WO | 2007130519 | 11/2007 |
| WO | 2008/016391 A2 | 2/2008 |
| WO | 2008016391 | 2/2008 |
| WO | 2007148971 | 7/2009 |
| WO | 2009134681 | 11/2009 |
| WO | 2011038187 | 3/2011 |
| WO | 2011054976 | 5/2011 |
| WO | 2011088081 A1 | 7/2011 |
| WO | 2011122950 | 10/2011 |
| WO | 2010109053 | 11/2011 |
| WO | 2012057363 | 5/2012 |
| WO | 2012114090 | 8/2012 |
| WO | 2012144446 | 10/2012 |
| WO | 2013014294 A2 | 1/2013 |
| WO | 2013078199 | 5/2013 |
| WO | 2013164793 | 11/2013 |
| WO | 2013170078 | 11/2013 |
| WO | 2014/127196 A1 | 8/2014 |
| WO | 2014127196 | 8/2014 |
| WO | 2014160092 | 10/2014 |
| WO | 2014168953 | 10/2014 |
| WO | 2014170470 | 10/2014 |
| WO | 2014172669 | 10/2014 |
| WO | 2014186579 | 11/2014 |
| WO | 2014194132 | 12/2014 |
| WO | 2014201252 | 12/2014 |
| WO | 2015012924 | 1/2015 |
| WO | 2015018503 | 2/2015 |
| WO | 2014186746 | 3/2015 |
| WO | 2015031686 | 4/2015 |
| WO | 2015044292 | 4/2015 |
| WO | 2015060722 | 4/2015 |
| WO | 2015108610 | 7/2015 |
| WO | 2015114365 | 8/2015 |
| WO | 2015121501 | 8/2015 |
| WO | 2015124546 | 8/2015 |
| WO | 2015137802 | 9/2015 |
| WO | 2015127128 | 11/2015 |
| WO | 2015196179 | 12/2015 |
| WO | 2016019364 | 2/2016 |
| WO | 2016054554 | 4/2016 |
| WO | 2016054557 | 4/2016 |
| WO | 2016065001 | 4/2016 |
| WO | 2016081811 | 5/2016 |
| WO | 2016081927 | 5/2016 |
| WO | 2016115382 | 7/2016 |
| WO | 2016122791 | 8/2016 |
| WO | 2016126857 | 8/2016 |
| WO | 2016130591 | 8/2016 |
| WO | 2016137949 | 9/2016 |
| WO | 2016154055 | 9/2016 |
| WO | 2016154344 | 9/2016 |
| WO | 2016164609 | 10/2016 |
| WO | 2016168728 | 10/2016 |
| WO | 2016172008 | 10/2016 |
| WO | 2016172155 | 10/2016 |
| WO | 2016179496 | 11/2016 |
| WO | 2016183297 | 11/2016 |
| WO | 2016191418 | 12/2016 |
| WO | 2016196507 | 12/2016 |
| WO | 2017004514 | 1/2017 |
| WO | 2017005806 | 1/2017 |
| WO | 2017015102 | 1/2017 |
| WO | 2017019876 A1 | 2/2017 |
| WO | 2017019994 | 2/2017 |
| WO | 2017058892 | 4/2017 |
| WO | 2017070476 | 4/2017 |
| WO | 2017070516 | 4/2017 |
| WO | 2017070525 | 4/2017 |
| WO | 2017070678 | 4/2017 |
| WO | 2017075335 | 5/2017 |
| WO | 2017083423 | 5/2017 |
| WO | 2017093330 | 6/2017 |
| WO | 2017096039 | 6/2017 |
| WO | 2017100671 | 6/2017 |
| WO | 2017100674 | 6/2017 |
| WO | 2017100676 | 6/2017 |
| WO | 2017100704 | 6/2017 |
| WO | 2017106236 | 6/2017 |
| WO | 2017112948 | 6/2017 |
| WO | 2017122789 | 7/2017 |
| WO | 2017123934 A1 | 7/2017 |
| WO | 2017136202 | 8/2017 |
| WO | 2017136536 | 8/2017 |
| WO | 2017139381 | 8/2017 |
| WO | 2017143100 | 8/2017 |
| WO | 2017147477 | 8/2017 |
| WO | 2017151884 | 9/2017 |
| WO | 2017152149 | 9/2017 |
| WO | 2017155973 | 9/2017 |
| WO | 2017160360 | 9/2017 |
| WO | 2017165167 | 9/2017 |
| WO | 2017165859 | 9/2017 |
| WO | 2017172772 | 10/2017 |
| WO | 2017173043 | 10/2017 |
| WO | 2017173283 | 10/2017 |
| WO | 2017180854 | 10/2017 |
| WO | 2017181162 | 10/2017 |
| WO | 2017184879 | 10/2017 |
| WO | 2017190031 | 11/2017 |
| WO | 2017192699 | 11/2017 |
| WO | 2017192750 | 11/2017 |

OTHER PUBLICATIONS

Grimm et al., Liver Transduction with Recombinant Adeno-Associated Virus is Primarily Restricted by Capsid Serotype Not Vector Genotype, Journal of Virology, Jan. 2006, p. 426-439.*

Ryan et al., Sequence Requirements for Binding of Rep68 to the Adeno-Associated Virus Terminal Repeats, Journal of Virology, Mar. 1996, p. 1542-1553.*

McCarty, DM Self-complementary AAV Vectors; Advances and Applications, Molecular Therapy. Aug. 5, 2008, vol. 10, pp. 1648-1656; abstract.

Negrete, A et al. Strategies for Manufacturing Recombinant Adeno-Associated Virus Vectors for Gene Therapy Applications Exploiting Baculovirus Technology. Briefings in Functional Genomics and Proteomics. Jul. 16, 2008, vol. 7, No. 4, pp. 303-211.

Wasilko DJ, et al. The titerless infected-cells preservation and scale-up (TIPS) method for large-scale production of NO-sensitive human soluble guanylate cyclase (sGC) from insect cells infected with recombinant baculovirus. Protein Expr Purif. Jun. 2009;65(2):122-32. doi: 10.1016/j.pep.2009.01.002. Epub Jan. 11, 2009.

Zhao KN, et al. BPV1 E2 protein enhances packaging of full-length plasmid DNA in BPV1 pseudovirions. Virology. Jul. 5, 2000;272(2):382-93.

Pierson EE, et al. Resolving adeno-associated viral particle diversity with charge detection mass spectrometry. Anal Chem. Jul. 2016;88(13):6718-25.

Rashnonejad A, et al. Large-Scale Production of Adeno-Associated Viral Vector Serotype-9 Carrying the Human Survival Motor Neuron Gene. Mol Biotechnol. Jan. 2016,58(1):30-6.

Ling C, et al. Strategies to generate high-titer, high-potency recombinant AAV3 serotype vectors. Mol Ther Methods Clin Dev. May 2016;3:16029.

Afione S, et al. Identification and Mutagenesis of the Adeno-Associated Virus 5 Sialic Acid Binding Region.J Virol. Feb. 2015, 89(3):1660-72.

Drouin LM, et al. Cryo-electron microscopy reconstruction and stability studies of Wild-Type and R432A Variant of AAV2 Reveals Capsid Structural Stability is a Major Factor in Genome Packaging. J Virol. Sep. 2016;90(19):8542-51.

Halder S, et al. Structure of neurotropic adeno-associated virus AAVrh.8. J Struct Biol. Oct. 2015;192(1):21-36.

Huang LY, et al. Characterization of the adeno-associated virus 1 and 6 sialic acid binding site. J Virol. May 2016;90(11):5219-30.

Mao Y, et al. Single point mutation in adeno-associated viral vectors—DJ capsid leads to improvement for gene delivery in vivo BMC Biotechnol. Jan. 2016;16:1, pp. 1-8.

(56) References Cited

OTHER PUBLICATIONS

Tu MY, et al. Role of capsid proteins in parvoviruses infection. Virol J. Aug. 2015, 4,12:114, pp. 1-8.
Zeng C, et al. Probing the Link between Genomic Cargo, Contact Mechanics and Nanoindentation in Recombinant Adeno-Associated Virus 2. J Phys Chem B. Mar. 2017;121(8):1843-1853.
Zinn E, et al. In Silico Reconstruction of the Viral Evolutionary Lineage Yields a Potent Gene Therapy Vector. Cell Rep. Aug. 2015, 12(6):1056-68.
Grimm D, et al. E Pluribus Unum: 50 years of research, millions of viruses and one goal—tailored acceleration of AAV evolution. Mol Ther. Dec. 2015;23(12):1819-1831.
Karamuthil-Melethil S, et al. Novel Vector Design and Hexosaminidase Variant Enabling Self-Complementary Adeno-Associated Virus for the Treatment of Tay-Sachs Disease. Hum Gene Ther. Jul. 2016;27(7):509-21.
Ling C, et al. Development of Optimized AAV Serotype Vectors for High-Efficiency Transduction at Further Reduced Doses. Hum Gene Ther Methods. Aug. 2016;27(4):143-9.
Pillay S, et al. An essential receptor for adeno-associated virus infection. Nature. Feb. 2016;530(7588):108-12.
Li BZ, et al. Site directed mutagenesis of surface-exposed lysine residues leads to improved transduction by AAV2 but not AAV8 vectors in murine hepatocytes in vivo. Hum Gene Ther Methods. Dec. 2015;26(6):211-20.
Shen S, et al. Functional Analysis of the Putative Integrin Recognition Motif on Adeno-associated virus 9. J Biol Them. Jan. 2015, 290(3):1496-504.
Steines B, et al. CFTR gene transfer with AAV improves early cystic fibrosis pig phenotypes. JCI Insight. Sep. 2016;1(14):e88728, pp. 1-14.
Bensky MJ, et al. Targeted gene delivery to the enteric nervous system using AAV: a comparison across serotypes and capsid mutants.Mol Ther Mar. 2015;23(3):488-500.
Castle MJ, et al. Controlling AAV Tropism in the Nervous System with Natural and Engineered Capsids. Methods Mol Biol. 2016;1382:133-49.
Choudhury SR, et al. Widespread CNS gene transfer and silencing after systemic delivery of novel AAV-AS vectors Mol Ther. Apr. 2016;24(4):726-35.
Davis AS, et al. Rational design and engineering of a modified adeno-associated virus (AAV1)-based vector system for enhanced retrograde gene delivery. Neurosurgery Feb. 2015;76(2):216-25.
Deverman BE et al. Cre-dependent selection yields AAV variants for widespread gene transfer to the adult brain. Nat Biotechnol. Feb. 2016;34(2):204-9.
Powell SK et al. Characterization of a novel adeno-associated viral vector with preferential oligodendrocyte tropism. Gene Ther Sep. 15, 2016, pp. 1-13.
Tervo et al. A Designer AAV Variant Permits Efficient Retrograde Access to Projection Neurons. Neuron. Oct. 19, 2016;92(2):372-382.
Choudhury et al. In Vivo Selection Yields AAV-B1 Capsid for Central Nervous System and Muscle Gene Therapy. Mol Ther. Aug. 2016;24(7):1247-57.
Keravala A, et al. Evaluating AAV Hybrid Variants for Improved Tropism after Intravitreal Gene Delivery to the Retina. Molecular Therapy, vol. 23, Supplement 1, May 2015, pp. S127-S128.
Vercauteren K, et al. Superior in vivo Transduction of Human Hepatocytes Using Engineered AAV3 Capsid. Mol Ther. Jun. 2016;24(6):1042-9.
Chen M, et al. Efficient Gene Delivery and Expression in Pancreas and Pancreatic Tumors by Capsid-optimized AAV8 Vectors. Hum Gene Ther Methods. Feb. 2017;28(1):49-59.
Earley LF, et al. Identification and Characterization of Nuclear and Nucleolar Localization Signals in the Adeno-Associated Virus Serotype 2 Assembly-Activating Protein. J Virol. Mar. 2015, 89(6):3038-48.
Zou W, et al. Nonstructural protein NP1 of human bocavirus 1 plays a critical role in the expression of viral capsid proteins. J Virol. Apr. 2016;90(9):4658-69.
Mingozzi F, et al. Adeno-associated viral vectors at the frontier between tolerance and immunity. Front Immunol.Mar. 2015, 6:120, pp. 1-3.
Ling C, et al. Enhanced Transgene Expression from Recombinant Single-Stranded D-Sequence-Substituted Adeno-Associated Virus Vectors in Human Cell Lines In Vitro and in Murine Hepatocytes In Vivo. J Virol. Jan. 2015, 89(2):952-61.
Xie J, et al. Short DNA Hairpins Compromise Recombinant Adeno-Associated Virus Genome Homogeneity. Mol Ther. Apr. 24, 2017. Epub ahead of print, pp. 1-12.
Davidsson M, et al. A novel process of viral vector barcoding and library preparation enables high-diversity library generation and recombination-free paired-end sequencing. Sci Rep. Nov. 2016;6:3563.
Chamberlain K, et al. Expressing transgenes that exceed the packaging capacity of AAV capsids. Hum Gene Ther Methods. Feb. 2016;27(1):1-12.
De Leeuw CN et al. rAAV-compatible MiniPromoters for Restricted Expression in the Brain and Eye. Mol Brain. May 10, 2016,9(1):52, pp. 1-13.
Hirsch ML, et al. Delivering Transgenic DNA Exceeding the Carrying Capacity of AAV Vectors. Methods Mol Biol. 2016;1382:21-39.
Lu J, et al. A 5'non-coding exon containing engineered intron enhances transgene expression from recombinant AAV vectors in vivo. Hum Gene Ther. Jan. 2017;28(1):125-134.
Powell SK, et al. Viral expression cassette elements to enhance transgene target specificity and expression in gene therapy. Discov Med. Jan. 2015;19(102):49-57.
Rosario AM et al. Microglia-specific Targeting by Novel Capsid-modified AAV6 Vectors. Mol Ther Methods Clin Dev. Apr. 13, 2016;3:16026, pp. 1-9.
Wang L, et al. Productive life cycle of adeno-associated virus serotype 2 in the complete absence of a conventional polyadenylation signal. J Gen Virol. Sep. 2015;96(9):2780-7.
Yan ZY, et al. Optimization of recombinant adeno-associated virus mediated expression for large transgenes, using a synthetic promoter and tandem array enhancers. Hum Gene Ther. Jun. 2015;26(6):334-46.
Jackson KL, et al. Better Targeting, Better Efficiency for Wide-Scale Neuronal Transduction with the Synapsin Promoter and AAV-PHP. B. Front Mol Neurosci. Nov. 2016;6:116, pp. 1-11.
McClements ME, et al. A fragmented adeno-associated viral dual vector strategy for treatment of diseases caused by mutations in large genes leads to expression of hybrid transcripts. J Genet Syndr Gene Ther. Nov. 2016;7(5):311.
Parr MJ, et al. Tumor-selective transgene expression in vivo mediated by an E2F-responsive adenoviral vector. Nat Med. Oct. 1997;3(10):1145-9.
Reid CA, et al. miRNA mediated post-transcriptional silencing of transgenes leads to increased adeno-associated viral vector yield and targeting specificity. Gene Ther. Jun. 15, 2017 Epub ahead of print, pp. 1-33.
Careter BJ. Adeno-associated virus and the development of adeno-associated virus vectors: a historical perspective. Mol Ther. Dec. 2004;10(6):981-9.
Grimm D, et al. Progress in adeno-associated virus type 2 vector production: promises and prospects for clinical use. Hum Gene Ther. Oct. 10, 1999;10(15):2445-50.
Grimson A, et al. MicroRNA targeting specificity in mammals: determinants beyond seed pairing. Mol Cell. Jul. 6, 2007;27(1):91-105.
Hastie E, et al. Adeno-Associated Virus at 50: A Golden Anniversary of Discovery, Research, and Gene Therapy Success—A Personal Perspective. Hum Gene Ther. May 2015, 26(5):257-65.
Aydemir F, et al. Mutants at the 2-fold interface of AAV2 structural proteins suggest a role in viral transcription for AAV capsids. J Virol. Jul. 2016;90(16):7196-204.
Bantel-Schaal U, et al. Human adeno-associated virus type 5 is only distantly related to other known primate helper-dependent parvoviruses. J Virol. Feb. 1999;73(2):939-47.
Berry GE, et al. Cellular transduction mechanisms of adeno-associated viral vectors. Curr Opin Virol. Dec. 2016;21:54-60.

(56) References Cited

OTHER PUBLICATIONS

Chiorini JA, et al. Adeno-associated virus (AAV) type 5 Rep protein cleaves a unique terminal resolution site compared with other AAV serotypes. J Virol. May 1999;73(5):4293-8.
Chiorini JA, et al. Cloning and characterization of adeno-associated virus type 5. J Virol. Feb. 1999;73(2):1309-19.
Chiorini JA, et al. Cloning of adeno-associated virus type 4 (AAV4) and generation of recombinant AAV4 particles. J Virol. Sep. 1997;71(9):6823-33.
Earley LF, et al. Adeno-Associated Virus Assembly-Activating Protein is Not an Essential Requirement for Capsid Assembly of AAV Serotypes 4, 5 and 11. J Virol. Jan. 2017;91(3):pii:e0198-16, pp. 1-62.
Ding C, et al., Biochemical Characterization of Junonia Coenia Densovirus Nonstructural Protein NS-1. J. Virol., 76(1):338-345 2002.
Adachi K, et al. Drawing a high-resolution functional map of adeno-associated virus capsid by massively parallel sequencing. Nat Commun. 2014;5:3075. doi: 10.1038/ncomms4075, pp. 1-14.
Altschul SF, et al. Basic local alignment search tool. J Mol Biol. Oct. 5, 1990;215(3):403-10.
Carillo H, et al. The Multiple Sequence Alignment Problem in Biology. Siam J. Appl. Math. 48-5 (1988), pp. 1073-1082.
Devereux J A comprehensive set of sequence analysis programs for the VAX. Nucleic Acids Res. Jan. 11, 1984;12(1 Pt 1):387-95.
Gribskov M, et al. Sequence Analysis Primer. M Stockton Press, New York, 1991, pp. 827-828.
Berge SM Pharmaceutical salts. J Pharm Sci. Jan. 1977;66(1):1-19, pp. 1-4.
Bell P, et al. Effects of self-complementarity, codon optimization, transgene, and dose on liver transduction with AAV8. Hum Gene Ther Methods. Dec. 2016;27(6):228-237.
Heim et al., Wavelength mutations and posttranslational autoxidation of green fluorescent protein. Proc. Natl. Acad. Sci. USA (1994), pp. 12501-12504.
Hastie E, et al. Recombinant adeno-associated virus vectors in the treatment of rare diseases. Expert Opin Orphan Drugs. 2015;3(6):675-689.
Fargnoli AS, et al. Liquid jet delivery method featuring S100A1 gene therapy in the rodent model following acute myocardial infarction. Gene Ther. Feb. 2016;23(2):151-7.
Aubourg P. Gene therapy for rare central nervous system diseases comes to age. Endocr Dev. 2016;30:141-6.
Bankiewicz KS et al. AAV Viral Vector Delivery to the Brain by Shape-conforming MR-guided Infusions. J Control Release. Oct. 28, 2016;240:434-442.
Bey K, et al. Efficient CNS targeting in adult mice by intrathecal infusion of single-stranded AAV9-GFP for gene therapy of neurological disorders. Gene Ther. Apr. 20, 2017. Epub ahead of print, pp. 1-8.
Brulet R, et al. NEUROD1 Instructs Neuronal Conversion in Non-Reactive Astrocytes. Stem Cell Reports. May 11, 2017. Epub ahead of print, pp. 1506-1515.
Chandler RJ, et al. Systemic AAV9 gene therapy improves the lifespan of mice with Niemann-Pick disease, type C1. Hum Mol Genet. Jan. 2017;26(1):52-64.
Dang CH, et al. In vivo dynamics of AAV-mediated gene delivery to sensory neurons of the trigeminal ganglia. Sci Rep. Apr. 19, 2017;7(1):927.
Dimidschstein J, et al. A viral strategy for targeting and manipulating interneurons across vertebrate species. Nat Neurosci. Dec. 2016;19(12):1743-1749.
Donsante A et al. Intracerebroventricular delivery of self-complementary adeno-associated virus serotype 9 to the adult rat brain. Gene Ther. May 2016;23(5):401-7.
El-Shamayleh Y, et al. Strategies for targeting primate neural circuits with viral vectors. J Neurophysiol. Jul. 2016;116(1):122-34.
Foust KD, et al. Intravascular AAV9 preferentially targets neonatal neurons and adult astrocytes. Nat Biotechnol. Jan. 2009;27(1):59-65. doi: 10.1038/nbt.1515. Epub Dec. 21, 2008, pp. 59-65.
Gessler DJ et al. Gene Therapy for the Treatment of Neurological Disorders: Metabolic Disorders. Methods Mol Biol. 2016;1382:429-65.
Gilkes JA et al. Preferred Transduction with AAV5 and AAV9 Via Thalamic Administration in the MPS IIIB Model: A Comparison of Four rAAV Serotypes. Mol Genet Metab Rep. Dec. 7, 2015;6:48-54.
Gombash SE, et al. Systemic Gene Therapy for Targeting the CNS. Methods Mol Biol. 2016;1382:231-7.
Gurda BL, et al. Evaluation of AAV-mediated gene therapy for central nervous system disease in canine mucopolysaccharidosis VII. Mol Ther. Feb. 2016;24(2):206-16.
Ahmed SS, et al. rAAV gene therapy in a Canavan's disease mouse model reveals immune impairments and an extended pathology beyond the central nervous system. Mol Ther Jun. 2016;24(6):1030-41.
Dashkoff J, et al. Tailored transgene expression to specific cell types in the central nervous system after peripheral injection with AAV9 Mol Ther Methods Clin Dev Dec. 2016;3:16081, pp. 1-9.
Gruntman AM, et al. Retro-Orbital Venous Sinus Delivery of rAAV9 Mediates High-Level Transduction of Brain and Retina Compared with Temporal Vein Delivery in Neonatal Mouse Pups. Hum Gene Ther. Mar. 2017;28(3):228-230.
Aoyama Y, et al. Wnt11 gene therapy with adeno-associated virus 9 improves the survival of mice with myocarditis induced by coxsackievirus B3 through the suppression of the inflammatory reaction. J Mol Cell Cardiol. Jul. 2015;84:45-51.
Greig JA, et al. Impact of intravenous infusion time on AAV8 vector pharmacokinetics, safety, and liver transduction in cynomolgus macaques. Mol Ther Methods Clin Dev. Dec. 2016;3:16079, pp. 1-7.
Gruntman AM, et al. Delivery of Adeno-associated virus gene therapy by intravascular limb infusion methods. Hum Gene Ther Clin Dev Sep. 2015;26(3):159-64.
Hagg A, et al. Using AAV vectors expressing the beta 2-adrenoceptor or associated G alpha proteins to modulate skeletal muscle mass and muscle fiber size. Sci Rep. Mar. 2016;6:23042, pp. 1-10.
Greig JA, et al. Intramuscular administration of AAV overcomes pre-existing neutralizing antibodies in rhesus macaques. Vaccine. Dec. 2016;34(50):6323-6329.
Ai J, et al. Adeno-associated virus serotype rh.10 displays strong muscle tropism following intraperitoneal delivery. Sci Rep. Jan. 2017;7:40336, pp. 1-6.
Baum BJ, et al. Advances in salivary gland gene therapy—oral and systemic implications. Expert Opinion on Biologica Therapy. 2015;15(10):1443-54.
Hai B, et al. Long-term transduction of miniature pig parotid glands using serotype 2 adeno-associated viral vectors. J Gene Med. Jun. 2009;11(6):506-14.
Muzyczka N, et al. AAV's Golden Jubilee. Mol Ther. May 2015;23(5):807-8.
Xie Q, et al. The 2.8 Å Electron Microscopy Structure of Adeno-Associated Virus-DJ Bound by a Heparinoid Pentasaccharide. Mol Ther Methods Clin Dev. Mar. 8, 2017,5:1-12.
Srivastava A. Adeno-Associated Virus: The Naturally Occurring Virus Versus the Recombinant Vector. Hum Gene Ther. Jan. 2016;27(1):1-6.
Tratschin JD, et al. Adeno-associated virus vector for high-frequency integration, expression, and rescue of genes in mammalian cells. Mol Cell Biol. Nov. 1985;5(11):3251-60.
Srivastava A, et al. Nucleotide sequence and organization of the adeno-associated virus 2 genome. J Virol. Feb. 1983;45(2):555-64.
Summerford C, et al. AAVR: A multi-serotype receptor for AAV. Mol Ther. Apr. 2016;24(4):663-6.
Wu P, et al. Mutational analysis of the adeno-associated virus type 2 (AAV2) capsid gene and construction of AAV2 vectors with altered tropism. J Virol. Sep. 2000;74(18):8635-47.
Yang C, et al. Sequential adeno-associated viral vector serotype 9-green fluorescent protein gene transfer causes massive inflammation and intense immune response in rat striatum. Hum Gene Ther. Jul. 2016;27(7):528-43.
Chandler RJ, et al. rAAV integration and genotoxicity: insights from animal models. Hum Gene Ther. Apr. 2017;28(4):314-322.

(56) References Cited

OTHER PUBLICATIONS

Wang S, et al. Direct brain infusion can be enhanced with focused ultrasound and microbubbles. J Cereb Blood Flow Metab. Feb. 2017;37(2):706-714.
Wang et al., Noninvasive, neuron-specific gene therapy can be facilitated by focused ultrasound and recombinant adeno-associated virus. Gene Therapy. 2004. November.. 22, 104-110.
Weber-Adrian D, et al. Gene delivery to the spinal cord using MRI-guided focused ultrasound. Gene Ther. Jul. 2015, 22(7):568-77.
Zhu W, et al. Soluble FLT1 Gene Therapy Alleviates Brain Arteriovenous Malformation Severity. Stroke. May 2017;48(5):1420-1423.
Watson ZL, et al. Adeno-associated Virus Vectors Efficiently Transduce Mouse and Rabbit Sensory Neurons Coinfected with Herpes Simplex Virus 1 following Peripheral Inoculation. J Virol. Aug. 12, 2016;90(17):7894-901.
Woodard KT et al. Heparan Sulfate Binding Promotes Accumulation of Intravitreally Delivered Adeno-associated Viral Vectors at the Retina for Enhanced Transduction but Weakly Influences Tropism. J Virol. Oct. 14, 2016,90(21):9878-9888.
Wang LL, et al. Comparative study of liver gene transfer with AAV vectors based on endogenous and engineered AAV capsids Mol Ther. Dec. 2015;23(12):1877-87.
Sondhi D, et al. Genetic Modification of the Lung Directed Toward Treatment of Human Disease. Hum Gene Ther. Jan. 2017;28(1):3-84.
Yalvac ME, et al. AAV1.NT-3 gene therapy attenuates spontaneous autoimmune peripheral polyneuropathy. Gene Ther. Jan. 2016;23(1):95-102.
Srivastava A. In Vivo Tissue-tropism of Adeno-associated Viral Vectors. CurrOpin Virol. Sep. 2, 2016;21:75-80.
Adamson-Small L, et al. Sodium chloride enhances rAAV production in a serum-free suspension manufacturing platform using the Herpes Simplex Virus System Hum Gene Ther Methods. Feb. 2017;28(1):1-14.
Burnham B, et al. Analytical ultracentrifugation as an approach to characterize recombinant adeno-associated viral vectors. Hum Gene Ther Methods. Dec. 2015;26(6):228-42.
Grieger JC, et al. Production of Recombinant Adeno-associated Virus Vectors Using Suspension HEK293 Cells and Continuous Harvest of Vector From the Culture Media for GMP FIX and FLT1 Clinical Vector. Mol Ther. Feb. 2016;24(2):287-97.
Gruntman AM, et al. Stability and Compatibility of Recombinant Adeno-Associated Virus Under Conditions Commonly Encountered in Human Gene Therapy Trials. Hum Gene Ther Methods. Apr. 2015, 26(2):71-6.
Kajigaya S, et al. Self-assembled B19 parvovirus capsids, produced in a baculovirus system, are antigenically and immunogenically similar to native virions. Proc Natl Acad Sci U S A. Jun. 1, 1991;88(11):4646-50.
Kirnbauer R, et al. Virus-like particles of bovine papillomavirus type 4 in prophylactic and therapeutic immunization. Virology May 1, 1996;219(1):37-44.
Kohlbrenner E, et al. Production and Characterization of Vectors Based on the Cardiotropic AAV Serotype 9. Methods Mol Biol. 2017;1521:91-107.
Kotterman MA, et al. Enhanced cellular secretion of AAV2 by expression of foreign viral envelope proteins. Biochemical Engineering Journal, vol. 93, Jan. 15, 2015, pp. 108-114.
Mietzsch M, et al. OneBac 2.0: Sf9 Cell Lines for Production of AAV1, AAV2 and AAV8 Vectors with Minimal Encapsidation of Foreign DNA Hum Gene Ther Methods. Feb. 2017;28(1):15-22.
Mietzsch M, et al. OneBac 2.0: Sf9 cell lines for production of AAV5 vectors with enhanced infectivity and minimal encapsidation of foreign DNA Hum Gene Ther. Oct. 26, 2015(10):688-97.
Nambiar B, et al. Characteristics of minimally oversized adeno-associated virus vectors encoding human Factor VIII generated using producer cell lines and triple transfection. Hum Gene Ther Methods. Feb. 2017;28(1):23-38.

Ruffing M, et al. Assembly of viruslike particles by recombinant structural proteins of adeno-associated virus type 2 in insect cells. J Virol. Dec. 1992;66(12):6922-30.
Samulski RJ, et al. Helper-free stocks of recombinant adeno-associated viruses: normal integration does not require viral gene expression. J Virol. Sep. 1989;63(9):3822-8.
Urabe M, et al. Scalable generation of high-titer recombinant adeno-associated virus type 5 in insect cells. J Virol. Feb. 2006;80(4):1874-85.
Van Der Loo JCM, et al. Progress and challenges in viral vector manufacturing. Hum Mol Genet. Apr. 2016;25(R1):R42-52.
Kailasan S, et al. Parvovirus Family Conundrum: What makes a killer? Annu Rev Virol. Nov. 2015;2(1):425-50.
Rutledge EA, et al. Infectious clones and vectors derived from adeno-associated virus (AAV) serotypes other than AAV type 2. J Virol. Jan. 1998;72(1):309-19.
Pillay S, et al. An essential receptor for adeno-associated virus infection. Nature. Nov. 17, 2016;539(7629):456.
Platt MP, et al. Embryonic disruption of the candidate dyslexia susceptibility gene homolog Kiaa0319-like results in neuronal migration disorders. Neuroscience. Sep. 17, 2013;248:585-93.
Poon MW, et al. Distribution of Kiaa0319-like immunoreactivity in the adult mouse brain—a novel protein encoded by the putative dyslexia susceptibility gene KIAA0319-like. Histol Histopathol Aug. 2011;26(8):953-63.
Poon MW, et al. Dyslexia-associated kiaa0319-like protein interacts with axon guidance receptor nogo receptor 1. Cell Mol Neurobiol. Jan. 2011;31(1):27-35.
Kozak M. Interpreting cDNA sequences: some insights from studies on translation. Mamm Genome. Aug. 1996;7(8):563-74.
Kozak M. Point mutations define a sequence flanking the AUG initiator codon that modulates translation by eukaryotic ribosomes Cell. Jan. 31, 1986,44(2):283-92.
Kozak M. The scanning model for translation: an update. J Cell Biol. Feb. 1989;108(2):229-41.
Heim R, et al. Engineering green fluorescent protein for improved brightness, longer wavelengths and fluorescence resonance energy transfer. Curr Biol. Feb. 1, 1996;6(2):178-82.
Oliva B, et al. An automated classification of the structure of protein loops. J Mol Biol. Mar. 7, 1997;266(4):814-30.
Samaranch L, et al. MR-guided parenchymal delivery of adeno-associated viral vector serotype 5 in non-human primate brain. Gene Ther. Apr. 2017;24(4):253-261.
Hordeaux J., et al. Efficient central nervous system AAVrhIO-mediated intrathecal gene transfers in adult and neonate rats. Gene Ther.Apr. 2015, 22(4):316-24.
Muralidharan G, et al. Unique glycan signatures regulate adeno-associated virus tropism in the developing brain. J Virol. Apr. 2015;89(7):3976-87.
Ponder K, et al. Intrathecal injection of lentiviral vector results in high expression in the brain of mucopolysaccharidosis VII dogs but the pattern of expression is different than for AAV9 or AAV-rh10. J Control Release. Dec. 2014, 196:71-8.
Salegio EA, et al. MRI-Guided Delivery of Viral Vectors. Methods Mol Viol. 2016;1382:217-30.
Samaranch L et al. Cerebellomedullary Cistern Delivery for AAV-Based Gene Therapy: A Technical Note for Monhuman Primates. Hum Gene Ther Methods. Feb. 2016;27(1):13-6.
Saraiva J et al. Gene Therapy for the CNS Using AAVs: The Impact of Systemic Delivery by AAV9. J Control Release Nov. 10, 2016;241:94-109.
Shen F, et al. Inhibition of pathological brain angiogenesis through systemic delivery of AAV vector expressing soluble FLT1. Gene Therapy. Nov. 22, 2015(11):893-900.
Hinderer C, et al. Neonatal Systemic AAV Induces Tolerance to CNS Gene Therapy in MPS I Dogs and Nonhuman Primates Mol Ther. Aug. 2015, 23(8):1298-307.
Ojala DS, et al. Adeno-associated virus vectors and neurological gene therapy. Neuroscientist. Feb. 2015;21(1):84-98.
Landegger LD, et al. A synthetic AAV vector enables safe and efficient gene transfer to the mammalian inner ear. Nat Biotechnol. Mar. 2017;35(3):280-284.

(56) References Cited

OTHER PUBLICATIONS

Mason JB, et al. Delivery and evaluation of recombinant adeno-associated viral vectors in the equine distal extremity for the treatment of laminitis. Equine Vet J. Jan. 2017;49(1):79-86.
Jeong D, et al. Matricellular Protein CCN5 Reverses Established Cardiac Fibrosis. J Am Coll Cardiol. Apr. 5, 2016;67(13):1556-68.
Knezevic T, et al. Adeno-associated Virus Serotype 9—Driven Expression of BAG3 Improves Left Ventricular Function in Murine Hearts with Left Ventricular Dysfunction Secondary to a Myocardial Infarction. JACC Basic Transl Sci. Dec. 2016;1(7):647-656.
Ibrahim S, et al. Stable liver specific expression of human IDOL in humanized mice raises plasma cholesterol. Cardiovasc Res. May 2016;110(1):23-9.
Li SY, et al. Efficient and targeted transduction of nonhuman primate liver with systemically delivered optimized AAV3E vectors Mol Ther. Dec. 2015;23(12):1867-76.
Heller KN, et al. Human alpha 7 integrin gene (ITGA7) delivered by adeno-associated virus extends survival of severely affected dystrophin/utrophin deficient mice. Oct. 2015;26(10):647-56.
Mendell Jr, et al. Follistatin Gene Therapy for Sporadic Inclusion Body Myositis Improves Functional Outcomes. Mol Ther. Apr. 2017;25(4):870-879.
Schnepp BC, et al. Recombinant adeno-associated virus vector genomes take the form of long-lived transcriptionally competent episomes in human muscle. Hum Gene Ther Jan. 2016;27(1):32-42.
Neuberger EWI, et al. Establishment of two quantitative nested qPCR assays targeting the human EPO transgene. Gene Ther Apr. 2016;23(4):330-9.
Lentz TB, et al. Insight into the Mechanism of Inhibition of Adeno-Associated Virus by the Mre11/Rad50/Nbs1 Complex J Virol. Jan. 2015, 89(1):181-94.
Nicolson SC, et al. Identification and validation of small molecules that enhance recombinant Adeno-associated virus transduction following high throughput screen. J Virol. Jul. 2016;90(16):7019-31.
Wang M, et al. Direct interaction of human serum proteins with AAV virions to enhance AAV transduction: Immediate impact on clinical applications. Gene Ther. Jan. 2017;24(1):49-59.
Watakabe A, et al. Comparative analyses of adeno-associated viral vector serotypes 1 2 5 8 and 9 in marmoset mouse and macaque cerebral cortex. Neurosci Res.Apr. 2015, 93:144-57.
Xiao P, et al. Disruption of microtubules post virus entry enhances adeno-associated virus vector transduction. Hum Gene Ther Apr. 2016;27(4):309-24.
Hudry EM, et al. Exosome-associated AAV vector as a robust and convenient neursocience tool. Gene Ther. Apr. 2016,23(4):380-92.
Nery FC, et al. New methods for investigation of neuronal migration in embryonic brain explants J Neurosci Methods.Jan. 2015, 239:80-4.
Su W et al. Recombinant adeno-associated viral (rAAV) vectors mediate efficient gene transduction in cultured neonatal and adult microglia. J Neurochem Jan. 2016;136 Suppl 1:49-62.
Ren XF, et al. Adeno-associated virus-mediated BMP-7 and SOX9 in vitro co-transfection of human degenerative intervertebral disc cells. Genet Mol Res. Apr. 22, 2015;14(2):3736-44.
Reichel FF, et al. AAV8 can induce innate and adaptive immune response in the primate eye. Mol Ther. Aug. 31, 2017 Epub ahead of print, pp. 1-13.
De Silva SR, Charbel Issa P, Singh MS, Lipinski DM, Barnea-Cramer AO, Walker NJ, Barnard AR, Hankins MW, MacLaren RE. Single residue AAV capsid mutation improves transduction of photoreceptors in the Abca4[−/−] mouse and bipolar cells in the rd1 mouse and human retina ex vivo Gene Ther Nov. 2016;23(11):767-774. doi: 10.1038/gt.2016.54. Epub Jul. 14, 2016, pp. 1-13.
Katz MG, et al. Use of Adeno-Associated Virus Vector for Cardiac Gene Delivery in Large Animal Surgical Models of Heart Failure Hum Gene Ther Clin Dev Jul. 20, 2017, pp. 1-31.
Watanabe S, et al. Protein Phosphatase Inhibitor-1 Gene Therapy in a Swine Model of Nonischemic Heart Failure. Journal of the American College of Cardiology 2017, pp. 1744-1756 plus supplementary pages.
Jin X, et al. Direct LC/MS Analysis for Complete Characterization of Recombinant Adeno-Associated Virus Capsid Proteins. Hum Gene Ther Methods. Jun. 18, 2017. Epub ahead of print, pp. 255-267.
Galli A, et al. Strategies to optimize capsid protein expression and single stranded DNA formation of Adeno-associated virus in *Saccharomyces cerevisiae*. J Appl Microbiol. Jun. 13, 2017 Epub ahead of print, pp. 414-428.
Wang Z, et al. Human Bocavirus 1 is a Novel Helper for Adeno-Associated Virus Replication. J Virol. Jun. 28, 2017. Epub ahead of print, pp. 1-18.
Grobe S, et al. Relevance of assembly-activating protein for Adeno-associated virus vector production and capsid protein stability in mammalian and insect cells. J Virol. Aug. 2, 2017. pii: JVI.01198-17. doi: 10.1128/JVI.01198-17, pp. 1-72.
Kondratov O, et al. Direct head-to-head evaluation of recombinant Adeno-associated viral (rAAV) vectors manufactured in human vs insect cells. Molecular Therapy Aug. 1, 2017, pp. 1-45.
Jungmann A, et al. Protocol for efficient generation and characterization of adeno-associated viral (AAV) vectors. Hum Gene Ther Methods Sep. 21, 2017 Epub ahead of print, pp. 1-39.
Luo Y, et al. AAVS1-Targeted Plasmid Integration in AAV Producer Cell Lines. Hum Gene Ther Methods. Jun. 2017;28(3):124-138.
Savy A, et al. Impact of ITR integrity on rAAV8 production using baculovirus/Sf9 cells system. Hum Gene Ther Methods. Oct. 1, 2017 Epub ahead of print, pp. 1-33.
GTEx Consortium et al. Genetic effects on gene expression across human tissues. Nature. Oct. 11, 2017;550(7675):204-213.
Li X, et al. The impact of rare variation on gene expression across tissues. Nature. Oct. 11, 2017;550(7675):239-243.
Ojala DS, et al. In Vivo Selection of a Computationally Designed Schema AAV Library Yields a Novel Variant for Infection of Adult Neural Stem Cells in the SVZ. Mol Ther Sep. 8, 2017 Epub ahead of print, pp. 1-16.
Chandran JS, et al. Site Specific Modification of Adeno-Associated Virus Enables Both Fluorescent Imaging of Viral Particles and Characterization of the Capsid Interactome. Sci Rep. Nov. 7, 2017;7(1):14766.
Chai Z, et al. Application of polyploid adeno-associated virus vectors for transduction enhancement and neutralizing antibody evasion. J Control Release. Aug. 5, 2017 pii: S0168-3659(17)30772-1. doi: 10.1016/j.jconrel.2017.08.005.
Hickey DG, et al. Tropism of engineered and evolved recombinant AAV serotypes in the rd1 mouse and ex vivo primate retina Gene Ther Sep. 5, 2017 Epub ahead of print, pp. 1-14.
Yan Z, et al. Human Bocavirus Type-1 Capsid Facilitates the Transductiogeof Ferret Airways by Adeno-Associated Virus Genomes Hum Gene Ther. May 10, 2017. Epub ahead of print, pp. 612-625.
Kanaan NM, et al. Rationally Engineered AAV Capsids Improve Transduction and Volumetric Spread in the CNS. Molecular Therapy-Nucleic Acids 8: 184-197 Sep. 15, 2017.
Powell SK, Khan N, Parker CL, Samulski RJ, Matsushima G, Gray SJ, McCown TJ. Characterization of a novel adeno-associated viral vector with preferential oligodendrocyte tropism. Gene Ther. Nov. 2016;23(11):807-814. doi: 10.1038/gt.2016.62. Epub Sep. 15, 2016.
Kanaan N, et al. Rationally Engineered AAV Capsids Improve Transduction and Volumetric Spread in the CNS. Molecular Therapy—Nucleic Acids, vol. 8, 184-197.
Chan KY, et al. Engineered AAVs for efficient noninvasive gene delivery to the central and peripheral nervous systems. Nat Neurosci. Jun. 26, 2017. Epub ahead of print, pp. 1172-1181.
Paulk NK, et al. Bioengineered AAV Capsids with Combined High Human Liver Transduction In Vivo and Unique Humoral Seroreactivity Mol Ther. Sep. 25, 2017 Epub ahead of print, pp. 1-15.
Hagedorn C, et al. S/MAR element facilitates episomal long-term persistence of Adeno-associated viral (AAV) vector genomes in proliferating cells. Hum Gene Ther. Jun. 30, 2017. Epub ahead of print, pp. 1-11.

(56) References Cited

OTHER PUBLICATIONS

Ziegler T, et al. Steerable induction of the Thymosin β4/MRTF-A pathway via AAV-based overexpression induces therapeutic neovascularization. Hum Gene Ther. Jul. 20, 2017, pp. 1-9.
Potter RA, et al. Systemic Delivery of Dysferlin Overlap Vectors Provides Long-Term Functional Improvement for Dysferlinopathy. Hum Gene Ther. Jul. 14, 2017. Epub ahead of print, pp. 1-37.
Huang W, et al. Targeting Visceral Fat by Intraperitoneal Delivery of Novel AAV Serotype Vector Restricting Off-Target Transduction in Liver Mol Ther Methods Clin Dev Jun. 19, 2017;6:68-78.
Herrera-Carrillo E, et al. Improving miRNA delivery by optimizing miRNA expression cassettes in viral vectors. Hum Gene Ther Methods. Jul. 16, 2017, pp. 177-190.
Krhac Levacic A, et al. Minicircle versus plasmid DNA delivery by receptor-targeted polyplexes. Hum Gene Ther. Aug. 21, 2017 Epub ahead of print, pp. 862-874.
Moffett HF, et al. Hit-and-run programming of therapeutic cytoreagents using mRNA nanocarriers. Nat Commun. Aug. 30, 2017;8(1):389.
Morabito G, Giannelli SG, Ordazzo G, Bido S, Castoldi V, Indrigo M, Cabassi T, Cattaneo S, Luoni M, Cancellieri C, Sessa A, Bacigaluppi M, Taverna S, Leocani L, Lanciego JL, Broccoli V. Mol Ther. Dec. 6, 2017;25(12):2727-2742. Epub Aug. 10, 2017.
Matsuzaki Y, Konno A, Mochizuki R, Shinohara Y, Nitta K, Okada Y, Hirai H. Neurosci Lett. Nov. 23, 2017. [Epub ahead of print].
European Search Report issued in corresponding EP Application No. EP 15867378 dated Sep. 4, 2018, pp. 1-13.
Kothari P, et al. Iodine-124 Labeled Adeno-Associated Virus: A Promising Tool for Tracking Gene Therapy. Journal of Nuclear Medicine. May 2015, 56 (supplement 3), 494-494.
Maniatis T. et al.,Molecular Cloning. CSH Laboratory, NY, N.Y. (1982), p. 82 , book surmmary only.
Marsic D et al. Altering Tropism of rAAV by Directed Evolution. Methods of Mol Biol. 2016;1382:151-73.
Myers EW, et al. Optimal alignments in linear space. Comput Appl Biosci. Mar. 1988;4(1):11-7.
O'Reilly DR, et al. Baculovirus expression vectors: a laboratory manual. Oxford University Press, 1994, cover, inside page and v-x.
Philiport, et al. Liposomes as tools in Basic Research and Industry. CRC Press, Ann Arbor, Mich. (1995), cover, title, copyright, table of contents.
Smith DW, et al. Biocomputing: Informatics and Genome Projects. Academic Press, New York, 1993, cover, title, copyright and pp. v-ix.
Stahl, PH, et al. Pharmaceutical Salts: Properties, Selection, and Use. Wiley-VCH, 2008, cover, title, copyright and table of contents only.
Von Heinje G. Sequence Analysis in Molecular Biology, Academic ZPress, 1987, title and contents page only.
Tarantal AF, et al. Systemic and Persistent Muscle Gene Expression in Rhesus Monkeys with a Liver De-targeted Adeno-Associated Virus (AAV) Vector Hum Gene Ther. May 2017;28(5):385-391.
Huang LY, et al. Characterization of the Adeno-Associated Virus 1 and 6 Sialic Acid Binding Site. J Virol. May 12, 2016;90(11):5219-30.
Kailasan S, et al. Structure of an Enteric Pathogen, Bovine Parvovirus.J Virol. Mar. 2015, 89(5):2603-14.
Alton EW, et al. Repeated nebulisation of non-viral CFIR gene therapy in patients with cystic fibrosis: a randomised, double-blind, placebo-controlled, phase 2b trial. Lancet Respir Med Sep. 2015;3(9):684-91.
Baum BJ, et al. Early responses to adenoviral-mediated transfer of the aquaporin-1 cDNA for radiation-induced salivary hypofunction. Proc Natl Acad Sci U S A. Nov. 20, 2012;109(47):19403-7.
Shen W, et al. Analysis of the Cis and Trans Requirements for DNA Replication at the Right End Hairpin of the Human Bocavirus 1 Genome. J Virol. Aug. 2016;90(17):7761-77.
Mingozzi F, et al. Overcoming the Host Immune Response to Adeno-Associated Virus Gene Delivery Vectors: The Race Between Clearance, Tolerance, Neutralization, and Escape. Annu Rev Virol Sep. 29, 2017;4(1):511-534.

Gil-Farina I, et al. Recombinant AAV Integration is Not Associated With Hepatic Genotoxicity in Nonhuman Primates and Patients Mol Ther. Jun. 2016;24(6):1100-5.
Bennett A, et al. Understanding capsid assembly and genome packaging for adeno-associated viruses. Future Virology Jun. 2017; 12(6): 283-297.
Grimm et al. Small but increasingly mightly—latest advances in AAV vector research, design and evolution. Hum Gene Ther. Nov. 2017 (Epub Aug. 23, 2017); 28(11):1075-1086.
Smith LJ, et al. Gene transfer properties and structural modeling of human stem cell-derived AAV. Molecular Therapy. Sep. 2014;22(9):1625-1634.
Eichler K, et al. The complete connectome of a learning and memory centre in an insect brain. Nature. Aug. 9, 2017,548(7666):175-182.
Kurosaki F, et al. Optimization of adeno-associated virus vector-mediated gene transfer to the respiratory tract. Gene Ther. May 2017;24(5):290-297.
Tardieu M, et al. Intracerebral gene therapy in children with mucopolysaccharidosis type IIIB syndrome: an uncontrolled phase 1/2 clinical trial. Lancet Neurol. Sep. 2017;16(9):712-720.
Allocca et al., Serotype-dependent packaging of large genes in adeno-associated viral vectors results in effective gene delivery in mice. J Clin Invest. May 2008;118(5):1955-64.
Brister et al., Rep-mediated nicking of the adeno-associated virus origin requires two biochemical activities, DNA helicase activity and transesterification. J Virol. Nov. 1999;73(11):9325-36.
Chiorini et al., Sequence requirements for stable binding and function of Rep68 on the adeno-associated virus type 2 inverted terminal repeats. J Virol. Nov. 1994;68(11):7448-57.
Chiorini et al., Determination of adeno-associated virus Rep68 and Rep78 binding sites by random sequence oligonucleotide selection. J Virol. Nov. 1995;69(11):7334 8.
Chiorini et al., Adeno-associated virus (AAV) type 5 Rep protein cleaves a unique terminal resolution site compared with other AAV serotypes J Virol May 1999;73(5):4293-8.
Dong et al., Quantitative analysis of the packaging capacity of recombinant adeno-associated virus. Hum Gene Ther. Nov. 10, 1996;7(17):2101-12.
Grieger et al., Packaging capacity of adeno-associated virus serotypes: impact of larger genomes on infectivity and postentry steps J Virol Aug. 2005;79(15):9933-44.
Hickman et al., The nuclease domain of adeno-associated virus rep coordinates replication initiation using two distinct DNA recognition interfaces. Mol Cell Feb. 13, 2004;13(3):403-14.
King et al., DNA helicase-mediated packaging of adeno-associated virus type 2 genomes into preformed capsids. EMBO J. Jun. 15, 2001;20(12):3282-91.
Matsushita et al., Adeno-associated virus vectors can be efficiently produced without helper virus. Gene Ther. Jul. 1998;5(7):938-45.
McAlister et al., Substitution of adeno-associated virus Rep protein binding and nicking sites with human chromosome 19 sequences. Virol J. Sep. 8, 2010;7:218.
Nakai et al., Increasing the size of rAAV-mediated expression cassettes in vivo by intermolecular joining of two complementary vectors. Nat Biotechnol. May 2000;18(5):527-32.
Rabinowitz et al., Cross-packaging of a single adeno-associated virus (AAV) type 2 vector genome into multiple AAV serotypes enables transduction with broad specificity. J Virol. Jan. 2002;76(2):791-801.
Smith et al., The Rep78 gene product of adeno-associated virus (AAV) self-associates to form a hexameric complex in the presence of AAV ori sequences. J Virol. Jun. 1997;71(6):4461-71.
Smith et al., An adeno-associated virus (AAV) initiator protein, Rep78, catalyzes the cleavage and ligation of single-stranded AAV ori DNA. J Virol. Apr. 2000;74(7):3122-9.
Sun et al., Overcoming adeno-associated virus vector size limitation through viral DNA heterodimerization. Nat Med. May 2000;6(5):599-602.
Weitzman et al., Adeno-associated virus (AAV) Rep proteins mediate complex formation between AAV DNA and its integration site in human DNA. Proc Natl Acad Sci U S A. Jun. 21, 1994;91(13):5808-12.

(56) References Cited

OTHER PUBLICATIONS

Wonderling et al., Binding sites for adeno-associated virus Rep proteins within the human genome. J Virol. Mar. 1997;71(3):2528-34.
Wu et al., Self-complementary recombinant adeno-associated viral vectors: packaging capacity and the role of rep proteins in vector purity Hum Gene Ther. Feb. 2007;18(2):171-82.
Wu et al., Optimization of self-complementary AAV vectors for liver-directed expression results in sustained correction of hemophilia B at low vector dose Mol Ther. Feb. 2008;16(2):280-9. Epub Dec. 4, 2007.
Wu et al., Effect of genome size on AAV vector packaging. Mol Ther. Jan. 2010;18(1):80-6.
Yan et al., Trans-splicing vectors expand the utility of adeno-associated virus for gene therapy. Proc Natl Acad Sci U S A. Jun. 6, 2000;97(12):6716-21.
Sawada Y., et al. "Inflammation-induced Reversible Switch of the Neuron-specific Enolase Promoter from Purkinje Neurons to Bergmann Glia," Sci Rep., vol. 6:27758 (2016).
Siu JJ, et al., "Improved gene delivery to adult mouse spinal cord through the use of engineered hybrid adeno-associated viral serotypes," Gene Ther., vol. 24 (6):361-369 (2017).
Smith RH, "A simplified baculovirus-AAV expression vector system coupled with one-step affinity purification yields high-titer rAAV stocks from insect cells," Mol Ther., vol. 17(11):1888-1896 (2009).
Smith RH, et al., "Germline viral "fossils" guide in silico reconstruction of a mid-Cenozoic era 7marsupial adeno-associated virus," Sci Rep., vol. 6:28965:17 pages (2016).
Sun J, et al., "Gene delivery of activated Factor VII Using Alternative Adeno-Associated Virus Serotype Improves Hemostasis in Hemophiliac Mice with FVIII Inhibitors and Adeno-Associated Virus Neutralizing antibodies," Hum Gene Ther., vo. 28(8):654-666 (2017).
Suzuki J, et al. "Cochlear gene therapy with ancestral AAV in adult mice: complete transduction of inner hair cells without cochlear dysfunction," Sci Rep., vol. 7:45524: 11 pages (2017).
Tadokoro T, et al., "Subpial Adeno-associated Virus 9 (AAV9) Vector Delivery in Adult Mice," J Vis Exp., vol. 125:55770 (2017).
Thorne B, et al. Gene Therapy. Adv Biochem Eng Biotechnol., vol. 165:351-399 (2018) Abstract Only.
Tse LV, et al., "Structure-guided evolution of antigenically distinct adeno-associated virus variants for immune evasion," PNAS, vol. 114(24):E4812-E4821 (2017).
Vandamme C, et al., "Unraveling the complex story of immune responses to AAV vectors trial after trial," Hum Gene Ther. , vol. 28 (11):1061-1074 (2017).
Wang M, et al. "Direct interaction of human serum proteins with AAV virions to enhance AAV transduction: immediate impact on clinical applications," Gene Ther., vol. 24(1):49-59. (2017).
Wooley DP, et al., "A directed evolution approach to select for novel Adeno-associated virus capsids on an HIV-1 producer T cell line," J Virol. Methods, vol. 250:47-54 (2017).
Xie Q, et al., "The atomic structure of adeno-associated virus (AAV-2), a vector for human gene therapy," PNAS vol. 99(16):10405-10 (2002).
Yazdan-Shahmorad A, et al., "Widespread Optogenetic Expression in Macaque Cortex Obtained with MR-Guided, Convection Enhanced Delivery (CED) of AAV vector to the Thalamus," J Neurosci Methods, vol. 293:347-358 (2018).
Ye L., et al., "Adeno-Associated Virus Vector Mediated Delivery of the HBV Genome Induces Chronic Hepatitis B Virus Infection and Liver Fibrosis in Mice," PLoS One, vol. 10(6):e0130052: 16 pages (2015).
Zhu, Z. et al., "Zika virus has oncolytic activity against glioblastoma stem cells," J Exp Med., vol. 214(10):2843-2857 (2017).
Ahmad M, et al., "Engineered Expression of Broadly Neutralizing Antibodies Against Human Immunodeficiency Virus," Annu Rev Virol., vol. 4(1):491-510 (2017).
Ai J, et al., "A Scalable and Accurate Method for Quantifying Vector Genomes of Recombinant Adeno-Associated Viruses in Crude Lysate," Hum Gene Ther Methods, vol. 28(3):139-147 (2017).
Alves S. et al., "Ultramicroscopy as a Novel Tool to Unravel the Tropism of AAV Gene Therapy Vectors in the Brain," Sci. Rep., vol. 6:28272:12 pages (2016).
Bennett A, et al., "Thermal Stability as a Determinant of AAV Serotype Identity," Mol Ther Methods Clin Dev., vol. 6:171-182 (2017).
Brady JM, et al. "Antibody gene transfer with adeno-associated viral vectors as a method for HIV prevention," Immunol Rev. vol. 275(1):324-333 (2017).
Buclez PO, et al., "Rapid, scalable, and low-cost purification of recombinant adeno-associated virus produced by baculovirus expression vector system," Mol Ther Methods Clin Dev., vol. 3:16035 (2016).
Cabral-Miranda F, et al., "rAAV8-733-Mediated Gene Transfer of CHIP/Stub-1 Prevents Hippocampal Neuronal Death in Experimental Brain Ischemia," Mol Ther., vol. 25(2):392-400 (2017).
Carvalho LS, et al., "Evaluating efficiencies of dual AAV approaches for retinal targeting," Front Neursci., vol. 11:503: 8 pages (2017).
Clement N, et al., "Manufacturing of recombinant adeno-associated viral vectors for clinical trials," Mol Ther Methods Clin Dev vol. 3:16002: 7 pages (2016).
D'Costa S, et al.," Practical utilization of recombinant AAV vector reference standards: focus on vector genome titration by free ITR qPCR," Mol Ther Methods Clin Dev, vol. 5:16019: 9 pages (2016).
Deng X., et al., "Replication of an autonomous human parvovirus in non-dividing human airway epithelium is facilitated through the DNA damage and repair pathways," PLoS Pathog., vol. 12(1):e1005399: 25 pages (2016).
Durost P, et al. "Gene therapy with an Adeno-Associated Virus vector expressing human Interleukin-2 alters immune system homeostasis in humanized mice," Hum Gene Ther., vol. 23(8): 352-365 (2017).
Eichler F, et al. "Hematopoietic Stem-Cell Gene Therapy for Cerebral Adrenoleukodystrophy," N Engl J Med., vol. 377(17):1630-1638 (2017).
Extended EP Search Report dated Sep. 4, 2018 received in corresponding EP Application No. 15867378.0, 13 pages.
Fu H, et al. "Differential prevalence of antibodies against adeno-associated virus in healthy children and patients with mucopolysaccharidosis III: perspective for AAV-mediated gene therapy," Human Gene Ther Clin Dev., vol. 28(4):187-196 (2017).
G. S. Banker, et al., "Modern Pharmaceutics, Drugs and the Pharmaceutical Sciences," vol. 72: 18 pages, Marcel Dekker, New York, Inc., 1996.
Gombash SE, et al. "Systemic gene delivery transduces the enteric nervous system of guinea pigs and cynomolgus macaques," Gene Ther., vol. 24(10):640-648 (2010).
Gray-Edwards H, et al. "AAV gene therapy in a sheep model of Tay-Sachs disease," Human Gene Therapy, 29(3):312-326 (2018).
Griffin AM, et al. Computer Analysis of Sequence Data, Part I. Humana Press, New Jersey, 1994.
Guggino W. et al., "A Preclinical Study in Rhesus Macaques for Cystic Fibrosis to Assess Gene Transfer and Transduction by AAV1 and AAV5 with a Dual-Luciferase Reporter System," Hum Gene Ther Clin Dev., vol. 28(3): 145-156 (2017).
Heim R,et al "Improved green fluorescence," Nature, vol. 373: 663-664 (1995).
Hinderer C, et al. Delivery of an Adeno-Associated Virus Vector into Cerebrospinal Fluid Attenuates Central Nervous System Disease in Mucopolysaccharidosis Type II Mice. Hum Gene Ther., vol. 27(11):906-915. Epub Aug. 10, 2016.
Hinderer C, et al., "Evaluation of intrathecal routes of administration for adeno-associated virus vectors in large animals," Hum Gene Ther., vol. 29(1):15-24 (2018).
Hordeaux J, et al., "Long-term neurologic and cardiac correction by intrathecal gene therapy in Pompe disease," Acta Neuropathol Commun., vol. 5 (1):66 (2017).
International Search Report dated Apr. 29, 2016 received in corresponding PCT Application No. PCT/US2015/065218.

(56) References Cited

OTHER PUBLICATIONS

Katz ML, et al. "AAV gene transfer delays disease onset in a TPP1-deficient canine model of the late infantile form of Batten Disease," Sci Transl Med., vol. 7(313):313ra180: 23 pages (2015).
Kim Y, et al. "Mutagenic Analysis of an Adeno-Associated Virus Variant Capable of Simultaneously Promoting Immune Resistance and Robust Gene Delivery," Hum Gene Ther., vol. 29(1):25-41 (2018).
Kothari P., et al. "Radioiodinated Capsids Facilitate In Vivo Non-Invasive Tracking of Adeno-Associated Gene Transfer Vectors," Sci Rep., vol. 7:39594: 10 pages (2017).
Kotin RM, "Large-scale recombinant adeno-associated virus production.," Hum Mol Genet. vol. 20(R1): R2-6. doi 10.1093/hmg/ddr141 (2011).
Kotin RM, et al. "Manufacturing clinical grade recombinant adeno-associated virus using invertebrate cell lines," Hum Gene Ther. vol. 28(4):350-360 (2017).
Le Pichon CE, et al., "Loss of dual leucine zipper kinase signaling is protective in animal models of neurodegenerative Disease," Sci Transl Med., vol. 9(403): 16 pages (2017).
Lee NC, et al., "A neuron-specific gene therapy relieves motor deficits in pompe disease mice," Mol Neurobiol., vol. 55(6):5299-5309 (2018).
Li L, et al. "Production and characterization of novel recombinant adeno-associated virus replicative-form genomes: a eukaryotic source of DNA for gene transfer," PLoS One, vol. 8(8):e69879: 14 pages (2013).
Ling C, et al., "High-Efficiency Transduction of Primary Human Hematopoietic Stem/Progenitor Cells by AAV6 Vectors: Strategies for Overcoming Donor-Variation and Implications in Genome Editing," Sci Rep., vol. 6:35495: 8 pages (2016).
Liu Z et al. "Single-cell transcriptomics reconstructs fate conversion from fibroblast to cardiomyocyte," Nature, vol. 551(7678):100-104 (2017).
Logan GJ, et al. "Identification of liver-specific enhancer-promoter activity in the 3' untranslated region of the wild-type AAV2 genome," Nat Genet., 49(8):1267-1273 (2017).
Lukashchuk, V et al., "AAV9-mediated central nervous system-targeted gene delivery via cisterna magna route in mice," Mol. Ther. Methods Clin Dev., vol. 3:15055 (2016).
Magnani DM et al., "Dengue virus evades AAV-mediated neutralizing antibody prophylaxis in rhesus monkeys," Mol Ther., vol. 25(10):2323-2331 (2017).
Majowicz A, et al., "Successful Repeated Hepatic Gene Delivery in Mice and Non-human Primates Achieved by Sequential Administration of AAV5ch and AAV1," Mol Ther., vol. 25(8):1831-1842 (2017).
Merkel SF, et al., "Trafficking of AAV virus vectors across a model of the blood-brain barrier; a comparative study of transcytosis and transduction using primary human brain endothelial cells," J Neurochem., vol. 140(2):216-230 (2017).
Merten, et al. "Viral vectors for gene therapy and gene modification approaches," Biochem Eng J., vol. 108:98-115 (2016).
"Gene Therapy for Neurological Disorders", Methods in Molecular Biology, Humana Press, NJ, 488 pages (1995).
Miyanohara A et al., "Potent Spinal Parenchymal AAV9-mediated Gene Delivery by Subpial Injection in Adult Rats and Pigs," Mol Ther Methods Clin Dev., vol. 3:16046: 10 pages (2016).
Murlidharan G et al. "Glymphatic Fluid Transport Controls Paravascular Clearance of AAV Vectors from the Brain," JCI Insight, vol. 1(14):e88034: 11 pages (2016).
Nygaard S, et al., "A universal system to select gene-modified hepatocytes in vivo," Sci Transl Med., vol. 8(342):342ra79: 22 pages (2016).
Pacouret S, et al., "AAV-ID: A Rapid and Robust Assay for Batch-to-Batch Consistency Evaluation of AAV Preparations," Mol Ther., vol. 25(6): 1375-1386 (2017).
Penaud-Budloo M, et al. "Accurate identification and quantification of DNA species by next-generation sequencing in adeno-associated viral vectors produced in insect cells," Hum Gene Ther Methods, vol. 28(3): 148-162 (2017).
Petit L, et al."Rod Outer Segment Development Influences AAV-Mediated Photoreceptor Transduction After Subretinal Injection," Hum Gene Ther., vol. 28(6): 464-481 (2017).
Pillay S, et al. "Host determinants of adeno-associated viral vector entry," Curr Opin Virol., vol. 24:124-131 (2017).
Pillay S, et al., "Adeno-associated Virus (AAV) serotypes have distinctive interactions with domains of the cellular AAV receptor," J Virol., vol. 91(18):e00391-17 (2017).
Durost P, et al. "Gene therapy with an Adeno-Associated Virus vector expressing human Interleukin-2 alters immune system homeostasis in humanized mice," Hum Gene Ther., vol. 23(8): 352-365 (2017).
Gray-Edwards H, et al. "AAV gene therapy in a sheep model of Tay-Sachs disease," Human Gene Therapy, 29(K3):312-326 (2018).
Griffin AM, et al. Computer Analysis of Sequence Data, Part L Humana Press, New Jersey, 1994.

\* cited by examiner

PRIOR ART

FIG. 8

| | | | |
|---|---|---|---|
| AAV-5 | (NC_006152.1) | SEQ ID NO: 269 | MATEYEVIVRVPFDVEEHLPGISDSFVDWVTGQIWELPPESDLNLTLVEQPQLTVADRIR 60 |
| AAV-2_Rep68 | (NC_001401.2) | SEQ ID NO: 265 | MPGFYEIVIKVPSDLDEHLPGISDSFVNWVAEKEWELPPDSDMDLNLIEQAPLTVAEKLQ 60 |
| AAV-2_Rep78 | (NC_001401.2) | SEQ ID NO: 266 | MPGFYEIVIKVPSILDEHLPGISDSFVNWVAEKEWELPPDSDMDLNLIEQAPLTVAEKLQ 60 |
| AAV-2_Rep40 | (NC_001401.2) | SEQ ID NO: 267 | ------------------------------------------------------------ 0 |
| AAV-2_Rep52 | (NC_001401.2) | SEQ ID NO: 268 | ------------------------------------------------------------ 0 |
| AAV-1 | (NC_002077.1) | SEQ ID NO: 270 | MPGFYEIVIKVPSDLDEHLPGISNSFVNWVAEKEWDVPDSDMDPNLIEQAPLTVAEKLQ 60 |
| AAV-3 | (NC_001729.1) | SEQ ID NO: 271 | MPGFYEIVLKVPSDLEKLPGISDSFVSWVAEKEWELPPDSDMDLNLIEQAPLTVAEKLQ 60 |
| AAV-4 | (NC_001829.1) | SEQ ID NO: 272 | MPGFYEIVIKVPSDLDSHLPGISDSFVSWVAEKEWELPPDSDMDLNLIEQAPLTVAEKLQ 60 |
| AAV-7 | (NC_006260.1) | SEQ ID NO: 273 | MPGFYEIVIKVPSDLDEHLPGISDSFVNWVAEKEWELPPDSDMDLNLIEQAPLTVAEKLQ 60 |
| AAV-8 | (NC_006261.1) | SEQ ID NO: 274 | MPGFYEIVIKVPSDLDEHLPGISDSFVNWVAEKEWELPPDSDMDRNLIEQAPLTVAEKLQ 60 |
| Avian_AAV_DA-1 | (NC_006263.1) | SEQ ID NO: 275 | MRSYYEVIVQLPNDVESQVPGISDSFVNWITSREWTLPEDADWDLDQVDQVQLTLGDKIQ 60 |
| Avian_AAV_VR-865 | (NC_004828.1) | SEQ ID NO: 276 | MRSYYEVIVQLPNDVESQVPGISDSFVNWITSREWTLPEDADWDLDQVDQVQLTLGDKIQ 60 |
| Bat | (NC_014468.1) | SEQ ID NO: 278 | -MEFYSIVIRLFGDFDSEVPGLQDSFYKWLSGFRRELPEWSDLDPGQIESAYQILADKIV 59 |
| Bovine | (NC_005889.1) | SEQ ID NO: 277 | MATFYEVIVRVPFDVEEHLPGISDMFVDWVTGQIWELPPESDLNLTLIEQPQLTVADRIR 60 |

| | | | |
|---|---|---|---|
| AAV-5 | (NC_006152.1) | SEQ ID NO: 269 | RVELYEWNKFSKQ-ESKFFVQERKGSEYFHLHTLVETSGISSMVLGRYVSQIRAQLVK-V 11 |
| AAV-2_Rep68 | (NC_001401.2) | SEQ ID NO: 265 | RDFLTEWRRVSKAPEALFFVQFEKGESYFHMHVLVETTGVKSMVLGRFLSQIREKLIQ-R 11 |
| AAV-2_Rep78 | (NC_001401.2) | SEQ ID NO: 266 | RDFLTEWRRVSKAPEALFFVQFEKGESYFHMHVLVETTGVKSMVLGRFLSQIREKLIQ-R 11 |
| AAV-2_Rep40 | (NC_001401.2) | SEQ ID NO: 267 | ------------------------------------------------------------ 0 |
| AAV-2_Rep52 | (NC_001401.2) | SEQ ID NO: 268 | ------------------------------------------------------------ 0 |
| AAV-1 | (NC_002077.1) | SEQ ID NO: 270 | RDFLVQWRRVSKAPEALFFVQFEKGESYFHLHILVETTGVKSMVLGRELSQIRDKLVQ-T 11 |
| AAV-3 | (NC_001729.1) | SEQ ID NO: 271 | REFLVEWRRVSKAPEALFFVQFEKGETYFHLHVLVLIETIGVKSMVVGRYVSQIKEKLVT-R 11 |
| AAV-4 | (NC_001829.1) | SEQ ID NO: 272 | REFLVEWRRVSKAPEALFFVQFEKGESYFHLHILVETVGVKSMVLGRYVSQIKEKLVT-R 11 |
| AAV-7 | (NC_006260.1) | SEQ ID NO: 273 | RDFLVQWRRVSKAPEALFFVQFEKGESYFHLHVLVETTGVKSMVLGRFLSQIREKLVQ-T 11 |
| AAV-8 | (NC_006261.1) | SEQ ID NO: 274 | RDELVQWRRVSKAPEALFFVQFEKGESYFHLHVLVETTGVKSMVLGRELSQIREKLGEDH 12 |
| Avian_AAV_DA-1 | (NC_006263.1) | SEQ ID NO: 275 | REIRNHWGTMAKEPDHYFIQLEGQEVFFHLHVLETCSVKPMVLGRYIRHIQQKIVS-K 11 |
| Avian_AAV_VR-865 | (NC_004828.1) | SEQ ID NO: 276 | REIRTRHWGTMAKEPDFHIFIQLEQGEVFFHLHVLLETCSVKPMVLGRYIRHIQQKIVS-K 11 |
| Bat | (NC_014468.1) | SEQ ID NO: 278 | REFAQKWAAHSEDPRAPYPAQLEKGRENEHVHVLASSKKVGSFVVGRYVKKMRQHLVD-V 11 |
| Bovine | (NC_005889.1) | SEQ ID NO: 277 | RVFLYEWNKFESKQ-ESKFFVQEKGSEYFHLHTLVETSGISSMVLGRYVSQIRAQLVK-V 11 |

FIG. 8 cont.

| | | | |
|---|---|---|---|
| AAV-5 | (NC_006152.1) | SEQ ID NO: 269 | VFQGIEPQINDWVAITKIK----KGGANKVVDSGYIPAYLLPKVQPELQWAWTNLDEYKLA 175 |
| AAV-2_Rep68 | (NC_001401.2) | SEQ ID NO: 265 | IYRGIEPTLPNWFAVTKTRN--GAGHGNKVVDECYIPNYLLPKTQPELQRAWTNMEQYLSA 178 |
| AAV-2_Rep78 | (NC_001401.2) | SEQ ID NO: 266 | IYRGIEPTLPNWFAVTKTRN--GAGHGNKVVDECYIPNYLLPKTQPELQRAWTNMEQYLSA 178 |
| AAV-2_Rep40 | (NC_001401.2) | SEQ ID NO: 267 | ------------------------------------------------------------ 0 |
| AAV-2_Rep52 | (NC_001401.2) | SEQ ID NO: 268 | ------------------------------------------------------------ 0 |
| AAV-1 | (NC_002077.1) | SEQ ID NO: 270 | IYRGVEPTLPNWFAVTKTR----MGAGGNKVVDDCYIPNYLLPKTQPELQRAWTNMEEYISA 178 |
| AAV-3 | (NC_001729.1) | SEQ ID NO: 271 | IYRGVEPQLPNWFAVTKTRN--GAGHGNKVVDDCYIPNYLLPKTQPELQRAWTNMDQYISA 178 |
| AAV-4 | (NC_001829.1) | SEQ ID NO: 272 | IYRGVEPQLPNWFAVTKTRN--GAGHGNKVVDDCYIPNYLLPKTQPELQRAWTNMDQYISA 178 |
| AAV-7 | (NC_006260.1) | SEQ ID NO: 273 | IYRGVEPTLPNWFAVTKTR----MGAGGNKVVDDCYIPNYLLPKTQPELQRAWTNMEEYISA 178 |
| AAV-8 | (NC_006261.1) | SEQ ID NO: 274 | LPAGSSPTLPNWFAVTKTR-AVMAPALGNKVVDECYIPNYLLPKTQPELQRAWTNMEEYISA 180 |
| Avian_AAV_DA-1 | (NC_006263.1) | SEQ ID NO: 275 | VYCGHEPAMEGSWMRVTKKRN--FGLANKVRAESYIPAYLIPKQQPEVQWAWTNVPEYIKA 177 |
| Avian_AAV_VR-865 | (NC_004828.1) | SEQ ID NO: 276 | VYCATSLRWKDGCVVTKKRN--FGLANKVRAESYIPAYLIPKQQPEVQWAWTNVPEYIKA 177 |
| Bat | (NC_014468.1) | SEQ ID NO: 278 | VFRKCEPVDADWLQVQKIG---NHKSNEIKDEGHIPAYLLPKQSELQWAWTNIEKYERA 175 |
| Bovine | (NC_005889.1) | SEQ ID NO: 277 | VFQNIEPKINDWVAITKIK----KGGAMKVVDSGYIPAYLLPKVQPELQWAWTNLEEYKLA 175 |

| | | | |
|---|---|---|---|
| AAV-5 | (NC_006152.1) | SEQ ID NO: 269 | ALNLEERKRLVAQFLAESSQRS-QEAASQREFSADPVIKSKTSQKYMALVNWLVEHGITS 234 |
| AAV-2_Rep68 | (NC_001401.2) | SEQ ID NO: 265 | CLNLTERKRLVAQHLTHVSQTQKENKENQNPNSDAPVIRSKTSARYMELVGWLVDRGITS 238 |
| AAV-2_Rep78 | (NC_001401.2) | SEQ ID NO: 266 | CLNLTERKRLVAQHLTHVSQTQKENKENQNPNSDAPVIRSKTSARYMELVGWLVDRGITS 238 |
| AAV-2_Rep40 | (NC_001401.2) | SEQ ID NO: 267 | ---------------------------------------MELVGWLVDKGITS 14 |
| AAV-2_Rep52 | (NC_001401.2) | SEQ ID NO: 268 | ---------------------------------------MELVGWLVDKGITS 14 |
| AAV-1 | (NC_002077.1) | SEQ ID NO: 270 | CLNLAERKRLVAQHLTHVSQTQKENKENQNPNSDAPVIRSKTSARYMELVGWLVDRGITS 239 |
| AAV-3 | (NC_001729.1) | SEQ ID NO: 271 | CLNLAERKRLVAQHLTHVSQTQKENKENQNPNSDAPVIRSKTSARYMELVGWLVDRGITS 239 |
| AAV-4 | (NC_001829.1) | SEQ ID NO: 272 | CLNLAERKRLVAQHLTHVSQTQKENKENQNPNSDAPVIRSKTSARYMELVGWLVDRGITS 238 |
| AAV-7 | (NC_006260.1) | SEQ ID NO: 273 | CLNLAERKRLVAQHLTHVSQTQKENKENLNPNSDAPVIRSKTSARYMELVGWLVDRGITS 238 |
| AAV-8 | (NC_006261.1) | SEQ ID NO: 274 | CLHRELRASLARLHFERAGLSQSK-ENLARTADGAPVIATRVSKRYMELVGWLVEKGITT 240 |
| Avian_AAV_DA-1 | (NC_006263.1) | SEQ ID NO: 275 | CLHRELRASLARLHFERAGVSQSK-ENLARTADGAPVMPTRVSKRYMELVGWLVEKGHTT 236 |
| Avian_AAV_VR-865 | (NC_004828.1) | SEQ ID NO: 276 | CLHRELRASLARLHFERAGVSQSK-ENLARTADGAPVMPTRVSKRYMELVGWLVEKGHTT 236 |
| Bat | (NC_014468.1) | SEQ ID NO: 278 | TLSVAERARLVEEWKRSLAAEESDP---AEPERRFRKSTKSASEIMALVRNLVDNGIAT 231 |
| Bovine | (NC_005889.1) | SEQ ID NO: 277 | ALNLEERKRLVAQFQLESSQRS-QEASSQRDVSADPVIKSKTSQKYMALVSWLVEHGITS 234 |
| | | | :  * *:,::  |

FIG. 8 cont.

| | | | |
|---|---|---|---|
| AAV-5 | (NC_006152.1) | SEQ ID NO: 269 | ERQWIQEMNQESYLSPNSTGNSRSQIKAALDNATKIMSLTKSAVDYLVGSSVPE--DISKN 292 |
| AAV-2_Rep68 | (NC_001401.2) | SEQ ID NO: 265 | EKQWIQEDQASYISFNAASNSRSQIKAALDNAGKIMSLTKTAPDYLVGQQPVE--DISSN 296 |
| AAV-2_Rep78 | (NC_001401.2) | SEQ ID NO: 266 | EKQWIQEDQASYISFNAASNSRSQIKAALDNAGKIMSLTKTAPDYLVGQQPVE--DISSN 296 |
| AAV-2_Rep40 | (NC_001401.2) | SEQ ID NO: 267 | EKQWIQEDQASYISFNAASNSRSQIKAALDNAGKIMSLTKTAPDYLVGQQPVE--DISSN 72 |
| AAV-2_Rep52 | (NC_001401.2) | SEQ ID NO: 268 | EKQWIQEDQASYISFNAASNSRSQIKAALDNAGKIMSLTKTAPDYLVGQQPVE--DISSN 72 |
| AAV-1 | (NC_002077.1) | SEQ ID NO: 270 | EKQWIQEDQASYISFNAASNSRSQIKAALDNAGKIMALTKSAPDYLVGPAPPA---DIKTN 296 |
| AAV-3 | (NC_001729.1) | SEQ ID NO: 271 | EKQWIQEDQASYISFNAASNSRSQIKAALDNASKIMSLTKTAPDYLVGSNPPE--DITKN 296 |
| AAV-4 | (NC_001829.1) | SEQ ID NO: 272 | EKQWIQEDQASYISFNAASNSRSQIKAALDNAGKIMSLTKTAPDYLVGQNPPE--DISSN 296 |
| AAV-7 | (NC_006260.1) | SEQ ID NO: 273 | ERQWIQEDQASYISFNAASNSRSQIKAALDNAGKIMALTKSAPDYLVGPSLPA---DIKTN 296 |
| AAV-8 | (NC_006261.1) | SEQ ID NO: 274 | EKQWIQEDQASYISFNAASNSRSQIKAALDNAGKIMALTKSAPDYLVGPSLPA---DITQN 298 |
| Avian_AAV_DA-1 | (NC_006263.1) | SEQ ID NO: 275 | EKEWLLENRESFRSFQASSNSARQIKTALQGAIQEMLLTKTAEDYLVGKEPVSDDEIRQN 296 |
| Avian_AAV_VR-865 | (NC_004828.1) | SEQ ID NO: 276 | EKEWLLENRESFRSFQASSNSARQIKTALQGAIQEMLLTKTAEDYLVGKDPVSDDIRQN 296 |
| Bat | (NC_014468.1) | SEQ ID NO: 278 | EREWMREDSDGYLSYNATGATRAQIKAALDNAARIMVNTTAADYLVGRNPPL--DVEDN 289 |
| Bovine | (NC_005889.1) | SEQ ID NO: 277 | EKQWIQENQESYLSFNSTGNSRSQIKAALDNASKIMSLTKSASDYLVGQTVPE---DISEN 292 |

| | | | |
|---|---|---|---|
| AAV-5 | (NC_006152.1) | SEQ ID NO: 269 | RIWQIFEMNGYDPAYAGSILYGWCQRSFNKKRNTVWLYGPATGKTNIAEAIAHTVPFYGC 352 |
| AAV-2_Rep68 | (NC_001401.2) | SEQ ID NO: 265 | RIYKILELNGYDPQYAASVFLGWATKKFGKRNTIWLFGPATGKTNIAEAIAHTVPFYGC 356 |
| AAV-2_Rep78 | (NC_001401.2) | SEQ ID NO: 266 | RIYKILELNGYDPQYAASVFLGWATKKFGKRNTIWLFGPATGKTNIAEAIAHTVPFYGC 356 |
| AAV-2_Rep40 | (NC_001401.2) | SEQ ID NO: 267 | RIYKILELNGYDPQYAASVFLGWATKKFGKRNTIWLFGPATGKTNIAEAIAHTVPFYGC 132 |
| AAV-2_Rep52 | (NC_001401.2) | SEQ ID NO: 268 | RIYKILELNGYDPQYAASVFLGWATKKFGKRNTIWLFGPATGKTNIAEAIAHTVPFYGC 132 |
| AAV-1 | (NC_002077.1) | SEQ ID NO: 270 | RITRILELNGYEPAYAGSVFLGWAQKRFGKRNTIWLFGPATGKTNIAEAIAHAVPFYGC 356 |
| AAV-3 | (NC_001729.1) | SEQ ID NO: 271 | RIYQILELMNGYDPQYAASVFLGWAQKFGKRNTIWLFGPATGKTNIAEAIAHAVPFYGC 356 |
| AAV-4 | (NC_001829.1) | SEQ ID NO: 272 | RIYRILELMNGYDPQYAASVFLGWAQKQKKFGKRNTIWLFGPATGKTNIAEAIAHAVPFYGC 356 |
| AAV-7 | (NC_006260.1) | SEQ ID NO: 273 | RIYRILELNGYDPAYAGSVFLGWAQKKFGKRNTIWLFGPATGKTNIAEAIAHAVPFYGC 356 |
| AAV-8 | (NC_006261.1) | SEQ ID NO: 274 | RIYRILALNGYDPAYAGSVFLGWAQKKFGKRNTIWLFGPATGKTNIAEAIAHAVPFYGC 358 |
| Avian_AAV_DA-1 | (NC_006263.1) | SEQ ID NO: 275 | RIYKILELNHYDPATYGWCRKWGKRNTLWLFGPATTGKTNIAEAIAHAVPFYGC 356 |
| Avian_AAV_VR-865 | (NC_004828.1) | SEQ ID NO: 276 | RIYKILELNHYDPATYGWCQKKWGKRRTLWLFGHATTGKTNIAEAIAHAVPFYGC 356 |
| Bat | (NC_014468.1) | SEQ ID NO: 278 | RITRLFRMNGYDPATGSVLIGWCRTGFGKRNTVWLFGPATTGKTNLAEAISHSVPFYGC 349 |
| Bovine | (NC_005889.1) | SEQ ID NO: 277 | RIWQIFDLNGYDPAYAGSVLYGWCTRAFGKRNTVWLYGPATTGKTNIAEAISHTVPFYGC 352 |

FIG. 8 cont.

| | | | |
|---|---|---|---|
| AAV-5 | (NC_006152.1) | SEQ ID NO: 269 | VNWTNENFPFNDCVDKRMLIWWEEGKMTNKVVESAKAILGGSKVRVDQKCKSSVQIDSTPV 412 |
| AAV-2_Rep68 | (NC_001401.2) | SEQ ID NO: 265 | VNWTNENFPFNDCVDKMVIWWEEGKMTAKVVESAKAILGGSKVRVDQKCKSSAQIDPTPV 416 |
| AAV-2_Rep78 | (NC_001401.2) | SEQ ID NO: 266 | VNWTNENFPFNDCVDKMVIWWEEGKMTAKVVESAKAILGGSKVRVDQKCKSSAQIDPTPV 416 |
| AAV-2_Rep40 | (NC_001401.2) | SEQ ID NO: 267 | VNWTNENFPFNDCVDKMVIWWEEGKMTAKVVESAKAILGGSKVRVDQKCKSSAQIDPTPV 192 |
| AAV-2_Rep52 | (NC_001401.2) | SEQ ID NO: 268 | VNWTNENFPFNDCVDKMVIWWEEGKMTAKVVESAKAILGGSKVRVDQKCKSSAQIDPTPV 192 |
| AAV-1 | (NC_002077.1) | SEQ ID NO: 270 | VNWTNENFPFNDCVDKMVIWWEEGKMTAKVVESAKAILGGSKVRVDQKCKSSAQIDPTPV 416 |
| AAV-3 | (NC_001729.1) | SEQ ID NO: 271 | VNWTNENFPFNDCVDKMVIWWEEGKMTAKVVESAKAILGGSKVRVDQKCKSSAQIDPTPV 416 |
| AAV-4 | (NC_001829.1) | SEQ ID NO: 272 | VNWTNENFPFNDCVDKMVIWWEEGKMTAKVVESAKAILGGSKVRVDQKCKSSAQIEPTPV 416 |
| AAV-7 | (NC_006260.1) | SEQ ID NO: 273 | VNWTNENFPFNDCVDKMVIWWEEGKMTAKVVESAKAILGGSKVRVDQKCKSSAQIDPTPV 416 |
| AAV-8 | (NC_006261.1) | SEQ ID NO: 274 | VNWTNENFPFNDCVDKMVIWWEEGKMTAKVVESAKAILGGSKVRVDQKCKSSAQIDPTPV 418 |
| Avian AAV DA-1 | (NC_006263.1) | SEQ ID NO: 275 | VNWTNENFPFNDCVERMIIWWEEGKMTAKVVETAKVETAKVETAVESAKAILGGSKVRVDQKCKASVPIEPTPV 416 |
| Avian_AAV_VR-865 | (NC_004828.1) | SEQ ID NO: 276 | VNWTNENFPFNDCVERMIIWWEEGKMTAKVVETAKVETAVESAKAILGGSKVRVDQKCKASVPIEPTPV 416 |
| Bat | (NC_014468.1) | SEQ ID NO: 279 | VNWTNENFPFNDCVDKMIIWWEEGKMTSKVVEEGKMTSKVVESAKAILGGSRVRVDQKCKNSQQIEPTPV 409 |
| Bovine | (NC_005889.1) | SEQ ID NO: 277 | VNWTNENFPFNDCVEKMLIWWEEGKMTSKVVEPAKAILGGSKVRVDQKCKSSVQVDSTPV 412 |
| | | | *:****** ;:***** : ***:;****** * :; *** |

| | | | |
|---|---|---|---|
| AAV-5 | (NC_006152.1) | SEQ ID NO: 269 | IVTSNTNMCVVVDGNSTTFEHQQPLEDRMFKFELTRLPDEGKITKQEVKDFFAWAKVN 472 |
| AAV-2_Rep68 | (NC_001401.2) | SEQ ID NO: 265 | IVTSNTNMCAVIDGNSTTFEHQQPLEDRMFKFELTRLLRRLDHFGKVTQEVKDFFRWAKDH 476 |
| AAV-2_Rep78 | (NC_001401.2) | SEQ ID NO: 266 | IVTSNTNMCAVIDGNSTTFEHQQPLQDRMFKFELTRLDHFGKVTQEVKDFFRWAKDH 476 |
| AAV-2_Rep40 | (NC_001401.2) | SEQ ID NO: 267 | IVTSNTNMCAVIDGNSTTFEHQQPLQDRMFKFELTRLDHFGKVTQEVKDFFRWAKDH 252 |
| AAV-2_Rep52 | (NC_001401.2) | SEQ ID NO: 268 | IVTSNTNMCAVIDGNSTTFEHQQPLQDRMFKFELTRLDHFGKVTQEVKDFFRWAKDH 252 |
| AAV-1 | (NC_002077.1) | SEQ ID NO: 270 | IVTSNTNMCAVIDGNSTTFEHQQPLQDRMFKFELTRLLHDKGKVTQEVKDFFRWAQDH 476 |
| AAV-3 | (NC_001729.1) | SEQ ID NO: 271 | IVTSNTNMCAVIDGNSTTFEHQQPLQDRMFKFELTRLLEHDFGKVTQEVKRFFRWAQDH 476 |
| AAV-4 | (NC_001829.1) | SEQ ID NO: 272 | IVTSNTNMCAVIDGNSTTFEHQQPLQDRMFKFELTRLLEHDFGKVTQEVKDFFRWASDH 476 |
| AAV-7 | (NC_006260.1) | SEQ ID NO: 273 | IVTSNTNMCAVIDGNSTTFEHQQPLQDRMFKFELTRLEHDFGKVTQEVKEFFRWASDH 476 |
| AAV-8 | (NC_006261.1) | SEQ ID NO: 274 | IVTSNTNMCYVIDGNTTFEHQQPLQDRMFKLELTRLEHDDFGKVTQEVKEFFRWASDH 478 |
| Avian AAV DA-1 | (NC_006263.1) | SEQ ID NO: 275 | IITSNTNMCYVIDGNTTFEHQQPLEDRMFKLELTRLPDDFGKVTQEVRQFFRWSQDH 476 |
| Avian_AAV_VR-865 | (NC_004828.1) | SEQ ID NO: 276 | IITSNTNMCYVIDGNTTFEHQQPLEDRMFKLELTRLPDDFGKVTQEVRQFFRWSQDH 476 |
| Bat | (NC_014468.1) | SEQ ID NO: 279 | IITSNTNMCEVVDGNSTFEHRQPLEDRMFKFELTVRLQPTEGKITKQEVREFFKWAELN 469 |
| Bovine | (NC_005889.1) | SEQ ID NO: 277 | IITSNTNMCYVVDGNSTTFEHQQPLEDRMFRFELMRRLPDFGKITHQEVKDFFAWAKVN 472 |
| | | | *:******* *;*:*:**;;  :** *.;** *. |

FIG. 8 cont.

| | | | | |
|---|---|---|---|---|
| AAV-5 | (NC_006152.1) | SEQ ID NO: 269 | QVPVTHEFKVPRELAGTKGAEKSLKRPLGDVTNTSYKSLEKRARLSFVPETPRSSDVTVD | 532 |
| AAV-2_Rep68 | (NC_001401.2) | SEQ ID NO: 265 | VVEVEHEFYVKKGG------A---KKRPAPSD----ADISEPKRVRESV-------AQPSTS | 518 |
| AAV-2_Rep78 | (NC_001401.2) | SEQ ID NO: 266 | VVEVEHEFYVKKGG------A---KKRPAPSD----ADISEPKRVRESV-------AQPSTS | 518 |
| AAV-2_Rep40 | (NC_001401.2) | SEQ ID NO: 267 | VVEVEHEFYVKKGG------A---KKRPAPSD----ADISEPKRVRESV-------AQPSTS | 294 |
| AAV-2_Rep52 | (NC_001401.2) | SEQ ID NO: 268 | VVEVEHEFYVKKGG------A---KKRPAPSD----ADISEPKRVRESV-------AQPSTS | 294 |
| AAV-1 | (NC_002077.1) | SEQ ID NO: 270 | VTEVAHEFYVRKGG------A---KKRPAPDD----ADKSEPKRACPSV-------ADPSTS | 518 |
| AAV-3 | (NC_001729.1) | SEQ ID NO: 271 | VTDVAHEFYVRKGG------A---KKRPASND----ADVSEPKRECTSL------AQPTTS | 518 |
| AAV-4 | (NC_001829.1) | SEQ ID NO: 272 | VTEVTHEFVVRKGG------A---RKRPAPND----ADISEPKRACPSV-------AQPSTS | 518 |
| AAV-7 | (NC_006260.1) | SEQ ID NO: 273 | VTEVAHEFYVRKGG------A---SKRPAPDD----ADISEPKRACPSV-------ADPSTS | 518 |
| AAV-8 | (NC_006261.1) | SEQ ID NO: 274 | VTEVAHEFYVRKGG------A---SKRPAPDD----ADKSEPKRACPSV-------ADPSTS | 520 |
| Avian_AAV_DA-1 | (NC_006263.1) | SEQ ID NO: 275 | LFPVIPERLVRKAE------SRKRPAPSG----EGYISPTKRPALAEQQ---------- | 515 |
| Avian_AAV_VR-865 | (NC_004828.1) | SEQ ID NO: 276 | LFPVIPERLVRKAE------SRKRPAPSG----EGYISPTKRPALAEQQ---------- | 515 |
| Bat | (NC_014468.1) | SEQ ID NO: 278 | AVDVEYDFLVRKIMQSDTGGG---VKRGAEPT----KDEPPAKRVFFYGAT-SEGEDVREGA | 523 |
| Bovine | (NC_005889.1) | SEQ ID NO: 277 | QVPVTHEFMVPKKVAGTERAETSRKRFLDDVTNTNYKSPEKRARLSVVPETRSSDVFVE | 532 |
| | | | *  :  :  **                              **         | |

| | | | | |
|---|---|---|---|---|
| AAV-5 | (NC_006152.1) | SEQ ID NO: 269 | PAPLRPLNWNSRYDCKCDYHAQFDNISNKCDECEYLNRGENGCICHNVTHCQICHGIPPW | 592 |
| AAV-2_Rep68 | (NC_001401.2) | SEQ ID NO: 265 | DAE-ASINYADRYQNKCSRHVGMLFCRQCERMNQNFNICFTHGQKDCLECFPV-SE | 536 |
| AAV-2_Rep78 | (NC_001401.2) | SEQ ID NO: 266 | DAE-ASINYADRYQNKCSRHVGMNLMLFPCRQCERMNQNSNICFTHGQKDCLECFPV-SE | 576 |
| AAV-2_Rep40 | (NC_001401.2) | SEQ ID NO: 267 | DAE-ASINYADRLARGHSL---------------------------------------- | 312 |
| AAV-2_Rep52 | (NC_001401.2) | SEQ ID NO: 268 | DAE-ASINYADRLARGHSL---------------------------------------- | 352 |
| AAV-1 | (NC_002077.1) | SEQ ID NO: 270 | DAEGAFVDFADRYQNKCSRHAGMLQMLFPCKTCERMNQNFNICFTHGTRDCSECFPGVSE | 579 |
| AAV-3 | (NC_001729.1) | SEQ ID NO: 271 | DAE-APADYADRYQNKCSRHVGMNLMLFPCKTCERMNQISNVCFTHGQRDCGECFPGMSE | 577 |
| AAV-4 | (NC_001829.1) | SEQ ID NO: 272 | DAE-APVDYADRYQNKCSRHVGMNLMLFPCRQCERMNQNVDICFTHGVMDCAECFPV-SE | 576 |
| AAV-7 | (NC_006260.1) | SEQ ID NO: 273 | DAEGAPVDFADRYQNKCSRHAGMIQMLFPCKTCERMNQNFNICFTHGVRDCLECFPGVSE | 578 |
| AAV-8 | (NC_006261.1) | SEQ ID NO: 274 | DAEGAPVDFADRYQNKCSRHAGMLQMLFPCKTCERMNQNFNICFTHGVRDCSECFPEYGD | 580 |
| Avian_AAV_DA-1 | (NC_006263.1) | SEQ ID NO: 275 | QASESAEPVPTRYRIKCSKHCGMDKMLFPCQICESMRRNINICAIHKTTECKECFPEYGD | 575 |
| Avian_AAV_VR-865 | (NC_004828.1) | SEQ ID NO: 276 | QASESADPVPTRYRIKCSKHCGMDKMLFPCQICESMRRDINICAIHKTDCKECFPDYGD | 575 |
| Bat | (NC_014468.1) | SEQ ID NO: 278 | PGESDSVNFAERYVSKCSKHLSWSNMRYPCRACERMNADVNVCTPHGCRDCPECFRPAP | 583 |
| Bovine | (NC_005889.1) | SEQ ID NO: 277 | PAPLRPLNWSSRYECRCDYHAKFDSVTGECDECEYLNRGKNGCIFNMATHCQICHAVPPW | 592 |
| | | | . *                                              . | |

FIG. 8 cont.

```
AAV-5          (NC_006152.1) SEQ ID NO: 269 EK---------------------------------ENLSD---------- 599
AAV-2_Rep68    (NC_001401.2) SEQ ID NO: 265 ------------------------------------------------- 536
AAV-2_Rep78    (NC_001401.2) SEQ ID NO: 266 SQPVSVV----------------------------KKAYQKLCYIHHIMGK 599
AAV-2_Rep40    (NC_001401.2) SEQ ID NO: 267 ------------------------------------------------- 312
AAV-2_Rep52    (NC_001401.2) SEQ ID NO: 268 SQPVSVV----------------------------KKAYQKLCYIHHIMGK 375
AAV-1          (NC_002077.1) SEQ ID NO: 270 SQPV--VR---------------------------KRTYRKLCAIHHILGR 600
AAV-3          (NC_001729.1) SEQ ID NO: 271 SQPVSVVK---------------------------KKTYQKLCPIHHILGR 601
AAV-4          (NC_001829.1) SEQ ID NO: 272 SQPVSVVR---------------------------KRTYQKLCPIHHIMGR 600
AAV-7          (NC_006260.1) SEQ ID NO: 273 SQPV--VR---------------------------KKTYRKLCAIHHILGR 600
AAV-8          (NC_006261.1) SEQ ID NO: 274 SQPV--VR---------------------------KRTYRKLCAIHHILGR 602
Avian_AAV_DA-1 (NC_006263.1) SEQ ID NO: 275 KDTVPELPPCTEHNVSRCYQCHSGELYRVTSDSDEKPAPESEKGTEPSYAPCTIHHILMGK 635
Avian_AAV_VR-865 (NC_004828.1) SEQ ID NO: 276 KDDV-ELPPCTEHNVSRCYQCHSGELYRVTSDSDEKPAPESDEGTEPSIAPCTIHHILMGK 634
Bat            (NC_014468.1) SEQ ID NO: 278 ---VPIAE---------------------------HDLCLAPI-EDS-- 599
Bovine         (NC_005889.1) SEQ ID NO: 277 EK---------------------------------ENVSD---------- 599

AAV-5          (NC_006152.1) SEQ ID NO: 269 ---------------FGDFD------DANKKQ 610
AAV-2_Rep68    (NC_001401.2) SEQ ID NO: 265 -------------------------------- 536
AAV-2_Rep78    (NC_001401.2) SEQ ID NO: 266 VP-D-ACTACDLVNVDLD--------DCIFEQ 621
AAV-2_Rep40    (NC_001401.2) SEQ ID NO: 267 -------------------------------- 312
AAV-2_Rep52    (NC_001401.2) SEQ ID NO: 268 VP-D-ACTACDLVNVDLD--------DCIFEQ 397
AAV-1          (NC_002077.1) SEQ ID NO: 270 AP-EIACSACDLVNVDLD--------DCVSEQ 623
AAV-3          (NC_001729.1) SEQ ID NO: 271 AP-EIACSACDLANVDLD--------DCVSEQ 624
AAV-4          (NC_001829.1) SEQ ID NO: 272 AP-EVACSACELANVDLD--------DCDMEQ 623
AAV-7          (NC_006260.1) SEQ ID NO: 273 AP-EIACSACDLVNVDLD--------DCDSEQ 623
AAV-8          (NC_006261.1) SEQ ID NO: 274 AP-EIACSACDLVNVDLD--------DCVSEQ 625
Avian_AAV_DA-1 (NC_006263.1) SEQ ID NO: 275 SRGIVSCAACRLKNSTLHDDLDDGDLEQ 663
Avian_AAV_VR-865 (NC_004828.1) SEQ ID NO: 276 SHGLVTCAACRLKNSTLHDDLDDGDLEQ 662
Bat            (NC_014468.1) SEQ ID NO: 278 DF-YVGC-------------ID----DVNKEQ 613
Bovine         (NC_005889.1) SEQ ID NO: 277 ---------------FNDFD------DCNKEQ 610
```

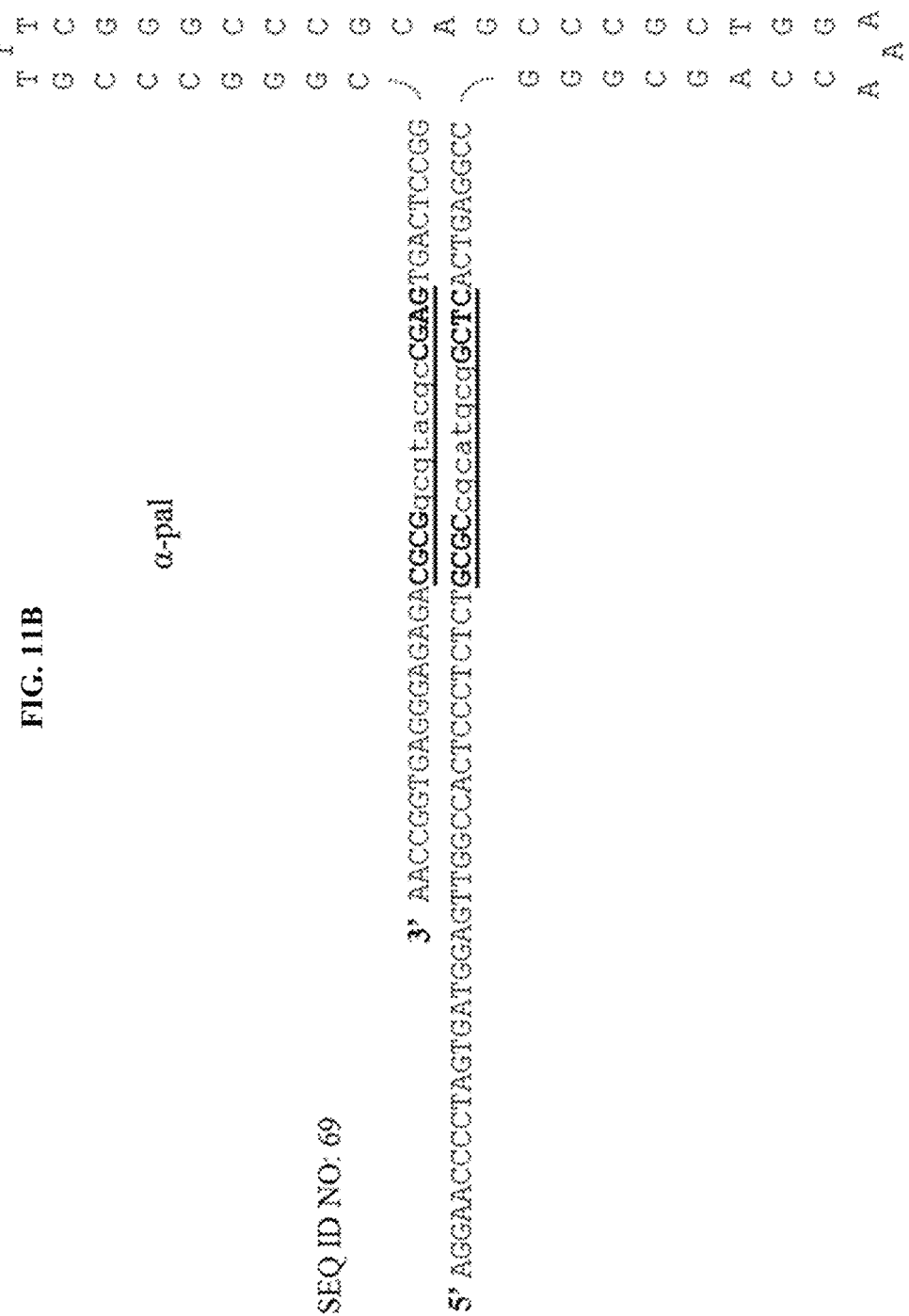

FIG. 11D 5-5/EGR

```
                         T T                           A A
                         T T C G G C C C C C C A G C C C G T G G A A
                         | | | | | | | | | | | | | | | | | | | | | |
                         G C C C G G G C G / A \ G G C G A C C A A
```

3' AACCGGTGAGGAGAGACTcgccccgcgCGAGTGACTCCGG
5' AGGAACCCCTAGTGATGGAGTTGGCCACTCCCTCTgagcgggcgcgGCTCACTGAGGCC

SEQ ID NO: 72

FIG. 11F

JcDNV NS1

```
                                   T T                         A
                                   T T C G G C C G C C A G C C C G T G A A
                                   | | | | | | | | | | | | | | | | | | | |
                                   G C C C G G C C C G G G C G A C C A A
```

SEQ ID NO: 75

3' AACCGTGAGGGAGA

SEQUENCE LISTING

```
<160> NUMBER OF SEQ ID NOS: 312

<210> SEQ ID NO 1
<211> LENGTH: 16
<212> TYPE: DNA
<213> ORGANISM: Adeno-associated virus

<400> SEQUENCE: 1
gcgcgctcgc tcgctc                                                     16

<210> SEQ ID NO 2
<211> LENGTH: 16
<212> TYPE: DNA
<213> ORGANISM: Adeno-associated virus

<400> SEQUENCE: 2
gagcgagcga gcgcgc                                                     16

<210> SEQ ID NO 3
<211> LENGTH: 16
<212> TYPE: DNA
<213> ORGANISM: Adeno-associated virus

<400> SEQUENCE: 3
gctcgctcgc tggctc                                                     16

<210> SEQ ID NO 4
<211> LENGTH: 16
<212> TYPE: DNA
<213> ORGANISM: Adeno-associated virus

<400> SEQUENCE: 4
gagccagcga gcgagc                                                     16

<210> SEQ ID NO 5
<211> LENGTH: 16
<212> TYPE: DNA
<213> ORGANISM: Adeno-associated virus

<400> SEQUENCE: 5
gcgcgctcgc tcgctc                                                     16

<210> SEQ ID NO 6
<211> LENGTH: 16
<212> TYPE: DNA
<213> ORGANISM: Adeno-associated virus
```

```
<400> SEQUENCE: 6
gagcgagcga gcgcgc                                                    16

<210> SEQ ID NO 7
<211> LENGTH: 16
<212> TYPE: DNA
<213> ORGANISM: Adeno-associated virus

<400> SEQUENCE: 7
gcgcactcgc tcgctc                                                    16

<210> SEQ ID NO 8
<211> LENGTH: 16
<212> TYPE: DNA
<213> ORGANISM: Adeno-associated virus

<400> SEQUENCE: 8
gagcgagcga gtgcgc                                                    16

<210> SEQ ID NO 9
<211> LENGTH: 16
<212> TYPE: DNA
<213> ORGANISM: Adeno-associated virus

<400> SEQUENCE: 9
gcgcgctcgc tcactc                                                    16

<210> SEQ ID NO 10
<211> LENGTH: 16
<212> TYPE: DNA
<213> ORGANISM: Adeno-associated virus

<400> SEQUENCE: 10
gagtgagcga gcgcgc                                                    16

<210> SEQ ID NO 11
<211> LENGTH: 16
<212> TYPE: DNA
<213> ORGANISM: Adeno-associated virus

<400> SEQUENCE: 11
gcgcgctcgc tcgctc                                                    16

<210> SEQ ID NO 12
<211> LENGTH: 16
<212> TYPE: DNA
<213> ORGANISM: Adeno-associated virus

<400> SEQUENCE: 12
gagcgagcga gcgcgc                                                    16

<210> SEQ ID NO 13
<211> LENGTH: 12
<212> TYPE: DNA
<213> ORGANISM: Avian adeno-associated virus

<400> SEQUENCE: 13
gctcgctcgc tc                                                        12

<210> SEQ ID NO 14
<211> LENGTH: 12
<212> TYPE: DNA
<213> ORGANISM: Avian adeno-associated virus
```

<400> SEQUENCE: 14
gagcgagcga gc                                                          12

<210> SEQ ID NO 15
<211> LENGTH: 12
<212> TYPE: DNA
<213> ORGANISM: Avian adeno-associated virus

<400> SEQUENCE: 15
gctcgctcgc tc                                                          12

<210> SEQ ID NO 16
<211> LENGTH: 12
<212> TYPE: DNA
<213> ORGANISM: Avian adeno-associated virus

<400> SEQUENCE: 16
gagcgagcga gc                                                          12

<210> SEQ ID NO 17
<211> LENGTH: 16
<212> TYPE: DNA
<213> ORGANISM: Bovine adeno-associated virus

<400> SEQUENCE: 17
gctcgttcgc tggctc                                                      16

<210> SEQ ID NO 18
<211> LENGTH: 16
<212> TYPE: DNA
<213> ORGANISM: Bovine adeno-associated virus

<400> SEQUENCE: 18
gagccagcga acgagc                                                      16

<210> SEQ ID NO 19
<211> LENGTH: 10
<212> TYPE: DNA
<213> ORGANISM: Snake parvovirus

<400> SEQUENCE: 19
gcgcgcgctc                                                             10

<210> SEQ ID NO 20
<211> LENGTH: 10
<212> TYPE: DNA
<213> ORGANISM: Snake parvovirus

<400> SEQUENCE: 20
gagcgcgcgc                                                             10

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(20)
<223> OTHER INFORMATION: a, c, t, g, unknown or other

<400> SEQUENCE: 21

```
gctcnnnnn nnnnnnnnnn                                            20

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(16)
<223> OTHER INFORMATION: a, c, t, g, unknown or other

<400> SEQUENCE: 22
gctcnnnnnn nnnnnn                                               16

<210> SEQ ID NO 23
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(12)
<223> OTHER INFORMATION: a, c, t, g, unknown or other

<400> SEQUENCE: 23
gctcnnnnnn nn                                                   12

<210> SEQ ID NO 24
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(8)
<223> OTHER INFORMATION: a, c, t, g, unknown or other

<400> SEQUENCE: 24 gctcnnnn                                                         8

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(16)
<223> OTHER INFORMATION: a, c, t, g, unknown or other

<400> SEQUENCE: 25
nnnnnnnnnn nnnnnngctc                                           20

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (1)..(12)
<223> OTHER INFORMATION: a, c, t, g, unknown or other

<400> SEQUENCE: 26
nnnnnnnnnn nngctc                                                         16

<210> SEQ ID NO 27
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, g, unknown or other

<400> SEQUENCE: 27
nnnnnnnngc tc                                                             12

<210> SEQ ID NO 28
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other

<400> SEQUENCE: 28 nnnngctc                                                                   8

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(16)
<223> OTHER INFORMATION: a, c, t, g, unknown or other

<400> SEQUENCE: 29
gctcnnnnnn nnnnnngctc                                                     20

<210> SEQ ID NO 30
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(12)
<223> OTHER INFORMATION: a, c, t, g, unknown or other

<400> SEQUENCE: 30
gctcnnnnnn nngctc                                                         16

<210> SEQ ID NO 31
```

```
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(8)
<223> OTHER INFORMATION: a, c, t, g, unknown or other

<400> SEQUENCE: 31
gctcnnnngc tc                                                           12

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(20)
<223> OTHER INFORMATION: a, c, t, g, unknown or other

<400> SEQUENCE: 32
gctcgctcnn nnnnnnnnnn                                                   20

<210> SEQ ID NO 33
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(16)
<223> OTHER INFORMATION: a, c, t, g, unknown or other

<400> SEQUENCE: 33
gctcgctcnn nnnnnn                                                       16

<210> SEQ ID NO 34
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(12)
<223> OTHER INFORMATION: a, c, t, g, unknown or other

<400> SEQUENCE: 34
gctcgctcnn nn                                                           12

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(20)
<223> OTHER INFORMATION: a, c, t, g, unknown or other
```

```
<400> SEQUENCE: 35
gctcgctcgc tcnnnnnnnn                                               20

<210> SEQ ID NO 36
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(16)
<223> OTHER INFORMATION: a, c, t, g, unknown or other

<400> SEQUENCE: 36
gctcgctcgc tcnnnn                                                   16

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t, g, unknown or other

<400> SEQUENCE: 37
nnnnnnnnnn nngctcgctc                                               20

<210> SEQ ID NO 38
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, g, unknown or other

<400> SEQUENCE: 38
nnnnnnnngc tcgctc                                                   16

<210> SEQ ID NO 39
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other

<400> SEQUENCE: 39
nnnngctcgc tc                                                       12

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
     oligonucleotide
<220> FEATURE:
<221> NAME/KEY: modified_base
<222> LOCATION: (1)..(8)
<223> OTHER INFORMATION: a, c, t, g, unknown or other

<400> SEQUENCE: 40
nnnnnnnngc tcgctcgctc                                                 20

<210> SEQ ID NO 41
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other

<400> SEQUENCE: 41
nnnngctcgc tcgctc                                                     16

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(16)
<223> OTHER INFORMATION: a, c, t, g, unknown or other

<400> SEQUENCE: 42
gctcgctcnn nnnnnngctc                                                 20

<210> SEQ ID NO 43
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(12)
<223> OTHER INFORMATION: a, c, t, g, unknown or other

<400> SEQUENCE: 43
gctcgctcnn nngctc                                                     16

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(12)
<223> OTHER INFORMATION: a, c, t, g, unknown or other

<400> SEQUENCE: 44
gctcnnnnnn nngctcgctc                                                 20
```

```
<210> SEQ ID NO 45
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(8)
<223> OTHER INFORMATION: a, c, t, g, unknown or other

<400> SEQUENCE: 45
gctcnnnngc tcgctc                                                  16

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: modified_base
<222> LOCATION: (17)..(20)
<223> OTHER INFORMATION: a, c, t, g, unknown or other

<400> SEQUENCE: 46
nnnngctcgc tcgctcnnnn                                              20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, g, unknown or other
<220> FEATURE:
<221> NAME/KEY: modified_base
<222> LOCATION: (17)..(20)
<223> OTHER INFORMATION: a, c, t, g, unknown or other

<400> SEQUENCE: 47
nnnnnnnngc tcgctcnnnn                                              20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: modified_base
<222> LOCATION: (13)..(20)
<223> OTHER INFORMATION: a, c, t, g, unknown or other

<400> SEQUENCE: 48
nnnngctcgc tcnnnnnnnn                                              20
```

```
<210> SEQ ID NO 49
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: modified_base
<222> LOCATION: (13)..(16)
<223> OTHER INFORMATION: a, c, t, g, unknown or other

<400> SEQUENCE: 49
nnnngctcgc tcnnnn                                                        16

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t, g, unknown or other
<220> FEATURE:
<221> NAME/KEY: modified_base
<222> LOCATION: (17)..(20)
<223> OTHER INFORMATION: a, c, t, g, unknown or other

<400> SEQUENCE: 50
nnnnnnnnnn nngctcnnnn                                                    20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, g, unknown or other
<220> FEATURE:
<221> NAME/KEY: modified_base
<222> LOCATION: (13)..(20)
<223> OTHER INFORMATION: a, c, t, g, unknown or other

<400> SEQUENCE: 51
nnnnnnnngc tcnnnnnnnn                                                    20

<210> SEQ ID NO 52
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, g, unknown or other
<220> FEATURE:
<221> NAME/KEY: modified_base
<222> LOCATION: (13)..(16)
<223> OTHER INFORMATION: a, c, t, g, unknown or other
```

```
<400> SEQUENCE: 52
nnnnnnnngc tcnnnn                                                  16

<210> SEQ ID NO 53
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: modified_base
<222> LOCATION: (9)..(12)
<223> OTHER INFORMATION: a, c, t, g, unknown or other

<400> SEQUENCE: 53
nnnngctcnn nn                                                      12

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: modified_base
<222> LOCATION: (9)..(20)
<223> OTHER INFORMATION: a, c, t, g, unknown or other

<400> SEQUENCE: 54
nnnngctcnn nnnnnnnnnn                                              20

<210> SEQ ID NO 55
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: modified_base
<222> LOCATION: (9)..(16)
<223> OTHER INFORMATION: a, c, t, g, unknown or other

<400> SEQUENCE: 55
nnnngctcnn nnnnnn                                                  16

<210> SEQ ID NO 56
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(8)
```

```
<223> OTHER INFORMATION: a, c, t, g, unknown or other
<220> FEATURE:
<221> NAME/KEY: modified_base
<222> LOCATION: (13)..(16)
<223> OTHER INFORMATION: a, c, t, g, unknown or other

<400> SEQUENCE: 56 gctcnnngc tcnnnn                                                       16

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(12)
<223> OTHER INFORMATION: a, c, t, g, unknown or other
<220> FEATURE:
<221> NAME/KEY: modified_base
<222> LOCATION: (17)..(20)
<223> OTHER INFORMATION: a, c, t, g, unknown or other

<400> SEQUENCE: 57
gctcnnnnnn nngctcnnnn                                                  20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(8)
<223> OTHER INFORMATION: a, c, t, g, unknown or other
<220> FEATURE:
<221> NAME/KEY: modified_base
<222> LOCATION: (13)..(20)
<223> OTHER INFORMATION: a, c, t, g, unknown or other

<400> SEQUENCE: 58 gctcnnngc tcnnnnnnnn                                                   20

<210> SEQ ID NO 59
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: modified_base
<222> LOCATION: (9)..(12)
<223> OTHER INFORMATION: a, c, t, g, unknown or other

<400> SEQUENCE: 59
nnnngctcnn nngctc                                                      16

<210> SEQ ID NO 60
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: modified_base
<222> LOCATION: (9)..(16)
<223> OTHER INFORMATION: a, c, t, g, unknown or other

<400> SEQUENCE: 60
nnnngctcnn nnnnnngctc                                                    20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, g, unknown or other
<220> FEATURE:
<221> NAME/KEY: modified_base
<222> LOCATION: (13)..(16)
<223> OTHER INFORMATION: a, c, t, g, unknown or other

<400> SEQUENCE: 61
nnnnnnnngc tcnnnngctc                                                    20

<210> SEQ ID NO 62
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62 gctcgggg                                                                  8

<210> SEQ ID NO 63
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63 gctcggggg                                                                 9

<210> SEQ ID NO 64
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gctcgggggg                                                               10

<210> SEQ ID NO 65
<211> LENGTH: 11
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 65 gctcggggggg g                                                         11

<210> SEQ ID NO 66
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gctcgggggg gg                                                         12

<210> SEQ ID NO 67
<211> LENGTH: 2303
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
cctgcaggca gctgcgccgc atgcggctca ctgaggccgc ccgggcaaag cccgggcgtc      60
gggcgacctt tggtcgcccg gcctcagtga gccgcatgcg gcgcagagag ggagtggcca     120
actccatcac taggggttcc ttgtagttaa tgattaaccc gccatgctac ttatctacgt     180
agccatgctc tagagcggcc gcacgcgtgt tactagttat taatagtaat caattacggg     240
gtcattagtt catagcccat atatggagtt ccgcgttaca taacttacgg taaatggccc     300
gcctggctga ccgcccaacg acccccgccc attgacgtca ataatgacgt atgttcccat     360
agtaacgtca atagggactt tccattgacg tcaatgggtg gagtatttac ggtaaactgc     420
ccacttggca gtacatcaag tgtatcatat gccaagtacg cccctattg acgtcaatga     480 cggtaaatgg cccgcctggc attatgccca gtacatgacc ttatgggact ttcctacttg     540
gcagtacatc tacgtattag tcatcgctat taccatggtg atgcggtttt ggcagtacat     600
caatgggcgt ggatagcggt ttgactcacg ggatttcca agtctccacc ccattgacgt     660
caatgggagt ttgttttgca ccaaaatcaa cgggactttc caaaatgtcg taacaactcc     720
gccccattga cgcaaatggg cggtaggcgt gtacggtggg aggtctatat aagcagagct     780
cgtttagtga accgtcagat cgcctggaga cgccatccac gctgttttga cctccataga     840
agacaccggg accgatccag cctccaaccg gttcgaacag gtaagcgccc ctaaaatccc     900
tttggcacaa tgtgtcctga ggggagaggc agcgacctgt agatgggacg ggggcactaa     960
ccctcagggt ttgggttct gaatgtgagt atcgccatgt aagcccagta tttggccaat    1020
ctcagaaagc tcctggctcc ctggaggatg agagagaaa acaaacagc tcctggagca    1080 gggagagtgc tggcctcttg ctctccggct ccctctgttg ccctctggtt tctccccagg    1140
ttcgaagcgc gcaaggagag ccgccatggt gagcaagggc gaggagctgt tcaccggggt    1200
ggtgcccatc ctggtcgagc tggacggcga cgtaaacggc cacaagttca gcgtgtccgg    1260
cgagggcgag ggcgatgcca cctacggcaa gctgaccctg aagttcatct gcaccaccgg    1320
caagctgccc gtgccctggc ccaccctcgt gaccaccctg acctacggcg tgcagtgctt    1380
```

| | |
|---|---|
| cagccgctac cccgaccaca tgaagcagca cgacttcttc aagtccgcca tgcccgaagg | 1440 |
| ctacgtccag gagcgcacca tcttcttcaa ggacgacggc aactacaaga cccgcgccga | 1500 |
| ggtgaagttc gagggcgaca ccctggtgaa ccgcatcgag ctgaagggca tcgacttcaa | 1560 |
| ggaggacggc aacatcctgg ggcacaagct ggagtacaac tacaacagcc acaacgtcta | 1620 |
| tatcatggcc gacaagcaga agaacggcat caaggtgaac ttcaagatcc gccacaacat | 1680 |
| cgaggacggc agcgtgcagc tcgccgacca ctaccagcag aacaccccca tcggcgacgg | 1740 |
| ccccgtgctg ctgcccgaca accactacct gagcacccag tccgccctga gcaaagaccc | 1800 |
| caacgagaag cgcgatcaca tggtcctgct ggagttcgtg accgccgccg ggatcactct | 1860 |
| cggcatggac gagctgtaca gtaaagcgg ccggccgcac agctgtatac acgtgcaagc | 1920 |
| cgcgcgcagc ggccgaccat ggcccaactt gtttattgca gcttataatg gttacaaata | 1980 |
| aagcaatagc atcacaaatt tcacaaataa agcatttttt tcactgcatt ctagttgtgg | 2040 |
| tttgtccaaa ctcatcaatg tatcttatca tgtctggatc tccggaccac gtgcggaccg | 2100 |
| agcggccgct ctagagcatg gctacgtaga taagtagcat ggcgggttaa tcattaacta | 2160 |
| caaggaaccc ctagtgatgg agttggccac tccctctctg cgcgctcgct cgctcactga | 2220 |
| ggccgggcga ccaaaggtcg cccgacgccc gggctttgcc cgggcggcct cagtgagcga | 2280 |
| gcgagcgcgc agctgcctgc agg | 2303 |

<210> SEQ ID NO 68
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gcgccgcatg cggctc                                                         16

<210> SEQ ID NO 69
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69

| | |
|---|---|
| aggaacccct agtgatggag ttggccactc cctctctgcg ccgcatgcgg ctcactgagg | 60 |
| ccgcccgggc aaagcccggg cgtcgggcga cctttggtcg cccggcctca gtgagcgagc | 120 |
| gagcgcgcag agggagtg gccaa | 145 |

<210> SEQ ID NO 70
<211> LENGTH: 2303
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70

| | |
|---|---|
| cctgcaggca gctgagcggg ggcgcgctca ctgaggccgc ccgggcaaag cccgggcgtc | 60 |
| gggcgacctt tggtcgcccg gcctcagtga gcgcgcccc gctcagagag ggagtggcca | 120 |
| actccatcac taggggttcc ttgtagttaa tgattaaccc gccatgctac ttatctacgt | 180 |

```
agccatgctc tagagcggcc gcacgcgtgt tactagttat taatagtaat caattacggg    240
gtcattagtt catagcccat atatggagtt ccgcgttaca taacttacgg taaatggccc    300
gcctggctga ccgcccaacg accccogccc attgacgtca ataatgacgt atgttcccat    360
agtaacgtca atagggactt tccattgacg tcaatgggtg gagtatttac ggtaaactgc    420
ccacttggca gtacatcaag tgtatcatat gccaagtacg ccccctattg acgtcaatga    480
cggtaaatgg cccgcctggc attatgccca gtacatgacc ttatgggact ttcctacttg    540
gcagtacatc tacgtattag tcatcgctat taccatggtg atgcggtttt ggcagtacat    600
caatgggcgt ggatagcggt ttgactcacg gggatttcca gtctccacc ccattgacgt     660 caatgggagt ttgttttgca ccaaaatcaa cgggactttc caaaatgtcg taacaactcc    720
gccccattga cgcaaatggg cggtaggcgt gtacggtggg aggtctatat aagcagagct    780
cgtttagtga accgtcagat cgcctggaga cgccatccac gctgttttga cctccataga    840
agacaccggg accgatccag cctcaaccg gttcgaacag gtaagcgccc ctaaaatccc     900
tttggcacaa tgtgtcctga ggggagaggc agcgacctgt agatgggacg ggggcactaa    960
ccctcagggt ttggggttct gaatgtgagt atcgccatgt aagcccagta tttggccaat   1020
ctcagaaagc tcctggctcc ctggaggatg gagagagaaa acaaacagc tcctggagca    1080 gggagagtgc tggcctcttg ctctccggct ccctctgttg ccctctggtt tctccccagg   1140
ttcgaagcgc gcaaggagag ccgccatggt gagcaagggc gaggagctgt tcaccggggt   1200
ggtgcccatc ctggtcgagc tggacggcga cgtaaacggc cacaagttca gcgtgtccgg   1260
cgagggcgag ggcgatgcca cctacggcaa gctgaccctg aagttcatct gcaccaccgg   1320
caagctgccc gtgccctggc ccaccctcgt gaccaccctg acctacggcg tgcagtgctt   1380
cagccgctac cccgaccaca tgaagcagca cgacttcttc aagtccgcca tgcccgaagg   1440
ctacgtccag gagcgcacca tcttcttcaa ggacgacggc aactacaaga cccgcgccga   1500
ggtgaagttc gagggcgaca ccctggtgaa ccgcatcgag ctgaagggca tcgacttcaa   1560
ggaggacggc aacatcctgg ggcacaagct ggagtacaac tacaacagcc acaacgtcta   1620
tatcatggcc gacaagcaga agaacggcat caaggtgaac ttcaagatcc gccacaacat   1680
cgaggacggc agcgtgcagc tcgccgacca ctaccagcag aacacccca tcggcgacgg    1740 ccccgtgctg ctgcccgaca accactacct gagcacccag tccgccctga gcaaagaccc   1800
caacgagaag cgcgatcaca tggtcctgct ggagttcgtg accgccgccg ggatcactct   1860
cggcatggac gagctgtaca gtaaagcgg ccggccgcac agctgtatac acgtgcaagc    1920
cgcgcgcagc ggccgaccat ggcccaactt gtttattgca gcttataatg gttacaaata   1980
aagcaatagc atcacaaatt tcacaaataa agcatttttt tcactgcatt ctagttgtgg   2040
tttgtccaaa ctcatcaatg tatcttatca tgtctggatc tccggaccac gtgcggaccg   2100
agcggccgct ctagagcatg gctacgtaga taagtagcat ggcgggttaa tcattaacta   2160
caaggaaccc ctagtgatgg agttggccac tccctctctg cgcgctcgct cgctcactga   2220
ggccgggcga ccaaaggtcg cccgacgccc gggctttgcc cggcggcct cagtgagcga    2280 gcgagcgcgc agctgcctgc agg                                           2303
```

<210> SEQ ID NO 71
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 71
gagcgggggc gcgctc                                                            16

<210> SEQ ID NO 72
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
aggaacccct agtgatggag ttggccactc cctctctgag cggggcgcg ctcactgagg           60 ccgcccgggc aaagcccggg cgtcgggcga cctttggtcg cccggcctca gtgagcgagc          120
gagcgcgcag agagggagtg gccaa                                                145

<210> SEQ ID NO 73
<211> LENGTH: 2303
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
cctgcaggca gctccgtcgt cgtggtcgga ctgaggccgc ccgggcaaag cccggggcgtc          60 gggcgaccatt tggtcgcccg gcctcagtcc gaccacgacg acgagagag ggagtggcca          120 actccatcac taggggttcc ttgtagttaa tgattaaccc gccatgctac ttatctacgt          180
agccatgctc tagagcggcc gcacgcgtgt tactagttat aatagtaat caattacggg           240 gtcattagtt catagcccat atatggagtt ccgcgttaca aacttacgg taaatggccc          300 gcctggctga ccgcccaacg accccgccc attgacgtca ataatgacgt atgttcccat           360
agtaacgtca tagggacttt ccattgacg tcaatgggtg gagtatttac ggtaaactgc           420
ccacttggca gtacatcaag tgtatcatat gccaagtacg cccctattg acgtcaatga           480 cggtaaatgg cccgcctggc attatgccca gtacatgacc ttatgggact ttcctacttg         540
gcagtacatc tacgtattag tcatcgctat taccatggtg atgcggtttt ggcagtacat          600
caatgggcgt ggatagcggt ttgactcacg ggatttcca agtctccacc ccattgacgt          660
caatgggagt ttgttttgca ccaaaatcaa cgggactttc caaaatgtcg taacaactcc          720
gccccattga cgcaaatggg cggtaggcgt gtacggtggg aggtctatat aagcagagct          780
cgtttagtga accgtcagat cgcctggaga cgccatccac gctgttttga cctccataga         840
agacaccggg accgatccag cctccaaccg gttcgaacag gtaagcgccc ctaaaatccc         900
tttggcacaa tgtgtcctga ggggagaggc agcgacctgt agatgggacg ggggcactaa          960
ccctcagggt ttggggttct gaatgtgagt atcgccatgt aagcccagta tttggccaat        1020
ctcagaaagc tcctggctcc ctggaggatg agagagaaa aacaaacagc tcctggagca         1080
gggagagtgc tggcctcttg ctctccggct ccctctgttg ccctctggtt tctcccagg          1140 ttcgaagcgc gcaaggagag ccgccatggt gagcaagggc gaggagctgt tcaccggggt        1200
ggtgcccatc ctggtcgagc tggacggcga cgtaaacggc cacaagttca gcgtgtccgg        1260
cgagggcgag ggcgatgcca cctacggcaa gctgaccctg aagttcatct gcaccaccgg        1320
caagctgccc gtgccctggc ccaccctcgt gaccacccctg acctacggcg tgcagtgctt        1380

```
cagccgctac cccgaccaca tgaagcagca cgacttcttc aagtccgcca tgcccgaagg    1440
ctacgtccag gagcgcacca tcttcttcaa ggacgacggc aactacaaga cccgcgccga    1500
ggtgaagttc gagggcgaca ccctggtgaa ccgcatcgag ctgaagggca tcgacttcaa    1560
ggaggacggc aacatcctgg ggcacaagct ggagtacaac tacaacagcc acaacgtcta    1620
tatcatggcc gacaagcaga agaacggcat caaggtgaac ttcaagatcc gccacaacat    1680
cgaggacggc agcgtgcagc tcgccgacca ctaccagcag aacacccca tcggcgacgg    1740 ccccgtgctg ctgcccgaca accactacct gagcacccag tccgccctga gcaaagaccc    1800
caacgagaag cgcgatcaca tggtcctgct ggagttcgtg accgccgccg ggatcactct    1860
cggcatggac gagctgtaca gtaaagcgg ccggccgcac agctgtatac acgtgcaagc    1920
cgcgcgcagc ggccgaccat ggcccaactt gtttattgca gcttataatg gttacaaata    1980
aagcaatagc atcacaaatt tcacaaataa agcatttttt tcactgcatt ctagttgtgg    2040
tttgtccaaa ctcatcaatg tatcttatca tgtctggatc tccggaccac gtgcggaccg    2100
agcggccgct ctagagcatg gctacgtaga taagtagcat ggcgggttaa tcattaacta    2160
caaggaaccc ctagtgatgg agttggccac tccctctctg cgcgctcgct cgctcactga    2220
ggccgggcga ccaaaggtcg cccgacgccc gggctttgcc cgggcggcct cagtgagcga    2280
gcgagcgcgc agctgcctgc agg                                           2303
```

<210> SEQ ID NO 74
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74

```
ccgaccacga cgacgg                                                     16
```

<210> SEQ ID NO 75
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75

```
aggaacccct agtgatggag ttggccactc cctctctccg accacgacga cggactgagg     60
ccgcccgggc aaagcccggg cgtcgggcga cctttggtcg cccggcctca gtgagcgagc    120
gagcgcgcag agagggagtg gccaa                                          145
```

<210> SEQ ID NO 76
<211> LENGTH: 2304
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggctc    120
gctcccatca ctaggggttc cttgtagtta atgattaacc cgccatgcta cttatctacg    180
```

```
tagccatgct ctagagcggc cgcacgcgtg ttactagtta ttaatagtaa tcaattacgg    240
ggtcattagt tcatagccca tatatggagt tccgcgttac ataacttacg gtaaatggcc    300
cgcctggctg accgcccaac gacccccgcc cattgacgtc aataatgacg tatgttccca    360
tagtaacgtc aatagggact ttccattgac gtcaatgggt ggagtattta cggtaaactg    420
cccacttggc agtacatcaa gtgtatcata tgccaagtac gccccctatt gacgtcaatg    480
acggtaaatg gcccgcctgg cattatgccc agtacatgac cttatgggac tttcctactt    540
ggcagtacat ctacgtatta gtcatcgcta ttaccatggt gatgcggttt tggcagtaca    600
tcaatgggcg tggatagcgg tttgactcac ggggatttcc aagtctccac cccattgacg    660
tcaatgggag tttgttttgc accaaaatca acgggacttt ccaaaatgtc gtaacaactc    720
cgccccattg acgcaaatgg gcggtaggcg tgtacggtgg gaggtctata taagcagagc    780
tcgtttagtg aaccgtcaga tcgcctggag acgccatcca cgctgttttg acctccatag    840
aagacaccgg gaccgatcca gcctccaacc ggttcgaaca ggtaagcgcc cctaaaatcc    900
ctttggcaca atgtgtcctg aggggagagg cagcgacctg tagatgggac ggggggcacta    960 accctcaggt tttggggttc tgaatgtgag tatcgccatg taagcccagt atttggccaa   1020
tctcagaaag ctcctggctc cctggaggat ggagagagaa aaacaaacag ctcctggagc   1080
agggagagtg ctggcctctt gctctccggc tccctctgtt gccctctggt ttctccccag   1140
gttcgaagcg cgcaaggaga gccgccatgg tgagcaaggg cgaggagctg ttcaccgggg   1200
tggtgcccat cctggtcgag ctggacggcg acgtaaacgg ccacaagttc agcgtgtccg   1260
gcgagggcga gggcgatgcc acctacggca agctgaccct gaagttcatc tgcaccaccg   1320
gcaagctgcc cgtgccctgg cccaccctcg tgaccaccct gacctacggc gtgcagtgct   1380
tcagccgcta ccccgaccac atgaagcagc acgacttctt caagtccgcc atgcccgaag   1440
gctacgtcca ggagcgcacc atcttcttca aggacgacgg caactacaag acccgcgccg   1500
aggtgaagtt cgagggcgac accctggtga accgcatcga gctgaagggc atcgacttca   1560
aggaggacgg caacatcctg ggcacaagc tggagtacaa ctacaacagc cacaacgtct   1620
atatcatggc cgacaagcag aagaacggca tcaaggtgaa cttcaagatc cgccacaaca   1680
tcgaggacgg cagcgtgcag ctcgccgacc actaccagca gaacacccc atcggcgacg   1740 gccccgtgct gctgcccgac aaccactacc tgagcaccca gtccgccctg agcaaagacc   1800
ccaacgagaa gcgcgatcac atggtcctgc tggagttcgt gaccgccgcc gggatcactc   1860
tcggcatgga cgagctgtac aagtaaagcg gccggccgca cagctgtata cacgtgcaag   1920
ccgcgcgcag cggccgacca tgcccaact tgtttattgc agcttataat ggttacaaat   1980
aaagcaatag catcacaaat ttcacaaata agcattttt ttcactgcat ctagttgtg   2040 gtttgtccaa actcatcaat gtatcttatc atgtctggat ctccggacca cgtgcggacc   2100
gagcggccgc tctagagcat ggctacgtag ataagtagca tggcgggtta atcattaact   2160
acaaggaacc cctagtgatg gagttggcca ctccctctct gcgcgctcgc tcgctcactg   2220
aggccgggcg accaaaggtc gcccgacgcc cgggctttgc ccgggcggcc tcagtgagcg   2280
agcgagcgcg cagctgcctg cagg                                          2304
```

<210> SEQ ID NO 77
<211> LENGTH: 13
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 77
gagtgtggca ctc                                                           13

<210> SEQ ID NO 78
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
aggaacccct agtgatggag tgtggcactc cctctctgcg cgctcgctcg ctcactgagg         60
ccgcccgggc aaagcccggg cgtcgggcga cctttggtcg cccggcctca gtgagcgagc        120
gagcgcgcag agagggagtg gccaa                                              145

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
atacgccgcc tcgcgctcag                                                    20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
atctgtcgct cgtccggcta                                                    20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
tccgcgctgg ctcatcgtcc                                                    20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
tccgcgctgg ctcatcgtcc                                                    20

<210> SEQ ID NO 83
<211> LENGTH: 20
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
tccccgcccc cgctcattct                                              20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gtgcccccgc tcagagtcca                                              20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
tttaccgccg ctcagataga                                              20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86 gaccccagg cgctcctatg                                               20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
atctcgctca tgccccttag                                              20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
tccccggtca ggggctcact                                              20

<210> SEQ ID NO 89
<211> LENGTH: 20
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 89
ccgccgctct atccactggt                                              20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ttgcctcgct gctactgttc                                              20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
catatctccg cttagttgcc                                              20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
tcgttaagaa ccttcctcat                                              20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
cccccgcatc ctccgccttc                                              20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
catatctccg cttagttgcc                                              20

<210> SEQ ID NO 95
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 95
cacagttctc gcctacccgt                                                20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
ctctccttca gggcctcagc                                                20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gctgcccgcg tactcacccg                                                20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
gctcgaagga agcggggaac                                                20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gtcagttcgc tgggtgattc                                                20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
atcggacggc ttcgttgtgc                                                20

<210> SEQ ID NO 101
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 101
tcgctgacca agccgcatgc                                               20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
ccagtattct gcgcagctgg                                               20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ggcgtcccct ttccttttcg                                               20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
taatcgtatg catcgtcgtg                                               20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
tgaacggtcg cgacgcagca                                               20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
acgttcaacc cgccgcgtcg                                               20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 107
atcggacggc ttcgttgtgc                                             20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
ccatgtgttg cgcccgtcgc                                             20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ggtcccccca tgcactgccc                                             20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
cccgtatcca cgccccacgc                                             20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
tgccccacgc gcgctcgtac                                             20

<210> SEQ ID NO 112
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
atgctttctc gctcagtcc                                              19

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
acacttctca ctcgctgcct                                                   20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ccttcgcgct cgttcgaata                                                   20

<210> SEQ ID NO 115
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
tgctttctcg ctcagtcc                                                     18

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
gcgattgcct cggtggctca                                                   20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
cttcacttac tcgcgcaccc                                                   20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
tgcccttggc ttgctcagtg                                                   20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 119
gtctcgctcg gtcagctact                                                    20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
atccgttcac tcgttcgcct                                                    20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
acgcactcac tcgccggcgc                                                    20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ctcttgctcg ctcaattgct                                                    20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
gggtgctcgc ctgggttgcg                                                    20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ccagtgctca ctcagctcgc                                                    20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
```
tcggcgctcg ctcggtcctc						20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
cgcgggttgt tttcactcac						20

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
tgtcatctgc tcgctcactt						20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
agatccttgt ggctcactcg						20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
actggctggt tcgctcagac						20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ccacagatgt agctcactca						20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131

```
ctggtatcgc tcacttgacc                                              20
```

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132

```
tcgcgctcgt tcgcctctgc                                              20
```

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133

```
agatccttgt ggctcactcg                                              20
```

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134

```
caattcagtc aaccactcaa                                              20
```

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135

```
ctcgcttgca gtcactcact                                              20
```

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136

```
gagtttatct catgttctgc                                              20
```

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137

```
caattcagcc aaccactcaa                                              20
```

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gctgactcgt tgactcatct                                                 20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
tctccgctgg ttcaccgtac                                                 20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
tgtgcggccc actgagacgt                                                 20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
ccacgtgctc gctcaacctt                                                 20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
tcctacagct tgctcactct                                                 20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
cacagttact ggctcactga                                                 20

```
<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144 gggggttggtt ggttcactcc                                                  20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
gggtgctcgc ctgggttgcg                                                   20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
gccacttagc gtactggttc                                                   20

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
ccctgttcgc ttgctcgttc                                                   20

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
ttaacatggc gcgttcactg                                                   20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
ccatcttatt ggttcactgg                                                   20
```

```
<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
ctcttcccgc gcactgactc                                                   20

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
ctaagatgcc ccgctcgctc                                                   20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
gtatggcact cgctcgctgg                                                   20

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
tgcatctgcc cttgctcact                                                   20

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
actcactcac tgagttgtcc                                                   20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
ttcgttggct cactcacccc                                                   20

<210> SEQ ID NO 156
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
gtgcccgttt ctactcactg                                              20

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
tggtcgctcg ccccagccgc                                              20

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
ttgcttgctc actccgcgct                                              20

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
cgccagctcc ctcctcatgc                                              20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
cctccactcg ctgggtgagc                                              20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
tcgtcgctcg ctctgcatcc                                              20

<210> SEQ ID NO 162
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
taccgcgatc tcgctctctg                                                    20

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
cccacgccct cgctcactgc                                                    20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
tctctgtcac tcgtctccgg                                                    20

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
ctcgtgcccc ggtgcgctca                                                    20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
cgtgtacttc gtgctcagcc                                                    20

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
cccgtgtagg tgcgctcgct                                                    20

<210> SEQ ID NO 168
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 168
tccaccctac tccgtcggcc                                                20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
ctcaccgcac tcactggccc                                                20

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
gcccctcctt tcgctcgttt                                                20

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
cctctccgcg tgcccactcg                                                20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
ccttcttttc cgctggctca                                                20

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
ctcgtgcccc ggtgcgctca                                                20

<210> SEQ ID NO 174
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 174
ggcgattcac tcatctgacc                                                 20

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
actgcccggc cgtttcgctc                                                 20

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
cctctccgcg tgcccactcg                                                 20

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gcttgctcga cccagccacg                                                 20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
cctggttcgg tccttctccc                                                 20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
atcctcctat ctcactcgct                                                 20

<210> SEQ ID NO 180
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 180
cccgggtact gactcgcgct                                                20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
tccatgccac ttggttcact                                                20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
ctgctatcgt taactcacct                                                20

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
tgcactcatt cgactgcctc                                                20

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
cgagcgagct tagtgaacgt                                                20

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
agctggtcgg tgttcactgc                                                20

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 186
attcagtcgc ggttgcgcac                                            20

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
tctcgctggt tcagtccttc                                            20

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
gcatttctgg gtagctcgct                                            20

<210> SEQ ID NO 189
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
tagctgaatc gccaggcttg                                            20

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
tggctcattc attgagtcca                                            20

<210> SEQ ID NO 191
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
cattggctgt tgctgact                                              18

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 192
tccatgccac ttggttcact                                              20

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
gcccctcctt tcgctcgttt                                              20

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
cggccccttc ccactggctc                                              20

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
cgccagctcc ctcctcatgc                                              20

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
gtcgctccct ccttaccgcg                                              20

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
ccagcgaacg ccctcccgca                                              20

<210> SEQ ID NO 198
<211> LENGTH: 23
<212> TYPE: DNA
<213> ORGANISM: Adeno-associated virus

<400> SEQUENCE: 198
agagggagtg gccaactcca tca                                          23
```

```
<210> SEQ ID NO 199
<211> LENGTH: 23
<212> TYPE: DNA
<213> ORGANISM: Adeno-associated virus

<400> SEQUENCE: 199
tgatggagtt ggccactccc tct                                          23

<210> SEQ ID NO 200
<211> LENGTH: 22
<212> TYPE: DNA
<213> ORGANISM: Adeno-associated virus

<400> SEQUENCE: 200
gggggagagt gccacactct ca                                           22

<210> SEQ ID NO 201
<211> LENGTH: 22
<212> TYPE: DNA
<213> ORGANISM: Adeno-associated virus

<400> SEQUENCE: 201
tgagagtgtg gcactctccc cc                                           22

<210> SEQ ID NO 202
<211> LENGTH: 23
<212> TYPE: DNA
<213> ORGANISM: Adeno-associated virus

<400> SEQUENCE: 202
agagggagtg ggcaactcca tca                                          23

<210> SEQ ID NO 203
<211> LENGTH: 23
<212> TYPE: DNA
<213> ORGANISM: Adeno-associated virus

<400> SEQUENCE: 203
tgatggagtt gcccactccc tct                                          23

<210> SEQ ID NO 204
<211> LENGTH: 23
<212> TYPE: DNA
<213> ORGANISM: Adeno-associated virus

<400> SEQUENCE: 204
agagggagtg gccaactcca tca                                          23

<210> SEQ ID NO 205
<211> LENGTH: 23
<212> TYPE: DNA
<213> ORGANISM: Adeno-associated virus

<400> SEQUENCE: 205
tgatggagtt ggccactccc tct                                          23

<210> SEQ ID NO 206
<211> LENGTH: 23
<212> TYPE: DNA
<213> ORGANISM: Adeno-associated virus

<400> SEQUENCE: 206
```

-continued agagggagtg gccaactcca tca                                          23

<210> SEQ ID NO 207
<211> LENGTH: 23
<212> TYPE: DNA
<213> ORGANISM: Adeno-associated virus

<400> SEQUENCE: 207
tgatggagtt ggccacatta gct                                          23

<210> SEQ ID NO 208
<211> LENGTH: 23
<212> TYPE: DNA
<213> ORGANISM: Adeno-associated virus

<400> SEQUENCE: 208
agagggagtg gccaactcca tca                                          23

<210> SEQ ID NO 209
<211> LENGTH: 23
<212> TYPE: DNA
<213> ORGANISM: Adeno-associated virus

<400> SEQUENCE: 209
tgatggagtt ggccactccc tct                                          23

<210> SEQ ID NO 210
<211> LENGTH: 20
<212> TYPE: DNA
<213> ORGANISM: Avian adeno-associated virus

<400> SEQUENCE: 210
actggccagc actccggtga                                              20

<210> SEQ ID NO 211
<211> LENGTH: 20
<212> TYPE: DNA
<213> ORGANISM: Avian adeno-associated virus

<400> SEQUENCE: 211
tcaccggagt gctggccagt                                              20

<210> SEQ ID NO 212
<211> LENGTH: 20
<212> TYPE: DNA
<213> ORGANISM: Avian adeno-associated virus

<400> SEQUENCE: 212
actggccagc actccggtga                                              20

<210> SEQ ID NO 213
<211> LENGTH: 20
<212> TYPE: DNA
<213> ORGANISM: Avian adeno-associated virus

<400> SEQUENCE: 213
tcaccggagt gctggccagt                                              20

<210> SEQ ID NO 214
<211> LENGTH: 22
<212> TYPE: DNA
<213> ORGANISM: Bovine adeno-associated virus

<400> SEQUENCE: 214

```
ggggggggagt gccacactct ct                                          22
```

<210> SEQ ID NO 215
<211> LENGTH: 22
<212> TYPE: DNA
<213> ORGANISM: Bovine adeno-associated virus

<400> SEQUENCE: 215

```
agagagtgtg gcactccccc cc                                           22
```

<210> SEQ ID NO 216
<211> LENGTH: 19
<212> TYPE: DNA
<213> ORGANISM: Snake parvovirus

<400> SEQUENCE: 216

```
tggggcgagt gccctgctc                                               19
```

<210> SEQ ID NO 217
<211> LENGTH: 19
<212> TYPE: DNA
<213> ORGANISM: Snake parvovirus

<400> SEQUENCE: 217

```
gagcagggca ctcgcccca                                               19
```

<210> SEQ ID NO 218
<211> LENGTH: 168
<212> TYPE: DNA
<213> ORGANISM: Adeno-associated virus

<400> SEQUENCE: 218

```
tacaaaaccc ccttgcttga tggagttggc cactccctct ctgtcgcgtt cgctcgctcg   60
ctggctcgtt tggggggggcg acggccagag ggccgtcgtc tggcagctct ttgagctgcc  120 accccccaa acgagccagc gagcgagcga acgcgacagg ggggagag                 168
```

<210> SEQ ID NO 219
<211> LENGTH: 168
<212> TYPE: DNA
<213> ORGANISM: Adeno-associated virus

<400> SEQUENCE: 219

```
tacaaaaccc ccttgcttga tggagttggc cacattagct ctgtcgcgtt cgctcgctcg   60
ctggctcgtt tggggggggcg acggccagag ggccgtcgtc tggcagctct ttgagctgcc  120 accccccaa acgagccagc gagcgagcga acgcgacagg ggggagag                 168
```

<210> SEQ ID NO 220
<211> LENGTH: 145
<212> TYPE: DNA
<213> ORGANISM: Adeno-associated virus

<400> SEQUENCE: 220

```
tggcaaacca gatgatggag ttggccactc cctctatgcg cgctcgctca ctcactcggc   60
cctggagacc aaaggtctcc agactgccgg cctctggccg gcagggccga gtgagtgagc  120
gagcgcgcat agagggagtg gccaa                                        145
```

<210> SEQ ID NO 221
<211> LENGTH: 144
<212> TYPE: DNA

-continued

<213> ORGANISM: Adeno-associated virus

<400> SEQUENCE: 221
aggaacccct agtgagagtg tggcactctc ccccctgcgc gctcgctcgc tcactgaggc    60
cgcccgggca aagcccgggc gtcgggcgac ctttggtcgc ccggcctcag tgagcgagcg   120
agcgcgcaga gagggagtgg ccaa                                         144

<210> SEQ ID NO 222
<211> LENGTH: 142
<212> TYPE: DNA
<213> ORGANISM: Adeno-associated virus

<400> SEQUENCE: 222 ttaccccctag tgagagtgtg gcactctccc ccctgcgcgc tcgctcgctc ggtggggccg    60
gcagagcaga gctctgccgt ctgcggacct ttggtccgca ggccccaccg agcgagcgag   120
cgcgcagaga gggagtgggc aa                                           142

<210> SEQ ID NO 223
<211> LENGTH: 145
<212> TYPE: DNA
<213> ORGANISM: Adeno-associated virus

<400> SEQUENCE: 223
gccatacctc tagtgagagt gtggcactct cccccatgcg cactcgctcg ctcggtgggg    60
ccggacgtgc aaagcacgtc cgtctggcga cctttggtcg ccaggcccca ccgagcgagc   120
gagtgcgcat agagggagtg gccaa                                        145

<210> SEQ ID NO 224
<211> LENGTH: 144
<212> TYPE: DNA
<213> ORGANISM: Adeno-associated virus

<400> SEQUENCE: 224 tggcaaaacca gatgagagtg tggcactctc cccatgcgc gctcgctcac tcactcggcc    60
ctggagacca aggtctcca gactgccggc ctctggccgg cagggccgag tgagtgagcg   120
agcgcgcata gagggagtgg ccaa                                         144

<210> SEQ ID NO 225
<211> LENGTH: 146
<212> TYPE: DNA
<213> ORGANISM: Adeno-associated virus

<400> SEQUENCE: 225
cgcggtaccc ctagtgagag tgtggcactc tcccccatgc gcgctcgctc gctcggtggg    60
gccggcagag cagagctctg ccgtctgcgg acctttggtc gcaggcccc accgagcgag   120 cgagcgcgca tagagggagt ggccaa                                       146

<210> SEQ ID NO 226
<211> LENGTH: 144
<212> TYPE: DNA
<213> ORGANISM: Bovine adeno-associated virus

<400> SEQUENCE: 226
aggaacccct agagagagtg tggcactccc ccccctgcgc gctcgctcgc tcactgaggc    60
cgcccgggca aagcccgggc gtcgggcgac ctttggtcgc ccggcctcag tgagcgagcg   120
agcgcgcaga gagggagtgg ccaa                                         144

<210> SEQ ID NO 227
<211> LENGTH: 142
<212> TYPE: DNA
<213> ORGANISM: Bovine adeno-associated virus

<400> SEQUENCE: 227
ttacccctag agagagtgtg gcactccccc ccctgcgcgc tcgctcgctc ggtggggccg       60
gcagagcaga gctctgccgt ctgcggacct ttggtccgca ggccccaccg agcgagcgag      120
cgcgcagaga gggagtgggc aa                                              142

<210> SEQ ID NO 228
<211> LENGTH: 145
<212> TYPE: DNA
<213> ORGANISM: Bovine adeno-associated virus

<400> SEQUENCE: 228
gccatacctc tagagagagt gtggcactcc cccccatgcg cactcgctcg ctcggtgggg       60
ccggacgtgc aaagcacgtc cgtctggcga cctttggtcg ccaggcccca ccgagcgagc      120
gagtgcgcat agagggagtg gccaa                                            145

<210> SEQ ID NO 229
<211> LENGTH: 144
<212> TYPE: DNA
<213> ORGANISM: Bovine adeno-associated virus

<400> SEQUENCE: 229
tggcaaacca gaagagagtg tggcactccc cccatgcgc gctcgctcac tcactcggcc        60
ctggagacca aggtctccag actgccggc ctctggccgg cagggccgag tgagtgagcg      120
agcgcgcata gagggagtgg ccaa                                             144

<210> SEQ ID NO 230
<211> LENGTH: 146
<212> TYPE: DNA
<213> ORGANISM: Bovine adeno-associated virus

<400> SEQUENCE: 230
cgcggtaccc ctagagagag tgtggcactc cccccatgc gcgctcgctc gctcggtggg        60
gccggcagag cagagctctg ccgtctgcgg acctttggtc gcaggcccc accgagcgag      120 cgagcgcgca tagagggagt ggccaa                                           146

<210> SEQ ID NO 231
<211> LENGTH: 141
<212> TYPE: DNA
<213> ORGANISM: Snake parvovirus

<400> SEQUENCE: 231
aggaacccct aggagcaggg cactcgcccc actgcgcgct cgctcgctca ctgaggccgc       60
ccgggcaaag cccgggcgtc gggcgacctt tggtcgcccg gcctcagtga gcgagcgagc      120
gcgcagagag ggagtggcca a                                                141

<210> SEQ ID NO 232
<211> LENGTH: 142
<212> TYPE: DNA
<213> ORGANISM: Snake parvovirus

<400> SEQUENCE: 232

```
ttaccnctag agagagtgtg gcactccccc cctgcgcgc tcgctcgctc ggtggggccg        60
gcagagcaga gctctgccgt ctgcggacct ttggtccgca ggccccaccg agcgagcgag      120
cgcgcagaga gggagtgggc aa                                              142
```

<210> SEQ ID NO 233
<211> LENGTH: 142
<212> TYPE: DNA
<213> ORGANISM: Snake parvovirus

<400> SEQUENCE: 233

```
gccatacctc taggagcagg gcactcgccc caatgcgcac tcgctcgctc ggtggggccg        60
gacgtgcaaa gcacgtccgt ctggcgacct ttggtcgcca ggccccaccg agcgagcgag      120
tgcgcataga gggagtggcc aa                                              142
```

<210> SEQ ID NO 234
<211> LENGTH: 141
<212> TYPE: DNA
<213> ORGANISM: Snake parvovirus

<400> SEQUENCE: 234

```
tggcaaacca gagagcaggg cactcgcccc aatgcgcgct cgctcactca ctcggccctg        60
gagaccaaag gtctccagac tgccggcctc tggccggcag ggccgagtga gtgagcgagc      120
gcgcatagag ggagtggcca a                                               141
```

<210> SEQ ID NO 235
<211> LENGTH: 143
<212> TYPE: DNA
<213> ORGANISM: Snake parvovirus

<400> SEQUENCE: 235

```
cgcggtaccc ctaggagcag ggcactcgcc ccaatgcgcg ctcgctcgct cggtggggcc        60
ggcagagcag agctctgccg tctgcggacc tttggtccgc aggccccacc gagcgagcga      120
gcgcgcatag agggagtggc caa                                             143
```

<210> SEQ ID NO 236
<211> LENGTH: 142
<212> TYPE: DNA
<213> ORGANISM: Avian adeno-associated virus

<400> SEQUENCE: 236

```
aggaacccct agtcaccgga gtgctggcca gtctgcgcgc tcgctcgctc actgaggccg        60
cccgggcaaa gcccgggcgt cgggcgacct ttggtcgccc ggcctcagtg agcgagcgag      120
cgcgcagaga gggagtggcc aa                                              142
```

<210> SEQ ID NO 237
<211> LENGTH: 140
<212> TYPE: DNA
<213> ORGANISM: Avian adeno-associated virus

<400> SEQUENCE: 237

```
ttaccccctag tcaccggagt gctggccagt ctgcgcgctc gctcgctcgg tggggccggc        60
agagcagagc tctgccgtct gcggaccttt ggtccgcagg ccccaccgag cgagcgagcg      120
cgcagagagg gagtgggcaa                                                 140
```

<210> SEQ ID NO 238
<211> LENGTH: 143

```
<212> TYPE: DNA
<213> ORGANISM: Avian adeno-associated virus

<400> SEQUENCE: 238
gccatacctc tagtcaccgg agtgctggcc agtatgcgca ctcgctcgct cggtggggcc    60
ggacgtgcaa agcacgtccg tctggcgacc tttggtcgcc aggccccacc gagcgagcga   120
gtgcgcatag agggagtggc caa                                          143

<210> SEQ ID NO 239
<211> LENGTH: 142
<212> TYPE: DNA
<213> ORGANISM: Avian adeno-associated virus

<400> SEQUENCE: 239 tggcaaaacca gatcaccgga gtgctggcca gtatgcgcgc tcgctcactc actcggccct    60
ggagaccaaa ggtctccaga ctgccggcct ctggccggca gggccgagtg agtgagcgag   120
cgcgcataga gggagtggcc aa                                           142

<210> SEQ ID NO 240
<211> LENGTH: 144
<212> TYPE: DNA
<213> ORGANISM: Avian adeno-associated virus

<400> SEQUENCE: 240
cgcggtaccc ctagtcaccg gagtgctggc cagtatgcgc gctcgctcgc tcggtggggc    60
cggcagagca gagctctgcc gtctgcggac cttttggtccg caggccccac cgagcgagcg   120
agcgcgcata gagggagtgg ccaa                                         144

<210> SEQ ID NO 241
<211> LENGTH: 145
<212> TYPE: DNA
<213> ORGANISM: Adeno-associated virus

<400> SEQUENCE: 241
ttggccactc cctctctgcg cgctcgctcg ctcactgagg ccgggcgacc aaaggtcgcc    60
cgacgcccgg gctttgcccg gcggcctca gtgagcgagc gagcgcgcag agagggagtg    120
gccaactcca tcactagggg ttcct                                        145

<210> SEQ ID NO 242
<211> LENGTH: 145
<212> TYPE: DNA
<213> ORGANISM: Adeno-associated virus

<400> SEQUENCE: 242
aggaacccct agtgatggag ttggccactc cctctctgcg cgctcgctcg ctcactgagg    60
ccgcccgggc aaagcccggg cgtcgggcga ccttttggtcg cccggcctca gtgagcgagc   120
gagcgcgcag agagggagtg gccaa                                        145

<210> SEQ ID NO 243
<211> LENGTH: 167
<212> TYPE: DNA
<213> ORGANISM: Adeno-associated virus

<400> SEQUENCE: 243
ctctcccccc tgtcgcgttc gctcgctcgc tggctcgttt ggggggggtgg cagctcaaag    60 agctgccaga cgacggccct ctggccgtcg ccccccaaa cgagccagcg agcgagcgaa   120
```

```
cgcgacaggg gggagagtgc cacactctca agcaagggg ttttgta              167

<210> SEQ ID NO 244
<211> LENGTH: 167
<212> TYPE: DNA
<213> ORGANISM: Adeno-associated virus

<400> SEQUENCE: 244
tacaaaaccc ccttgcttga gagtgtggca ctctccccc tgtcgcgttc gctcgctcgc   60
tggctcgttt ggggggcga cggccagagg gccgtcgtct ggcagctctt tgagctgcca  120 ccccccaaa cgagccagcg agcgagcgaa cgcgacaggg gggagag                167

<210> SEQ ID NO 245
<211> LENGTH: 143
<212> TYPE: DNA
<213> ORGANISM: Adeno-associated virus

<400> SEQUENCE: 245
ttgcccactc cctctctgcg cgctcgctcg ctcggtgggg cctgcggacc aaaggtccgc   60
agacggcaga gctctgctct gccggcccca ccgagcgagc gagcgcgcag agagggagtg  120
ggcaactcca tcactagggg taa                                         143

<210> SEQ ID NO 246
<211> LENGTH: 143
<212> TYPE: DNA
<213> ORGANISM: Adeno-associated virus

<400> SEQUENCE: 246 ttaccctag tgatggagtt gcccactccc tctctgcgcg ctcgctcgct cggtggggcc   60
ggcagagcag agctctgccg tctgcggacc tttggtccgc aggccccacc gagcgagcga  120
gcgcgcagag agggagtggg caa                                          143

<210> SEQ ID NO 247
<211> LENGTH: 146
<212> TYPE: DNA
<213> ORGANISM: Adeno-associated virus

<400> SEQUENCE: 247
ttggccactc cctctatgcg cactcgctcg ctcggtgggg cctggcgacc aaaggtcgcc   60
agacggacgt gctttgcacg tccggcccca ccgagcgagc gagtgcgcat agagggagtg  120
gccaactcca tcactagagg tatggc                                       146

<210> SEQ ID NO 248
<211> LENGTH: 146
<212> TYPE: DNA
<213> ORGANISM: Adeno-associated virus

<400> SEQUENCE: 248 gccataccte tagtgatgga gttggccact ccctctatgc gcactcgctc gctcggtggg   60
gccggacgtg caaagcacgt ccgtctggcg acctttggtc gccaggcccc accgagcgag  120
cgagtgcgca tagagggagt ggccaa                                       146

<210> SEQ ID NO 249
<211> LENGTH: 145
<212> TYPE: DNA
<213> ORGANISM: Adeno-associated virus

<400> SEQUENCE: 249
```

-continued

```
ttggccactc cctctatgcg cgctcgctca ctcactcggc cctggagacc aaaggtctcc      60
agactgccgg cctctggccg gcagggccga gtgagtgagc gagcgcgcat agagggagtg     120
gccaactcca tcatctaggt ttgcc                                           145

<210> SEQ ID NO 250
<211> LENGTH: 145
<212> TYPE: DNA
<213> ORGANISM: Adeno-associated virus

<400> SEQUENCE: 250
tggcaaacca gatgatggag ttggccacat tagctatgcg cgctcgctca ctcactcggc      60
cctggagacc aaaggtctcc agactgccgg cctctggccg gcagggccga gtgagtgagc     120
gagcgcgcat agagggagtg gccaa                                           145

<210> SEQ ID NO 251
<211> LENGTH: 147
<212> TYPE: DNA
<213> ORGANISM: Adeno-associated virus

<400> SEQUENCE: 251
ttggccactc cctctatgcg cgctcgctcg ctcggtgggg cctgcggacc aaaggtccgc      60
agacggcaga gctctgctct gccggcccca ccgagcgagc gagcgcgcat agagggagtg     120
gccaactcca tcactagggg taccgcg                                         147

<210> SEQ ID NO 252
<211> LENGTH: 147
<212> TYPE: DNA
<213> ORGANISM: Adeno-associated virus

<400> SEQUENCE: 252
cgcggtaccc ctagtgatgg agttggccac tccctctatg cgcgctcgct cgctcggtgg      60
ggccggcaga gcagagctct gccgtctgcg gacctttggt ccgcaggccc caccgagcga     120
gcgagcgcgc atagagggag tggccaa                                         147

<210> SEQ ID NO 253
<211> LENGTH: 150
<212> TYPE: DNA
<213> ORGANISM: Adeno-associated virus

<400> SEQUENCE: 253
cagagaggga gtggccaact ccatcactag gggtagcgcg aagcgcctcc cacgctgccg      60
cgtcagcgct gacgtaaatt acgtcatagg ggagtggtcc tgtattagct gtcacgtgag     120
tgcttttgcg gcattttgcg acaccacgtg                                      150

<210> SEQ ID NO 254
<211> LENGTH: 150
<212> TYPE: DNA
<213> ORGANISM: Adeno-associated virus

<400> SEQUENCE: 254
cacgtggtgt cgcaaaatgc cgcaaaagca ctcacgtgac agctaataca ggaccactcc      60
cctatgacgt aatttacgtc agcgctgacg cggcagcgtg ggaggcgctt cgcgctaccc     120
ctagtgatgg agttggccac tccctctctg                                      150

<210> SEQ ID NO 255
```

```
<211> LENGTH: 143
<212> TYPE: DNA
<213> ORGANISM: Avian adeno-associated virus

<400> SEQUENCE: 255
tggccagttt ccaaaacagg ctcgctcgct cactcgggcc ccggccccaa gggggccggt    60
agcgacgcct ttggcgtcgc ggcccgagtg agcgagcgag cctgttttgg aaactggcca   120
gcactccggt gaggtaatgc cgt                                           143

<210> SEQ ID NO 256
<211> LENGTH: 143
<212> TYPE: DNA
<213> ORGANISM: Avian adeno-associated virus

<400> SEQUENCE: 256
acggcattac ctcaccggag tgctggccag tttccaaaac aggctcgctc gctcactcgg    60
gccgcgacgc caaaggcgtc gctaccggcc cccttggggc cggggcccga gtgagcgagc   120
gagcctgttt tggaaactgg cca                                           143

<210> SEQ ID NO 257
<211> LENGTH: 142
<212> TYPE: DNA
<213> ORGANISM: Avian adeno-associated virus

<400> SEQUENCE: 257
tggccagttt ccaagacagg ctcgctcgct cactcgggcc ggggccccaa aggggcccct    60
agcgaccgct tcgcggtcgc ggcccgagtg agcgagcgag cctgtcttgg aaactggcca   120
gcactccggt gaggtaatgc cg                                            142

<210> SEQ ID NO 258
<211> LENGTH: 142
<212> TYPE: DNA
<213> ORGANISM: Avian adeno-associated virus

<400> SEQUENCE: 258
cggcattacc tcaccggagt gctggccagt ttccaagaca ggctcgctcg ctcactcggg    60
ccgcgaccgc gaagcggtcg ctaggggccc ctttggggcc ccggcccgag tgagcgagcg   120
agcctgtctt ggaaactggc ca                                            142

<210> SEQ ID NO 259
<211> LENGTH: 173
<212> TYPE: DNA
<213> ORGANISM: Bovine adeno-associated virus

<400> SEQUENCE: 259
gtggcactcc ccccctgtc gcgttcgctc gttcgctggc tcgattgggg gggtggcagc     60
tcaaagagct gccagacgac ggccctctgg gccgtcgccc ccccaatcga gccagcgaac   120
gagcgaacgc gacagggggg ggagtgccac actctctagc aagggggttt tgt          173

<210> SEQ ID NO 260
<211> LENGTH: 173
<212> TYPE: DNA
<213> ORGANISM: Bovine adeno-associated virus

<400> SEQUENCE: 260
acaaaacccc cttgctagag agtgtggcac tcccccccct gtcgcgttcg ctcgttcgct    60
ggctcgattg gggggcgac ggcccagagg gccgtcgtct ggcagctctt tgagctgcca   120
```

```
cccccccaat cgagccagcg aacgagcgaa cgcgacaggg gggggagtgc cac            173
```

<210> SEQ ID NO 261
<211> LENGTH: 150
<212> TYPE: DNA
<213> ORGANISM: Bat adeno-associated virus

<400> SEQUENCE: 261

```
aagaaacctc taatcatcat ctgtactttg tgagggtgtg gtcgtgagaa cgggcatgcc     60
cgggcatgtc ctgttaatca ttaaccagaa tggactttgg acttaataag ttacgtatta   120
atgggtgtgt atataagtaa gtgtatttcc                                    150
```

<210> SEQ ID NO 262
<211> LENGTH: 150
<212> TYPE: DNA
<213> ORGANISM: Bat adeno-associated virus

<400> SEQUENCE: 262

```
ggaaatacac ttacttatat acacacccat taatacgtaa cttattaagt ccaaagtcca     60
ttctggttaa tgattaacag gacatgcccg gcatgcccg ttctcacgac cacaccctca   120
caaagtacag atgatgatta gaggtttctt                                    150
```

<210> SEQ ID NO 263
<211> LENGTH: 154
<212> TYPE: DNA
<213> ORGANISM: Snake parvovirus

<400> SEQUENCE: 263

```
cgccccaccc ctagtgatcg cgcgcgctct ctcttggggc ctgacggccg aaggccgtca     60
gctgccgagc ttcgctcggc aggccccaag agagagcgcg cgcgatcact aggggtgggg   120
cgagtgccct gctcaacggg ttttttggtg ggcg                               154
```

<210> SEQ ID NO 264
<211> LENGTH: 154
<212> TYPE: DNA
<213> ORGANISM: Snake parvovirus

<400> SEQUENCE: 264

```
cgcccaccaa aaacccgtt gagcagggca ctcgccccac ccctagtgat cgcgcgcgct      60
ctctcttggg gcctgccgag cgaagctcgg cagctgacgg ccttcggccg tcaggcccca   120
agagagagcg cgcgcgatca ctaggggtgg ggcg                               154
```

<210> SEQ ID NO 265
<211> LENGTH: 536
<212> TYPE: PRT
<213> ORGANISM: Adeno-associated virus

<400> SEQUENCE: 265

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60
```

```
Thr Glu Trp Arg Arg Val Ser Lys Ala Pro Glu Ala Leu Phe Phe Val
 65                  70                  75                  80

Gln Phe Glu Lys Gly Glu Ser Tyr Phe His Met His Val Leu Val Glu
                 85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
        450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
```

|              | 485 |     |     |     | 490 |     |     |     | 495 |     |
|---|---|---|---|---|---|---|---|---|---|---|

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
            515                 520                 525

Arg Leu Ala Arg Gly His Ser Leu
            530                 535

<210> SEQ ID NO 266
<211> LENGTH: 621
<212> TYPE: PRT
<213> ORGANISM: Adeno-associated virus

<400> SEQUENCE: 266

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

-continued

```
Thr Lys Lys Phe Gly Lys Arg Asn Thr Ile Trp Leu Phe Gly Pro Ala
            325                 330                 335
Thr Thr Gly Lys Thr Asn Ile Ala Glu Ala Ile Ala His Thr Val Pro
        340                 345                 350
Phe Tyr Gly Cys Val Asn Trp Thr Asn Glu Asn Phe Pro Phe Asn Asp
    355                 360                 365
Cys Val Asp Lys Met Val Ile Trp Trp Glu Gly Lys Met Thr Ala
370                 375                 380
Lys Val Val Glu Ser Ala Lys Ala Ile Leu Gly Gly Ser Lys Val Arg
385                 390                 395                 400
Val Asp Gln Lys Cys Lys Ser Ser Ala Gln Ile Asp Pro Thr Pro Val
                405                 410                 415
Ile Val Thr Ser Asn Thr Asn Met Cys Ala Val Ile Asp Gly Asn Ser
            420                 425                 430
Thr Thr Phe Glu His Gln Gln Pro Leu Gln Asp Arg Met Phe Lys Phe
        435                 440                 445
Glu Leu Thr Arg Arg Leu Asp His Asp Phe Gly Lys Val Thr Lys Gln
    450                 455                 460
Glu Val Lys Asp Phe Phe Arg Trp Ala Lys Asp His Val Val Glu Val
465                 470                 475                 480
Glu His Glu Phe Tyr Val Lys Lys Gly Gly Ala Lys Lys Arg Pro Ala
                485                 490                 495
Pro Ser Asp Ala Asp Ile Ser Glu Pro Lys Arg Val Arg Glu Ser Val
            500                 505                 510
Ala Gln Pro Ser Thr Ser Asp Ala Glu Ala Ser Ile Asn Tyr Ala Asp
        515                 520                 525
Arg Tyr Gln Asn Lys Cys Ser Arg His Val Gly Met Asn Leu Met Leu
    530                 535                 540
Phe Pro Cys Arg Gln Cys Glu Arg Met Asn Gln Asn Ser Asn Ile Cys
545                 550                 555                 560
Phe Thr His Gly Gln Lys Asp Cys Leu Glu Cys Phe Pro Val Ser Glu
                565                 570                 575
Ser Gln Pro Val Ser Val Val Lys Lys Ala Tyr Gln Lys Leu Cys Tyr
            580                 585                 590
Ile His His Ile Met Gly Lys Val Pro Asp Ala Cys Thr Ala Cys Asp
        595                 600                 605
Leu Val Asn Val Asp Leu Asp Cys Ile Phe Glu Gln
    610                 615                 620

<210> SEQ ID NO 267
<211> LENGTH: 312
<212> TYPE: PRT
<213> ORGANISM: Adeno-associated virus

<400> SEQUENCE: 267

Met Glu Leu Val Gly Trp Leu Val Asp Lys Gly Ile Thr Ser Glu Lys
1               5                   10                  15
Gln Trp Ile Gln Glu Asp Gln Ala Ser Tyr Ile Ser Phe Asn Ala Ala
            20                  25                  30
Ser Asn Ser Arg Ser Gln Ile Lys Ala Ala Leu Asp Asn Ala Gly Lys
        35                  40                  45
Ile Met Ser Leu Thr Lys Thr Ala Pro Asp Tyr Leu Val Gly Gln Gln
    50                  55                  60
Pro Val Glu Asp Ile Ser Ser Asn Arg Ile Tyr Lys Ile Leu Glu Leu
65                  70                  75                  80
```

Asn Gly Tyr Asp Pro Gln Tyr Ala Ala Ser Val Phe Leu Gly Trp Ala
                85                  90                  95

Thr Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Thr Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Lys Asp His Val Val Glu Val
                245                 250                 255

Glu His Glu Phe Tyr Val Lys Lys Gly Gly Ala Lys Lys Arg Pro Ala
            260                 265                 270

Pro Ser Asp Ala Asp Ile Ser Glu Pro Lys Arg Val Arg Glu Ser Val
        275                 280                 285

Ala Gln Pro Ser Thr Ser Asp Ala Glu Ala Ser Ile Asn Tyr Ala Asp
    290                 295                 300

Arg Leu Ala Arg Gly His Ser Leu
305                 310

<210> SEQ ID NO 268
<211> LENGTH: 397
<212> TYPE: PRT
<213> ORGANISM: Adeno-associated virus

<400> SEQUENCE: 268

Met Glu Leu Val Gly Trp Leu Val Asp Lys Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ser Leu Thr Lys Thr Ala Pro Asp Tyr Leu Val Gly Gln Gln
    50                  55                  60

Pro Val Glu Asp Ile Ser Ser Asn Arg Ile Tyr Lys Ile Leu Glu Leu
65                  70                  75                  80

Asn Gly Tyr Asp Pro Gln Tyr Ala Ala Ser Val Phe Leu Gly Trp Ala
                85                  90                  95

Thr Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Thr Val Pro
        115                 120                 125

Phe Tyr Gly Cys Val Asn Trp Thr Asn Glu Asn Phe Pro Phe Asn Asp

```
            130                 135                 140
Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
                195                 200                 205

Thr Thr Phe Glu His Gln Gln Pro Leu Gln Asp Arg Met Phe Lys Phe
            210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Lys Asp His Val Val Glu Val
                245                 250                 255

Glu His Glu Phe Tyr Val Lys Lys Gly Gly Ala Lys Lys Arg Pro Ala
            260                 265                 270

Pro Ser Asp Ala Asp Ile Ser Glu Pro Lys Arg Val Arg Glu Ser Val
            275                 280                 285

Ala Gln Pro Ser Thr Ser Asp Ala Glu Ala Ser Ile Asn Tyr Ala Asp
            290                 295                 300

Arg Tyr Gln Asn Lys Cys Ser Arg His Val Gly Met Asn Leu Met Leu
305                 310                 315                 320

Phe Pro Cys Arg Gln Cys Glu Arg Met Asn Gln Asn Ser Asn Ile Cys
                325                 330                 335

Phe Thr His Gly Gln Lys Asp Cys Leu Glu Cys Phe Pro Val Ser Glu
            340                 345                 350

Ser Gln Pro Val Ser Val Val Lys Lys Ala Tyr Gln Lys Leu Cys Tyr
                355                 360                 365

Ile His His Ile Met Gly Lys Val Pro Asp Ala Cys Thr Ala Cys Asp
            370                 375                 380

Leu Val Asn Val Asp Leu Asp Asp Cys Ile Phe Glu Gln
385                 390                 395

<210> SEQ ID NO 269
<211> LENGTH: 610
<212> TYPE: PRT
<213> ORGANISM: Adeno-associated virus

<400> SEQUENCE: 269

Met Ala Thr Phe Tyr Glu Val Ile Val Arg Val Pro Phe Asp Val Glu
1                   5                   10                  15

Glu His Leu Pro Gly Ile Ser Asp Ser Phe Val Asp Trp Val Thr Gly
                20                  25                  30

Gln Ile Trp Glu Leu Pro Pro Glu Ser Asp Leu Asn Leu Thr Leu Val
            35                  40                  45

Glu Gln Pro Gln Leu Thr Val Ala Asp Arg Ile Arg Arg Val Phe Leu
        50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
                100                 105                 110
```

```
Ala Gln Leu Val Lys Val Val Phe Gln Gly Ile Glu Pro Gln Ile Asn
            115                 120                 125

Asp Trp Val Ala Ile Thr Lys Val Lys Gly Gly Ala Asn Lys Val
130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Leu Asp Glu Tyr Lys Leu Ala Ala
                165                 170                 175

Leu Asn Leu Glu Glu Arg Lys Arg Leu Val Ala Gln Phe Leu Ala Glu
            180                 185                 190

Ser Ser Gln Arg Ser Gln Glu Ala Ala Ser Gln Arg Glu Phe Ser Ala
        195                 200                 205

Asp Pro Val Ile Lys Ser Lys Thr Ser Gln Lys Tyr Met Ala Leu Val
210                 215                 220

Asn Trp Leu Val Glu His Gly Ile Thr Ser Glu Lys Gln Trp Ile Gln
225                 230                 235                 240

Glu Asn Gln Glu Ser Tyr Leu Ser Phe Asn Ser Thr Gly Asn Ser Arg
                245                 250                 255

Ser Gln Ile Lys Ala Ala Leu Asp Asn Ala Thr Lys Ile Met Ser Leu
            260                 265                 270

Thr Lys Ser Ala Val Asp Tyr Leu Val Gly Ser Ser Val Pro Glu Asp
        275                 280                 285

Ile Ser Lys Asn Arg Ile Trp Gln Ile Phe Glu Met Asn Gly Tyr Asp
        290                 295                 300

Pro Ala Tyr Ala Gly Ser Ile Leu Tyr Gly Trp Cys Gln Arg Ser Phe
305                 310                 315                 320

Asn Lys Arg Asn Thr Val Trp Leu Tyr Gly Pro Ala Thr Thr Gly Lys
                325                 330                 335

Thr Asn Ile Ala Glu Ala Ile Ala His Thr Val Pro Phe Tyr Gly Cys
            340                 345                 350

Val Asn Trp Thr Asn Glu Asn Phe Pro Phe Asn Asp Cys Val Asp Lys
        355                 360                 365

Met Leu Ile Trp Trp Glu Glu Gly Lys Met Thr Asn Lys Val Val Glu
370                 375                 380

Ser Ala Lys Ala Ile Leu Gly Gly Ser Lys Val Arg Val Asp Gln Lys
385                 390                 395                 400

Cys Lys Ser Ser Val Gln Ile Asp Ser Thr Pro Val Ile Val Thr Ser
                405                 410                 415

Asn Thr Asn Met Cys Val Val Asp Gly Asn Ser Thr Thr Phe Glu
            420                 425                 430

His Gln Gln Pro Leu Glu Asp Arg Met Phe Lys Phe Glu Leu Thr Lys
        435                 440                 445

Arg Leu Pro Pro Asp Phe Gly Lys Ile Thr Lys Gln Glu Val Lys Asp
        450                 455                 460

Phe Phe Ala Trp Ala Lys Val Asn Gln Val Pro Val Thr His Glu Phe
465                 470                 475                 480

Lys Val Pro Arg Glu Leu Ala Gly Thr Lys Gly Ala Glu Lys Ser Leu
                485                 490                 495

Lys Arg Pro Leu Gly Asp Val Thr Asn Thr Ser Tyr Lys Ser Leu Glu
            500                 505                 510

Lys Arg Ala Arg Leu Ser Phe Val Pro Glu Thr Pro Arg Ser Ser Asp
        515                 520                 525

Val Thr Val Asp Pro Ala Pro Leu Arg Pro Leu Asn Trp Asn Ser Arg
```

```
                530                 535                 540
Tyr Asp Cys Lys Cys Asp Tyr His Ala Gln Phe Asp Asn Ile Ser Asn
545                 550                 555                 560

Lys Cys Asp Glu Cys Glu Tyr Leu Asn Arg Gly Lys Asn Gly Cys Ile
                565                 570                 575

Cys His Asn Val Thr His Cys Gln Ile Cys His Gly Ile Pro Pro Trp
                580                 585                 590

Glu Lys Glu Asn Leu Ser Asp Phe Gly Asp Phe Asp Asp Ala Asn Lys
                595                 600                 605

Glu Gln
    610

<210> SEQ ID NO 270
<211> LENGTH: 623
<212> TYPE: PRT
<213> ORGANISM: Adeno-associated virus

<400> SEQUENCE: 270

Met Pro Gly Phe Tyr Glu Ile Val Ile Lys Val Pro Ser Asp Leu Asp
1               5                   10                  15

Glu His Leu Pro Gly Ile Ser Asp Ser Phe Val Ser Trp Val Ala Glu
                20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Ile Leu Val Glu
                85                  90                  95

Thr Thr Gly Val Lys Ser Met Val Leu Gly Arg Phe Leu Ser Gln Ile
                100                 105                 110

Arg Asp Lys Leu Val Gln Thr Ile Tyr Arg Gly Ile Glu Pro Thr Leu
            115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
                180                 185                 190

Leu Thr His Val Ser Gln Thr Gln Glu Gln Asn Lys Glu Asn Leu Asn
            195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
                260                 265                 270

Ile Met Ala Leu Thr Lys Ser Ala Pro Asp Tyr Leu Val Gly Pro Ala
            275                 280                 285
```

Pro Pro Ala Asp Ile Lys Thr Asn Arg Ile Tyr Arg Ile Leu Glu Leu
    290                 295                 300

Asn Gly Tyr Glu Pro Ala Tyr Ala Gly Ser Val Phe Leu Gly Trp Ala
305                 310                 315                 320

Gln Lys Arg Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Glu His Asp Phe Gly Lys Val Thr Lys Gln
450                 455                 460

Glu Val Lys Glu Phe Phe Arg Trp Ala Gln Asp His Val Thr Glu Val
465                 470                 475                 480

Ala His Glu Phe Tyr Val Arg Lys Gly Gly Ala Asn Lys Arg Pro Ala
                485                 490                 495

Pro Asp Asp Ala Asp Lys Ser Glu Pro Lys Arg Ala Cys Pro Ser Val
            500                 505                 510

Ala Asp Pro Ser Thr Ser Asp Ala Glu Gly Ala Pro Val Asp Phe Ala
        515                 520                 525

Asp Arg Tyr Gln Asn Lys Cys Ser Arg His Ala Gly Met Leu Gln Met
530                 535                 540

Leu Phe Pro Cys Lys Thr Cys Glu Arg Met Asn Gln Asn Phe Asn Ile
545                 550                 555                 560

Cys Phe Thr His Gly Thr Arg Asp Cys Ser Glu Cys Phe Pro Gly Val
                565                 570                 575

Ser Glu Ser Gln Pro Val Val Arg Lys Arg Thr Tyr Arg Lys Leu Cys
            580                 585                 590

Ala Ile His His Leu Leu Gly Arg Ala Pro Glu Ile Ala Cys Ser Ala
        595                 600                 605

Cys Asp Leu Val Asn Val Asp Leu Asp Asp Cys Val Ser Glu Gln
610                 615                 620

<210> SEQ ID NO 271
<211> LENGTH: 624
<212> TYPE: PRT
<213> ORGANISM: Adeno-associated virus

<400> SEQUENCE: 271

Met Pro Gly Phe Tyr Glu Ile Val Leu Lys Val Pro Ser Asp Leu Asp
1               5                   10                  15

Glu Arg Leu Pro Gly Ile Ser Asn Ser Phe Val Asn Trp Val Ala Glu
            20                  25                  30

Lys Glu Trp Asp Val Pro Pro Asp Ser Asp Met Asp Pro Asn Leu Ile
        35                  40                  45

```
Glu Gln Ala Pro Leu Thr Val Ala Glu Lys Leu Gln Arg Glu Phe Leu
     50                  55                  60

Val Glu Trp Arg Arg Val Ser Lys Ala Pro Glu Ala Leu Phe Phe Val
65                   70                  75                  80

Gln Phe Glu Lys Gly Glu Thr Tyr Phe His Leu His Val Leu Ile Glu
                 85                  90                  95

Thr Ile Gly Val Lys Ser Met Val Val Gly Arg Tyr Val Ser Gln Ile
                100                 105                 110

Lys Glu Lys Leu Val Thr Arg Ile Tyr Arg Gly Val Glu Pro Gln Leu
            115                 120                 125

Pro Asn Trp Phe Ala Val Thr Lys Thr Arg Asn Gly Ala Gly Gly Gly
            130                 135                 140

Asn Lys Val Val Asp Asp Cys Tyr Ile Pro Asn Tyr Leu Leu Pro Lys
145                 150                 155                 160

Thr Gln Pro Glu Leu Gln Trp Ala Trp Thr Asn Met Asp Gln Tyr Leu
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Gln Asn
            195                 200                 205

Pro Asn Ser Asp Ala Pro Val Ile Arg Ser Lys Thr Ser Ala Arg Tyr
210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Ser Lys
            260                 265                 270

Ile Met Ser Leu Thr Lys Thr Ala Pro Asp Tyr Leu Val Gly Ser Asn
            275                 280                 285

Pro Pro Glu Asp Ile Thr Lys Asn Arg Ile Tyr Gln Ile Leu Glu Leu
290                 295                 300

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Glu Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Glu Phe
            435                 440                 445

Glu Leu Thr Arg Arg Leu Asp His Asp Phe Gly Lys Val Thr Lys Gln
450                 455                 460
```

Glu Val Lys Asp Phe Phe Arg Trp Ala Ser Asp His Val Thr Asp Val
465                 470                 475                 480

Ala His Glu Phe Tyr Val Arg Lys Gly Gly Ala Lys Lys Arg Pro Ala
            485                 490                 495

Ser Asn Asp Ala Asp Val Ser Glu Pro Lys Arg Glu Cys Thr Ser Leu
            500                 505                 510

Ala Gln Pro Thr Thr Ser Asp Ala Glu Ala Pro Ala Asp Tyr Ala Asp
            515                 520                 525

Arg Tyr Gln Asn Lys Cys Ser Arg His Val Gly Met Asn Leu Met Leu
            530                 535                 540

Phe Pro Cys Lys Thr Cys Glu Arg Met Asn Gln Ile Ser Asn Val Cys
545                 550                 555                 560

Phe Thr His Gly Gln Arg Asp Cys Gly Glu Cys Phe Pro Gly Met Ser
            565                 570                 575

Glu Ser Gln Pro Val Ser Val Val Lys Lys Thr Tyr Gln Lys Leu
            580                 585                 590

Cys Pro Ile His His Ile Leu Gly Arg Ala Pro Glu Ile Ala Cys Ser
            595                 600                 605

Ala Cys Asp Leu Ala Asn Val Asp Leu Asp Asp Cys Val Ser Glu Gln
610                 615                 620

<210> SEQ ID NO 272
<211> LENGTH: 623
<212> TYPE: PRT
<213> ORGANISM: Adeno-associated virus

<400> SEQUENCE: 272

Met Pro Gly Phe Tyr Glu Ile Val Leu Lys Val Pro Ser Asp Leu Asp
1                   5                   10                  15

Glu His Leu Pro Gly Ile Ser Asp Ser Phe Val Ser Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Glu Phe Leu
    50                  55                  60

Val Glu Trp Arg Arg Val Ser Lys Ala Pro Glu Ala Leu Phe Phe Val
65                  70                  75                  80

Gln Phe Glu Lys Gly Asp Ser Tyr Phe His Leu His Ile Leu Val Glu
                85                  90                  95

Thr Val Gly Val Lys Ser Met Val Val Gly Arg Tyr Val Ser Gln Ile
            100                 105                 110

Lys Glu Lys Leu Val Thr Arg Ile Tyr Arg Gly Val Glu Pro Gln Leu
        115                 120                 125

Pro Asn Trp Phe Ala Val Thr Lys Thr Arg Asn Gly Ala Gly Gly Gly
    130                 135                 140

Asn Lys Val Val Asp Asp Cys Tyr Ile Pro Asn Tyr Leu Leu Pro Lys
145                 150                 155                 160

Thr Gln Pro Glu Leu Gln Trp Ala Trp Thr Asn Met Asp Gln Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

```
Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
            245                 250                 255

Ser Asn Ser Arg Ser Gln Ile Lys Ala Ala Leu Asp Asn Ala Ser Lys
        260                 265                 270

Ile Met Ser Leu Thr Lys Thr Ala Pro Asp Tyr Leu Val Gly Gln Asn
    275                 280                 285

Pro Pro Glu Asp Ile Ser Ser Asn Arg Ile Tyr Arg Ile Leu Glu Met
290                 295                 300

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
            325                 330                 335

Thr Thr Gly Lys Thr Asn Ile Ala Glu Ala Ile Ala His Ala Val Pro
        340                 345                 350

Phe Tyr Gly Cys Val Asn Trp Thr Asn Glu Asn Phe Pro Phe Asn Asp
    355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
            405                 410                 415

Ile Val Thr Ser Asn Thr Asn Met Cys Ala Val Ile Asp Gly Asn Ser
        420                 425                 430

Thr Thr Phe Glu His Gln Gln Pro Leu Gln Asp Arg Met Phe Lys Phe
    435                 440                 445

Glu Leu Thr Lys Arg Leu Glu His Asp Phe Gly Lys Val Thr Lys Gln
450                 455                 460

Glu Val Lys Asp Phe Phe Arg Trp Ala Ser Asp His Val Thr Glu Val
465                 470                 475                 480

Thr His Glu Phe Tyr Val Arg Lys Gly Gly Ala Arg Lys Arg Pro Ala
            485                 490                 495

Pro Asn Asp Ala Asp Ile Ser Glu Pro Lys Arg Ala Cys Pro Ser Val
        500                 505                 510

Ala Gln Pro Ser Thr Ser Asp Ala Glu Ala Pro Val Asp Tyr Ala Asp
    515                 520                 525

Arg Tyr Gln Asn Lys Cys Ser Arg His Val Gly Met Asn Leu Met Leu
530                 535                 540

Phe Pro Cys Arg Gln Cys Glu Arg Met Asn Gln Asn Val Asp Ile Cys
545                 550                 555                 560

Phe Thr His Gly Val Met Asp Cys Ala Glu Cys Phe Pro Val Ser Glu
            565                 570                 575

Ser Gln Pro Val Ser Val Val Arg Lys Arg Thr Tyr Gln Lys Leu Cys
        580                 585                 590

Pro Ile His His Ile Met Gly Arg Ala Pro Glu Val Ala Cys Ser Ala
    595                 600                 605

Cys Glu Leu Ala Asn Val Asp Leu Asp Asp Cys Asp Met Glu Gln
610                 615                 620

<210> SEQ ID NO 273
<211> LENGTH: 623
```

<212> TYPE: PRT
<213> ORGANISM: Adeno-associated virus

<400> SEQUENCE: 273

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Ser Tyr Phe His Leu His Val Leu Val Glu
                85                  90                  95

Thr Thr Gly Val Lys Ser Met Val Leu Gly Arg Phe Leu Ser Gln Ile
            100                 105                 110

Arg Glu Lys Leu Val Gln Thr Ile Tyr Arg Gly Val Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ser
        275                 280                 285

Leu Pro Ala Asp Ile Lys Thr Asn Arg Ile Tyr Arg Ile Leu Glu Leu
    290                 295                 300

Asn Gly Tyr Asp Pro Ala Tyr Ala Gly Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400
```

```
Val Asp Gln Lys Cys Lys Ser Ser Ala Gln Ile Asp Pro Thr Pro Val
            405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Arg Arg Leu Glu His Asp Phe Gly Lys Val Thr Lys Gln
            450                 455                 460

Glu Val Lys Glu Phe Phe Arg Trp Ala Ser Asp His Val Thr Glu Val
465                 470                 475                 480

Ala His Glu Phe Tyr Val Arg Lys Gly Gly Ala Ser Lys Arg Pro Ala
            485                 490                 495

Pro Asp Asp Ala Asp Ile Ser Glu Pro Lys Arg Ala Cys Pro Ser Val
            500                 505                 510

Ala Asp Pro Ser Thr Ser Asp Ala Glu Gly Ala Pro Val Asp Phe Ala
            515                 520                 525

Asp Arg Tyr Gln Asn Lys Cys Ser Arg His Ala Gly Met Ile Gln Met
            530                 535                 540

Leu Phe Pro Cys Lys Thr Cys Glu Arg Met Asn Gln Asn Phe Asn Ile
545                 550                 555                 560

Cys Phe Thr His Gly Val Arg Asp Cys Leu Glu Cys Phe Pro Gly Val
            565                 570                 575

Ser Glu Ser Gln Pro Val Val Arg Lys Lys Thr Tyr Arg Lys Leu Cys
            580                 585                 590

Ala Ile His His Leu Leu Gly Arg Ala Pro Glu Ile Ala Cys Ser Ala
            595                 600                 605

Cys Asp Leu Val Asn Val Asp Leu Asp Asp Cys Val Ser Glu Gln
            610                 615                 620

<210> SEQ ID NO 274
<211> LENGTH: 625
<212> TYPE: PRT
<213> ORGANISM: Adeno-associated virus

<400> SEQUENCE: 274

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Arg Asn Leu Ile
            35                  40                  45

Glu Gln Ala Pro Leu Thr Val Ala Glu Lys Leu Gln Arg Asp Phe Leu
        50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
            85                  90                  95

Thr Thr Gly Val Lys Ser Met Val Leu Gly Arg Phe Leu Ser Gln Ile
            100                 105                 110

Arg Glu Lys Leu Gly Pro Asp His Leu Pro Ala Gly Ser Ser Pro Thr
            115                 120                 125

Leu Pro Asn Trp Phe Ala Val Thr Lys Asp Ala Val Met Ala Pro Ala
            130                 135                 140

Gly Gly Asn Lys Val Val Asp Glu Cys Tyr Ile Pro Asn Tyr Leu Leu
```

-continued

```
           145                 150                 155                 160
Pro Lys Thr Gln Pro Glu Leu Gln Trp Ala Trp Thr Asn Met Glu Glu
                    165                 170                 175

Tyr Ile Ser Ala Cys Leu Asn Leu Ala Glu Arg Lys Arg Leu Val Ala
                180                 185                 190

Gln His Leu Thr His Val Ser Gln Thr Gln Gln Asn Lys Glu Asn
            195                 200                 205

Leu Asn Pro Asn Ser Asp Ala Pro Val Ile Arg Ser Lys Thr Ser Ala
        210                 215                 220

Arg Tyr Met Glu Leu Val Gly Trp Leu Val Asp Arg Gly Ile Thr Ser
225                 230                 235                 240

Glu Lys Gln Trp Ile Gln Glu Asp Gln Ala Ser Tyr Ile Ser Phe Asn
                    245                 250                 255

Ala Ala Ser Asn Ser Arg Ser Gln Ile Lys Ala Ala Leu Asp Asn Ala
                260                 265                 270

Gly Lys Ile Met Ala Leu Thr Lys Ser Ala Pro Asp Tyr Leu Val Gly
            275                 280                 285

Pro Ser Leu Pro Ala Asp Ile Thr Gln Asn Arg Ile Tyr Arg Ile Leu
        290                 295                 300

Ala Leu Asn Gly Tyr Asp Pro Ala Tyr Ala Gly Ser Val Phe Leu Gly
305                 310                 315                 320

Trp Ala Gln Lys Lys Phe Gly Lys Arg Asn Thr Ile Trp Leu Phe Gly
                    325                 330                 335

Pro Ala Thr Thr Gly Lys Thr Asn Ile Ala Glu Ala Ile Ala His Ala
                340                 345                 350

Val Pro Phe Tyr Gly Cys Val Asn Trp Thr Asn Glu Asn Phe Pro Phe
            355                 360                 365

Asn Asp Cys Val Asp Lys Met Val Ile Trp Trp Glu Glu Gly Lys Met
        370                 375                 380

Thr Ala Lys Val Val Glu Ser Ala Lys Ala Ile Leu Gly Gly Ser Lys
385                 390                 395                 400

Val Arg Val Asp Gln Lys Cys Lys Ser Ser Ala Gln Ile Asp Pro Thr
                    405                 410                 415

Pro Val Ile Val Thr Ser Asn Thr Asn Met Cys Ala Val Ile Asp Gly
                420                 425                 430

Asn Ser Thr Thr Phe Glu His Gln Gln Pro Leu Gln Asp Arg Met Phe
            435                 440                 445

Lys Phe Glu Leu Thr Arg Arg Leu Glu His Asp Phe Gly Lys Val Thr
        450                 455                 460

Lys Gln Glu Val Lys Glu Phe Phe Arg Trp Ala Ser Asp His Val Thr
465                 470                 475                 480

Glu Val Ala His Glu Phe Tyr Val Arg Lys Gly Gly Ala Ser Lys Arg
                    485                 490                 495

Pro Ala Pro Asp Asp Ala Asp Lys Ser Glu Pro Lys Arg Ala Cys Pro
                500                 505                 510

Ser Val Ala Asp Pro Ser Thr Ser Asp Ala Glu Gly Ala Pro Val Asp
            515                 520                 525

Phe Ala Asp Arg Tyr Gln Asn Lys Cys Ser Arg His Ala Gly Met Leu
        530                 535                 540

Gln Met Leu Phe Pro Cys Lys Thr Cys Glu Arg Met Asn Gln Asn Phe
545                 550                 555                 560

Asn Ile Cys Phe Thr His Gly Val Arg Asp Cys Ser Glu Cys Phe Pro
                    565                 570                 575
```

```
Gly Val Ser Glu Ser Gln Pro Val Val Arg Lys Arg Thr Tyr Arg Lys
            580                 585                 590

Leu Cys Ala Ile His His Leu Leu Gly Arg Ala Pro Glu Ile Ala Cys
    595                 600                 605

Ser Ala Cys Asp Leu Val Asn Val Asp Leu Asp Asp Cys Val Ser Glu
610                 615                 620

Gln
625

<210> SEQ ID NO 275
<211> LENGTH: 663
<212> TYPE: PRT
<213> ORGANISM: Avian adeno-associated virus

<400> SEQUENCE: 275

Met Arg Ser Tyr Tyr Glu Val Ile Val Gln Leu Pro Asn Asp Val Glu
1               5                   10                  15

Ser Gln Val Pro Gly Ile Ser Asp Ser Phe Val Asn Trp Ile Thr Ser
            20                  25                  30

Arg Glu Trp Thr Leu Pro Glu Asp Ala Asp Trp Asp Leu Asp Gln Val
        35                  40                  45

Asp Gln Val Gln Leu Thr Leu Gly Asp Lys Ile Gln Arg Glu Ile Arg
50                  55                  60

Asn His Trp Gly Thr Met Ala Lys Glu Pro Asp Phe His Tyr Phe Ile
65                  70                  75                  80

Gln Leu Glu Gln Gly Glu Val Phe Phe His Leu His Val Leu Leu Glu
                85                  90                  95

Thr Cys Ser Val Lys Pro Met Val Leu Gly Arg Tyr Ile Arg His Ile
            100                 105                 110

Gln Gln Lys Ile Val Ser Lys Val Tyr Cys Gly His Glu Pro Ala Met
        115                 120                 125

Glu Gly Trp Met Arg Val Thr Lys Thr Lys Asn Phe Gly Gly Ala Asn
    130                 135                 140

Lys Val Arg Ala Glu Ser Tyr Ile Pro Ala Tyr Leu Ile Pro Lys Gln
145                 150                 155                 160

Gln Pro Glu Val Gln Trp Ala Trp Thr Asn Val Pro Glu Tyr Ile Lys
                165                 170                 175

Ala Cys Leu His Arg Glu Leu Arg Ala Ser Leu Ala Arg Leu His Phe
            180                 185                 190

Glu Glu Ala Gly Leu Ser Gln Ser Lys Glu Asn Leu Ala Arg Thr Ala
        195                 200                 205

Asp Gly Ala Pro Val Ile Ala Thr Arg Val Ser Lys Arg Tyr Met Glu
    210                 215                 220

Leu Val Asp Trp Leu Val Glu Lys Gly Ile Thr Thr Glu Lys Glu Trp
225                 230                 235                 240

Leu Leu Glu Asn Arg Glu Ser Phe Arg Ser Phe Gln Ala Ser Ser Asn
                245                 250                 255

Ser Ala Arg Gln Ile Lys Thr Ala Leu Gln Gly Ala Ile Gln Glu Met
            260                 265                 270

Leu Leu Thr Lys Thr Ala Glu Asp Tyr Leu Val Gly Lys Glu Pro Val
        275                 280                 285

Ser Asp Asp Glu Ile Arg Gln Asn Arg Ile Tyr Lys Ile Leu Glu Leu
    290                 295                 300

Asn His Tyr Asp Pro Ala Tyr Val Gly Ser Ile Leu Val Gly Trp Cys
```

```
            305                 310                 315                 320
Gln Lys Lys Trp Gly Lys Arg Asn Thr Leu Trp Leu Phe Gly Pro Ala
                325                 330                 335
Thr Thr Gly Lys Thr Asn Ile Ala Glu Ala Ile Ala His Ala Val Pro
                340                 345                 350
Phe Tyr Gly Cys Val Asn Trp Thr Asn Glu Asn Phe Pro Phe Asn Asp
                355                 360                 365
Cys Val Glu Lys Met Ile Ile Trp Trp Glu Gly Lys Met Thr Ala
            370                 375                 380
Lys Val Val Glu Thr Ala Lys Ala Ile Leu Gly Gly Ser Arg Val Arg
385                 390                 395                 400
Val Asp Gln Lys Cys Lys Ala Ser Val Pro Ile Glu Pro Thr Pro Val
                405                 410                 415
Ile Ile Thr Ser Asn Thr Asn Met Cys Tyr Val Ile Asp Gly Asn Thr
                420                 425                 430
Thr Thr Phe Glu His Lys Gln Pro Leu Glu Asp Arg Met Phe Lys Leu
            435                 440                 445
Glu Leu Leu Thr Arg Leu Pro Asp Asp Phe Gly Lys Val Thr Lys Gln
450                 455                 460
Glu Val Arg Gln Phe Phe Arg Trp Ser Gln Asp His Leu Thr Pro Val
465                 470                 475                 480
Ile Pro Glu Phe Leu Val Arg Lys Ala Glu Ser Arg Lys Arg Pro Ala
                485                 490                 495
Pro Ser Gly Glu Gly Tyr Ile Ser Pro Thr Lys Arg Pro Ala Leu Ala
                500                 505                 510
Glu Gln Gln Gln Ala Ser Glu Ser Ala Glu Pro Val Pro Thr Arg Tyr
            515                 520                 525
Arg Ile Lys Cys Ser Lys His Cys Gly Met Asp Lys Met Leu Phe Pro
                530                 535                 540
Cys Gln Ile Cys Glu Ser Met Asn Arg Asn Ile Asn Ile Cys Ala Ile
545                 550                 555                 560
His Lys Thr Thr Glu Cys Lys Glu Cys Phe Pro Glu Tyr Gly Asp Lys
                565                 570                 575
Asp Thr Val Pro Glu Leu Pro Pro Cys Thr Glu His Asn Val Ser Arg
            580                 585                 590
Cys Tyr Gln Cys His Ser Gly Glu Leu Tyr Arg Val Thr Ser Asp Ser
            595                 600                 605
Asp Glu Lys Pro Ala Pro Glu Ser Asp Glu Gly Thr Glu Pro Ser Tyr
        610                 615                 620
Ala Pro Cys Thr Ile His His Leu Met Gly Lys Ser Arg Gly Leu Val
625                 630                 635                 640
Ser Cys Ala Ala Cys Arg Leu Lys Asn Ser Thr Leu His Asp Asp Leu
                645                 650                 655
Asp Asp Gly Asp Leu Glu Gln
            660

<210> SEQ ID NO 276
<211> LENGTH: 662
<212> TYPE: PRT
<213> ORGANISM: Avian adeno-associated virus

<400> SEQUENCE: 276

Met Arg Ser Tyr Tyr Glu Val Ile Val Gln Leu Pro Asn Asp Val Glu
1               5                   10                  15
```

```
Ser Gln Val Pro Gly Ile Ser Asp Ser Phe Val Asn Trp Ile Thr Ser
            20                  25                  30

Arg Glu Trp Thr Leu Pro Glu Asp Ala Asp Trp Asp Leu Asp Gln Val
        35                  40                  45

Asp Gln Val Gln Leu Thr Leu Gly Asp Lys Ile Gln Arg Glu Ile Arg
50                  55                  60

Thr His Trp Gly Thr Met Ala Lys Glu Pro Asp Phe His Tyr Phe Ile
65                  70                  75                  80

Gln Leu Glu Gln Gly Glu Val Phe Phe His Leu His Val Leu Leu Glu
                85                  90                  95

Thr Cys Ser Val Lys Pro Met Val Leu Gly Arg Tyr Ile Arg His Ile
            100                 105                 110

Gln Gln Lys Ile Val Ser Lys Val Tyr Cys Ala Thr Ser Leu Arg Trp
        115                 120                 125

Lys Asp Gly Cys Val Val Thr Lys Thr Lys Asn Phe Gly Gly Ala Asn
130                 135                 140

Lys Val Arg Ala Glu Ser Tyr Ile Pro Ala Tyr Leu Ile Pro Lys Gln
145                 150                 155                 160

Gln Pro Glu Val Gln Trp Ala Trp Thr Asn Val Pro Glu Tyr Ile Lys
                165                 170                 175

Ala Cys Leu His Arg Glu Leu Arg Ala Ser Leu Ala Arg Leu His Phe
            180                 185                 190

Glu Glu Ala Gly Val Ser Gln Ser Lys Glu Asn Leu Ala Arg Thr Ala
        195                 200                 205

Asp Gly Ala Pro Val Met Pro Thr Arg Val Ser Lys Arg Tyr Met Glu
210                 215                 220

Leu Val Asp Trp Leu Val Glu Lys Gly Ile Thr Thr Glu Lys Glu Trp
225                 230                 235                 240

Leu Leu Glu Asn Arg Glu Ser Phe Arg Ser Phe Gln Ala Ser Ser Asn
                245                 250                 255

Ser Ala Arg Gln Ile Lys Thr Ala Leu Gln Gly Ala Ile Gln Glu Met
            260                 265                 270

Leu Leu Thr Lys Thr Ala Glu Asp Tyr Leu Val Gly Lys Asp Pro Val
        275                 280                 285

Ser Asp Asp Asp Ile Arg Gln Asn Arg Ile Tyr Lys Ile Leu Glu Leu
290                 295                 300

Asn His Tyr Asp Pro Ala Tyr Val Gly Ser Ile Leu Val Gly Trp Cys
305                 310                 315                 320

Gln Lys Lys Trp Gly Lys Arg Asn Thr Leu Trp Leu Phe Gly His Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Glu Lys Met Ile Ile Trp Trp Glu Gly Lys Met Thr Ala
370                 375                 380

Lys Val Val Glu Thr Ala Lys Ala Ile Leu Gly Gly Ser Arg Val Arg
385                 390                 395                 400

Val Asp Gln Lys Cys Lys Ala Ser Val Pro Ile Glu Pro Thr Pro Val
                405                 410                 415

Ile Ile Thr Ser Asn Thr Asn Met Cys Tyr Val Ile Asp Gly Asn Thr
            420                 425                 430

Thr Thr Phe Glu His Lys Gln Pro Leu Glu Asp Arg Met Phe Lys Leu
```

```
                435                 440                 445
Glu Leu Leu Thr Arg Leu Pro Asp Asp Phe Gly Lys Val Thr Lys Gln
    450                 455                 460

Glu Val Arg Gln Phe Phe Arg Trp Ser Gln Asp His Leu Thr Pro Val
465                 470                 475                 480

Ile Pro Glu Phe Leu Val Arg Lys Ala Glu Ser Arg Lys Arg Pro Ala
                485                 490                 495

Pro Ser Gly Glu Gly Tyr Ile Ser Pro Thr Lys Arg Pro Ala Leu Ala
                500                 505                 510

Glu Gln Gln Gln Ala Ser Glu Ser Ala Asp Pro Val Pro Thr Arg Tyr
                515                 520                 525

Arg Ile Lys Cys Ser Lys His Cys Gly Met Asp Lys Met Leu Phe Pro
                530                 535                 540

Cys Gln Ile Cys Glu Ser Met Asn Arg Asp Ile Asn Ile Cys Ala Ile
545                 550                 555                 560

His Lys Thr Thr Asp Cys Lys Glu Cys Phe Pro Asp Tyr Gly Asp Lys
                565                 570                 575

Asp Asp Val Glu Leu Pro Pro Cys Thr Glu His Asn Val Ser Arg Cys
                580                 585                 590

Tyr Gln Cys His Ser Gly Glu Leu Tyr Arg Val Thr Ser Asp Ser Asp
                595                 600                 605

Glu Lys Pro Ala Pro Glu Ser Asp Glu Gly Thr Glu Pro Ser Tyr Ala
610                 615                 620

Pro Cys Thr Ile His His Leu Met Gly Lys Ser His Gly Leu Val Thr
625                 630                 635                 640

Cys Ala Ala Cys Arg Leu Lys Asn Ser Thr Leu His Asp Asp Leu Asp
                645                 650                 655

Asp Gly Asp Leu Glu Gln
            660

<210> SEQ ID NO 277
<211> LENGTH: 610
<212> TYPE: PRT
<213> ORGANISM: Bovine adeno-associated virus

<400> SEQUENCE: 277

Met Ala Thr Phe Tyr Glu Val Ile Val Arg Val Pro Phe Asp Val Glu
1               5                   10                  15

Glu His Leu Pro Gly Ile Ser Asp Asn Phe Val Asp Trp Val Thr Gly
                20                  25                  30

Gln Ile Trp Glu Leu Pro Pro Glu Ser Asp Leu Asn Leu Thr Leu Ile
            35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65              70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
                100                 105                 110

Ala Gln Leu Val Lys Val Phe Gln Asn Ile Glu Pro Arg Ile Asn
            115                 120                 125

Asp Trp Val Ala Ile Thr Lys Val Lys Lys Gly Gly Ala Asn Lys Val
    130                 135                 140
```

```
Val Asp Ser Gly Tyr Ile Pro Ala Tyr Leu Leu Pro Lys Val Gln Pro
145                 150                 155                 160

Glu Leu Gln Trp Ala Trp Thr Asn Leu Glu Glu Tyr Lys Leu Ala Ala
            165                 170                 175

Leu Asn Leu Glu Glu Arg Lys Arg Leu Val Ala Gln Phe Gln Leu Glu
                180                 185                 190

Ser Ser Gln Arg Ser Gln Ala Ser Ser Gln Arg Asp Val Ser Ala
        195                 200                 205

Asp Pro Val Ile Lys Ser Lys Thr Ser Gln Lys Tyr Met Ala Leu Val
        210                 215                 220

Ser Trp Leu Val Glu His Gly Ile Thr Ser Glu Lys Gln Trp Ile Gln
225                 230                 235                 240

Glu Asn Gln Glu Ser Tyr Leu Ser Phe Asn Ser Thr Gly Asn Ser Arg
                245                 250                 255

Ser Gln Ile Lys Ala Ala Leu Asp Asn Ala Ser Lys Ile Met Ser Leu
            260                 265                 270

Thr Lys Ser Ala Ser Asp Tyr Leu Val Gly Gln Thr Val Pro Glu Asp
        275                 280                 285

Ile Ser Glu Asn Arg Ile Trp Gln Ile Phe Asp Leu Asn Gly Tyr Asp
290                 295                 300

Pro Ala Tyr Ala Gly Ser Val Leu Tyr Gly Trp Cys Thr Arg Ala Phe
305                 310                 315                 320

Gly Lys Arg Asn Thr Val Trp Leu Tyr Gly Pro Ala Thr Gly Lys
                325                 330                 335

Thr Asn Ile Ala Glu Ala Ile Ser His Thr Val Pro Phe Tyr Gly Cys
                340                 345                 350

Val Asn Trp Thr Asn Glu Asn Phe Pro Phe Asn Asp Cys Val Glu Lys
                355                 360                 365

Met Leu Ile Trp Trp Glu Glu Gly Lys Met Thr Ser Lys Val Val Glu
370                 375                 380

Pro Ala Lys Ala Ile Leu Gly Gly Ser Arg Val Arg Val Asp Gln Lys
385                 390                 395                 400

Cys Lys Ser Ser Val Gln Val Asp Ser Thr Pro Val Ile Ile Thr Ser
                405                 410                 415

Asn Thr Asn Met Cys Val Val Asp Gly Asn Ser Thr Thr Phe Glu
            420                 425                 430

His Gln Gln Pro Leu Glu Asp Arg Met Phe Arg Phe Glu Leu Met Arg
        435                 440                 445

Arg Leu Pro Pro Asp Phe Gly Lys Ile Thr Lys Gln Glu Val Lys Asp
450                 455                 460

Phe Phe Ala Trp Ala Lys Val Asn Gln Val Pro Val Thr His Glu Phe
465                 470                 475                 480

Met Val Pro Lys Lys Val Ala Gly Thr Glu Arg Ala Glu Thr Ser Arg
            485                 490                 495

Lys Arg Pro Leu Asp Asp Val Thr Asn Tyr Lys Ser Pro Glu
        500                 505                 510

Lys Arg Ala Arg Leu Ser Val Val Pro Glu Thr Pro Arg Ser Ser Asp
        515                 520                 525

Val Pro Val Glu Pro Ala Pro Leu Arg Pro Leu Asn Trp Ser Ser Arg
        530                 535                 540

Tyr Glu Cys Arg Cys Asp Tyr His Ala Lys Phe Asp Ser Val Thr Gly
545                 550                 555                 560

Glu Cys Asp Glu Cys Glu Tyr Leu Asn Arg Gly Lys Asn Gly Cys Ile
```

```
                          565                 570                 575
Phe His Asn Ala Thr His Cys Gln Ile Cys His Ala Val Pro Pro Trp
                580                 585                 590

Glu Lys Glu Asn Val Ser Asp Phe Asn Asp Phe Asp Asp Cys Asn Lys
            595                 600                 605

Glu Gln
    610

<210> SEQ ID NO 278
<211> LENGTH: 613
<212> TYPE: PRT
<213> ORGANISM: Bat adeno-associated virus

<400> SEQUENCE: 278

Met Glu Phe Tyr Ser Ile Val Leu Arg Leu Pro Gly Asp Phe Asp Ser
1               5                   10                  15

Glu Val Pro Gly Leu Gln Asp Ser Phe Tyr Lys Trp Ile Ser Gly Pro
                20                  25                  30

Arg Arg Glu Leu Pro Glu Trp Ser Asp Leu Asp Pro Gly Gln Ile Glu
            35                  40                  45

Ser Ala Tyr Gln Ile Leu Ala Asp Lys Leu Val Arg Glu Phe Ala Gln
        50                  55                  60

Lys Trp Ala Ala Phe Ser Glu Asp Pro Arg Ala Pro Tyr Phe Ala Gln
65                  70                  75                  80

Leu Glu Lys Gly Arg Glu Asn Phe His Val His Val Leu Ala Ser Ser
                85                  90                  95

Lys Lys Val Gly Ser Phe Val Val Gly Arg Tyr Val Arg Lys Met Arg
            100                 105                 110

Gln His Leu Val Asp Val Val Phe Arg Lys Cys Glu Pro Val Asp Ala
        115                 120                 125

Asp Trp Leu Gln Val Gln Lys Ser Gly Asn His Lys Ser Asn Glu Ile
130                 135                 140

Lys Asp Glu Gly Phe Ile Pro Ala Tyr Leu Leu Pro Lys Arg Gln Ser
145                 150                 155                 160

Glu Leu Gln Trp Ala Trp Thr Asn Ile Glu Lys Tyr Glu Arg Ala Thr
                165                 170                 175

Leu Ser Val Ala Glu Arg Ala Arg Leu Val Glu Glu Trp Lys Arg Ser
            180                 185                 190

Leu Ala Ala Glu Glu Ser Asp Pro Ala Glu Pro Glu Arg Arg Pro Arg
        195                 200                 205

Lys Ser Thr Lys Ser Ala Ser Glu Tyr Met Ala Leu Val Arg Trp Leu
    210                 215                 220

Val Asp Asn Gly Ile Ala Thr Glu Arg Glu Trp Met Arg Glu Asp Ser
225                 230                 235                 240

Asp Gly Tyr Leu Ser Tyr Asn Ala Thr Gly Ala Thr Arg Ala Gln Ile
                245                 250                 255

Lys Ala Ala Leu Asp Asn Ala Ala Arg Ile Met Val Asn Thr Lys Thr
            260                 265                 270

Ala Ala Asp Tyr Leu Val Gly Arg Asn Pro Pro Leu Asp Val Glu Asp
        275                 280                 285

Asn Arg Ile Tyr Arg Leu Phe Arg Met Asn Gly Tyr Asp Pro Ala Tyr
    290                 295                 300

Ala Gly Ser Val Leu Leu Gly Trp Cys Arg Thr Gly Phe Gly Lys Arg
305                 310                 315                 320
```

```
Asn Thr Val Trp Leu Phe Gly Pro Ala Thr Thr Gly Lys Thr Asn Leu
                325                 330                 335

Ala Glu Ala Ile Ser His Ser Val Pro Phe Tyr Gly Cys Val Asn Trp
            340                 345                 350

Thr Asn Glu Asn Phe Pro Phe Asn Asp Cys Val Asp Lys Met Ile Ile
        355                 360                 365

Trp Trp Glu Glu Gly Lys Met Thr Ser Lys Val Val Glu Ser Ala Lys
370                 375                 380

Ala Ile Leu Gly Gly Ser Lys Val Arg Val Asp Gln Lys Cys Lys Asn
385                 390                 395                 400

Ser Gln Gln Ile Glu Pro Thr Pro Val Ile Ile Thr Ser Asn Thr Asn
                405                 410                 415

Met Cys Glu Val Val Asp Gly Asn Ser Thr Thr Phe Glu His Arg Gln
            420                 425                 430

Pro Leu Glu Asp Arg Met Phe Lys Phe Glu Leu Thr Val Arg Leu Gln
        435                 440                 445

Pro Thr Phe Gly Lys Ile Thr Lys Gln Glu Val Arg Glu Phe Phe Lys
    450                 455                 460

Trp Ala Glu Leu Asn Ala Val Asp Val Glu Tyr Asp Phe Leu Val Arg
465                 470                 475                 480

Lys Ile Asn Gln Ser Asp Thr Gly Gly Val Lys Arg Gly Ala Glu
                485                 490                 495

Pro Thr Lys Asp Glu Pro Pro Ala Lys Arg Val Phe Phe Tyr Gly Ala
            500                 505                 510

Thr Ser Glu Gly Glu Asp Val Arg Glu Gly Ala Pro Gly Ser Asp
        515                 520                 525

Ser Val Asn Phe Ala Glu Arg Tyr Val Ser Lys Cys Ser Lys His Leu
    530                 535                 540

Ser Trp Ser Asn Met Arg Tyr Pro Cys Arg Ala Cys Glu Arg Met Asn
545                 550                 555                 560

Ala Asp Val Asn Val Cys Thr Pro His Gly Cys Arg Asp Cys Pro Glu
                565                 570                 575

Cys Phe Pro Arg Pro Ala Pro Val Pro Ile Ala Glu His Asp Leu Cys
            580                 585                 590

Leu Ala Pro Ile Glu Asp Ser Asp Phe Tyr Val Gly Cys Ile Asp Asp
        595                 600                 605

Val Asn Lys Glu Gln
    610

<210> SEQ ID NO 279
<211> LENGTH: 562
<212> TYPE: PRT
<213> ORGANISM: Snake parvovirus

<400> SEQUENCE: 279

Met Ala Phe Tyr Glu Val Val Phe Arg Leu Pro Arg Asp Asn Asn Asn
1               5                   10                  15

Leu Leu Asp Glu Asp Arg Tyr Gln Pro Glu Leu Lys Glu Glu Asp Asp
                20                  25                  30

Trp Pro Glu Glu Tyr Leu Thr Ser Glu Asp Ala Ser Phe Ile Gly Leu
            35                  40                  45

Ala Tyr Ala Val Leu Ser Glu Ile Arg Arg Phe Phe Gly Lys Glu Leu
        50                  55                  60

Gln Trp Phe Ala Gln Val Glu Trp Cys Pro Thr Ala Gly Tyr His Met
65                  70                  75                  80
```

```
His Val Leu Leu Asn His Pro Lys Leu Ser Asn Gln Thr Tyr Gly Arg
                85                  90                  95
Lys Val Asn Glu Leu Ala Cys Arg Ile Val Asp Thr Phe Gly Leu Ile
            100                 105                 110
Asn Pro Glu Glu Val Ile Ser Thr His Tyr Val Lys Ser Asn Tyr Gly
        115                 120                 125
His Lys Lys Val Arg Val Ile His Leu Glu Ser Tyr Leu Lys Asn Tyr
    130                 135                 140
Phe Phe Arg Lys Thr Leu Ala Pro Pro Asn Tyr Thr Glu Glu Gly Asp
145                 150                 155                 160
Tyr Lys Arg Glu Glu Glu Val Val Leu Trp Ala Phe Thr Asn Ile Val
                165                 170                 175
Ala Trp Lys Pro Phe Val Arg Asn Leu Ile Lys Arg Ser Glu Leu Ala
            180                 185                 190
Thr Val Pro Lys Gln Pro Glu Asn Pro Ala Gly Asp Gly Pro Ala Pro
        195                 200                 205
Arg Val Thr Ala Gly Thr Arg His Phe Met Glu Thr Ile Asp Trp Leu
    210                 215                 220
Val Lys His Gly Ile Thr Thr Glu Arg Glu Phe Cys His Ala Asn Arg
225                 230                 235                 240
Pro Leu Tyr Leu Ser Met Leu Ala Ser Thr Ser Gly Ala Gly Gln Ile
                245                 250                 255
Lys Arg Ala Leu Asp Gln Ala Lys His Met Met Thr Ser Thr Met Ser
            260                 265                 270
Ala Glu Asp Tyr Leu Thr Thr Glu Asp Val Ile Glu Pro Pro Thr
        275                 280                 285
Glu Asn Arg Ile Tyr Lys Ile Met Lys Leu Asn Arg Tyr Asp Pro Glu
    290                 295                 300
Leu Ala Ala Ala Leu Phe Tyr Gly Trp Thr Cys Lys Asn Phe Gly Lys
305                 310                 315                 320
Arg Asn Thr Ile Trp Leu Tyr Gly Pro Ala Thr Thr Gly Lys Thr Ile
                325                 330                 335
Ile Ala Gln Ala Ile Ala His Ala Val Lys Leu Phe Ala Gly Val Asn
            340                 345                 350
Trp Thr Asn Glu Asn Phe Pro Phe Cys Asn Cys Pro Gly Lys Leu Leu
        355                 360                 365
Ile Trp Trp Glu Glu Gly Lys Met Thr Asn Lys Met Val Glu Thr Ala
    370                 375                 380
Lys Cys Ile Leu Gly Gly Ser Ala Val Pro Val Asp Ile Lys Gly Lys
385                 390                 395                 400
Pro Ala Glu Met Cys Pro Gln Thr Pro Cys Ile Ile Thr Ser Asn Thr
                405                 410                 415
Asn Met Cys Gln Val Tyr Asp Gly Asn Ser Ser Ser Phe Glu His Gln
            420                 425                 430
Glu Pro Leu Glu Glu Arg Met Phe Met Phe Arg Leu Asn Thr Lys Leu
        435                 440                 445
Pro Ser Thr Phe Gly Lys Ile Thr Glu Glu Val Lys Gln Phe Ile
    450                 455                 460
Thr Trp Gly Arg Ser Leu Lys Val Gln Val Pro His Gln Phe Arg Val
465                 470                 475                 480
Pro Thr Thr Gly Glu Tyr Lys Arg Pro Ala Pro Glu Ala Lys Ala His
                485                 490                 495
```

Ser Ser Asp Glu Pro Pro Lys Glu Lys Val Ala Arg Ile Asp Asp Ser
        500                 505                 510

Leu Thr Arg Tyr Val Asn Asn Ile Asp Glu Ser Ala Thr Ser Arg Glu
        515                 520                 525

Met Phe Leu Glu Ile Ala Asn Thr Asn Gln Cys Met Leu His His Cys
        530                 535                 540

Phe Ser Cys Thr Glu Cys Tyr Pro Glu Leu Leu Asp Asp Met Asp Lys
545                 550                 555                 560

Glu Gln

<210> SEQ ID NO 280
<211> LENGTH: 4718
<212> TYPE: DNA
<213> ORGANISM: Adeno-associated virus

<400> SEQUENCE: 280

```
ttgcccactc cctctctgcg cgctcgctcg ctcggtgggg cctgcggacc aaaggtccgc      60
agacggcaga gctctgctct gccggcccca ccgagcgagc gagcgcgcag agagggagtg     120
ggcaactcca tcactagggg taatcgcgaa gcgcctccca cgctgccgcg tcagcgctga     180
cgtaaattac gtcatagggg agtggtcctg tattagctgt cacgtgagtg cttttgcgac     240
attttgcgac accacgtggc catttagggt atatatggcc gagtgagcga gcaggatctc     300
cattttgacc gcgaaatttg aacgagcagc agccatgccg ggcttctacg agatcgtgat     360
caaggtgccg agcgacctgg acgagcacct gccgggcatt tctgactcgt tgtgagctg     420
ggtggccgag aaggaatggg agctgccccc ggattctgac atggatctga atctgattga     480
gcaggcaccc ctgaccgtgg ccgagaagct gcagcgcgac ttcctggtcc aatggcgccg     540
cgtgagtaag gccccggagg ccctcttctt tgttcagttc gagaagggcg agtcctactt     600
ccacctccat attctggtgg agaccacggg ggtcaaatcc atggtgctgg ccgcttcct      660
gagtcagatt agggacaagc tggtgcagac catctaccgc gggatcgagc cgaccctgcc     720
caactggttc gcggtgacca agacgcgtaa tggcgccgga ggggggaaca aggtggtgga     780
cgagtgctac atccccaact acctcctgcc caagactcag cccgagctgc agtgggcgtg     840
gactaacatg gaggagtata taagcgcctg tttgaacctg gccgagcgca acggctcgt      900
ggcgcagcac ctgacccacg tcagccagac ccaggagcag aacaaggaga atctgaaccc     960
caattctgac gcgcctgtca tccggtcaaa aacctccgcg cgctacatgg agctggtcgg    1020
gtggctggtg gaccgggggca tcacctccga gaagcagtgg atccaggagg accaggcctc    1080
gtacatctcc ttcaacgccg cttccaactc gcggtcccag atcaaggccg ctctggacaa    1140
tgccggcaag atcatggcgc tgaccaaaatc cgcgcccgac tacctggtag ccccgctcc    1200
gccccgcggac attaaaacca accgcatcta ccgcatcctg gagctgaacg gctacgaacc    1260
tgcctacgcc ggctcgtct ttctcggctg ggcccagaaa aggttcggga agcgcaacac    1320
catctggctg tttgggccgg ccaccacggg caagaccaac atcgcggaag ccatcgccca    1380
cgccgtgccc ttctacggct gcgtcaactg gaccaatgag aactttccct tcaatgattg    1440
cgtcgacaag atggtgatct ggtgggagga gggcaagatg acggccaagg tcgtggagtc    1500
cgccaaggcc attctcggcg gcagcaaggt gcgcgtggac caaaagtgca gtcgtccgc    1560
ccagatcgac cccacccccg tgatcgtcac ctccaacacc aacatgtgcg ccgtgattga    1620
cgggaacagc accaccttcg agcaccagca gccgttgcag gaccggatgt tcaaatttga    1680
actcacccgc cgtctggagc atgactttgg caaggtgaca aagcaggaag tcaaagagtt    1740
```

```
cttccgctgg gcgcaggatc acgtgaccga ggtggcgcat gagttctacg tcagaaaggg    1800
tggagccaac aaaagacccg cccccgatga cgcggataaa agcgagccca agcgggcctg    1860
cccctcagtc gcggatccat cgacgtcaga cgcggaagga gctccggtgg actttgccga    1920
caggtaccaa aacaaatgtt ctcgtcacgc gggcatgctt cagatgctgt ttccctgcaa    1980
gacatgcgag agaatgaatc agaatttcaa catttgcttc acgcacggga cgagagactg    2040
ttcagagtgc ttccccggcg tgtcagaatc tcaaccggtc gtcagaaaga ggacgtatcg    2100
gaaactctgt gccattcatc atctgctggg gcgggctccc gagattgctt gctcggcctg    2160
cgatctggtc aacgtggacc tggatgactg tgtttctgag caataaatga cttaaaccag    2220
gtatggctgc cgatggttat cttccagatt ggctcgagga caacctctct gagggcattc    2280
gcgagtggtg ggacttgaaa cctggagccc gaagcccaa agccaaccag caaaagcagg    2340
acgacggccg gggtctggtg cttcctggct acaagtacct cggacccttc aacggactcg    2400
acaaggggga gcccgtcaac gcggcggacg cagcggccct cgagcacgac aaggcctacg    2460
accagcagct caaagcgggt gacaatccgt acctgcggta taaccacgcc gacgccgagt    2520
ttcaggagcg tctgcaagaa gatacgtctt ttgggggcaa cctcgggcga gcagtcttcc    2580
aggccaagaa gcgggttctc gaacctctcg gtctggttga ggaaggcgct aagacggctc    2640
ctggaaagaa acgtccggta gagcagtcgc cacaagagcc agactcctcc tcgggcatcg    2700
gcaagacagg ccagcagccc gctaaaaaga gactcaattt tggtcagact ggcgactcag    2760
agtcagtccc cgatccacaa cctctcggag aacctccagc aaccccgct gctgtgggac    2820 ctactacaat ggcttcaggc ggtggcgcac caatggcaga caataacgaa ggcgccgacg    2880
gagtgggtaa tgcctcagga aattggcatt gcgattccac atggctgggc gacagagtca    2940
tcaccaccag cacccgcacc tgggccttgc ccacctacaa taaccactc tacaagcaaa    3000 tctccagtgc ttcaacgggg gccagcaacg acaaccacta cttcggctac agcacccct    3060 gggggtattt tgatttcaac agattccact gccactttc accacgtgac tggcagcgac    3120
tcatcaacaa caattgggga ttccggccca agagactcaa cttcaaactc ttcaacatcc    3180
aagtcaagga ggtcacgacg aatgatggcg tcacaaccat cgctaataac cttaccagca    3240
cggttcaagt cttctcggac tcggagtacc agcttccgta cgtcctcggc tctgcgcacc    3300
agggctgcct ccctccgttc ccggcggacg tgttcatgat tccgcaatac ggctacctga    3360
cgctcaacaa tggcagccaa gccgtgggac gttcatcctt ttactgcctg gaatatttcc    3420
cttctcagat gctgagaacg ggcaacaact ttaccttcag ctacaccttt gaggaagtgc    3480
ctttccacag cagctacgcg cacagccaga gcctggaccg gctgatgaat cctctcatcg    3540
accaatacct gtattacctg aacagaactc aaaatcagtc cggaagtgcc caaacaagg    3600 acttgctgtt tagccgtggg tctccagctg gcatgtctgt tcagcccaaa aactggctac    3660
ctggaccctg ttatcggcag cagcgcgttt ctaaaacaaa aacagacaac aacaacagca    3720
attttacctg gactggtgct tcaaaatata acctcaatgg gcgtgaatcc atcatcaacc    3780
ctggcactgc tatggcctca cacaaagacg acgaagacaa gttctttccc atgagcggtg    3840
tcatgatttt tggaaaagag agcgccggag cttcaaacac tgcattggac aatgtcatga    3900
ttacagacga agaggaaatt aaagccacta accctgtggc caccgaaaga tttgggaccg    3960
tggcagtcaa tttccagagc agcagcacag accctgcgac cggagatgtg catgctatg    4020 gagcattacc tggcatggtg tggcaagata gagacgtgta cctgcagggt cccatttggg    4080
```

```
ccaaaattcc tcacacagat ggacactttc acccgtctcc tcttatgggc ggctttggac    4140
tcaagaaccc gcctcctcag atcctcatca aaaacacgcc tgttcctgcg aatcctccgg    4200
cggagttttc agctacaaag tttgcttcat tcatcaccca atactccaca ggacaagtga    4260
gtgtggaaat tgaatgggag ctgcagaaag aaaacagcaa gcgctggaat cccgaagtgc    4320
agtacacatc caattatgca aaatctgcca acgttgattt tactgtggac aacaatggac    4380
tttatactga gcctcgcccc attggcaccc gttaccttac ccgtcccctg taattacgtg    4440
ttaatcaata aaccggttga ttcgtttcag ttgaactttg gtctcctgtc cttcttatct    4500
tatcggttac catggttata gcttacacat taactgcttg gttgcgcttc gcgataaaag    4560
acttacgtca tcgggttacc cctagtgatg gagttgccca ctccctctct gcgcgctcgc    4620
tcgctcggtg gggcctgcgg accaaaggtc cgcagacggc agagctctgc tctgccggcc    4680
ccaccgagcg agcgagcgcg cagagaggga gtgggcaa                           4718

<210> SEQ ID NO 281
<211> LENGTH: 4679
<212> TYPE: DNA
<213> ORGANISM: Adeno-associated virus

<400> SEQUENCE: 281
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcctggagg ggtggagtcg tgacgtgaat tacgtcatag    180
ggttagggag gtcctgtatt agaggtcacg tgagtgtttt gcgacatttt gcgacaccat    240
gtggtcacgc tgggtattta agcccgagtg agcacgcagg gtctccattt tgaagcggga    300
ggtttgaacg cgcagccgcc atgccggggt tttacgagat tgtgattaag gtccccagcg    360
accttgacga gcatctgccc ggcatttctg acagctttgt gaactgggtg gccgagaagg    420
aatgggagtt gccgccagat tctgacatgg atctgaatct gattgagcag gcacccctga    480
ccgtggccga gaagctgcag cgcgactttc tgacggaatg gcgccgtgtg agtaaggccc    540
cggaggccct tttctttgtg caatttgaga agggagagag ctacttccac atgcacgtgc    600
tcgtggaaac caccggggtg aaatccatgg ttttgggacg tttcctgagt cagattcgcg    660
aaaaactgat tcagagaatt taccgcggga tcgagccgac tttgccaaac tggttcgcgg    720
tcacaaagac cagaaatggc gccggaggcg ggaacaaggt ggtggatgag tgctacatcc    780
ccaattactt gctccccaaa acccagcctg agctccagtg ggcgtggact aatatggaac    840
agtatttaag cgcctgtttg aatctcacgg agcgtaaacg gttggtggcg cagcatctga    900
cgcacgtgtc gcagacgcag gagcagaaca aagagaatca gaatcccaat tctgatgcgc    960
cggtgatcag atcaaaaact tcagccaggt acatggagct ggtcgggtgg ctcgtggaca   1020
agggggattac ctcggagaag cagtggatcc aggaggacca ggcctcatac atctccttca   1080
atgcggcctc caactcgcgg tcccaaatca aggctgcctt ggacaatgcg ggaaagatta   1140
tgagcctgac taaaaccgcc cccgactacc tggtgggcca gcagcccgtg gaggacattt   1200
ccagcaatcg gatttataaa attttggaac taaacgggta cgatccccaa tatgcggctt   1260
ccgtcttcct gggatgggcc acgaaaaagt tcggcaagag gaacaccatc tggctgtttg   1320
ggcctgcaac taccgggaag accaacatcg cggaggccat agcccacact gtgcccttct   1380
acgggtgcgt aaactggacc aatgagaact tccccttcaa cgactgtgtc gacaagatgg   1440
tgatctggtg ggaggagggg aagatgaccg ccaaggtcgt ggagtcggcc aaagccattc   1500
```

```
tcggaggaag caaggtgcgc gtggaccaga aatgcaagtc ctcggcccag atagacccga   1560
ctcccgtgat cgtcacctcc aacaccaaca tgtgcgccgt gattgacggg aactcaacga   1620
ccttcgaaca ccagcagccg ttgcaagacc ggatgttcaa atttgaactc acccgccgtc   1680
tggatcatga ctttgggaag gtcaccaagc aggaagtcaa agactttttc cggtgggcaa   1740
aggatcacgt ggttgaggtg gagcatgaat tctacgtcaa aaagggtgga gccaagaaaa   1800
gacccgcccc cagtgacgca gatataagtg agcccaaacg ggtgcgcgag tcagttgcgc   1860
agccatcgac gtcagacgcg gaagcttcga tcaactacgc agacaggtac caaaacaaat   1920
gttctcgtca cgtgggcatg aatctgatgc tgtttccctg cagacaatgc gagagaatga   1980
atcagaattc aaatatctgc ttcactcacg gacagaaaga ctgtttagag tgctttcccg   2040
tgtcagaatc tcaacccgtt tctgtcgtca aaaaggcgta tcagaaactg tgctacattc   2100
atcatatcat gggaaaggtg ccagacgctt gcactgcctg cgatctggtc aatgtggatt   2160
tggatgactg catctttgaa caataaatga tttaaatcag gtatggctgc cgatggttat   2220
cttccagatt ggctcgagga cactctctct gaaggaataa gacagtggtg gaagctcaaa   2280
cctggcccac caccaccaaa gcccgcagag cggcataagg acgacagcag gggtcttgtg   2340
cttcctgggt acaagtacct cggacccttc aacggactcg acaagggaga gccggtcaac   2400
gaggcagacg ccgcggccct cgagcacgac aaagcctacg accggcagct cgacagcgga   2460
gacaacccgt acctcaagta caaccacgcc gacgcggagt tcaggagcg ccttaaagaa   2520 gatacgtctt ttgggggcaa cctcggacga gcagtcttcc aggcgaaaaa gagggttctt   2580
gaacctctgg gcctggttga ggaacctgtt aagacggctc cgggaaaaaa gaggccggta   2640
gagcactctc ctgtggagcc agactcctcc tcgggaaccg gaaaggcggg ccagcagcct   2700
gcaagaaaaa gattgaattt tggtcagact ggagacgcag actcagtacc tgaccccag   2760 cctctcggac agccaccagc agcccccctct ggtctgggaa ctaatacgat ggctacaggc   2820
agtggcgcac caatggcaga caataacgag ggcgccgacg gagtgggtaa ttcctcggga   2880
aattggcatt gcgattccac atggatgggc gacagagtca tcaccaccag cacccgaacc   2940
tgggccctgc ccacctacaa caaccacctc tacaaacaaa tttccagcca atcaggagcc   3000
tcgaacgaca atcactactt tggctacagc accccttggg ggtattttga cttcaacaga   3060
ttccactgcc acttttcacc acgtgactgg caaagactca tcaacaacaa ctggggattc   3120
cgacccaaga gactcaactt caagctcttt aacattcaag tcaaagaggt cacgcagaat   3180
gacggtacga cgacgattgc caataacctt accagcacgg ttcaggtgtt tactgactcg   3240
gagtaccagc tcccgtacgt cctcggctcg gcgcatcaag gatgcctccc gccgttccca   3300
gcagacgtct tcatggtgcc acagtatgga tacctcaccc tgaacaacgg gagtcaggca   3360
gtaggacgct cttcatttta ctgcctggag tactttcctt ctcagatgct gcgtaccgga   3420
aacaacttta ccttcagcta cacttttgag gacgttcctt tccacagcag ctacgctcac   3480
agccagagtc tggaccgtct catgaatcct ctcatcgacc agtacctgta ttacttgagc   3540
agaacaaaca ctccaagtgg aaccaccacg cagtcaaggc ttcagttttc tcaggccgga   3600
gcgagtgaca ttcgggacca gtctaggaac tggcttcctg accctgttta ccgccagcag   3660
cgagtatcaa agacatctgc ggataacaac aacagtgaat actcgtggac tggagctacc   3720
aagtaccacc tcaatggcag agactctctg gtgaatccgg gccgccat ggcaagccac   3780 aaggacgatg aagaaaagtt ttttcctcag agcggggttc tcatctttgg gaagcaaggc   3840
```

-continued

```
tcagagaaaa caaatgtgga cattgaaaag gtcatgatta cagacgaaga ggaaatcagg   3900
acaaccaatc ccgtggctac ggagcagtat ggttctgtat ctaccaacct ccagagaggc   3960
aacagacaag cagctaccgc agatgtcaac acacaaggcg ttcttccagg catggtctgg   4020
caggacagag atgtgtacct tcaggggccc atctgggcaa agattccaca cacggacgga   4080
cattttcacc cctctcccct catgggtgga ttcggactta aacaccctcc tccacagatt   4140
ctcatcaaga acaccccggt acctgcgaat ccttcgacca ccttcagtgc ggcaaagttt   4200
gcttccttca tcacacagta ctccacggga caggtcagcg tggagatcga gtgggagctg   4260
cagaaggaaa acagcaaacg ctggaatccc gaaattcagt acacttccaa ctacaacaag   4320
tctgttaatg tggactttac tgtggacact aatggcgtgt attcagagcc tcgccccatt   4380
ggcaccagat acctgactcg taatctgtaa ttgcttgtta atcaataaac cgtttaattc   4440
gtttcagttg aactttggtc tctgcgtatt tctttcttat ctagtttcca tggctacgta   4500
gataagtagc atggcgggtt aatcattaac tacaaggaac ccctagtgat ggagttggcc   4560
actccctctc tgcgcgctcg ctcgctcact gaggccgggc gaccaaaggt cgcccgacgc   4620
ccgggctttg cccgggcggc ctcagtgagc gagcgagcgc gcagagaggg agtggccaa    4679
```

```
<210> SEQ ID NO 282
<211> LENGTH: 4726
<212> TYPE: DNA
<213> ORGANISM: Adeno-associated virus

<400> SEQUENCE: 282
ttggccactc cctctatgcg cactcgctcg ctcggtgggg cctggcgacc aaaggtcgcc     60
agacggacgt gctttgcacg tccggcccca ccgagcgagc gagtgcgcat agagggagtg    120
gccaactcca tcactagagg tatggcagtg acgtaacgcg aagcgcgcga agcgagacca    180
cgcctaccag ctgcgtcagc agtcaggtga cccttttgcg acagtttgcg acaccacgtg    240
gccgctgagg gtatatattc tcgagtgagc gaaccaggag ctccattttg accgcgaaat    300
ttgaacgagc agcagccatg ccggggttct acgagattgt cctgaaggtc ccgagtgacc    360
tggacgagcg cctgccgggc atttctaact cgtttgttaa ctgggtggcc gagaaggaat    420
gggacgtgcc gccggattct gacatggatc cgaatctgat tgagcaggca cccctgaccg    480
tggccgaaaa gcttcagcgc gagttcctgg tggagtggcg ccgcgtgagt aaggccccgg    540
aggccctctt ttttgtccag ttcgaaaagg gggagaccta cttccacctg cacgtgctga    600
ttgagaccat cggggtcaaa tccatggtgg tcggccgcta cgtgagccag attaaagaga    660
agctggtgac ccgcatctac cgcggggtcg agccgcagct tccgaactgg ttcgcggtga    720
ccaaaacgcg aaatggcgcc gggggcggga acaaggtggt ggacgactgc tacatcccca    780
actacctgct ccccaagacc cagcccgagc tccagtgggc gtggactaac atggaccagt    840
atttaagcgc ctgtttgaat ctcgcggagc gtaaacggct ggtggcgcag catctgacgc    900
acgtgtcgca gacgcaggag cagaacaaag agaatcagaa ccccaattct gacgcgccgg    960
tcatcaggtc aaaaacctca gccaggtaca tggagctggt cgggtggctg gtggaccgcg   1020
ggatcacgtc agaaaagcaa tggattcagg aggaccaggc ctcgtacatc tccttcaacg   1080
ccgcctccaa ctcgcggtcc cagatcaagg ccgcgctgga caatgcctcc aagatcatga   1140
gcctgacaaa gacggctccg gactacctgg tgggcagcaa cccgccggag gacattacca   1200
aaaatcggat ctaccaaatc ctggagctga acgggtacga tccgcagtac gcggcctccg   1260
tcttcctggg ctgggcgcaa aagaagttcg ggaagaggaa caccatctgg ctctttgggc   1320
```

```
cggccacgac gggtaaaacc aacatcgcgg aagccatcgc ccacgccgtg cccttctacg   1380
gctgcgtaaa ctggaccaat gagaactttc ccttcaacga ttgcgtcgac aagatggtga   1440
tctggtggga ggagggcaag atgacggcca aggtcgtgga gagcgccaag gccattctgg   1500
gcggaagcaa ggtgcgcgtg gaccaaaagt gcaagtcatc ggcccagatc gaacccactc   1560
ccgtgatcgt cacctccaac accaacatgt gcgccgtgat tgacgggaac agcaccacct   1620
tcgagcatca gcagccgctg caggaccgga tgtttgaatt tgaacttacc cgccgttttgg   1680 accatgactt tgggaaggtc accaaacagg aagtaaagga cttttttccgg tgggcttccg   1740 atcacgtgac tgacgtggct catgagttct acgtcagaaa gggtggagct aagaaacgcc   1800
ccgcctccaa tgacgcggat gtaagcgagc caaaacggga gtgcacgtca cttgcgcagc   1860
cgacaacgtc agacgcggaa gcaccggcgg actacgcgga caggtaccaa aacaaatgtt   1920
ctcgtcacgt gggcatgaat ctgatgcttt ttccctgtaa aacatgcgag agaatgaatc   1980
aaatttccaa tgtctgtttt acgcatggtc aaagagactg tggggaatgc ttccctggaa   2040
tgtcagaatc tcaacccgtt tctgtcgtca aaagaagac ttatcagaaa ctgtgtccaa   2100
ttcatcatat cctgggaagg cacccgaga ttgcctgttc ggcctgcgat ttggccaatg   2160
tggacttgga tgactgtgtt tctgagcaat aaatgactta aaccaggtat ggctgctgac   2220
ggttatcttc cagattggct cgaggacaac ctttctgaag gcattcgtga gtggtgggct   2280
ctgaaacctg gagtccctca acccaaagcg aaccaacaac accaggacaa ccgtcggggt   2340
cttgtgcttc cgggttacaa ataccctcgga cccggtaacg gactcgacaa aggagagccg   2400
gtcaacgagg cggacgcggc agccctcgaa cacgacaaag cttacgacca gcagctcaag   2460
gccggtgaca acccgtacct caagtacaac cacgccgacg ccgagtttca ggagcgtctt   2520
caagaagata cgtcttttgg gggcaaccct ggcagagcag tcttccaggc caaaaagagg   2580
atccttgagc tcttggtct ggttgaggaa gcagctaaaa cggctcctgg aaagaagggg   2640
gctgtagatc agtctcctca ggaaccggac tcatcatctg gtgttggcaa atcgggcaaa   2700
cagcctgcca gaaaaagact aaatttcggt cagactggag actcagagtc agtcccagac   2760
cctcaacctc tcggagaacc accagcagcc cccacaagtt tgggatctaa tacaatggct   2820
tcaggcggtg gcgcaccaat ggcagacaat aacgagggtg ccgatggagt gggtaattcc   2880
tcaggaaatt ggcattgcga ttcccaatgg ctgggcgaca gagtcatcac caccagcacc   2940
agaacctggg ccctgcccac ttacaacaac catctctaca gcaaatctc cagccaatca   3000 ggagcttcaa acgacaacca ctactttggc tacagcaccc cttgggggta ttttgacttt   3060
aacagattcc actgccactt ctcaccacgt gactggcagc gactcattaa caacaactgg   3120
ggattccggc caagaaact cagcttcaag ctcttcaaca tccaagttag aggggtcacg   3180
cagaacgatg gcacgacgac tattgccaat aaccttacca gcacggttca agtgtttacg   3240
gactcggagt atcagctccc gtacgtgctc gggtcggcgc accaaggctg tctcccgccg   3300
tttccagcgg acgtcttcat ggtccctcag tatggatacc tcaccctgaa caacggaagt   3360
caagcggtgg gacgctcatc ctttactgc ctggagtact tcccttcgca gatgctaagg   3420
actggaaata acttccaatt cagctatacc ttcgaggatg tacctttca cagcagctac   3480 gctcacagcc agagtttgga tcgcttgatg aatcctctta ttgatcagta tctgtactac   3540
ctgaacagaa cgcaaggaac aacctctgga acaaccaacc aatcacgcg gcttttagc   3600 caggctgggc ctcagtctat gtctttgcag gccagaaatt ggctacctgg gcctgctac   3660
```

| | |
|---|---|
| cggcaacaga gactttcaaa gactgctaac gacaacaaca acagtaactt tccttggaca | 3720 |
| gcggccagca aatatcatct caatggccgc gactcgctgg tgaatccagg accagctatg | 3780 |
| gccagtcaca aggacgatga agaaaaattt ttccctatgc acggcaatct aatatttggc | 3840 |
| aaagaaggga caacggcaag taacgcagaa ttagataatg taatgattac ggatgaagaa | 3900 |
| gagattcgta ccaccaatcc tgtggcaaca gagcagtatg gaactgtggc aaataacttg | 3960 |
| cagagctcaa atacagctcc cacgactgga actgtcaatc atcagggggc cttacctggc | 4020 |
| atggtgtggc aagatcgtga cgtgtacctt caaggaccta tctgggcaaa gattcctcac | 4080 |
| acggatggac actttcatcc ttctcctctg atgggaggct ttggactgaa acatccgcct | 4140 |
| cctcaaatca tgatcaaaaa tactccggta ccggcaaatc ctccgacgac tttcagcccg | 4200 |
| gccaagtttg cttcatttat cactcagtac tccactggac aggtcagcgt ggaaattgag | 4260 |
| tgggagctac agaaagaaaa cagcaaacgt tggaatccag agattcagta cacttccaac | 4320 |
| tacaacaagt ctgttaatgt ggactttact gtagacacta atggtgttta tagtgaacct | 4380 |
| cgccctattg aacccggta tctcacacga aacttgtgaa tcctggttaa tcaataaacc | 4440 |
| gtttaattcg tttcagttga actttggctc ttgtgcactt ctttatcttt atcttgtttc | 4500 |
| catggctact gcgtagataa gcagcggcct gcggcgcttg cgcttcgcgg tttacaactg | 4560 |
| ctggttaata tttaactctc gccatacctc tagtgatgga gttggccact ccctctatgc | 4620 |
| gcactcgctc gctcggtggg gcctggcgac caaaggtcgc cagacggacg tgctttgcac | 4680 |
| gtccggcccc accgagcgag cgagtgcgca tagagggagt ggccaa | 4726 |

```
<210> SEQ ID NO 283
<211> LENGTH: 4767
<212> TYPE: DNA
<213> ORGANISM: Adeno-associated virus

<400> SEQUENCE: 283
```

| | |
|---|---|
| ttggccactc cctctatgcg cgctcgctca ctcactcggc cctggagacc aaaggtctcc | 60 |
| agactgccgg cctctggccg gcagggccga gtgagtgagc gagcgcgcat agagggagtg | 120 |
| gccaactcca tcatctaggt ttgcccactg acgtcaatgt gacgtcctag ggttagggag | 180 |
| gtccctgtat tagcagtcac gtgagtgtcg tatttcgcgg agcgtagcgg agcgcatacc | 240 |
| aagctgccac gtcacagcca cgtggtccgt ttgcgacagt ttgcgacacc atgtggtcag | 300 |
| gagggtatat aaccgcgagt gagccagcga ggagctccat tttgcccgcg aattttgaac | 360 |
| gagcagcagc catgccgggg ttctacgaga tcgtgctgaa ggtgcccagc gacctggacg | 420 |
| agcacctgcc cggcatttct gactcttttg tgagctgggt ggccgagaag gaatgggagc | 480 |
| tgccgccgga ttctgacatg gacttgaatc tgattgagca ggcaccctg accgtggccg | 540 |
| aaaagctgca acgcgagttc ctggtcgagt ggcgccgcgt gagtaaggcc ccggaggccc | 600 |
| tcttctttgt ccagttcgag aaggggggaca gctacttcca cctgcacatc ctggtggaga | 660 |
| ccgtgggcgt caaatccatg gtggtgggcc gctacgtgag ccagattaaa gagaagctgg | 720 |
| tgacccgcat ctaccgcggg gtcgagccgc agcttccgaa ctggttcgcg gtgaccaaga | 780 |
| cgcgtaatgg cgccggaggc gggaacaagg tggtggacga ctgctacatc ccaactacc | 840 |
| tgctccccaa gacccagccc gagctccagt gggcgtggac taacatggac cagtatataa | 900 |
| gcgcctgttt gaatctcgcg gagcgtaaac ggctggtggc gcagcatctg acgcacgtgt | 960 |
| cgcagacgca ggagcagaac aaggaaaacc agaaccccaa ttctgacgcg ccggtcatca | 1020 |
| ggtcaaaaac ctccgccagg tacatggagc tggtcgggtg gctggtggac cgcgggatca | 1080 |

```
cgtcagaaaa gcaatggatc caggaggacc aggcgtccta catctccttc aacgccgcct    1140
ccaactcgcg gtcacaaatc aaggccgcgc tggacaatgc ctccaaaatc atgagcctga    1200
caaagacggc tccggactac ctggtgggcc agaacccgcc ggaggacatt tccagcaacc    1260
gcatctaccg aatcctcgag atgaacgggt acgatccgca gtacgcggcc tccgtcttcc    1320
tgggctgggc gcaaaagaag ttcgggaaga ggaacaccat ctggctcttt gggccggcca    1380
cgacgggtaa aaccaacatc gcggaagcca tcgcccacgc cgtgcccttc tacggctgcg    1440
tgaactggac caatgagaac tttccgttca acgattgcgt cgacaagatg gtgatctggt    1500
gggaggaggg caagatgacg gccaaggtcg tagagagcgc caaggccatc ctgggcggaa    1560
gcaaggtgcg cgtggaccaa aagtgcaagt catcggccca gatcgaccca actcccgtga    1620
tcgtcacctc caacaccaac atgtgcgcgg tcatcgacgg aaactcgacc accttcgagc    1680
accaacaacc actccaggac cggatgttca agttcgagct caccaagcgc ctggagcacg    1740
actttggcaa ggtcaccaag caggaagtca aagactttt ccggtgggcg tcagatcacg    1800
tgaccgaggt gactcacgag ttttacgtca gaaagggtgg agctagaaag aggcccgccc    1860
ccaatgacgc agatataagt gagcccaagc gggcctgtcc gtcagttgcg cagccatcga    1920
cgtcagacgc ggaagctccg gtggactacg cggacaggta ccaaaacaaa tgttctcgtc    1980
acgtgggtat gaatctgatg cttttccct gccggcaatg cgagagaatg aatcagaatg    2040
tggacatttg cttcacgcac ggggtcatgg actgtgccga gtgcttcccc gtgtcagaat    2100
ctcaacccgt gtctgtcgtc agaaagcgga cgtatcagaa actgtgtccg attcatcaca    2160
tcatggggag ggcgcccgag gtggcctgct cggcctgcga actggccaat gtggacttgg    2220
atgactgtga catggaacaa taaatgactc aaaccagata tgactgacgg ttaccttcca    2280
gattggctag aggacaacct ctctgaaggc gttcgagagt ggtgggcgct gcaacctgga    2340 gccctaaac ccaaggcaaa tcaacaacat caggacaacg ctcggggtct tgtgcttccg    2400
ggttacaaat acctcggacc cggcaacgga ctcgacaagg gggaacccgt caacgcagcg    2460
gacgcggcag ccctcgagca cgacaaggcc tacgaccagc agctcaaggc cggtgacaac    2520
ccctacctca gtacaaacca cgccgacgcg gagttccagc agcggcttca gggcgacaca    2580
tcgtttgggg gcaacctcgg cagagcagtc ttccaggcca aaaagagggt tcttgaacct    2640
cttggtctgg ttgagcaagc gggtgagacg gctcctggaa agaagagacc gttgattgaa    2700
tccccccagc agcccgactc ctccacgggt atcggcaaaa aaggcaagca gccggctaaa    2760
aagaagctcg ttttcgaaga cgaaactgga gcaggcgacg gaccccctga gggatcaact    2820
tccggagcca tgtctgatga cagtgagatg cgtgcagcag ctggcggagc tgcagtcgag    2880
ggcggacaag gtgccgatgg agtgggtaat gcctcgggtg attggcattg cgattccacc    2940
tggtctgagg gccacgtcac gaccaccagc accagaacct gggtcttgcc cacctacaac    3000
aaccacctct acaagcgact cggagagagc ctgcagtcca acacctacaa cggattctcc    3060
accccctggg gatactttga cttcaaccgc ttccactgcc acttctcacc acgtgactgg    3120
cagcgactca tcaacaacaa ctgggggcat cgacccaaag ccatgcgggt caaaatcttc    3180
aacatccagg tcaaggaggt cacgacgtcg aacggcgaga caacggtggc taataacctt    3240
accagcacgg ttcagatctt tgcggactcg tcgtacgaac tgccgtacgt gatggatgcg    3300
ggtcaagagg gcagcctgcc tccttttccc aacgacgtct ttatggtgcc ccagtacggc    3360
tactgtggac tggtgaccgg caacacttcg cagcaacaga ctgacagaaa tgccttctac    3420
```

```
tgcctggagt actttccttc gcagatgctg cggactggca acaactttga aattacgtac    3480
agttttgaga aggtgccttt ccactcgatg tacgcgcaca gccagagcct ggaccggctg    3540
atgaaccctc tcatcgacca gtacctgtgg ggactgcaat cgaccaccac cggaaccacc    3600
ctgaatgccg ggactgccac caccaacttt accaagctgc ggcctaccaa ctttccaac     3660
```
(Note: line 3660 as printed: `ctgaatgccg ggactgccac caccaacttt accaagctgc ggcctaccaa cttttccaac`)

```
ctgaatgccg ggactgccac caccaacttt accaagctgc ggcctaccaa cttttccaac    3660
tttaaaaaga actggctgcc cgggccttca atcaagcagc agggcttctc aaagactgcc    3720
aatcaaaact acaagatccc tgccaccggg tcagacagtc tcatcaaata cgagacgcac    3780
agcactctgg acggaagatg gagtgccctg accccggac ctccaatggc cacggctgga    3840
```
(correction: `agcactctgg acggaagatg gagtgccctg acccccggac tccaatggc cacggctgga`)

```
agcactctgg acggaagatg gagtgccctg acccccggac tccaatggcc acggctgga    3840 cctgcggaca gcaagttcag caacagccag ctcatctttg cggggcctaa acagaacggc    3900
aacacggcca ccgtacccgg gactctgatc ttcacctctg aggaggagct ggcagccacc    3960
aacgccaccg atacggacat gtggggcaac ctacctggcg tgaccagag caacagcaac     4020
```
(correction: `aacgccaccg atacggacat gtggggcaac ctacctggcg tgaccagag caacagcaac`)

```
aacgccaccg atacggacat gtggggcaac ctacctggcg tgaccagag caacagcaac    4020 ctgccgaccg tggacagact gacagccttg ggagccgtgc ctggaatggt ctggcaaaac    4080
agagacattt actaccaggg tcccatttgg gccaagattc tcataccga tggacacttt     4140
```

 

```
tgcctggagt actttccttc gcagatgctg cggactggca acaactttga aattacgtac    3480
agttttgaga aggtgccttt ccactcgatg tacgcgcaca gccagagcct ggaccggctg    3540
atgaaccctc tcatcgacca gtacctgtgg ggactgcaat cgaccaccac cggaaccacc    3600
ctgaatgccg ggactgccac caccaacttt accaagctgc ggcctaccaa cttttccaac    3660
tttaaaaaga actggctgcc cgggccttca atcaagcagc agggcttctc aaagactgcc    3720
aatcaaaact acaagatccc tgccaccggg tcagacagtc tcatcaaata cgagacgcac    3780
agcactctgg acggaagatg gagtgccctg acccccggac tccaatggcc acggctgga    3840
cctgcggaca gcaagttcag caacagccag ctcatctttg cggggcctaa acagaacggc    3900
aacacggcca ccgtacccgg gactctgatc ttcacctctg aggaggagct ggcagccacc    3960
aacgccaccg atacggacat gtggggcaac ctacctggcg tgaccagag caacagcaac    4020
ctgccgaccg tggacagact gacagccttg ggagccgtgc ctggaatggt ctggcaaaac    4080
agagacattt actaccaggg tcccatttgg gccaagattc tcataccga tggacacttt    4140
cacccctcac cgctgattgg tgggtttggg ctgaaacacc cgcctcctca aatttttatc    4200
aagaacaccc cggtacctgc gaatcctgca acgaccttca gctctactcc ggtaaactcc    4260
ttcattactc agtacagcac tggccaggtg tcggtgcaga ttgactggga gatccagaag    4320
gagcggtcca aacgctggaa ccccgaggtc cagtttacct ccaactacgg acagcaaaac    4380
tctctgttgt gggctcccga tgcggctggg aaatacactg agcctaggc tatcggtacc    4440
cgctacctca cccaccacct gtaataacct gttaatcaat aaaccggttt attcgtttca    4500
gttgaacttt ggtctccgtg tccttcttat cttatctcgt ttccatggct actgcgtaca    4560
taagcagcgg cctgcggcgc ttgcgcttcg cggtttacaa ctgccggtta atcagtaact    4620
tctggcaaac cagatgatgg agttggccac attagctatg cgcgctcgct cactcactcg    4680
gccctggaga ccaaaggtct ccagactgcc ggcctctggc cggcagggcc gagtgagtga    4740
gcgagcgcgc atagagggag tggccaa                                       4767
```

<210> SEQ ID NO 284
<211> LENGTH: 4642
<212> TYPE: DNA
<213> ORGANISM: Adeno-associated virus

<400> SEQUENCE: 284

```
ctctccccc tgtcgcgttc gctcgctcgc tggctcgttt gggggggtgg cagctcaaag      60
agctgccaga cgacgccct ctggccgtcg ccccccaaa cgagccagcg agcgagcgaa      120
cgcgacaggg gggagagtgc cacactctca agcaaggggg ttttgtaagc agtgatgtca    180
taatgatgta atgcttattg tcacgcgata gttaatgatt aacagtcatg tgatgtgttt    240
tatccaatag gaagaaagcg cgcgtatgag ttctcgcgag acttccgggg tataaaagac    300
cgagtgaacg agcccgccgc cattctttgc tctggactgc tagaggaccc tcgctgccat    360
ggctaccttc tatgaagtca ttgttcgcgt cccatttgac gtggaggaac atctgcctgg    420
aatttctgac agctttgtgg actgggtaac tggtcaaatt tgggagctgc ctccagagtc    480
agatttaaat ttgactctgg ttgaacagcc tcagttgacg gtggctgata gaattcgccg    540
cgtgttcctg tacgagtgga acaaattttc caagcaggag tccaaattct tgtgcagtt    600
tgaaaaggga tctgaatatt ttcatctgca cacgcttgtg gagacctccg gcatctcttc    660
catggtcctc ggccgctacg tgagtcagat tcgcgcccag ctggtgaaag tggtcttcca    720
gggaattgaa ccccagatca acgactgggt cgccatcacc aaggtaaaga agggcggagc    780
```

```
caataaggtg gtggattctg ggtatattcc cgcctacctg ctgccgaagg tccaaccgga      840
gcttcagtgg gcgtggacaa acctggacga gtataaattg gccgccctga atctggagga      900
gcgcaaacgg ctcgtcgcgc agtttctggc agaatcctcg cagcgctcgc aggaggcggc      960
ttcgcagcgt gagttctcgg ctgacccggt catcaaaagc aagacttccc agaaatacat     1020
ggcgctcgtc aactggctcg tggagcacgg catcacttcc gagaagcagt ggatccagga     1080
aaatcaggag agctacctct ccttcaactc caccggcaac tctcggagcc agatcaaggc     1140
cgcgctcgac aacgcgacca aaattatgag tctgacaaaa agcgcggtgg actacctcgt     1200
ggggagctcc gttcccgagg acatttcaaa aaacagaatc tggcaaattt ttgagatgaa     1260
tggctacgac ccggcctacg cgggatccat cctctacggc tggtgtcagc gctccttcaa     1320
caagaggaac accgtctggc tctacggacc cgccacgacc ggcaagacca acatcgcgga     1380
ggccatcgcc cacactgtgc ccttttacgg ctgcgtgaac tggaccaatg aaaactttcc     1440
ctttaatgac tgtgtggaca aaatgctcat ttggtgggag gagggaaaga tgaccaacaa     1500
ggtggttgaa tccgccaagg ccatcctggg gggctcaaag gtgcgggtcg atcagaaatg     1560
taaatcctct gttcaaattg attctacccc tgtcattgta acttccaata caaacatgtg     1620
tgtggtggtg gatgggaatt ccacgacctt tgaacaccag cagccgctgg aggaccgcat     1680
gttcaaattt gaactgacta gcggctcccg ccagattttt ggcaagatta ctaagcagga     1740
agtcaaggac tttttttgctt gggcaaaggt caatcaggtg ccggtgactc acgagtttaa     1800
agttcccagg gaattggcgg gaactaaagg ggcggagaaa tctctaaaac gcccactggg     1860
tgacgtcacc aatactagct ataaaagtct ggagaagcgg gccaggctct catttgttcc     1920
cgagacgcct cgcagttcag acgtgactgt tgatcccgct cctctgcgac cgctcaattg     1980
gaattcaagg tatgattgca aatgtgacta tcatgctcaa tttgacaaca tttctaacaa     2040
atgtgatgaa tgtgaatatt tgaatcgggg caaaaatgga tgtatctgtc acaatgtaac     2100
tcactgtcaa atttgtcatg ggattccccc ctgggaaaag gaaaacttgt cagattttgg     2160
ggattttgac gatgccaata agaacagtaa aataaagcga gtagtcatgt cttttgttga     2220
tcaccctcca gattggttgg aagaagttgg tgaaggtctt cgcgagtttt tgggccttga     2280
agcgggccca ccgaaaccaa acccaatca gcagcatcaa gatcaagccc gtggtcttgt     2340
gctgcctggt tataactatc tcggacccgg aaacggtctc gatcgaggag agcctgtcaa     2400
cagggcagac gaggtcgcgc gagagcacga catctcgtac aacgagcagc ttgaggcggg     2460
agacaacccc tacctcaagt acaaccacgc ggacgccgag tttcaggaga agctcgccga     2520
cgacacatcc ttcgggggaa acctcggaaa ggcagtcttt caggccaaga aaagggttct     2580 cgaaccttt ggcctggttg aagagggtgc taagacggcc cctaccggaa agcggataga     2640
cgaccacttt ccaaaaagaa agaaggctcg gaccgaagag gactccaagc cttccacctc     2700
gtcagacgcc gaagctggac ccagcggatc ccagcagctg caaatcccag cccaaccagc     2760
ctcaagtttg ggagctgata caatgtctgc gggaggtggc ggcccattgg gcgacaataa     2820
ccaaggtgcc gatggagtgg gcaatgcctc gggagattgg cattgcgatt ccacgtggat     2880
gggggacaga gtcgtcacca gtccacccg aacctgggtg ctgcccagct acaacaacca     2940
ccagtaccga gagatcaaaa gcggctccgt cgacggaagc aacgccaacg cctactttgg     3000
atacagcacc ccctgggggt actttgactt taaccgcttc cacagccact ggagcccccg     3060
agactggcaa agactcatca acaactactg gggcttcaga ccccggtccc tcagagtcaa     3120
```

```
aatcttcaac attcaagtca aagaggtcac ggtgcaggac tccaccacca ccatcgccaa    3180
caacctcacc tccaccgtcc aagtgtttac ggacgacgac taccagctgc cctacgtcgt    3240
cggcaacggg accgagggat gcctgccggc cttccctccg caggtcttta cgctgccgca    3300
gtacggttac gcgacgctga accgcgacaa cacagaaaat cccaccgaga ggagcagctt    3360
cttctgccta gagtactttc ccagcaagat gctgagaacg ggcaacaact ttgagtttac    3420
ctacaacttt gaggaggtgc ccttccactc cagcttcgct cccagtcaga acctgttcaa    3480
gctggccaac ccgctggtgg accagtactt gtaccgcttc gtgagcacaa ataacactgg    3540
cggagtccag ttcaacaaga acctggccgg gagatacgcc aacacctaca aaaactggtt    3600 cccgggccc atgggccgaa cccagggctg gaacctgggc tccggggtca accgcgccag    3660
tgtcagcgcc ttcgccacga ccaataggat ggagctcgag ggcgcgagtt accaggtgcc    3720
cccgcagccg aacggcatga ccaacaacct ccagggcagc aacacctatg ccctggagaa    3780
cactatgatc ttcaacagcc agccggcgaa cccgggcacc accgcacgt acctcgaggg    3840 caacatgctc atcaccagcg agagcgagac gcagccggtg aaccgcgtgg cgtacaacgt    3900
cggcgggcag atggccacca acaaccagag ctccaccact gcccccgcga ccggcacgta    3960
caacctccag gaaatcgtgc ccggcagcgt gtggatggag agggacgtgt acctccaagg    4020
acccatctgg gccaagatcc cagagacggg ggcgcacttt caccccctctc cggccatggg    4080 cggattcgga ctcaaacacc caccgccat gatgctcatc aagaacacgc ctgtgcccgg    4140
aaatatcacc agcttctcgg acgtgcccgt cagcagcttc atcacccagt acagcaccgg    4200
gcaggtcacc gtggagatgg agtgggagct caagaaggaa aactccaaga ggtggaaccc    4260
agagatccag tacacaaaca actacaacga cccccagttt gtggactttg ccccggacag    4320 caccgggaa tacagaacca ccagacctat cggaacccga taccttaccc gacccctta    4380 acccattcat gtcgcatacc ctcaataaac cgtgtattcg tgtcagtaaa atactgcctc    4440
ttgtggtcat tcaatgaata acagcttaca acatctacaa aacctccttg cttgagagtg    4500
tggcactctc cccctgtcg cgttcgctcg ctcgctggct cgtttggggg ggtggcagct    4560
caaagagctg ccagacgacg gccctctggc cgtcgccccc ccaaacgagc cagcgagcga    4620
gcgaacgcga caggggggag ag    4642
```

<210> SEQ ID NO 285
<211> LENGTH: 4721
<212> TYPE: DNA
<213> ORGANISM: Adeno-associated virus

<400> SEQUENCE: 285

```
ttggccactc cctctatgcg cgctcgctcg ctcggtgggg cctgcggacc aaaggtccgc      60
agacggcaga gctctgctct gccggcccca ccgagcgagc gagcgcgcat agagggagtg     120
gccaactcca tcactagggg taccgcgaag cgcctccac gctgccgcgt cagcgctgac     180
gtaaatcacg tcatagggga gtggtcctgt attagctgtc acgtgagtgc ttttgcgaca     240
ttttgcgaca ccacgtggcc atttgaggta tatatggccg agtgagcgag caggatctcc     300
attttgaccg cgaaatttga acgagcagca gccatgccgg gttctacga gatcgtgatc     360 aaggtgccga gcgacctgga cgagcacctg ccgggcattt ctgactcgtt tgtgaactgg     420
gtggccgaga aggaatggga gctgccccg gattctgaca tggatctgaa tctgatcgag     480
caggcacccc tgaccgtggc cgagaagctg cagcgcgact cctggtccca atggcgccgc     540
gtgagtaagg ccccggaggc cctgttcttt gttcagttcg agaagggcga gagctacttc     600
```

-continued

```
cacctt cacg ttctggtgga gaccacgggg gtcaagtcca tggtgctagg ccgcttcctg    660
agtcagattc gggagaagct ggtccagacc atctaccgcg gggtcgagcc cacgctgccc    720
aactggttcg cggtgaccaa gacgcgtaat ggcgccggcg ggggaacaa ggtggtggac     780
gagtgctaca tccccaacta cctcctgccc aagacccagc ccgagctgca gtgggcgtgg    840
actaacatgg aggagtatat aagcgcgtgt tgaacctgg ccgaacgcaa acggctcgtg    900
gcgcagcacc tgacccacgt cagccagacg caggagcaga acaaggagaa tctgaacccc    960
aattctgacg cgcccgtgat caggtcaaaa acctccgcgc gctacatgga gctggtcggg   1020
tggctggtgg accggggcat cacctccgag aagcagtgga tccaggagga ccaggcctcg   1080
tacatctcct tcaacgccgc ctccaactcg cggtcccaga tcaaggccgc gctggacaat   1140
gccggcaaga tcatggcgct gaccaaatcc gcgcccgact acctggtggg gccctcgctg   1200
cccgcggaca ttaaaaccaa ccgcatctac cgcatcctgg agctgaacgg gtacgatcct   1260
gcctacgccg gctccgtctt tctcggctgg gcccagaaaa agttcgggaa gcgcaacacc   1320
atctggctgt ttgggcccgc caccaccggc aagaccaaca ttgcggaagc catcgcccac   1380
gccgtgccct tctacggctg cgtcaactgg accaatgaga actttccctt caacgattgc   1440
gtcgacaaga tggtgatctg gtgggaggag ggcaagatga cggccaaggt cgtggagtcc   1500
gccaaggcca ttctcggcgg cagcaaggtg gcgtggacc aaaagtgcaa gtcgtccgcc    1560
cagatcgacc ccaccccgt gatcgtcacc tccaacacca acatgtgcgc cgtgattgac    1620
gggaacagca ccaccttcga gcaccagcag ccgttgcagg accggatgtt caaatttgaa   1680
ctcacccgcc gtctggagca cgactttggc aaggtgacga agcaggaagt caaagagttc   1740
ttccgctggg ccagtgatca cgtgaccgag gtggcgcatg agttctacgt cagaaagggc   1800
ggagccagca aaagacccgc ccccgatgac gcggatataa gcgagcccaa gcgggcctgc   1860
ccctcagtcg cggatccatc gacgtcagac gcggaaggag ctccggtgga ctttgccgac   1920
aggtaccaaa acaaatgttc tcgtcacgcg ggcatgattc agatgctgtt tccctgcaaa   1980
acgtgcgaga gatgaatca gaatttcaac atttgcttca cacacggggt cagagactgt   2040
ttagagtgtt tccccggcgt gtcagaatct caaccggtcg tcagaaaaaa gacgtatcgg   2100
aaactctgcg cgattcatca tctgctgggg cgggcgcccg agattgcttg ctcggcctgc   2160
gacctggtca acgtggacct ggacgactgc gtttctgagc aataaatgac ttaaaccagg   2220
tatggctgcc gatggttatc ttccagattg gctcgaggac aacctctctg agggcattcg   2280
cgagtggtgg gacctgaaac ctggagcccc gaaacccaaa gccaaccagc aaaagcagga   2340
caacggccgg ggtctggtgc ttcctggcta caagtacctc ggaccccttca acggactcga   2400
caaggggag cccgtcaacg cggcggacg agcggccctc gagcacgaca aggcctacga   2460
ccagcagctc aaagcgggtg acaatccgta cctgcggtat aaccacgccg acgccgagtt   2520
tcaggagcgt ctgcaagaag atacgtcatt tggggggcaac ctcggggcgag cagtcttcca   2580
ggccaagaag cgggttctcg aacctctcgg tctggttgag gaaggcgcta agacggctcc   2640
tgcaaagaag agaccggtag agccgtcacc tcagcgttcc cccgactcct ccacgggcat   2700
cggcaagaaa ggccagcagc ccgccagaaa gagactcaat ttcggtcaga ctggcgactc   2760
agagtcagtc cccgaccctc aacctctcgg agaacctcca gcagcgccct ctagtgtggg   2820
atctggtaca gtggctgcag gcggtggcgc accaatggca gacaataacg aaggtgccga   2880
cggagtgggt aatgcctcag gaaattggca ttgcgattcc acatggctgg gcgacagagt   2940
```

```
cattaccacc agcacccgaa cctgggccct gcccacctac aacaaccacc tctacaagca    3000
aatctccagt gaaactgcag gtagtaccaa cgacaacacc tacttcggct acagcacccc    3060
ctgggggtat tttgacttta acagattcca ctgccacttc tcaccacgtg actggcagcg    3120
actcatcaac aacaactggg gattccggcc caagaagctg cggttcaagc tcttcaacat    3180
ccaggtcaag gaggtcacga cgaatgacgg cgttacgacc atcgctaata accttaccag    3240
cacgattcag gtattctcgg actcggaata ccagctgccg tacgtcctcg gctctgcgca    3300
ccagggctgc ctgcctccgt tcccggcgga cgtcttcatg attcctcagt acggctacct    3360
gactctcaac aatggcagtc agtctgtggg acgttcctcc ttctactgcc tggagtactt    3420
cccctctcag atgctgagaa cgggcaacaa ctttgagttc agctacagct cgaggacgt    3480 gcctttccac agcagctacg cacacagcca gagcctggac cggctgatga atccccctcat    3540 cgaccagtac ttgtactacc tggccagaac acagagtaac ccaggaggca cagctggcaa    3600
tcgggaactg cagttttacc agggcgggcc ttcaactatg gccgaacaag ccaagaattg    3660
gttacctgga ccttgcttcc ggcaacaaag agtctccaaa cgctggatc aaaacaacaa    3720 cagcaacttt gcttggactg gtgccaccaa atatcacctg aacggcagaa actcgttggt    3780
taatcccggc gtcgccatgg caactcacaa ggacgacgag gaccgctttt tcccatccag    3840
cggagtcctg attttggaa aaactggagc aactaacaaa actacattgg aaaatgtgtt    3900
aatgacaaat gaagaagaaa ttcgtcctac taatcctgta gccacggaag aatacgggat    3960
agtcagcagc aacttacaag cggctaatac tgcagcccag acacaagttg tcaacaacca    4020
gggagcctta cctggcatgg tctgcagaa ccgggacgtg tacctgcagg gtcccatctg    4080
ggccaagatt cctcacacgg atggcaactt tcacccgtct cctttgatgg gcggctttgg    4140
acttaaacat ccgcctcctc agatcctgat caagaacact cccgttcccg ctaatcctcc    4200
ggaggtgttt actcctgcca gtttgcttc gttcatcaca cagtacagca ccggacaagt    4260
cagcgtggaa atcgagtggg agctgcagaa ggaaaacagc aagcgctgga acccggagat    4320
tcagtacacc tccaactttg aaaagcagac tggtgtggac tttgccgttg acagccaggg    4380
tgtttactct gagcctcgcc ctattggcac tcgttacctc acccgtaatc tgtaattgca    4440
tgttaatcaa taaaccggtt gattcgtttc agttgaactt tggtctcctg tgcttcttat    4500
cttatcggtt tccatagcaa ctggttacac attaactgct tgggtgcgct tcacgataag    4560
aacactgacg tcaccgcggt acccctagtg atggagttgg ccactccctc tatgcgcgct    4620
cgctcgctcg gtggggcctg cggaccaaag gtccgcagac ggcagagctc tgctctgccg    4680
gccccaccga gcgagcgagc gcgcatagag ggagtggcca a                        4721
```

<210> SEQ ID NO 286
<211> LENGTH: 4393
<212> TYPE: DNA
<213> ORGANISM: Adeno-associated virus

<400> SEQUENCE: 286

```
cagagaggga gtggccaact ccatcactag gggtagcgcg aagcgcctcc cacgctgccg      60
cgtcagcgct gacgtaaatt acgtcatagg ggagtggtcc tgtattagct gtcacgtgag    120
tgcttttgcg gcattttgcg acaccacgtg gccatttgag gtatatatgg ccgagtgagc    180
gagcaggatc tccattttga ccgcgaaatt tgaacgagca gcagccatgc cgggcttcta    240
cgagatcgta atcaaggtgc cgagcgacct ggacgagcac ctgccgggca tttctgactc    300
gtttgtgaac tgggtggccg agaaggaatg ggagctgccc ccggattctg acatggatcg    360
```

```
gaatctgatc gagcaggcac ccctgaccgt ggccgagaag ctgcagcgcg acttcctggt    420
ccaatggcgc cgcgtgagta aggccccgga ggccctcttc tttgttcagt tcgagaaggg    480
cgagagctac tttcacctgc acgttctggt cgagaccacg ggggtcaagt ccatggtgct    540
aggccgcttc ctgagtcaga ttcgggaaaa gcttggtcca gaccatctac ccgcggggtc    600
gagccccacc ttgcccaact ggttcgcggt gaccaaagac gcggtaatgg cgccggcggg    660
ggggaacaag gtggtggacg agtgctacat ccccaactac ctcctgccca agactcagcc    720
cgagctgcag tgggcgtgga ctaacatgga ggagtatata agcgcgtgct gaacctggc    780 cgagcgcaaa cggctcgtgg cgcagcacct gacccacgtc agccagacgc aggagcagaa    840
caaggagaat ctgaacccca attctgacgc gcccgtgatc aggtcaaaaa cctccgcgcg    900
ctatatggag ctggtcgggt ggctggtgga ccggggcatc acctccgaga agcagtggat    960
ccaggaggac caggcctcgt acatctcctt caacgccgcc tccaactcgc ggtcccagat   1020
caaggccgcg ctggacaatg ccggcaagat catggcgctg accaaatccg cgcccgacta   1080
cctggtgggg ccctcgctgc ccgcggacat tacccagaac cgcatctacc gcatcctcgc   1140
tctcaacggc tacgaccctg cctacgccgg ctccgtcttt ctcggctggg ctcagaaaaa   1200
gttcgggaaa cgcaacacca tctggctgtt tggacccgcc accaccggca agaccaacat   1260
tgcggaagcc atcgcccacg ccgtgcccct ctacggctgc gtcaactgga ccaatgagaa   1320
cttccccttc aatgattgcg tcgacaagat ggtgatctgg tgggaggagg gcaagatgac   1380
ggccaaggtc gtggagtccg ccaaggccat tctcggcggc agcaaggtgc gcgtggacca   1440
aaagtgcaag tcgtccgccc agatcgaccc cacccccgtg atcgtcacct ccaacaccaa   1500
catgtgcgcc gtgattgacg ggaacagcac caccttcgag caccagcagc ctctccagga   1560
ccggatgttt aagttcgaac tcacccgccg tctggagcac gactttggca aggtgacaaa   1620
gcaggaagtc aaagagttct ccgctgggc cagtgatcac gtgaccgagg tggcgcatga   1680
gttttacgtc agaaagggcg gagccagcaa aagacccgcc ccgatgacg cggataaaag   1740 cgagcccaag cgggcctgcc cctcagtcgc ggatccatcg acgtcagacg cggaaggagc   1800
tccggtggac tttgccgaca ggtaccaaaa caaatgttct cgtcacgcgg gcatgcttca   1860
gatgctgttt ccctgcaaaa cgtgcgagag aatgaatcag aatttcaaca tttgcttcac   1920
acacggggtc agagactgct cagagtgttt ccccggcgtg tcagaatctc aaccggtcgt   1980
cagaaagagg acgtatcgga aactctgtgc gattcatcat ctgctggggc gggctcccga   2040
gattgcttgc tcggcctgcg atctggtcaa cgtggacctg gatgactgtg tttctgagca   2100
ataaatgact taaaccaggt atggctgccg atggttatct tccagattgg ctcgaggaca   2160
acctctctga gggcattcgc gagtggtggg cgctgaaacc tggagccccg aagcccaaag   2220
ccaaccagca aaagcaggac gacggccggg gtctggtgct tcctggctac aagtacctcg   2280
gacccttcaa cggactcgac aagggggagc cgtcaacgc ggcggacgca gcggccctcg   2340
agcacgacaa ggcctacgac cagcagctgc aggcgggtga caatccgtac ctgcggtata   2400
accacgccga cgccgagttt caggagcgtc tgcaagaaga tacgtctttt ggggcaacc   2460 tcgggcgagc agtcttccag gccaagaagc gggttctcga acctcgggt ctggttgagg   2520 aaggcgctaa gacggctcct ggaaagaaga gaccggtaga gccatcaccc cagcgttctc   2580
cagactcctc tacgggcatc ggcaagaaag gccaacagcc cgccagaaaa agactcaatt   2640
ttggtcagac tggcgactca gagtcagttc cagacccctca acctctcgga gaacctccag   2700
```

| | |
|---|---|
| cagcgccctc tggtgtggga cctaatacaa tggctgcagg cggtggcgca ccaatggcag | 2760 |
| acaataacga aggcgccgac ggagtgggta gttcctcggg aaattggcat tgcgattcca | 2820 |
| catggctggg cgacagagtc atcaccacca gcacccgaac ctgggccctg cccacctaca | 2880 |
| acaaccacct ctacaagcaa atctccaacg ggacatcggg aggagccacc aacgacaaca | 2940 |
| cctacttcgg ctacagcacc ccctgggggt attttgactt taacagattc cactgccact | 3000 |
| tttcaccacg tgactggcag cgactcatca acaacaactg gggattccgg cccaagagac | 3060 |
| tcagcttcaa gctcttcaac atccaggtca aggaggtcac gcagaatgaa ggcaccaaga | 3120 |
| ccatcgccaa taacctcacc agcaccatcc aggtgtttac ggactcggag taccagctgc | 3180 |
| cgtacgttct cggctctgcc caccagggct gcctgcctcc gttcccggcg acgtgttca | 3240 |
| tgattcccca gtacggctac ctaacactca acaacggtag tcaggccgtg ggacgctcct | 3300 |
| ccttctactg cctggaatac tttccttcgc agatgctgag aaccggcaac aacttccagt | 3360 |
| ttacttacac cttcgaggac gtgcctttcc acagcagcta cgcccacagc cagagcttgg | 3420 |
| accggctgat gaatcctctg attgaccagt acctgtacta cttgtctcgg actcaaacaa | 3480 |
| caggaggcac ggcaaatacg cagactctgg gcttcagcca aggtgggcct aatacaatgg | 3540 |
| ccaatcaggc aaagaactgg ctgccaggac cctgttaccg ccaacaacgc gtctcaacga | 3600 |
| caaccgggca aaacaacaat agcaactttg cctggactgc tgggaccaaa taccatctga | 3660 |
| atggaagaaa ttcattggct aatcctggca tcgctatggc aacacacaaa gacgacgagg | 3720 |
| agcgtttttt tcccagtaac gggatcctga ttttggcaa acaaaatgct gccagagaca | 3780 |
| atgcggatta cagcgatgtc atgctcacca gcgaggaaga aatcaaaacc actaaccctg | 3840 |
| tggctacaga ggaatacggt atcgtggcag ataacttgca gcagcaaaac acggctcctc | 3900 |
| aaattggaac tgtcaacagc cagggggcct acccggtat ggtctggcag aaccgggacg | 3960 |
| tgtacctgca gggtcccatc tgggccaaga ttcctcacac ggacggcaac ttccacccgt | 4020 |
| ctccgctgat gggcggcttt ggcctgaaac atcctccgcc tcagatcctg atcaagaaca | 4080 |
| cgcctgtacc tgcggatcct ccgaccacct tcaaccagtc aaagctgaac tctttcatca | 4140 |
| cgcaatacag caccggacag gtcagcgtgg aaattgaatg ggagctgcag aaggaaaaca | 4200 |
| gcaagcgctg gaaccccgag atccagtaca cctccaacta ctacaaatct acaagtgtgg | 4260 |
| actttgctgt taatacagaa ggcgtgtact ctgaaccccg ccccattggc acccgttacc | 4320 |
| tcacccgtaa tctgtaattg cctgttaatc aataaaccgg ttgattcgtt tcagttgaac | 4380 |
| tttggtctct gcg | 4393 |

<210> SEQ ID NO 287
<211> LENGTH: 4286
<212> TYPE: DNA
<213> ORGANISM: Bat adeno-associated virus

<400> SEQUENCE: 287

| | |
|---|---|
| aagaaacctc taatcatcat ctgtactttg tgagggtgtg gtcgtgagaa cgggcatgcc | 60 |
| cgggcatgtc ctgttaatca ttaaccagaa tggactttgg acttaataag ttacgtatta | 120 |
| atgggtgtgt atataagtaa gtgtatttcc ggactcactc attcgacttc cggcggtcga | 180 |
| ggagcgaaga cgcgaagcca tggagttcta cagcatcgtt ctccgcctgc ccggcgactt | 240 |
| tgactcggag gtgccgggcc tgcaggacag cttctacaag tggatatccg gccccggcg | 300 |
| ggagctgccg gagtggtcgg acctggaccc gggtcagatc gagtcggcgt atcagattct | 360 |
| cgccgacaag ctggtccgcg agtttgcgca gaagtgggcc gccttcagcg aggacccgag | 420 |

```
ggcgccgtac tttgcgcagc tcgagaaggg ccgggagaac ttccacgtgc acgtgctcgc   480
ctcctccaag aaggtcgggt cgttcgtggt cggccgctac gtcaggaaga tgcgccagca   540
cctcgtcgac gtcgtcttcc ggaagtgcga gcccgtcgac gccgattggc tgcaggtgca   600
aaagagcggg aaccacaagt ccaacagagt caaggacgag gctttatcc ccgcctacct   660 gctgccgaag cgccaatcgg agctgcagtg ggcgtggacg aacatagaaa agtacgagcg   720
cgccacgctg agcgtcgcag agcgcgccag actcgtcgag gagtggaagc ggagcctcgc   780
cgccgaggaa tctgaccccg cggaacccga acgccgtccg cgaaagtcga ccaaatccgc   840
gtcagaatac atggcgctcg tcaggtggct cgtggacaac ggcatcgcga ccgagcgcga   900
gtggatgcgc gaggactcgg acgggtacct gagctacaac gccacgggcg ccacgcgcgc   960
ccagatcaag gccgcgctcg acaacgcggc ccgcatcatg gtcaacacga agacggccgc  1020
cgactacctg gtcggcagga acccgccccct cgacgtggag gacaacagga tctaccggct  1080
gtttcgcatg aacggctacg accccgccta cgcgggcagc gtgctgctcg gctggtgccg  1140
caccggcttc ggcaagcgca acaccgtctg gctcttcggg ccggccacga ccggcaagac  1200
gaacctcgcc gaggccatca gccactcggt gcccttctac ggctgcgtca actggaccaa  1260
cgagaacttc cccttcaacg actgcgtgga caagatgatc atctggtggg aggagggcaa  1320
gatgacgtcc aaggtcgtcg agagcgccaa ggcatcctc ggcggcagca aggtgcgcgt  1380
cgaccagaag tgcaagaact cgcagcagat cgagcccacg cccgtcatca tcaccagcaa  1440
caccaacatg tgcgaggtcg tcgacgggaa ctcgaccacg ttcgagcacc ggcagccgct  1500
cgaggacagg atgttcaagt tcgagctcac cgtcaggctg cagcccacct tcggcaagat  1560
caccaagcag gaggtgcgcg agttctttaa gtgggcggag ctcaacgccg tcgacgtgga  1620
gtacgacttt ctcgtgcgca agatcaacca atcggacact gggggcgggg ttaagcgcgg  1680
ggcagagcct acaaaggacg agcctcccgc gaagcgcgtg ttcttctacg gcgcgacttc  1740
ggagggagag gacgtccgcg agggagcccc gggggaatct gactccgtga acttcgccga  1800
gaggtacgtg tcaaaatgct cgaagcacct gtcctggtca aatatgcgct atccctgccg  1860
cgcctgcgag cgcatgaacg cggacgtgaa cgtctgcacc ccccacggat gcagagactg  1920
tcccgagtgc tttccccgcc ccgccccgt cccgatagcc gagcacgacc tgtgcctggc  1980
cccgatcgag gactctgact tttacgtcgg ctgtatcgac gacgtcaata agagcaata  2040 aaatgattta cagcagtcat gtcgtttgtc gatcaccccc cagactggct cgaggagatc  2100
ggagaggggc tctccgagtt catcggacta gaggcggac cgccgaagcc taagccgggc  2160
taccaggacc gcgcgcgcgg cctcgtcgtc cccggctaca agtacctcgg gcccttcaac  2220
ggactcgaca ggggcgagcc cgtcaacgcg gcgacgcgg cggccaagaa gcacgacgag  2280
gagtacgacc ggctcctcaa ggcggggac aacccgtacc tcgcctacaa ccacgcggac  2340
gccgagttcc agaaggacct cagcggcgac tccagcctag ccggcaacgc cgcgaacgcg  2400
ctcttccagg ccaagaagag ggtcctcgag cccttcggac tggtcgaggg agagccggag  2460
cccaagaaga cgccttccgt caagaggccg cacgcatcgc cggactcgtc gagcggcgtc  2520
gggaagaagg gcgaccagcc cgcgcggaag aggctcgact ttgggacgga gcccgcgggt  2580
caagacggag cgggacgagc ggcccaggca gccggagata tggcatctgc tgaggtggct  2640
gcgggtggtg gcgaccagt gggcgacgat gcacaaggtg ccgatggagt gggtaatgcc  2700
tcaggaaatt ggcattacga ttccgttttgg atggacggcg ctgtcatcac caagtccacc  2760
```

```
cgaacctgga gcctgcccgc ctacaacaac cacctctacc gccagatcca gtccagcggc    2820
accggagacg gcacgtactt tggttacagc acgccttggg gatacttcga tttcaatcga    2880
ttccactgcc acttttctcc cagggactgg cagcggctca tcaacaacca ctggggcatc    2940
cgccccaagc ggctccactt taagctcttc aacatccagg tcaaggaggt cacgacgacc    3000
gacggcacca cgaccatcgc caacaacctc accagcacca tacaggtctt tgcggacacg    3060
gagtaccagc tcccgtacgt gctcggcaac gcccacgagg gctgcctgcc gccgttcccg    3120
gcggacgtct tcatgctgcc gcagtacgcg tacctgacgc tcaacgccaa ccccacgaac    3180
cagggcgcgg ccgcgctcag cctgccgcag agcgccttct actgcctgga gtactttccg    3240
agccagatgc tgaggaccgg gaacaacttc tcgttcagct acgagttcga gaagctgccc    3300
ttccactcga tgttcatgca cagccagagc ctggaccggc tcatgaaccc gctcatcgac    3360
cagtacctct ggtacctcaa cgccacgacc ggcaacaacc tctccttcaa caaggccggc    3420
gccaagaact ccccgagta cttccgcaac tggctgcccg ggcccggcca gcgcgtgcag    3480
cagtggagca cgatcggaac ccagaacaac gcgcagaccg gcacgtgggc cagcgccaac    3540
aagtggatcc tcatgggcag gtccagcaag atggcccccg ggctggccca gccggtcagg    3600
aacgcccaga ccgtcaccaa cggctcgcag ctcatcttca caacgagac catcaagggc    3660 tccaccgcga cggcctccac cgtacactcg gggctgctcg tcaccaacga gtcggagacc    3720
gccccgacca cccccaactc ggcgacaaag tggggcgtca tgacgacaa ccagcagacc    3780 acctccacta cgccgaccgt cagcgacgac ctcgaggcgc acgtcttccc gggcatggtc    3840
tggcaggacc gcgacatcta cctgcagggc ccgatatggg ccaagatccc ggagacggac    3900
ggccacttcc acccgtcccc gctcatgggc ggcttcgggc tcaagaaccc gccgccgcag    3960
atcctcgtca gaacacgcc cgtgcccgcc gtgccgccca cgaccttcac accgcagaag    4020
gtcaactcct tcatcacgca gtactccacc ggccaggtca ccgtcgagat cgagtgggag    4080
ctgcgcaagg agaagagcaa cgcgctggaa cccgagatcc agtacacctc caacttcgag    4140
aactcggcca acgtacagtt ctccgtcaac ggcgacggcg cgtacatcga ccgcgaccg    4200 atcggaaccc ggtacctcac ccacaacctg taaataaatc ccccaataaa ccgtgtattc    4260
gtttcagttg aactttggtc tctgcg    4286
```

<210> SEQ ID NO 288  
<211> LENGTH: 4693  
<212> TYPE: DNA  
<213> ORGANISM: Bovine adeno-associated virus

<400> SEQUENCE: 288

```
gtggcactcc cccccctgtc gcgttcgctc gttcgctggc tcgattgggg gggtggcagc      60
tcaaagagct gccagacgac ggccctctgg gccgtcgccc ccccaatcga gccagcgaac     120
gagcgaacgc gacaggggg gggagtgccac actctctagc aagggggttt tgtaggtggt     180
gatgtcattg ttgatgtcat tatagttgtc acgcgatagt taatgattaa cagtcatgtg     240
atgtgtgtta tccaatagga tgaaagcgcg cgaatgagat ctcgcgagac ttccggggta     300
taaaaggggt gagtgaacga gcccgccgcc attctctgct ctggactgct agaggaccct     360
cgctgccatg gctaccttct atgaagtcat tgttcgcgtt ccatttgatg tggaagagca     420
cctgcctgga atttctgaca actttgtaga ctgggtaact ggtcaaattt gggagctgcc     480
tcccgagtca gatttgaatt tgactctgat tgagcagcct cagctgacgg tggctgacag     540
aattcgccgc gtgttcctgt acgagtggaa caaattttcc aagcaggaga gcaaattctt     600
```

```
tgtgcagttt gaaaagggat ctgaatattt tcatctgcac acgctcgtgg agacctccgg    660
catctcttct atggtccttg gccgctacgt gagtcagatt cgcgcccagc tggtgaaggt    720
ggtgttccag aacattgagc gcggattaac gactgggtc gccatcacca aggtaaagaa     780
gggcggagcc aataaggtgg tggattctgg gtatattccc gcctacctgc tgccgaaggt    840
ccaaccagag cttcagtggg cgtggactaa cctcgaagag tataaattgg ccgccctcaa    900
tctggaggag cgcaaacggc tcgtcgctca gtttcagctt gagtcctcgc agcgctcgca    960
agaggcatct tcccagaggg acgtttcggc tgacccggtc atcaagagca agacttccca   1020
gaaatacatg gcgctggtaa gctggctggt ggaacatggc atcacttccg agaagcagtg   1080
gattcaggag aatcaggaga gctacctgtc cttcaactcc acgggaaaact ctcggagcca   1140 gattaaagcc gcgcttgaca acgcgtcaaa aattatgagt ctgaccaaat ctgcctcaga   1200
ctatctcgtg ggacagactg ttccagagga catttctgaa acagaatct ggcagatttt    1260 tgatctcaac ggctacgacc cggcatacgc gggctctgtt ctctacggct ggtgcactcg   1320
cgcctttgga agaggaaca ccgtctggct gtatggaccc gcgaccaccg aaagaccaa     1380 catcgcggaa gccatctctc acaccgtgcc cttttatggc tgtgtgaact ggactaatga   1440
gaactttccc tttaatgact gtgtggaaaa aatgttgatc tggtgggagg agggaaagat   1500
gaccagcaag gtggtggaac ccgccaaggc catcttgggg gggtctagag tacgagtgga   1560
tcaaaaatgt aaatcctctg tacaagtaga ctctaccccg gtgattatca cctccaatac   1620
taacatgtgt gtggtggtgg atgggaactc cacgacctt gaacaccagc agccgctgga   1680
agaccgcatg ttcagatttg aactcatgcg gcggctcccg ccagatttg gcaagattac    1740 caagcaggaa gtcaaagact tttttgcttg ggcaaaggtc aaccaggtgc cggtgactca   1800
cgagtttatg gttcccaaga agtggcggg aactgagagg gcggagactt ctagaaaacg    1860
cccactggat gacgtcacca ataccaacta taaaagtccg gagaagcggg cccggctctc   1920
agttgttcct gagacgcctc gcagttcaga cgtgcctgta gagcccgctc ctctgcgacc   1980
tctcaactgg tcttccaggt atgaatgcag atgtgactat catgctaaat ttgactctgt   2040
aacgggggaa tgtgacgagt gtgaatattt gaatcggggc aaaaatggct gtatctttca   2100
taatgctaca cattgtcaaa tttgtcacgc tgttcctcca tgggaaaagg aaaatgtgtc   2160
agattttaat gattttgatg actgtaataa agagcagtaa ataaagtgag tagtcatgtc   2220
ttttgttgac caccctccag attggttgga atcgatcggc gacggctttc gtgaatttct   2280
cggccttgag gcgggtcccc cgaaacccaa ggccaatcaa cagaagcaag ataacgctcg   2340
aggtcttgtg cttcctgggt acaagtatct tggtcctggg aacggccttg ataagggcga   2400
tcctgtcaat tttgctgacg aggttgcccg agagcacgac ctctcctacc agaaacagct   2460
tgaggcgggc gataacccctt acctcaagta caaccacgcg gacgcagagt tcaggagaa    2520 actcgcttct gacacttctt ttggggggaaa ccttgggaag ctgttttcc aggctaaaaa    2580 gaggattctc gaacctcttg gcctggttga gacgccggat aaaacggcgc ctgcggcaaa   2640
aaagaggcct ctagagcaga gtcctcaaga gccagactcc tcgagcggag ttggcaagaa   2700
aggcaaacag cctgccagaa agagactcaa cttttgacgac gaacctggag ccggagacgg   2760
gcctccccca gaaggaccat cttccggagc tatgtctact gagactgaaa tgcgtgcagc   2820
agctggcgga aatggtggcg atgcgggaca aggtgccgag ggagtgggta atgcctccgg   2880
tgattggcat tgcgattcca cttggtcaga gagccacgtc accaccacct caacccgcac   2940
```

```
ctgggtcctg ccgacctaca acaaccacct gtacctgcgg ctcggctcga gcaacgccag    3000
cgacaccttc aacggattct ccaccccctg gggatacttt gactttaacc gcttccactg    3060
ccacttctcg ccaagagact ggcaaaggct catcaacaac cactggggac tgcgccccaa    3120
aagcatgcaa gtccgcatct tcaacatcca agttaaggag gtcacgacgt ctaacgggga    3180
gacgaccgta tccaacaacc tcaccagcac ggtccagatc tttgcggaca gcacgtacga    3240
gctcccgtac gtgatggatg caggtcagga gggcagcttg cctcctttcc caacgacgt    3300 gttcatggtg cctcagtacg ggtactgcgg actggtaacc ggaggcagct ctcaaaacca    3360
gacagacaga aatgccttct actgtctgga gtactttccc agccagatgc tgagaaccgg    3420
aaacaacttt gagatggtgt acaagtttga aaacgtgccc ttccactcca tgtacgctca    3480
cagccagagc ctggataggc tgatgaaccc gctgctggac cagtacctgt gggagctcca    3540
gtctaccacc tctggaggaa ctctcaacca gggcaattca gccaccaact tgccaagct    3600 gaccaaaaca aacttttctg gctaccgcaa aaactggctc ccggggccca tgatgaagca    3660
gcagagattc tccaagactg ccagtcaaaa ctacaagatt ccccagggaa gaaacaacag    3720
tctgctccat tatgagacca gaactaccct cgacggaaga tggagcaatt ttgccccggg    3780 aacgccatg gcaaccgcag ccaacgacgc caccgacttc tctcaggccc agctcatctt    3840
tgcggggccc aacatcaccg gcaacaccac cacagatgcc aataacctga tgttcacttc    3900
agaagatgaa cttagggcca ccaaccccg ggacactgac ctgtttggcc acctggcaac    3960
caaccagcaa aacgccacca ccgttcctac cgtagacgac gtggacggag tcggcgtgta    4020
cccgggaatg gtgtgcaggg acagagcat ttactaccaa gggcccattt gggccaaaat    4080
tccacacacg gatggacact ttcacccgtc tcctctcatt ggcggatttg gactgaaaag    4140
cccgcctcca caaatattca tcaaaaacac tcctgtaccc gccaatcccg caacgacctt    4200
ctctccggcc agaatcaaca gcttcatcac ccagtacagc accggacagg tggctgtcaa    4260
aatagaatgg gaaatccaga aggagcggtc caagagatgg aacccagagg tccagttcac    4320
gtccaactac ggagcacagg actcgcttct ctgggctccc gacaacgccg gagcctacaa    4380
agagcccagg gccattggat cccgatacct caccaaccac ctctagccca attctgttgc    4440
ataccctcaa taaaccgtgt attcgtttca gtaaaatact gcctcttgtg gtcattcggc    4500
gtacaacagc ttacaacaac aacaaaaccc ccttgctaga gagtgtggca ctccccccc    4560 tgtcgcgttc gctcgttcgc tggctcgatt ggggggtgg cagctcaaag agctgccaga    4620
cgacggccct ctgggccgtc gccccccaa tcgagccagc gaacgagcga acgcgacagg    4680
ggggggagtg cca    4693
```

<210> SEQ ID NO 289
<211> LENGTH: 4432
<212> TYPE: DNA
<213> ORGANISM: Snake parvovirus

<400> SEQUENCE: 289

```
cgccccaccc ctagtgatcg cgcgcgctct ctcttggggc ctgacggccg aaggccgtca    60
gctgccgagc ttcgctcggc aggccccaag agagagcgcg cgcgatcact aggggtgggg    120
cgagtgccct gctcaacggg ttttttggtg ggcggagcaa tgacgtcagc ggacatgtct    180
ggacatgtct ttgagcaagt ccatataagg agttccgccg gatatgcaaa tgagcaatcg    240
cgcaaagcat tttgggtagt caccatgaat aaaaaggaca gcaagaaaga tgacgcccca    300 taatttaat aggaatttta accatggcgt tttacgaggt tgtgtttcgt ttgccaagag    360
```

```
acaataacaa cttgttggat gaagatagat atcagccaga gttgaaagaa gaagatgact      420
ggcctgagga atatttaacc agtgaagatg ccagctttat cggactagcg tatgctgtgc      480
taagtgaaat tcggagattc tttggaaagg aactacaatg gtttgcccag gttgaatggt      540
gtcctactgc tggttaccac atgcatgttt tgttgaacca tcctaagctg agtaaccaga      600
cttatggaag aaaggtcaat gaactggctt gccgtatagt cgatacctt  ggcctaatta      660 atccagaaga agtcatcagt acccattatg ttaaaagcaa ctatggacat aaaaaggtga      720
gagtcattca cctagagtct tatttgaaga actacttttt cagaaagact ttagctcctc      780
ccaattatac cgaggaagga gactataaaa gagaggaaga agtcgtgctg tgggcattta      840
cgaatatcgt cgcttggaag ccattcgtgc ggaatctcat caagagatcg gagctagcga      900
ctgttcctaa gcaaccagag aatccggcgg gagacggacc ggcacctcga gtgactgcag      960
gaacccgcca ttttatggaa accatcgact ggttggtgaa acatggaatt actacagaac     1020
gagaattctg ccacgccaac cgcccttgt  acctgtctat gctggcttct acttcgggtg     1080
ctgggcagat taaaagagcg ctggaccagg cgaaacacat gatgaccagc accatgtcag     1140
cagaggatta cctgacaaca gaagaggatg tgatcgaacc acctactgaa aatagaatct     1200
acaagattat gaaactgaat cgctatgatc cagaactagc agctgctctc ttctacggct     1260
ggacctgcaa gaactttggc aagagaaaca ccatctggct gtatggtcca gctactaccg     1320
gcaaaaccat catcgctcaa gctattgcac atgctgttaa actgtttgct ggtgttaatt     1380
ggactaatga aaactttccc ttctgtaact gtccagggaa actgcttatc tggtgggagg     1440
agggcaagat gacaaacaaa atggtggaga cggctaaatg tatactgggg ggatctgctg     1500
tacctgtaga catcaaaggc aaacccgctg aaatgtgtcc tcaaacaccc tgtattatta     1560
ctagcaatac taacatgtgt caagtatatg atggtaatag ttctagcttt gagcaccaag     1620 aaccccctaga ggaacgcatg tttatgttca gacttaatac taaactgcca tcgacctttg     1680
gcaagatcac agaagaggaa gtcaaacagt ttattacctg ggggaggagc ttaaaggttc     1740
aagttccaca tcagttcaga gtgcctacca caggagagta taaaaggcca gcccccgagg     1800
cgaaagctca ttcttcggat gagccgccaa aagagaaggt cgcgcgtatt gatgactctc     1860
taaccaggta tgttaacaat attgatgagt cagctaccag tagagaaatg tttctagaga     1920
ttgctaatac taatcaatgt atgttgcatc attgcttttc ttgtaccgaa tgttatcctg     1980
aattgcttga tgacatggac aaggaacaat aaacttactg ataacagata tggattttct     2040
cgatgatttc tttgcagata aatataaaga gactgttaac gaactcggta accggtcaa     2100 tcctaaacct gtaaaacaca ttagcgaagc tcactcgcaa cctggcagca ggaggggctt     2160
tgtggtgcct gggtatcggt atcttgggcc tggtaatagc ttggaccgtg gaaagcccgt     2220
taacaaagca gacgaggctg ctaaaaagca cgatcaagaa tacgatcaac agcttaaagc     2280
gggagacaat ccctacataa aatataatca cgcggacgaa cagttccaga agacctaca      2340 aggtgatacc agtctagccg gcaacgcggc taacgctcta tttcaaggca aaaagactct     2400
actagcgccc cttggcctag tagagacccc tgtcggcaaa acgtctgaaa agcacaaatt     2460
agacgaatac tatcctaaag ctaaaaaggc caaacaaggc ttgcagatac cagctccacc     2520
taaaggcgga gaagaagaag ctacatcgtc acaatctgga gggagcccag caggttccga     2580
tactagcggc acatctgtca tggctacagg aggaggcggt ccgatggcag acgataacca     2640
gggcgccgag ggagtgggta attcctcagg tgattggcat tgcgatacca agtggatggg     2700
```

```
agaccacgtc attacaaagt caaccagaac ttgggtgctc cccacttacg ggaatcatct    2760
ctacgggcct atcaactttg acggcaccac aggttcgggt gctaatgcag cctatgcagg    2820
atacaagact ccctgggggt actttgactt caatcgattc cattgccact tctcccccg     2880 agactggcaa agactcatca acaaccacac aggcatcagg ccgaaaggac tcaaaatcaa    2940
agtctttaac gtccaagtca agaagttac  aacacaagat tcaacgaaaa caattgccaa    3000
caatctcacc agcaccgtac agatctttgc ggacgagaac tacgacttac catatgtatt    3060
aggcagtgct acacaaggca catttcctcc atttcccaat gatgtattta tgttaccaca    3120
atatgcttat tgtacacttc aaggaaattc ggggaaattt gtagatagaa gtgccttta    3180 ttgtttagaa tattttcctt cacaaatgct gagaacagga acaattttg  agttccagtt    3240 taaatttgaa gaagttccct ttcattctgg atgggcacag agtcaaagcc tagacagatt   3300
gatgaatccg ttgcttgatc aatatctgat aggagactat ggaacagatg catcaggaaa   3360
ccttatttat cacagagctg gtccaaatga tttgaatgaa ttctacaaga attgggcacc   3420
tgcaccctat gaatgtatcc agaatattaa cagcagtgat aataccaaga atgctaattc   3480
tataaatggt tcaaattcta ccaacaaatg gggactacaa ggaagacaag catgggatgc   3540
tccaggattt gttcaagcta gtacctatga aggtgcagca gcaggacaat ctcttcttaa   3600
tggcgtactt actttcgata aaagttcagc tactacttca tctccagctg ctactgcagt   3660
aaacagaaca attgaagacg aaatacaggg taccaataat tttggtaatg ctagaaataa   3720
cattgttgct atcaatcaac aaacgaaagg aacaaatcca acaacaggta gtacatctca   3780
atttgagaca atgccaggta tggtgtggtc taatagagac atttacttac aggggcctat   3840
ttgggctaaa attccaaata cagatggaca ttttcatcct tctcccagaa tgggtggttt   3900
tggattaaaa catcctccgc ctatgattct gatcaaaaat acaccagttc ctgctgatcc   3960
tccaactacc ttcaatccaa tgccacagac tagtttcatt actgaataca gtacaggaca   4020
agtaactgtt gaaatgttgt gggaggtaca gaaagaatcc tccaaaagat ggaatccaga   4080
agtacagttt acttccaatt ttggaacttc agatccagct gttgatggaa taccgtttgg   4140
aattaataat ttgggtactt atgttgaatc tagacctatt ggaactcgtt atatttctaa   4200
acacttgtaa ataataaaaa ttgtcaaatt tgcactaaga attgttgtca cgtggttgtt   4260
tacatgcttg ctaaaacacg ccccaccaaaa aaccgcttga gcagggcact cgccccaccc   4320
ctagtgatcg cgcgcgctct ctcttggggc ctgccgagcg aagctcggca gctgacggcc   4380
ttcggccgtc aggccccaag agagagcgcg cgcgatcact aggggtgggg cg           4432
```

<210> SEQ ID NO 290
<211> LENGTH: 4682
<212> TYPE: DNA
<213> ORGANISM: Avian adeno-associated virus

<400> SEQUENCE: 290

```
tggccagttt ccaaaacagg ctcgctcgct cactcgggcc ccggcccaa  ggggccggt      60 agcgacgcct ttggcgtcgc ggcccgagtg agcgagcgag cctgttttgg aaactggcca   120
gcactccggt gaggtaatgc cgtcacgtgg tcggaacgg  gaacgggaaa tctcgcgaga   180
acgtaaacaa atataagacg acgccacacg gcgctgcgtc atacgcgcgc gcgcaccggc   240
gagatgaggt cgtactacga ggtcatcgtt caactgccga acgacgtcga gagtcaggta   300
cctggaatct ccgattcatt cgtcaactgg attacgtcgc gagaatggac gttgccggaa   360
gacgccgatt gggatttgga ccaggtcgat caagttcaac tgacgctcgg cgacaaaatc   420
```

-continued

```
caacgggaga ttcgaaatca ctgggggacg atggcgaaag aaccggactt tcactatttt    480
atccaactgg aacaaggtga ggtgttcttt catttgcacg tcctgctgga aacgtgttcc    540
gtgaagccga tggtactcgg aagatatatt cgacatattc aacaaaaaat tgtcagtaaa    600
gtctactgcg gccacgagcc cgcgatggaa ggatggatgc gggtgaccaa gaccaaaaat    660 ttcggggggcg cgaacaaggt ccgggccgag tcgtatattc ccgcctacct gattccgaaa    720
cagcaaccga agtgcagtg gcgtggact aacgtgcccg agtatataaa agcgtgcctg    780
caccgagaac tgcgtgccag tctcgcgcga cttcacttcg aggaggcggg gctctcgcaa    840
tccaaggaaa atctcgcgag aactgcagac ggcgctcccg tgatcgcgac ccgcgtcagc    900
aaacgctaca tggagctcgt ggattggctc gtggagaagg ggatcaccac cgagaaggaa    960
tggctgctgg aaaacagaga aagctttcgg agcttccagg cctcgagcaa ctcggcgcgt   1020
cagatcaaga cggccctgca aggcgccatc caggagatgc ttctgaccaa gacggcggag   1080
gactacctcg tcggaaaaga acccgtctcg gacgacgaga ttcgtcagaa ccgcatctac   1140
aagattttgg aactgaacca ctacgaccca gcgtacgtgg ggagtatttt ggtcgggtgg   1200
tgccagaaga aatggggcaa gcgaaacacg ctgtggctgt tcggacctgc gaccaccggc   1260
aagaccaaca tcgcggaggc tattgcccat gctgtgccgt tctatggatg cgttaactgg   1320
accaacgaga acttccgtt caacgactgc gtcgaaaaga tgattatctg gtgggaagag   1380
ggcaaaatga ccgccaaggt ggtggaaacg gctaaagcga ttctgggagg atctcgggtg   1440
agagtggacc aaaaatgcaa agcttcggtt ccgatcgaac cgacgccggt cattattacc   1500
agtaacacca acatgtgtta tgtcatcgac gggaacacga ctacgttcga gcataagcag   1560
ccgttggagg acaggatgtt taagctcgag ctgttgactc gtttacccga tgactttggt   1620
aaggtgacca acaggaggt gcgtcaattc ttcaggtggt cccaggatca cctgacccct   1680
gtgatcccag aattcctggt gcggaaggcg gagtctcgca aaagacccgc cccctccggg   1740
gaaggctata taagcccgac aaagcggccc gcgctcgcag agcagcagca ggcgtcggag   1800
agcgcggagc cggttcccac caggtatcgt atcaaatgct cgaaacattg cgggatggat   1860
aaaatgttgt ttccttgcca aatttgtgaa tcgatgaaca gaaatattaa tatatgtgcg   1920
attcataaaa caacggaatg taaagaatgt tttccggaat acggggataa ggacactgtg   1980
ccagaactac ccccctgtac agaacataac gtgtctcgtt gttatcaatg tcattcgggc   2040
gaattgtatc gcgtgacttc ggactctgac gagaaacccg cccccgagag tgatgaaggc   2100
actgagccat cctatgctcc ctgcacgatt caccatttga tgggcaagag tcgcgggtta   2160
gtgtcgtgtg ctgcatgtcg tttgaaaaat agtacgttgc atgatgactt ggatgacggt   2220
gatcttgaac aataaatgat tgaaatatag ccatgtctct catttctgat gcgattccag   2280
attggttgga gcggttggtc aaaaagggag tgaatgctgc ggctgatttc taccatttgg   2340
aaagcggtcc tcctcatcct aaggcaaatc agcaaactca gaatctcct gaaaaggacg   2400 attcgagagg tctcgtgttc ccgggttaca agtatctagg cccttttcaac ggtctagata   2460 aaggaaaacc cgtcaacgag gcagacgctg ccgccttaga gcacgacaag gcttacgacc   2520
tcgaactcaa ggacgggcac aacccgtact ttgagtacaa cgaggccgat agacgtttcc   2580
aggaacgtct caaagacgat acctcttttcg gagggaatct cggtaaagcc atctttcagg   2640
ccaaaaagag ggtcctcgag ccctttggtc tgattgaaca cccgacaac acggccggga   2700 ccggggagaa gcgtcccgaa cgcgtcgacg acttttttccc gaaaaagaag aaggccaaga   2760
```

| | |
|---|---|
| ccgagcaagg caaagcccct gctcaaacgg gcgaagaccc cggagaagga acctcttcca | 2820 |
| acgctggatc aagcgccccc tctagtgtgg gatcatctgt catggctgaa ggaggtggcg | 2880 |
| gtccaatggg cgatgcaggc caaggtgccg acggagtggg caattcctcg ggaaattggc | 2940 |
| attgcgattc ccaatggctg gacaacgagt tcgttacccg aaccactcga acctgggtcc | 3000 |
| tgcccagcta caacaaccac ttgtacaagc ggatccaagg accgggagga accgacccca | 3060 |
| acaataaatt ctttggattc agcaccccct gggggtactt tgactacaac cgattccact | 3120 |
| gccacttctc cccccgagac tggcaacgac tcatcaacaa caactggggc atccgaccca | 3180 |
| aagcgatgcg ctttagactc tttaacatcc aggttaaaga agtcactgtc caagactcca | 3240 |
| acaccaccat cgccaacaac ctcaccagca cggtccaagt ctttgcggac aaggactacc | 3300 |
| agctgccgta cgtcctcgga tcggctacag agggcacctt cccgccgttc ccagcggata | 3360 |
| tctacacgat cccgcagtat ggttactgca cgctaaacta caacaacgag gcggtggatc | 3420 |
| gttcggcctt ctactgtcta gactatttcc cctcagacat gctgcggaca ggaaataact | 3480 |
| ttgaattcac ttacacgttc gaggacgttc ctttccatag catgtttgct cacaaccaga | 3540 |
| cgctagaccg gctgatgaat cctctcgtcg atcagtacct gtgggctttc agttccgtca | 3600 |
| gccaaacagg ctcgtctgga cgggcactca attattcacg cgcgaccaaa accaatatgg | 3660 |
| caacccagta cagaaactgg ttacctggac ccttcgtccg ggatcagcaa atctttacgg | 3720 |
| gggctagcaa catcacccaa aacaacgtgt caacgtttg gataaaggc aagcagtggg | 3780 |
| tgatagacaa tcggatcaat atgatgcagc ccggccctgc agcagcgacc acctttagcg | 3840 |
| gagaacccga ccgtcaagcc atgcaaaaca cgctggcctt tagtcggacg gtctacgacc | 3900 |
| agacaaccag tacgaccgat cgtaaccagt tgctcattac caacgaagat gaaatcagac | 3960 |
| ccaccaactc ggtcggcatc gacacgtggg gagtagttcc caacaacaac cagtccaagg | 4020 |
| tgaccgccgg cactcgcgcg gccatcaaca accaaggggc gcttcccggg atggtgtggc | 4080 |
| aaaacagaga catttacctc caaggaccca tttgggccaa atcccccgac acagacaatc | 4140 |
| acttccatcc gtccccgctt attggcgggt ttggctgcaa gcatccccct ccccagattt | 4200 |
| tcattaaaaa cacacccgtc ccggccaacc cttcggaaac gttccagacg gccaaggtgg | 4260 |
| cctccttcat caaccagtac tcgaccggac agtgcaccgt cgaaatcttt tgggaactca | 4320 |
| agaaggaaac ctccaagcgc tggaaccccg aaatccagtt cacctccaac tttggcaacg | 4380 |
| cggccgacat ccagtttgct gtctccgaca ccggatccta ttccgaacct cgtcccatcg | 4440 |
| gtacccggta ccttaccaaa cctctgtaaa ttaaaccctt caataaaccg tttatgcgta | 4500 |
| actgtacttc cgtctcctgt cgttattcag tcacatgata cggcattacc tcaccggagt | 4560 |
| gctggccagt ttccaaaaca ggctcgctcc tcactcgggc ccgcgacgcc aaaggcgtcg | 4620 |
| ctaccggccc ccttggggcc ggggcccgag tgagcgagcg agcctgtttt ggaaactggc | 4680 |
| ca | 4682 |

<210> SEQ ID NO 291
<211> LENGTH: 4694
<212> TYPE: DNA
<213> ORGANISM: Avian adeno-associated virus

<400> SEQUENCE: 291

| | |
|---|---|
| tggccagttt ccaagacagg ctcgctcgct cactcgggcc ggggcccaa aggggcccct | 60 |
| agcgaccgct tcgcggtcgc ggcccgagtg agcgagcgag cctgtcttgg aaactggcca | 120 |
| gcactccggt gaggtaatgc cgtcacgtgg tcgggaatgg gaacgggaaa tctcgcgaga | 180 |

```
acgtaaacaa atataagacg gcgccacacg gcgctgcgtc atacgcgcgc gcgcaccggc    240
gagatgaggt cgtactacga ggtcatcgtt cagctgccca acgacgtcga gagtcaggta    300
cctggaatct ccgattcgtt cgtcaactgg attacgtcgc gagaatggac gttgcctgag    360
gacgccgatt gggatttgga ccaggtcgat caagttcaac tgacgctcgg cgacaaaatc    420
caacgggaga ttcgaactca ttggggacg atggccaaag aaccggactt tcactatttt    480
atccaactgg aacaaggtga ggtgttcttt catttacacg tcctgctgga aacgtgttcc    540
gtaaagccga tggtactcgg aagatatatc cgacatattc aacaaaaaat tgtgagtaaa    600
gtctactgcg ccacgagcct acgatggaag gatggatgcg tggtgaccaa gaccaaaaat    660 ttcggggcg cgaacaaggt ccgggccgag tcgtatattc ccgcctacct gatcccgaaa    720
cagcaaccgg aagtgcagtg ggcgtggact aacgtgcccg agtatataaa agcgtgcttg    780
caccgagaac tgcgtgccag tctcgcgcga cttcacttcg aggaggcggg cgtctcgcaa    840
tccaaggaaa atctcgcgag aactgcgacg gcgctcccg tgatgccgac ccgcgtcagc    900
aaacgctaca tggagctcgt ggattggctc gtggagaagg ggatcaccac cgagaaggaa    960
tggctgctgg aaaacagaga aagctttcgg agctttcagg cctcgagcaa ctcggcgcgt   1020
cagatcaaga cggccctgca aggcgccatt caggagatgc ttctgaccaa gacggcggag   1080
gactacctcg tcggaaagga tcccgtctcg gacgacgaca tccgtcagaa ccgcatctac   1140
aagattctgg aactgaacca ctacgaccca gcgtacgtgg ggagtatttt ggtcgggtgg   1200
tgccagaaga aatggggcaa gcgaaacacg ctgtggctgt tcggacatgc gaccaccggc   1260
aagaccaaca tcgcggaggc tattgcccat gctgtgccgt tctatggatg cgttaactgg   1320
accaacgaga actttccgtt caacgactgc gtcgaaaaaa tgattatctg gtgggaggag   1380
ggcaaaatga ccgccaaagt ggtggaaaca gccaaggcga ttctgggagg atctcgggtg   1440
agagtggacc aaaaatgcaa agcttcggtt ccgatcgaac cgacgccggt cattattacc   1500
agtaacacca acatgtgtta tgtcatcgac gggaacacga ccacgttcga gcataagcag   1560
ccgttggagg acaggatgtt taagctcgaa ttgctgactc ggttgcctga tgactttggt   1620
aaggtgacca acaggaggt gcgtcaattc ttcaggtgg ctcaggatca cctgacccct   1680
gtgatcccag aattcctagt gcggaaggcg gagtctcgca aaagaccgc ccttccggg   1740 gaaggctata taagcccgac aaagcggccc gcgctcgcag agcagcagca ggcgtcggag   1800
agcgcggacc cggttcccac caggtatcgt atcaaatgct cgaaacattg cggtatggat   1860
aaaatgttgt ttccttgcca aatttgtgaa tcgatgaaca gagatattaa tatttgtgct   1920
attcataaaa cgaccgactg taaagagtgt ttccccgact acggggataa agatgatgta   1980
gaactacccc cctgtacaga acacaacgtg tctcgttgtt atcaatgtca ttcgggcgaa   2040
ttgtatcgcg tgacttcgga ctctgacgag aaacctgccc ccgagagtga tgaaggcacc   2100
gagccatcct atgctccctg cacgattcac cacctgatgg gcaagagtca cgggttagtc   2160
acttgcgcgg cgtgtcggtt gaaaaatagt acgttgcatg atgacttgga tgacggtgat   2220
ctcgaacaat aaatgattga aatgtagcca tgtctctcat ttctgatgcg attccagatt   2280
ggttggagcg gttggtcaaa aagggagtga atgctgcagc tgatttctac catttggaaa   2340
gcggtcctcc tcgtcctaag gcaaatcagc aaactcaaga atctcttgaa aaggacgatt   2400
cgagaggtct cgtgttccca ggctacaatt atctaggccc tttcaacggt ctagataaag   2460
gagaacccgt caacgaggca gacgctgccg ccttagaaca cgacaaggct tacgacctcg   2520
```

| | |
|---|---|
| aaatcaagga cgggcacaac ccgtactttg agtacaacga ggccgacaga cgtttccagg | 2580 |
| aacgtctcaa agacgatacc tcctttggag gcaatttagg taaagccatc ttccaggcca | 2640 |
| aaaagagggt tctcgaaccc tttggtctgg tggaagactc aaagacggct ccgaccggag | 2700 |
| acaagcggaa aggcgaagac gaacctcgtt tgcccgacac ttcttcacag actcccaaga | 2760 |
| aaaacaagaa gcctcgcaag gaaagacctt ccggcggggc agaagatccg ggcgaaggca | 2820 |
| cctcttccaa cgctggagca gcagcacccg cctctagtgt gggatcatct atcatggctg | 2880 |
| aaggaggtgg cggcccagtg ggcgatgcag gccaggtgc cgatggagtg ggcaattcct | 2940 |
| ccggaaattg gcattgcgat tcccaatggc tggaaaacgg agtcgtcact cgaaccaccc | 3000 |
| gaacctgggt cttgcccagc tacaacaacc acctgtacaa acgaatccaa ggacccagcg | 3060 |
| gaggcgacaa caacaacaaa ttctttggat tcagcacccc ctggggatac tttgactaca | 3120 |
| atcgattcca ctgccacttt tccccgcgag actggcaacg actcatcaac aacaactggg | 3180 |
| gcatccgtcc caaagcgatg cgctttagac tctttaacat ccaggttaaa gaggtcacgg | 3240 |
| tccaagactt caacaccacc atcggcaaca acctcaccag tacggtccag gtctttgcgg | 3300 |
| acaaggacta ccaactgccg tacgtcctcg gatcggctac cgaaggcacc ttcccgccgt | 3360 |
| tcccagcgga tatctacacg atcccgcagt acgggtactg cacgctaaac tacaacaacg | 3420 |
| aggcggtgga tcgttcggcc ttctactgtc tggactactt ccctcagac atgctgcgga | 3480 |
| caggaaataa ctttgagttt acttacacct tcgaggacgt tcctttccat agcatgtttg | 3540 |
| cccacaacca gacgctagac cggctgatga tcccctcgt ggatcagtac ctctgggctt | 3600 |
| tcagctccgt cagccaagca ggctcatctg gacgagctct tcattactcg cgggcgacta | 3660 |
| aaaccaacat ggcggctcaa tataggaact ggttacctgg gcctttcttc cgtgatcagc | 3720 |
| aaatctttac gggcgctagc aacatcacta aaaataacgt cttagcgtt tgggaaaaag | 3780 |
| gcaagcaatg ggaactcgac aatcggacca acctaatgca gcccggtcct gcggcagcga | 3840 |
| ccaccttag cggagaacct gaccgtcaag ccatgcaaaa cacgctggct tttagcagga | 3900 |
| ccgtctacga tcaaacgacc gccacgaccg atcgtaacca gatactcatc accaacgaag | 3960 |
| acgaaatcag acccaccaac tcggtcggta tcgacgcgtg gggagcagtt cccaccaaca | 4020 |
| accagtcgat cgtgaccccc ggcactcgcg cggccgtcaa caatcaaggg gcgcttcccg | 4080 |
| ggatggtgtg gcaaaacaga gacatttacc ctacagggac ccatttggcc aaaattcccg | 4140 |
| acactgacaa tcacttccat ccgtccccgc ttattgggcg gtttggctgc aagcatcccc | 4200 |
| ctcccccagat tttcattaaa aacacacccg tccctgccaa cccttcggaa acgttccaga | 4260 |
| cggccaaagt ggcctccttc atcaaccagt actcgaccgg acagtgcacc gtcgaaatct | 4320 |
| tttgggaact caagaaggaa acctccaagc gctggaaccc cgaaatccag ttcacctcca | 4380 |
| actttggcaa cgcggccgac atccagtttg ccgtctccga cacgggatcc tattccgaac | 4440 |
| ctcgtcccat cggtacccgt taccttacca aacctctgta aattaaaccc ttcaataaac | 4500 |
| cgtttatgcg taactgtatt tccgtctcct gtcgttattc agtcacatga tgcggcatta | 4560 |
| cctcaccgga gtgctggcca gtttccaaga caggctcgct cgctcactcg gccgggggcc | 4620 |
| ccaaaggggc ccctagcgac cgcttcgcgg tcgcggcccg agtgagcgag cgagcctgtc | 4680 |
| ttggaaactg gcca | 4694 |

<210> SEQ ID NO 292
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(20)
<223> OTHER INFORMATION: a, c, t, g, unknown or other
<220> FEATURE:
<221> NAME/KEY: misc_feature
<222> LOCATION: (5)..(20)
<223> OTHER INFORMATION: This region may encompass 0-16 nucleotides
<220> FEATURE:
<223> OTHER INFORMATION: see specification as filed for detailed
      description of substitutions and preferred embodiments

<400> SEQUENCE: 292
gctcnnnnnn nnnnnnnnnn                                                     20

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(16)
<223> OTHER INFORMATION: a, c, t, g, unknown or other
<220> FEATURE:
<221> NAME/KEY: misc_feature
<222> LOCATION: (1)..(16)
<223> OTHER INFORMATION: This region may encompass 0-16 nucleotides
<220> FEATURE:
<223> OTHER INFORMATION: see specification as filed for detailed
      description of substitutions and preferred embodiments

<400> SEQUENCE: 293
nnnnnnnnnn nnnnnngctc                                                     20

<210> SEQ ID NO 294
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(20)
<223> OTHER INFORMATION: a, c, t, g, unknown or other
<220> FEATURE:
<221> NAME/KEY: misc_feature
<222> LOCATION: (9)..(20)
<223> OTHER INFORMATION: This region may encompass 0-12 nucleotides
<220> FEATURE:
<223> OTHER INFORMATION: see specification as filed for detailed
      description of substitutions and preferred embodiments

<400> SEQUENCE: 294
gctcgctcnn nnnnnnnnnn                                                     20

<210> SEQ ID NO 295
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t, g, unknown or other
```

```
<220> FEATURE:
<221> NAME/KEY: misc_feature
<222> LOCATION: (1)..(12)
<223> OTHER INFORMATION: This region may encompass 0-12 nucleotides
<220> FEATURE:
<223> OTHER INFORMATION: see specification as filed for detailed
      description of substitutions and preferred embodiments

<400> SEQUENCE: 295
nnnnnnnnnn nngctcgctc                                              20

<210> SEQ ID NO 296
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(16)
<223> OTHER INFORMATION: a, c, t, g, unknown or other
<220> FEATURE:
<221> NAME/KEY: misc_feature
<222> LOCATION: (5)..(16)
<223> OTHER INFORMATION: This region may encompass 0-12 nucleotides
<220> FEATURE:
<221> NAME/KEY: modified_base
<222> LOCATION: (21)..(32)
<223> OTHER INFORMATION: a, c, t, g, unknown or other
<220> FEATURE:
<221> NAME/KEY: misc_feature
<222> LOCATION: (21)..(32)
<223> OTHER INFORMATION: This region may encompass 0-12 nucleotides
<220> FEATURE:
<223> OTHER INFORMATION: see specification as filed for detailed
      description of substitutions and preferred embodiments

<400> SEQUENCE: 296
gctcnnnnnn nnnnnngctc nnnnnnnnnn nn                                32

<210> SEQ ID NO 297
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t, g, unknown or other
<220> FEATURE:
<221> NAME/KEY: misc_feature
<222> LOCATION: (1)..(12)
<223> OTHER INFORMATION: This region may encompass 0-12 nucleotides
<220> FEATURE:
<221> NAME/KEY: modified_base
<222> LOCATION: (17)..(28)
<223> OTHER INFORMATION: a, c, t, g, unknown or other
<220> FEATURE:
<221> NAME/KEY: misc_feature
<222> LOCATION: (17)..(28)
<223> OTHER INFORMATION: This region may encompass 0-12 nucleotides
<220> FEATURE:
<223> OTHER INFORMATION: see specification as filed for detailed
      description of substitutions and preferred embodiments

<400> SEQUENCE: 297
nnnnnnnnnn nngctcnnnn nnnnnnnngc tc                                32

<210> SEQ ID NO 298
<211> LENGTH: 32
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t, g, unknown or other
<220> FEATURE:
<221> NAME/KEY: misc_feature
<222> LOCATION: (1)..(12)
<223> OTHER INFORMATION: This region may encompass 0-12 nucleotides
<220> FEATURE:
<221> NAME/KEY: modified_base
<222> LOCATION: (21)..(32)
<223> OTHER INFORMATION: a, c, t, g, unknown or other
<220> FEATURE:
<221> NAME/KEY: misc_feature
<222> LOCATION: (21)..(32)
<223> OTHER INFORMATION: This region may encompass 0-12 nucleotides
<220> FEATURE:
<223> OTHER INFORMATION: see specification as filed for detailed
      description of substitutions and preferred embodiments

<400> SEQUENCE: 298
nnnnnnnnnn nngctcgctc nnnnnnnnnn nn                                       32

<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(16)
<223> OTHER INFORMATION: a, c, t, g, unknown or other
<220> FEATURE:
<221> NAME/KEY: misc_feature
<222> LOCATION: (5)..(16)
<223> OTHER INFORMATION: This region may encompass 0-12 nucleotides
<220> FEATURE:
<223> OTHER INFORMATION: see specification as filed for detailed
      description of substitutions and preferred embodiments

<400> SEQUENCE: 299
gctcnnnnnn nnnnnngctc                                                     20

<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(20)
<223> OTHER INFORMATION: a, c, t, g, unknown or other
<220> FEATURE:
<221> NAME/KEY: misc_feature
<222> LOCATION: (13)..(20)
<223> OTHER INFORMATION: This region may encompass 0-8 nucleotides
<220> FEATURE:
<223> OTHER INFORMATION: see specification as filed for detailed
      description of substitutions and preferred embodiments

<400> SEQUENCE: 300
gctcgctcgc tcnnnnnnnn                                                     20

<210> SEQ ID NO 301
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, g, unknown or other
<220> FEATURE:
<221> NAME/KEY: misc_feature
<222> LOCATION: (1)..(8)
<223> OTHER INFORMATION: This region may encompass 0-8 nucleotides
<220> FEATURE:
<223> OTHER INFORMATION: see specification as filed for detailed
      description of substitutions and preferred embodiments

<400> SEQUENCE: 301
nnnnnnnngc tcgctcgctc                                                     20

<210> SEQ ID NO 302
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(12)
<223> OTHER INFORMATION: a, c, t, g, unknown or other
<220> FEATURE:
<221> NAME/KEY: misc_feature
<222> LOCATION: (5)..(12)
<223> OTHER INFORMATION: This region may encompass 0-8 nucleotides
<220> FEATURE:
<221> NAME/KEY: modified_base
<222> LOCATION: (21)..(28)
<223> OTHER INFORMATION: a, c, t, g, unknown or other
<220> FEATURE:
<221> NAME/KEY: misc_feature
<222> LOCATION: (21)..(28)
<223> OTHER INFORMATION: This region may encompass 0-8 nucleotides
<220> FEATURE:
<223> OTHER INFORMATION: see specification as filed for detailed
      description of substitutions and preferred embodiments

<400> SEQUENCE: 302
gctcnnnnnn nngctcgctc nnnnnnnn                                            28

<210> SEQ ID NO 303
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, g, unknown or other
<220> FEATURE:
<221> NAME/KEY: misc_feature
<222> LOCATION: (1)..(8)
<223> OTHER INFORMATION: This region may encompass 0-8 nucleotides
<220> FEATURE:
<221> NAME/KEY: modified_base
<222> LOCATION: (13)..(20)
<223> OTHER INFORMATION: a, c, t, g, unknown or other
<220> FEATURE:
<221> NAME/KEY: misc_feature
<222> LOCATION: (13)..(20)
<223> OTHER INFORMATION: This region may encompass 0-8 nucleotides
<220> FEATURE:
```

```
<223> OTHER INFORMATION: see specification as filed for detailed
      description of substitutions and preferred embodiments

<400> SEQUENCE: 303
nnnnnnnngc tcnnnnnnnn gctcgctc                                              28

<210> SEQ ID NO 304
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(16)
<223> OTHER INFORMATION: a, c, t, g, unknown or other
<220> FEATURE:
<221> NAME/KEY: misc_feature
<222> LOCATION: (9)..(16)
<223> OTHER INFORMATION: This region may encompass 0-8 nucleotides
<220> FEATURE:
<221> NAME/KEY: modified_base
<222> LOCATION: (21)..(28)
<223> OTHER INFORMATION: a, c, t, g, unknown or other
<220> FEATURE:
<221> NAME/KEY: misc_feature
<222> LOCATION: (21)..(28)
<223> OTHER INFORMATION: This region may encompass 0-8 nucleotides
<220> FEATURE:
<223> OTHER INFORMATION: see specification as filed for detailed
      description of substitutions and preferred embodiments

<400> SEQUENCE: 304
gctcgctcnn nnnnngctc nnnnnnnn                                               28

<210> SEQ ID NO 305
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, g, unknown or other
<220> FEATURE:
<221> NAME/KEY: misc_feature
<222> LOCATION: (1)..(8)
<223> OTHER INFORMATION: This region may encompass 0-8 nucleotides
<220> FEATURE:
<221> NAME/KEY: modified_base
<222> LOCATION: (17)..(24)
<223> OTHER INFORMATION: a, c, t, g, unknown or other
<220> FEATURE:
<221> NAME/KEY: misc_feature
<222> LOCATION: (17)..(24)
<223> OTHER INFORMATION: This region may encompass 0-8 nucleotides
<220> FEATURE:
<223> OTHER INFORMATION: see specification as filed for detailed
      description of substitutions and preferred embodiments

<400> SEQUENCE: 305
nnnnnnnngc tcgctcnnnn nnnngctc                                              28

<210> SEQ ID NO 306
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (1)..(8)
<223> OTHER INFORMATION: a, c, t, g, unknown or other
<220> FEATURE:
<221> NAME/KEY: misc_feature
<222> LOCATION: (1)..(8)
<223> OTHER INFORMATION: This region may encompass 0-8 nucleotides
<220> FEATURE:
<221> NAME/KEY: modified_base
<222> LOCATION: (21)..(28)
<223> OTHER INFORMATION: a, c, t, g, unknown or other
<220> FEATURE:
<221> NAME/KEY: misc_feature
<222> LOCATION: (21)..(28)
<223> OTHER INFORMATION: This region may encompass 0-8 nucleotides
<220> FEATURE:
<223> OTHER INFORMATION: see specification as filed for detailed
      description of substitutions and preferred embodiments

<400> SEQUENCE: 306
nnnnnnnngc tcgctcgctc nnnnnnnn                                              28

<210> SEQ ID NO 307
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(12)
<223> OTHER INFORMATION: a, c, t, g, unknown or other
<220> FEATURE:
<221> NAME/KEY: misc_feature
<222> LOCATION: (5)..(12)
<223> OTHER INFORMATION: This region may encompass 0-8 nucleotides
<220> FEATURE:
<221> NAME/KEY: modified_base
<222> LOCATION: (17)..(24)
<223> OTHER INFORMATION: a, c, t, g, unknown or other
<220> FEATURE:
<221> NAME/KEY: misc_feature
<222> LOCATION: (17)..(24)
<223> OTHER INFORMATION: This region may encompass 0-8 nucleotides
<220> FEATURE:
<223> OTHER INFORMATION: see specification as filed for detailed
      description of substitutions and preferred embodiments

<400> SEQUENCE: 307
gctcnnnnnn nngctcnnnn nnnngctc                                              28

<210> SEQ ID NO 308
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(16)
<223> OTHER INFORMATION: This sequence may encompass 1-4 'gctc'
      repeating units
<220> FEATURE:
<223> OTHER INFORMATION: see specification as filed for detailed
      description of substitutions and preferred embodiments

<400> SEQUENCE: 308
gctcgctcgc tcgctc                                                           16

<210> SEQ ID NO 309
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(8)
<223> OTHER INFORMATION: This region may encompass 0-2 'gctc' repeating
      units
<220> FEATURE:
<221> NAME/KEY: modified_base
<222> LOCATION: (9)..(16)
<223> OTHER INFORMATION: a, c, t, g, unknown or other
<220> FEATURE:
<221> NAME/KEY: misc_feature
<222> LOCATION: (9)..(16)
<223> OTHER INFORMATION: This region may encompass 0-8 nucleotides
<220> FEATURE:
<221> NAME/KEY: misc_feature
<222> LOCATION: (17)..(24)
<223> OTHER INFORMATION: This region may encompass 0-2 'gctc' repeating
      units
<220> FEATURE:
<223> OTHER INFORMATION: see specification as filed for detailed
      description of substitutions and preferred embodiments

<400> SEQUENCE: 309
gctcgctcnn nnnnnngctc gctc                                             24

<210> SEQ ID NO 310
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(8)
<223> OTHER INFORMATION: This region may encompass 0-2 'gctc' repeating
      units
<220> FEATURE:
<221> NAME/KEY: modified_base
<222> LOCATION: (9)..(16)
<223> OTHER INFORMATION: a, c, t, g, unknown or other
<220> FEATURE:
<221> NAME/KEY: misc_feature
<222> LOCATION: (9)..(16)
<223> OTHER INFORMATION: This region may encompass 0-8 nucleotides
<220> FEATURE:
<221> NAME/KEY: misc_feature
<222> LOCATION: (17)..(24)
<223> OTHER INFORMATION: This region may encompass 0-2 'gctc' repeating
      units
<220> FEATURE:
<221> NAME/KEY: modified_base
<222> LOCATION: (25)..(32)
<223> OTHER INFORMATION: a, c, t, g, unknown or other
<220> FEATURE:
<221> NAME/KEY: misc_feature
<222> LOCATION: (25)..(32)
<223> OTHER INFORMATION: This region may encompass 0-8 nucleotides
<220> FEATURE:
<221> NAME/KEY: misc_feature
<222> LOCATION: (33)..(40)
<223> OTHER INFORMATION: This region may encompass 0-2 'gctc' repeating
      units
<220> FEATURE:
<223> OTHER INFORMATION: see specification as filed for detailed
      description of substitutions and preferred embodiments

<400> SEQUENCE: 310
gctcgctcnn nnnnnngctc gctcnnnnnn nngctcgctc                            40
```

```
<210> SEQ ID NO 311
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
gcgcgctcgc tcgctc                                                        16

<210> SEQ ID NO 312
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
gagttggcca ctc                                                           13
```

COMPOSITIONS AND METHODS FOR THE PRODUCTION OF SCAAV

CROSS REFERENCE TO RELATED APPLICATIONS

This application is a 35 U.S.C. § 371 U.S. National Stage Entry of International Application No. PCT/US2015/065218 filed Dec. 11, 2015, which claims the benefit of U.S. Provisional Patent Application No. 62/091,062, entitled Compositions and Method for the Production of scAAV, filed Dec. 12, 2014, the contents of which are herein incorporated by reference in their entirety.

REFERENCE TO SEQUENCE LISTING

The instant application contains a Sequence Listing which has been submitted electronically in ASCII format and is hereby incorporated by reference in its entirety. Said ASCII copy, created on Jun. 12, 2017 is named 2057-1500US371_SL.txt and is 241,983 bytes in size.

FIELD OF THE INVENTION

The present invention relates to compositions and methods for the production of self-complementary genome-containing viral particles with improved transduction efficiencies and gene expression and therapeutic uses of these scAAV.

BACKGROUND OF THE INVENTION

Viruses of the Parvoviridae family are small non-enveloped icosahedral capsid viruses characterized by a single stranded DNA genome, Parvoviridae family viruses consist of two subfamilies: Parvoviridae, which infect vertebrates, and Densovirinae, which infect invertebrates.

Viruses of the Parvoviridae family are used as biological tools due to a relatively simple structure that may be easily manipulated with standard molecular biology techniques. The genome of the virus may be modified to contain a minimum of components for the assembly of a functional recombinant virus, or viral particle, which is loaded with, or engineered to deliver and/or express, a desired payload nucleic acid construct, e.g., a transgene, genome-editing sequence, miR, polypeptide-encoding polynucleotide, or a modulatory nucleic acid.

Preclinical studies have demonstrated the efficacy of recombinant adeno-associated virus (rAAV) as payload delivery viral particles, and recently rAAVs have been successfully used in clinical trials of gene therapy. Transduction efficiencies generally range from 25 to several hundred viral genome-containing particles (VGP) per transducing unit, depending on the cell type. However, the transduction efficiency of these viral genomes, in terms of the number of VGP required for transduction, is hindered by the need to convert the single-stranded DNA (ssDNA) genome into double-stranded DNA (dsDNA) prior to expression.

This rate-limiting step can be entirely circumvented through the use of scAAV, which package an inverted repeat genome that can fold into dsDNA without the requirement for DNA synthesis or base-pairing between multiple viral genomes.

Like all viral particle-based approaches to gene therapy, in addition to the production of large quantities of highly concentrated virus, another obstacle in translating therapies from pre-clinical trials into a human clinical application is the efficient transduction and delivery of the therapeutic payload nucleic acid construct.

In view of these issues there remains a need for alternative and improved methods of efficiently, safely, and economically producing viral particles with improved transduction efficiencies. The present invention provides compositions and methods for the production of self-complementary parvoviral genome-containing particles, e.g. scAAV particles, with improved transduction efficiencies and consequently more efficacious therapeutic outcomes.

SUMMARY OF THE INVENTION

The present disclosure provides compositions and methods for the production of viral particles with improved transduction efficiencies and increased gene expression useful as therapeutic modalities which employ viral delivery methods. Also provided are engineered nucleic acid and vector constructs for viral vector design and production which are useful components for viral particle production methods. Further provided are modified regulatory proteins engineered to improve viral particle transduction efficiencies and increase gene expression used alone or in conjunction with the engineered nucleic acid and vector constructs. The viral particles of the invention comprise one or more engineered polynucleotides or polypeptides as described herein. In addition, the present disclosure provides methods for producing viral particles which comprise one or more engineered polynucleotides or polypeptides, e.g., engineered genomes and/or engineered ITRs and/or engineered regulatory proteins and/or engineered payloads or any combination thereof.

The single-stranded nature of the parvoviral genome requires the use of cellular mechanisms to provide a complementary-strand for gene expression, the recruitment of which is considered to be a rate-limiting factor in the efficiency of transduction and gene expression in parvoviruses and parvoviral particles. This problem can be circumvented by packaging both strands as a single duplex DNA molecule. Parvoviral particles comprising such duplexed DNA have been shown to have increased transduction efficiency and a higher level of transgene expression than their single-stranded counterparts.

The present disclosure provides parvoviral particles having a duplexed genome resulting from the presence of a self-complementary viral genome sequence which may be packaged in a viral particle. The present disclosure thus provides a parvoviral particle comprising a parvovirus capsid and a parvoviral genome encoding a heterologous nucleotide sequence, e.g., a payload sequence, in which the parvoviral genome may be self-complementary, i.e., forms a dimeric inverted repeat via intra-strand base-pairing. In this manner, a double-stranded sequence may be formed by the base-pairing between complementary heterologous nucleotide sequences, thus producing the requisite structure for gene expression in a host cell without the need for host cell machinery to convert the viral genome into a double-stranded form.

Such a parvoviral genome may be formed by employing the use of one or more parvoviral genome sequences that are altered in a manner that results in the formation of a self-complementary viral genome during replication.

In one embodiment, the altered parvoviral genome sequence comprises at least one parvoviral inverted terminal repeat (ITR) sequence having an engineered. Rep binding sequence region (eRBSR). In this embodiment, the Rep binding sequence region may be altered such that binding with the Rep protein is decreased. The decrease in Rep binding affects the Rep nicking activity in a manner that promotes the formation of a self-complementary viral genome during replication.

In another embodiment, the altered parvoviral genome sequence comprises at least one parvoviral inverted terminal repeat sequence having a chimeric nicking stem loop, which abolishes Rep mediated nicking such that a self-complementary viral genome is formed during replication.

In another embodiment, the Rep protein, or polynucleotide sequence encoding the Rep protein, is engineered such that Rep protein binding to its cognate Rep binding sequence region is decreased in a manner that likewise promotes the formation of a self-complementary viral genome during replication.

In one embodiment, a parvoviral particle comprising a self-complementary viral genome is provided. The parvoviral particle may comprise a parvoviral capsid and a self-complementary parvoviral genome comprising: a first parvoviral inverted terminal repeat sequence, a first heterologous sequence, a parvoviral inverted terminal repeat nucleotide sequence comprising an engineered Rep binding sequence region, a second heterologous sequence, wherein the second heterologous sequence is complementary to the first heterologous sequence, and a second parvoviral inverted terminal repeat sequence. The viral genome may be capable of intra-strand base-pairing between the heterologous nucleotide sequences.

In another embodiment, the parvoviral particle comprises a parvoviral capsid and a self-complementary parvoviral genome comprising: a first parvoviral inverted terminal repeat sequence, a first heterologous sequence, a parvoviral inverted terminal repeat nucleotide sequence comprising a chimeric nicking stem loop, a second heterologous sequence, wherein the second heterologous sequence is complementary to the first heterologous sequence, and a second parvoviral inverted terminal repeat sequence. The viral genome may be capable of intra-strand base-pairing between the heterologous nucleotide sequences.

In another embodiment, the parvoviral particle comprises a parvoviral capsid and a self-complementary parvoviral genome comprising: a first parvoviral inverted terminal repeat sequence, a first heterologous sequence, a parvoviral inverted terminal repeat nucleotide sequence comprising an engineered Rep binding sequence region and a chimeric nicking stem loop, a second heterologous sequence, wherein the second heterologous sequence is complementary to the first heterologous sequence, and a second parvoviral inverted terminal repeat sequence. The viral genome may be capable of intra-strand base-pairing between the heterologous nucleotide sequences.

In any of the embodiments where the parvoviral particle comprises an engineered Rep binding sequence region and/or a chimeric nicking stem loop, production of the parvoviral particle can optionally further comprise a sequence encoding an engineered Rep protein which binds to the Rep binding sequence region and/or engineered Rep binding sequence region with decreased affinity.

The present disclosure additionally provides compositions and methods for improving the transduction efficiency and heterologous gene expression of viral particles having parvoviral polynucleotide sequences (e.g., a parvoviral genome encoding heterologous nucleotide sequence or a payload sequence or a fragment thereof) by altering one or more of several Rep binding activities to effect the production of viral particles having a self-complementary or duplexed genome. As a non-limiting example, the transduction efficiency and heterologous gene expression of viral particles having parvoviral polynucleotide sequences may be increased by altering the Rep binding sequence region and/or by altering the Rep nicking sequence found in parvoviral ITR sequences, and/or altering one or more Rep proteins. Thus, the present disclosure provides, among other things, a parvoviral polynucleotide, such as an adeno-associated viral (AAV) polynucleotide, comprising an engineered Rep binding sequence region and/or an altered Rep nicking sequence. In addition, the present disclosure provides an engineered Rep protein, and a polynucleotide sequence encoding the engineered Rep protein, which can be used independently in the production of a viral particle having a self-complementary or duplexed genome (i.e., with wild-type Rep binding sequence region and wild-type Rep nicking stem loop) or can be used in conjunction with an engineered Rep binding sequence region and/or an altered Rep nicking sequence in the production of a viral particle having a self-complementary or duplexed genome.

The present disclosure provides a polynucleotide (e.g., a parvoviral polynucleotide) comprising an engineered Rep binding sequence region (eRBSR). In one embodiment, the eRBSR comprises a sequence in which one or more of the nucleotides are altered or modified as compared to the native or reference Rep binding sequence region. In one embodiment, the eRBSR is altered as a result of one or more nucleotide insertions, deletions, substitutions, or any combination thereof as compared to the native Rep binding sequence region. In another embodiment, the eRBSR is altered by swapping the native Rep binding sequence region with the Rep binding sequence region of a different parvoviral serotype or species. In one embodiment, the entire Rep binding sequence region is swapped. In another embodiment, a portion or partial sequence of the Rep binding sequence region is swapped. In one embodiment, the engineered Rep binding sequence region can comprise a non-native Rep binding sequence region from an AAV viral genome, including, but not limited to, the Rep binding sequence regions of AAV1, AAV2, AAV3, AAV4, AAV5, AAV 5, AAV7, AAV8, AAV9, AAV10, AAV 11, AAV12, AAVrh8, AAVrh10, AAV-DJ, and AAV-DJ8.

In one embodiment, one or more of the nucleotides in the eRBSR are chemically modified as compared with the native Rep binding sequence region. In individual embodiments, the chemical modification(s) is on the nucleobase and/or the sugar and/or the phosphate backbone, or any combination thereof. In another embodiment, the eRBSR has one or more altered nucleotides and one or more chemically-modified nucleotides. In one embodiment, the Rep binding to the sequence is decreased.

Studies have shown that Rep protein recognizes and binds to a series of about four to five GCTC consensus motifs. Thus, decreased binding with Rep protein can be affected by altering the number and/or position of the GCTC motifs present in the Rep binding sequence region and/or by altering the sequence of the individual GCTC motif(s). Thus, in one embodiment, the eRBSR comprises one to three GCTC consensus motifs. In another embodiment, the eRBSR comprises about one to about five GCTC consensus motifs in which one or more nucleotides in at least one of the GCTC consensus motifs is altered or modified.

The present disclosure also provides polynucleotides comprising any of the eRBSRs described herein. In one embodiment, the polynucleotide comprises one or more parvoviral inverted terminal repeat (ITR) sequences wherein one of the ITR sequences comprises an eRBSR. In one embodiment, the polynucleotide comprising at least one parvoviral ITR sequence with an eRBSR is capable of forming a double-stranded Rep binding sequence region. In one embodiment, the engineered Rep binding sequence region is located between a 5' parvoviral inverted terminal repeat sequence and a 3' parvoviral inverted terminal repeat sequence. In another embodiment, the engineered Rep binding sequence region is located within a parvoviral inverted terminal repeat sequence.

In one embodiment, the polynucleotides described herein comprising the eRBSR can further comprise a heterologous or payload sequence, which can be, for example, a regulatory sequence, a sequence encoding a nucleic acid (e.g., such as a miR or an antisense sequence), or a sequence encoding a polypeptide (e.g., such as a transgene). In one embodiment, the heterologous sequence may be operatively linked to one or more regulatory sequence(s) that allows or controls expression of the heterologous sequence. In one embodiment, the polynucleotide comprises a first ITR sequence comprising an eRBSR and a second ITR sequence, wherein the heterologous sequence is flanked by the first and second ITR sequences.

In one embodiment, a parvoviral polynucleotide (e.g., a parvoviral genome) comprises in the 5' to 3' direction: (a) a 5' parvoviral inverted terminal repeat sequence; (b) a first payload encoding region; (c) an engineered Rep binding sequence region; (d) a second payload encoding region; and (e) a 3' parvoviral inverted terminal repeat sequence. In this embodiment, the first and second payload encoding regions are essentially self-complementary and may form a hairpin structure that comprises the parvoviral polynucleotide.

In one embodiment, the parvoviral ITR sequence(s) can be an adeno-associated virus (AAV) ITR or derived from an adeno-associated virus (AAV) ITR. AAV ITR sequences include, but are not limited to, any of those having an AAV1, AAV2, AAV3, AAV4, AAV5, AAV6, AAV7, AAV8, AAV9, AAV10, AAV11, AAV12, AAVrh8, AAVrh10, AAV-DJ, and AAV-DJ8 ITR sequence or a sequence derived therefrom.

Another way to promote the generation of self-complementary parvoviral genome sequences is to alter or modify the Rep nicking stem loop such that nicking by the Rep protein is decreased. This alteration or modification can promote the generation of self-complementary parvoviral genome sequences. The present disclosure thus provides a polynucleotide comprising a chimeric nicking stem loop, in which the native nicking stem loop sequence of one parvoviral serotype or species is substituted or swapped with the nicking stem loop sequence of a different parvoviral serotype or species. In one embodiment, the entire nicking stem loop sequence is swapped. In another embodiment, a portion or partial sequence of the nicking stem loop sequence is swapped. In one embodiment, the chimeric nicking stem loop can comprise a non-native nicking stem loop from an AAV viral genome, including the Rep binding sequence region of AAV1, AAV2, AAV3, AAV4, AAV5, AAV6, AAV7, AAV8, AAV9, AAV 10, AAV11, AAV12, AAVrh8, AAVrh10, AAV-DJ, and AAV-DJ8.

The present disclosure also provides a polynucleotide comprising the chimeric nicking stem loop. The polynucleotide comprising the chimeric nicking stem loop can further comprise a heterologous or payload sequence, which can be, for example, a regulatory sequence, a sequence encoding a nucleic acid, or a sequence encoding a polypeptide. In one embodiment, the heterologous sequence is operatively linked to one or more regulatory sequence(s) that allows expression of the heterologous sequence. In one embodiment, the polynucleotide comprises a first ITR sequence comprising a chimeric nicking stem loop and a second ITR sequence, wherein the heterologous sequence is flanked by the first and second ITR sequences.

In one embodiment, the disclosure provides a parvoviral polynucleotide (e.g., a parvoviral genome) comprising in the 5' to 3' direction: (a) a 5' parvoviral inverted terminal repeat sequence; (h) a first payload encoding region; (c) a chimeric nicking stem loop sequence; (d) a second payload encoding region; and (e) a 3' parvoviral inverted terminal repeat sequence. In this embodiment, the first and second payload encoding regions are essentially self-complementary and may form a hairpin structure that comprises the parvoviral polynucleotide.

The present disclosure also provides a polypeptide comprising an engineered Rep protein and a polynucleotide encoding the polypeptide comprising the engineered Rep protein. The engineered Rep protein comprises at least one amino acid that may be altered or modified as compared to the corresponding wild-type Rep protein. In one embodiment, the engineered Rep protein comprises one or more amino acids involved with DNA binding that are altered or modified as compared to the corresponding wild-type Rep protein. The engineered Rep protein has decreased binding to its cognate Rep binding sequence region and, as a consequence, promotes the formation of a self-complementary viral genome during replication.

The engineered Rep binding sequence region, chimeric nicking stem loop, and engineered Rep protein are each altered and/or modified, and used individually or in combination, such that binding to and/or nicking of the parvoviral ITR sequence is decreased. Thus, the present disclosure provides a parvoviral polynucleotide (e.g., a parvoviral genome) comprising an engineered Rep binding sequence region in which the binding affinity between a Rep protein and the engineered Rep binding sequence region is decreased relative to a parvoviral polynucleotide (e.g., a parvoviral genome) comprising the native Rep binding sequence region. The present disclosure provides a parvoviral polynucleotide (e.g., a parvoviral genome) comprising an engineered Rep binding sequence region in which the binding affinity between an engineered Rep protein and the engineered Rep binding sequence region is decreased relative to a parvoviral polynucleotide (e.g., a parvoviral genome) comprising the native Rep binding sequence region.

The present disclosure also provides a parvoviral polynucleotide (e.g., a parvoviral genome) encoding an engineered Rep protein in which the binding affinity between the engineered Rep protein and a Rep binding sequence region is decreased relative to a parvoviral polynucleotide a parvoviral genome) encoding the native Rep protein. The present disclosure additionally provides a parvoviral polynucleotide (e.g., a parvoviral genome) encoding an engineered Rep protein in which the binding affinity between the engineered Rep protein and an engineered Rep binding sequence region is decreased relative to a parvoviral polynucleotide (e.g., a parvoviral genome) encoding the native Rep protein.

The present disclosure further provides a parvoviral polynucleotide (e.g., a parvoviral genome) comprising an engineered Rep binding sequence region and/or a chimeric nicking stem loop in which the nicking by a Rep protein is decreased relative to a parvoviral polynucleotide (e.g., a parvoviral genome) comprising the native Rep binding sequence region and/or native Rep nicking stem loop. The present disclosure also provides a parvoviral polynucleotide (e.g., a parvoviral genome) comprising an engineered. Rep binding sequence region and/or chimeric nicking stem loop in which the nicking by an engineered Rep protein is decreased relative to a parvoviral polynucleotide (e.g., a parvoviral genome) comprising the native Rep binding sequence region and/or native Rep nicking stem loop.

The present disclosure also provides a parvoviral polynucleotide (e.g., a parvoviral genome) encoding an engineered Rep protein in which the nicking of the native Rep nicking stem loop is decreased relative to a parvoviral polynucleotide (e.g., a parvoviral genome) encoding the native Rep protein. The present disclosure additionally provides a parvoviral polynucleotide (e.g., a parvoviral genome) encoding an engineered Rep protein in which the nicking of the chimeric nicking stem loop Rep is decreased relative to a parvoviral polynucleotide (e.g., a parvoviral genome) encoding the native Rep protein.

The present disclosure also provides a parvoviral polynucleotide (e.g., a parvoviral genome) comprising an engineered Rep binding sequence region and/or a chimeric nicking stem loop in which a self-complementary (SC) parvoviral polynucleotide (e.g., a parvoviral genome) is produced during genome replication. The present disclosure also provides a parvoviral polynucleotide (e.g., a parvoviral genome) encoding an engineered Rep protein in which a self-complementary (SC) parvoviral polynucleotide (e.g., a parvoviral genome) is produced during genome replication.

The present disclosure provides a method of delivering to a cell or tissues a parvoviral particle comprising a payload, which method comprises contacting the cell or tissue with the parvoviral particle. The method of delivering the parvoviral particle to a cell or tissue can be accomplished using in vitro, ex vivo, or in vivo methods.

The present disclosure additionally provides a method of delivering to a subject, including a mammalian subject, parvoviral particle described herein, which method comprises administering to the subject the parvoviral particle.

The present disclosure additionally provides a method for treating a disease, disorder and/or condition in a mammalian subject, including a human subject, comprising administering to the subject parvoviral payload particle described herein. In one embodiment, the disease, disorder and/or condition is a neurological disease, disorder and/or condition.

BRIEF DESCRIPTION OF THE FIGURES

The foregoing and other objects, features and advantages will be apparent from the following description of particular embodiments of the invention, as illustrated in the accompanying drawings. The drawings are not necessarily to scale, emphasis instead being placed upon illustrating the principles of various embodiments of the invention.

FIG. 3 shows an alignment of 5' and 3' ITR sequences from selected AAV sequences aligned to AAV2 ITR sequence. Rep binding sequence regions are underlined and the nicking stem loop sequences are boxed.

FIG. 4 shows an alignment of 5' and 3' ITR sequences from selected AAV sequences aligned to AAV5 ITR sequence, Rep binding sequence regions are underlined and the nicking stem loop sequences are boxed.

FIG. 8 shows an alignment of selected AAV Rep protein sequences aligned to AAV5 Rep protein. Beta sheet 4 and Beta sheet 5 sequence regions are underlined; alpha helix C sequences are bold, residues involved in binding to the Rep binding sequence region are boxed.

FIG. 11A-FIG. 11F are schematic diagrams of polynucleotides comprising an engineered Rep binding sequence region and in which the eRBSR sequences are underlined. FIG. 11A is a schematic diagram comprising an α-pal payload construct (SEQ ID NO: 67). FIG. 11B is a schematic diagram comprising α-pal sequence (SEQ ID NO: 68) inserted into the Rep binding sequence region of an AAV2. ITR sequence (SEQ ID NO: 69). FIG. 11C is a schematic diagram comprising the 5-5/EGR payload construct (SEQ ID NO: 70). FIG. 11D is a schematic diagram comprising 5-5/EGR sequence (SEQ ID NO: 71) inserted into the Rep binding sequence region of an AAV2. ITR sequence (SEQ ID NO: 72). FIG. 11E is a schematic diagram comprising the JcDNV NS1 payload construct (SEQ ID NO: 73). FIG. 11F is a schematic diagram comprising JcDNV NS1 sequence (SEQ ID NO: 74) inserted into the Rep binding sequence region of an AAV2 ITR sequence (SEQ ID NO: 75).

DETAILED DESCRIPTION

Figure 1:
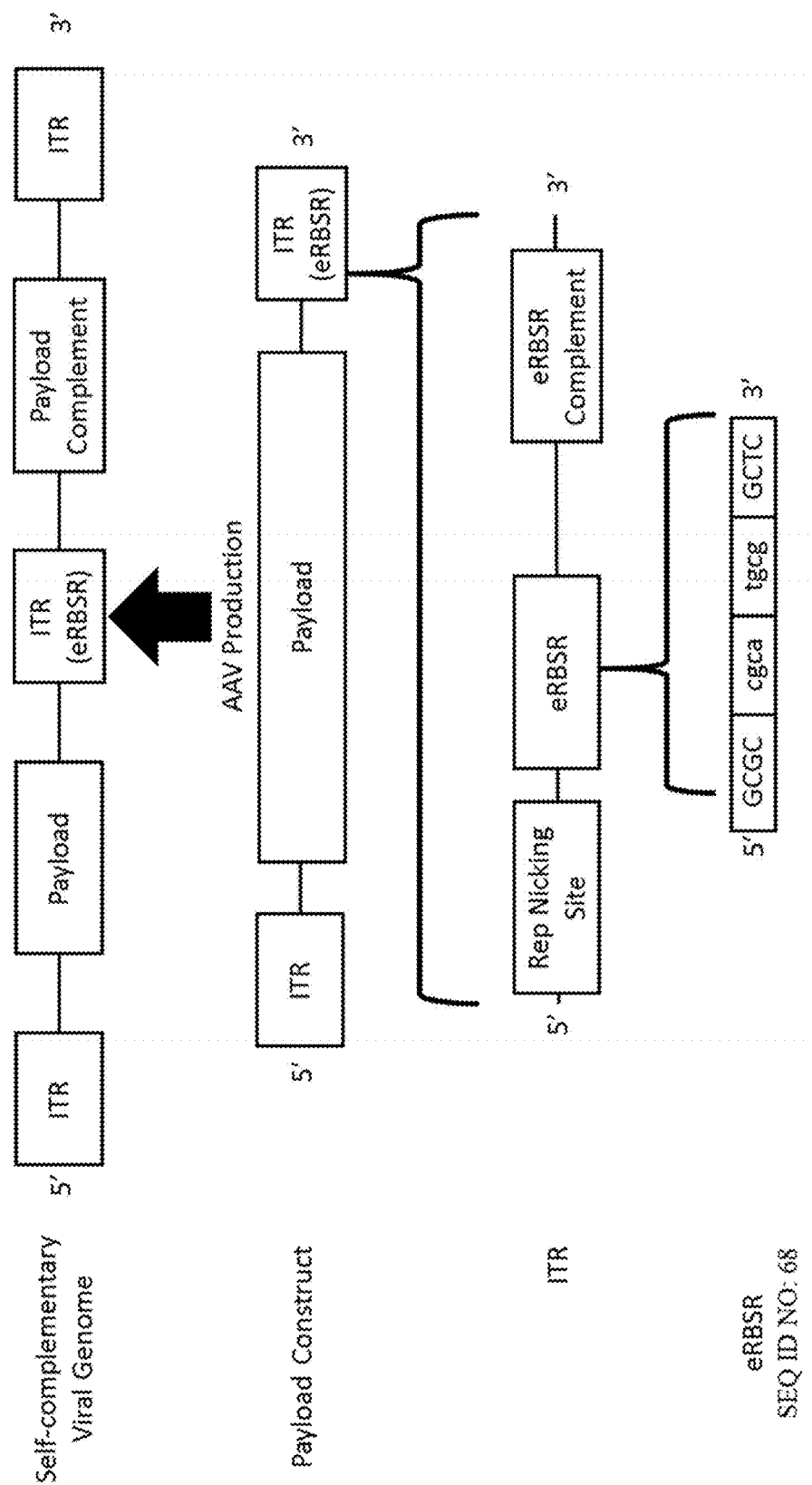
FIG. 1 is a schematic showing the structure of the self-complementary parvoviral genome that is produced by a parvoviral payload construct comprising an engineered Rep binding sequence region (eRBSR).

Like all parvoviruses, the adeno-associated (AAV) genome is packaged as a linear ssDNA molecule with palindromic inverted terminal repeat (ITR) sequences forming dsDNA hairpin structures at each end. The wild-type AAV2 genome encodes four replication proteins from a single Rep gene open reading frame, three capsid proteins from a single Cap gene open reading frame and a viral assembly protein (APP). The self-complementary ITR sequences serve as priming sites for host-cell DNA polymerase to begin synthesis of the second (complementary) strand and as replication origins during productive infection. Thus, the wild-type replication scheme of AAV requires de novo synthesis of the complementary DNA strand before subsequent steps of genome replication and genome transcription can begin. The second strand synthesis is considered to be one of several blocks to efficient infection.

Transduction of a target cell by wild-type AAV is dependent on a stepwise series of events including, but not limited to, cell surface binding, endocytic uptake, endosomal escape, nuclear entry, capsid uncoating, release of the ssDNA genome, second strand synthesis, transcription of the genome, and replication of the genome (Murlidharan et al. 2014, Frontiers in Molecular Neuroscience. 2014 Sep. 19; 7:76; the contents of which are herein incorporated by reference their entirety). In addition to the few gene products of the AAV genome, productive wild-type AAV infection is dependent on the presence of adenovirus co-infection which supplies helper genes E1a, E1b, E2a, E4, and VA. These helper genes provide transactivation activity, aid in transcription of the AAV genome, and facilitate AAV mRNA processing.

Replication of wild-type ssDNA AAV genomes begins at the 3' end of the genome where the self-complementary portion of the ITR forms a double stranded region that acts as a primer for the initiation of DNA synthesis. Replication continues in the 5' to 3' direction until a double stranded hairpin structure has been formed with a loop at one end. Rep protein binds to the Rep binding sequence region near the end of the hairpin comprising the loop and nicks the DNA, allowing the resolution of the loop and formation of a linear double stranded DNA molecule. The complementary strands are then separated and the replication cycle continues on both resultant strands of ssDNA.

Self-complementary or scAAV is formed in the event that Rep protein does not nick the DNA. Replication of the genome may still proceed by an alternative pathway wherein the complementary strands of the hairpin are separated, forming a replication species that comprises an ITR on either end and an ITR region in the center of the ssDNA strand. An AAV genome comprising scAAV is efficiently packaged within a viral capsid and transduces target cells wherein the double stranded genome that is delivered does not require the rate limiting second strand synthesis step before expression of the payload.

Recombinant adeno-associated virus (rAAV) comprises the minimal number of components to produce a non-replicative virus designed to deliver a payload to a target cell. The genome of the rAAV is comprised of ITRs flanking a payload sequence that replaces the wild-type Rep and Cap genes. Genes provided in trans for AAV replication comprise Rep and Cap genes expressing the three capsid proteins VP1, VP2, and VP3 and the non-structural protein. Rep78. The ITR sequences are the only required cis acting element required for AAV replication.

I. SELF-COMPLEMENTARY ADENO-ASSOCIATED VIRUS (SCAAV)

The present disclosure provides compositions and methods for the production of viral particles (e.g., parvoviral particles) with improved transduction efficiencies and gene expression.

The single-stranded nature of the parvoviral genome requires the use of cellular mechanisms to provide a complementary strand for gene expression. Recruitment of cellular factors and second strand synthesis are considered to be the rate-limiting factors in the efficiency of transduction and gene expression in parvoviral particles. This problem can be circumvented by packaging both strands as a single duplex DNA molecule.

The scAAV duplex molecule of the invention is produced by engineering certain components of the AAV genome to promote the generation of scAAV during the replication process. In one non-limiting example of the invention, the payload construct polynucleotide sequences encoding an ITR are altered to comprise an engineered Rep binding sequence region (eRBSR) that promotes production of self-complementary genomes during genome replication (FIG. 1). The final self-complementary ssDNA genome comprises in the 5' to 3' direction an ITR, a first complementary payload sequence, an ITR comprising an engineered Rep binding sequence region, a second complementary payload sequence, and an ITR. The ssDNA spontaneously folds to form a double stranded hairpin comprising an engineered Rep binding sequence region forming a closed loop at one end of the molecule, a double stranded DNA payload encoding region, and at least two ITR hairpins at the end of the molecule opposite the closed end.

The present disclosure provides viral particles, e.g., parvoviral particles, comprising a duplexed genome resulting from the presence of a self-complementary viral genomic sequence which is packaged in a single viral particle. In general, the parvovirus particle comprises a parvovirus capsid and a parvoviral genome encoding a heterologous nucleotide sequence, e.g. a payload sequence, in which the parvoviral genome is self-complementary. Such parvoviral particles are produced by employing the use of different parvoviral genome sequences that are altered in a manner that result in the formation of a self-complementary viral genome during replication. For example, a parvoviral particle comprising a parvoviral capsid and a duplexed genome can be produced using a parvoviral inverted terminal repeat nucleotide sequence comprising an engineered Rep binding sequence region which has decreased binding with its cognate Rep protein during viral replication. Similarly, a parvoviral particle comprising a parvoviral capsid and a duplexed genome can be produced using a parvoviral inverted terminal repeat nucleotide sequence comprising a chimeric nicking stem loop which has decreased nicking activity during viral replication. Parvoviral particles having a duplexed genome can also be produced using a sequence encoding an engineered Rep protein which binds to the Rep binding sequence region with decreased affinity. The parvoviral particles of the invention can further be produced using a combination of these nucleotide sequence components which can function individually or in combination to produce the parvoviral particles having duplexed genome.

Figure 2:
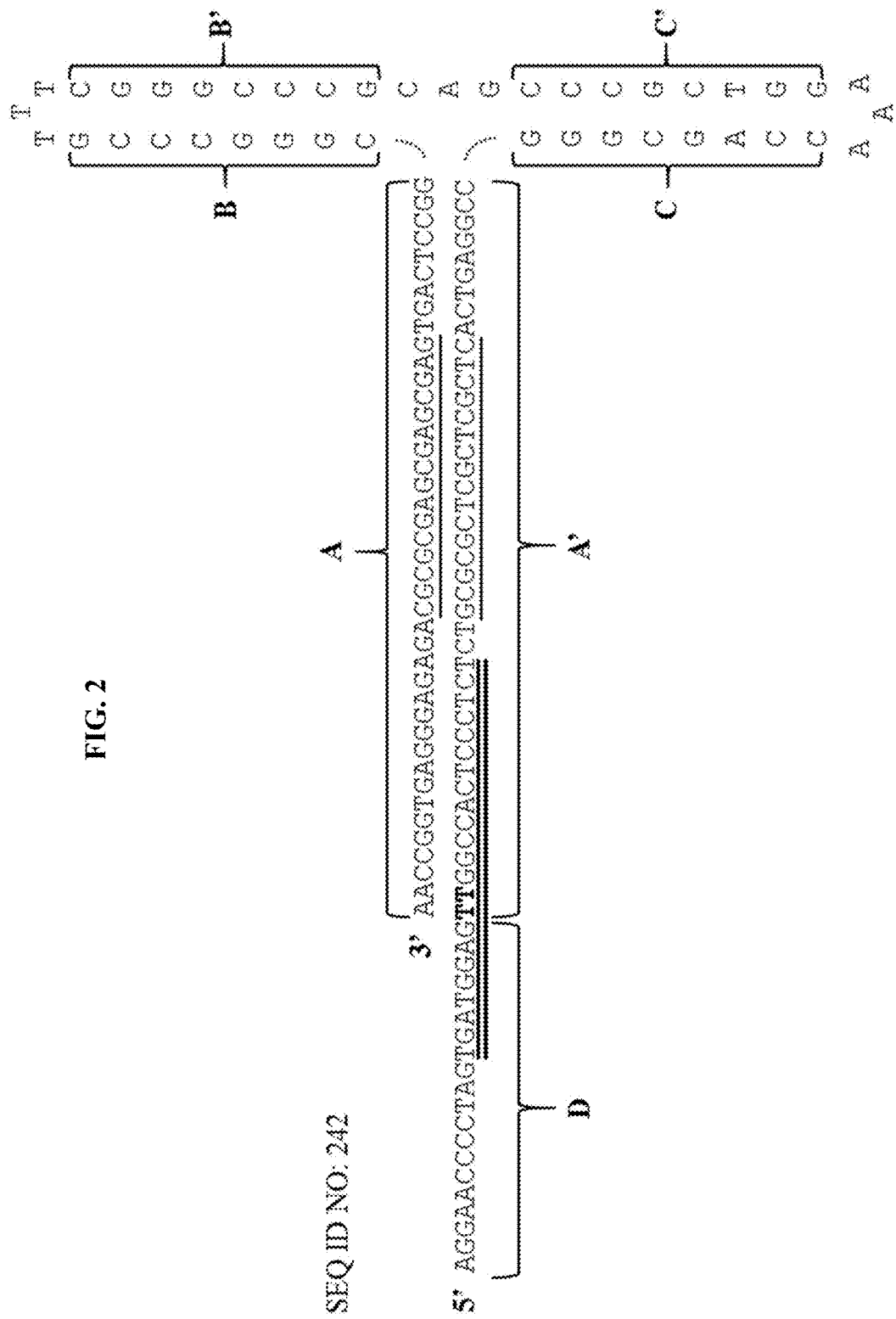
FIG. 2 is a schematic showing the structure of the 3' ITR from AAV2 (SEQ ID NO: 242). The strands of the double stranded Rep binding sequence region are underlined (SEQ ID NO: 1 and SEQ ID NO: 2), the terminal resolution site is bolded; and the nicking stein loop (SEQ ID NO: 199) is double-underlined.

Parvoviral ITRs are palindromic sequences, comprising complementary, symmetrically arranged sequences referred to as "A," "B," "C" and regions (FIG. 2). The ITR functions as an origin of replication comprising recognition sites for replication proteins Rep 78 and Rep68. The "D" region of the ITR is an asymmetrical region of the ITR where DNA replication initiates and provides directionality to the nucleic acid replication step.

Rep78 and Rep68 function in two distinct roles as part of a replication mechanism that is characteristic of Rep proteins from parvoviruses. Rep78 and Rep68 comprise both exonuclease activity and DNA helicase activity. Rep exonuclease activity comprises the steps of binding to a specific site within the ITR and nicking the DNA phosphodiester backbone at a specific location. Either Rep78 and/or Rep68 bind to unique and known sites within the 'A' region of the ITR (FIG. 2). The Rep binding sequence region comprises a sequence of repeated consensus 'GCTC' motifs located on the 'A' region of the ITR hairpin. The 'A' region of the AAV genome is a dsDNA region formed by base pairing of two complementary ssDNA sequence regions encoded in the ITR. The nicking stem loop region is comprised of a sequence that spans the border of the dsDNA 'A' and ssDNA 'D' regions that further comprises a specific nicking stem loop of the DNA backbone at the border of the 'A' and 'D' regions. In a second mode of activity, Rep78 or Rep68 exerts an ATP-dependent helicase activity for unwinding double-stranded DNA. Consequently, Rep78 and Rep68 act to break and unwind the hairpin structures on the end of the parvoviral genome, thereby providing access to replication machinery of the viral replication cell.

A single ITR may be engineered with Rep binding sites or sequence regions on both strands of the A regions and two symmetrical D regions on each side of the ITR palindrome. Such an engineered construct on a double-stranded circular DNA template allows Rep78 or Rep68 initiated nucleic acid replication that proceeds in both directions. A single ITR is sufficient for AAV replication of a circular vector.

Although similar to other AAV serotypes in many respects, AAV5 differs from other human and simian AAV serotypes more than other known human and simian serotypes. For example, AAV5 Rep and ITR sequences are unable to efficiently cross-complement corresponding Rep and ITR sequences from AAV2 in mammalian cells. See, e.g., Chiorini et al., J. Virol., 73(5):4293-4298 (1999) and Chiorini et al., J. Virol., 73(2):1309-1.319 (1999) the contents of which are herein incorporated by reference in their entirety. This lack of functional homology in AAV5 Rep and ITR sequences may be due to the relatively significant differences in the nucleotide and amino acid sequences of AAV5 from the corresponding sequences of other AAV serotypes. See, e.g., Bantel-Schaal et al., J. Virol., 73(2): 939-947 (1999) the contents of which are herein incorporated by reference in their entirety.

Figure 3:
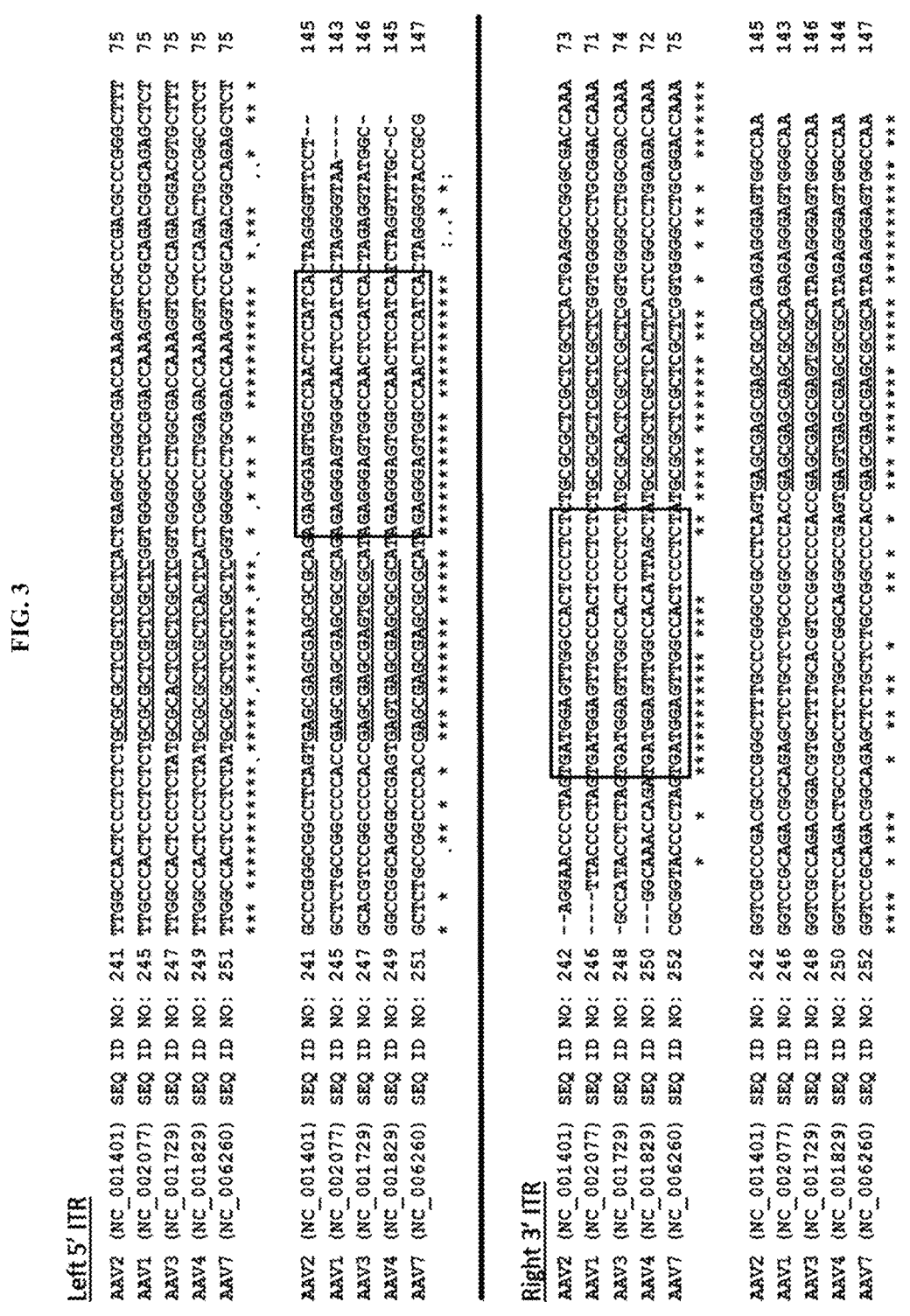
Figure 4:
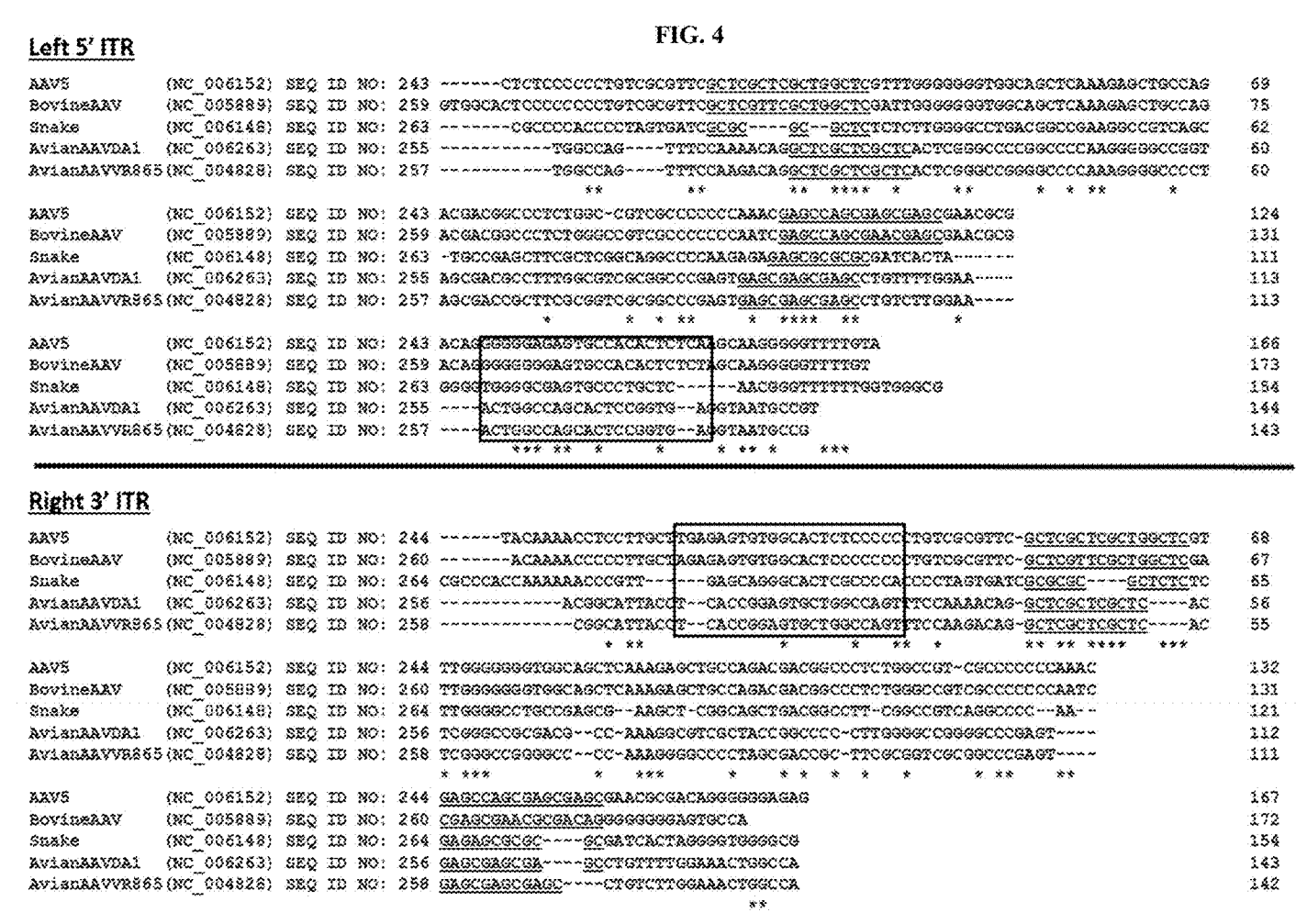

To identify the Rep binding sequence regions at the genomic sequence level, the genome sequences of several different AAV serotypes and species including AAV1, AAV2, AAV3, AAV4, AAV5, AAV7, AAV8, Bat AAV, Bovine AAV, Snake AAV, Avian AAV DA-1, and Avian AAV VR865 (SEQ ID NO: 280-291) were obtained from the NCBI Genome database. The 5' and 3' inverted terminal repeat sequences of selected genomes were aligned with the Clustal Omega multiple sequence alignment program using either AAV2 or AAV5 as the parent sequence, as shown in FIG. 3 and FIG. 4, respectively. Additional Rep binding sequence regions found in the ITR sequences of other parvoviral serotypes and species, including AAV8 5' ITR (SEQ ID NO: 253), AAV8 3' ITR (SEQ ID NO: 254), Bat AAV 5' ITR (SEQ ID NO: 261). Bat AAV 3' ITR (SEQ ID NO: 262) are obtained in the same manner using this alignment program.

Based on the genomic sequence alignments, two groups of Rep binding sequence regions, "AAV2-like" and "AAV5-like," were identified as regions of interest. FIG. 3 shows the sequences having the AAV2-like Rep binding sequence region and FIG. 4 shows the sequences having the AAV5-like Rep binding sequence region, in which the underlined regions represent the complementary Rep binding sequence in the 5' and 3' ITR regions. The Rep binding sequence regions share a consensus GCTC motif that is repeated four to five times. In total, the identified consensus Rep binding sequence regions are about 16-20 nucleotides in length.

In one embodiment, the altered parvoviral genome sequence comprises an engineered Rep binding sequence region. In this embodiment, the Rep binding sequence region is altered such that binding with its cognate Rep protein is decreased. Decreasing Rep binding to the Rep binding sequence region reduces the ability of the Rep protein exonuclease to successfully nick the DNA at the Rep nicking stem loop. Failure of the Rep protein to successfully nick DNA promotes an alternative pathway of genome replication and formation of a self-complementary viral genome during replication.

The affinity of Rep protein for a Rep binding sequence region is described as the affinity constant or $K_D$. The kinetics of binding between a Rep protein and a polynucleotide comprising a Rep binding sequence region is a dynamic process defined by the rate of association ($k_a$) and the rate of dissociation ($k_d$). The affinity constant ($K_D$) is determined by the following formula: $K_D = k_d/k_a$. At equilibrium, the rate of protein-DNA association is equal to the rate of dissociation wherein the measurement of reaction rate constants are used to define an equilibrium constant $1/K_D$. Due to the inverse nature of this constant, a smaller affinity constant represents a greater binding affinity. The affinity constant describing the binding of an engineered Rep binding sequence region and a Rep protein will be larger than the affinity constant describing the binding of a wild-type Rep binding sequence region and a Rep protein.

Figure 5:
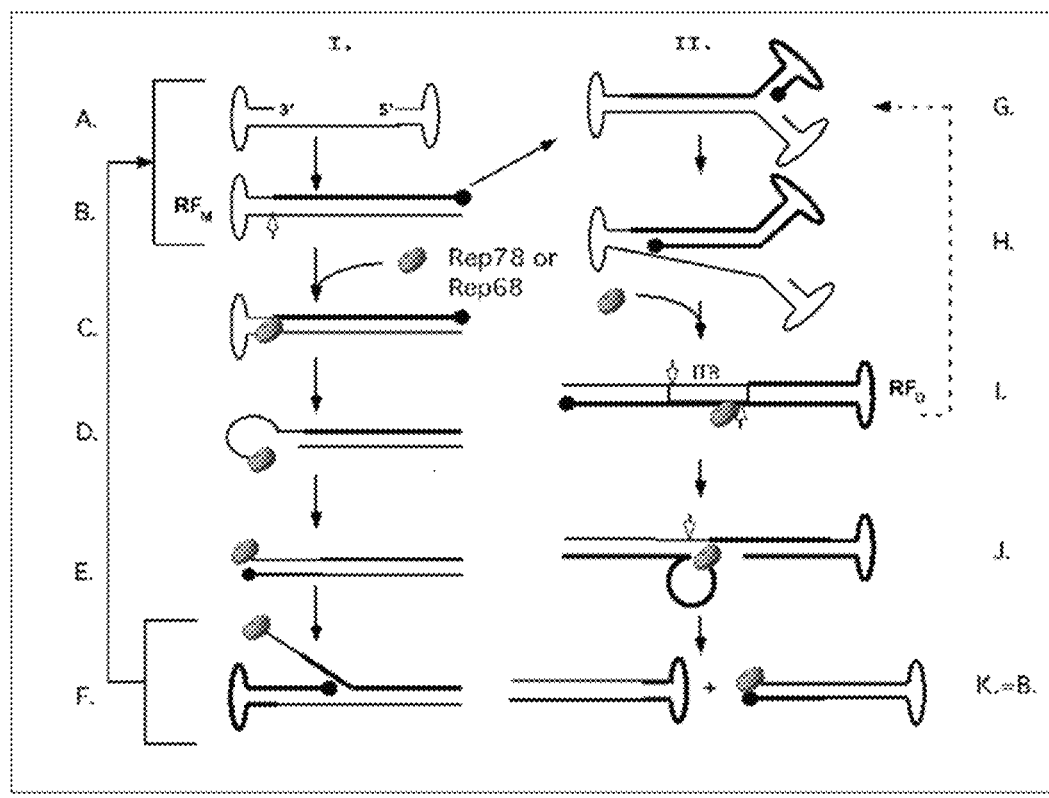
FIG. 5 is a PRIOR ART schematic depicting an example of parvovirus (AAV) replication in which single-stranded genomes are derived and showing the various unprocessed replicative intermediates that produce self-complementary genomes. The figure is from N. L. Craig et al. *Mobile DNA II*. ASM Press, Washington, D.C. 2002, the contents of which are herein incorporated by reference in their entirety.
Figure 6A:
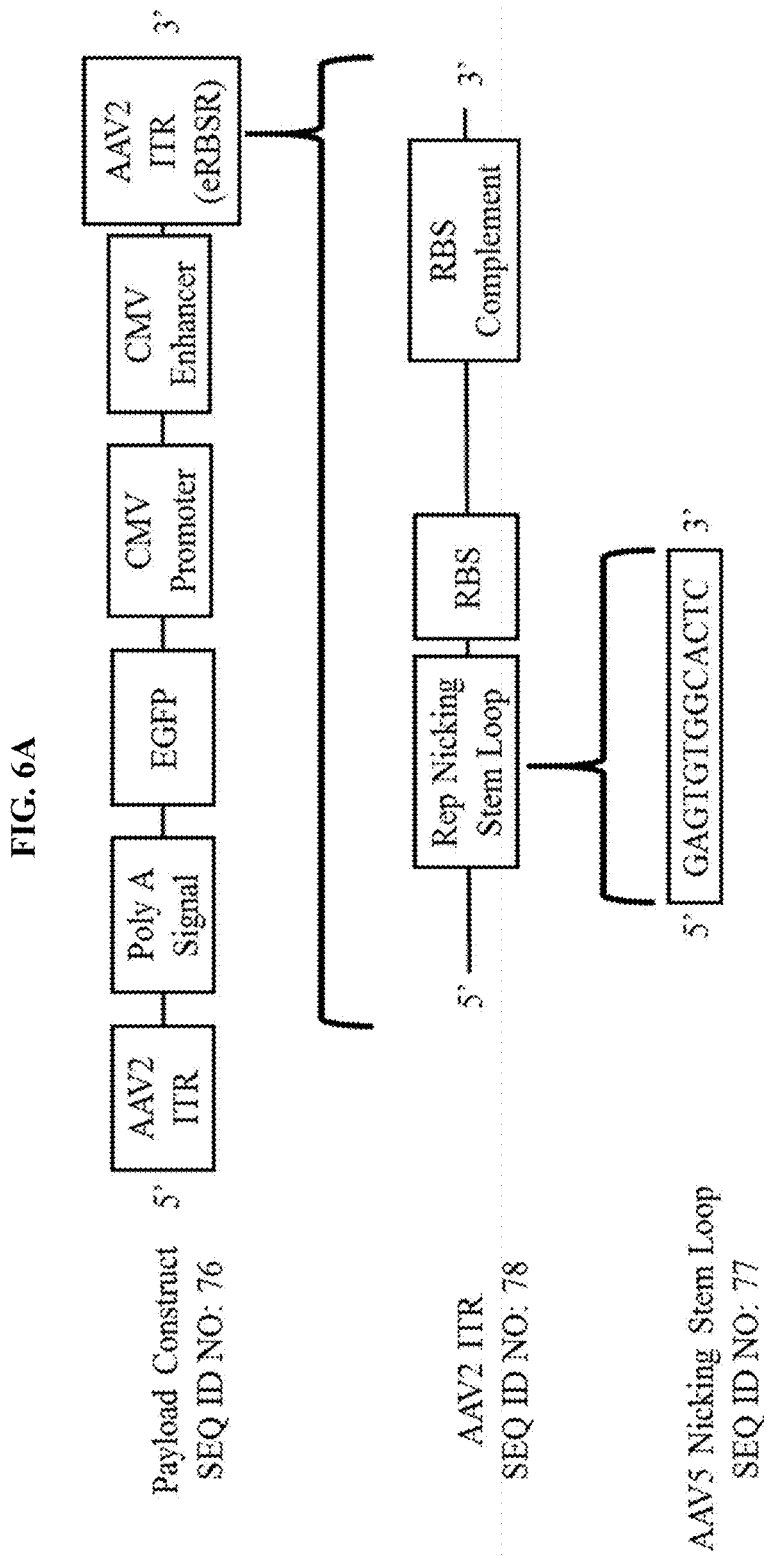
FIG. 6A is a schematic diagram of a polynucleotide having a swapped nicking stem loop payload construct (SEQ ID NO: 76).
Figure 6B:
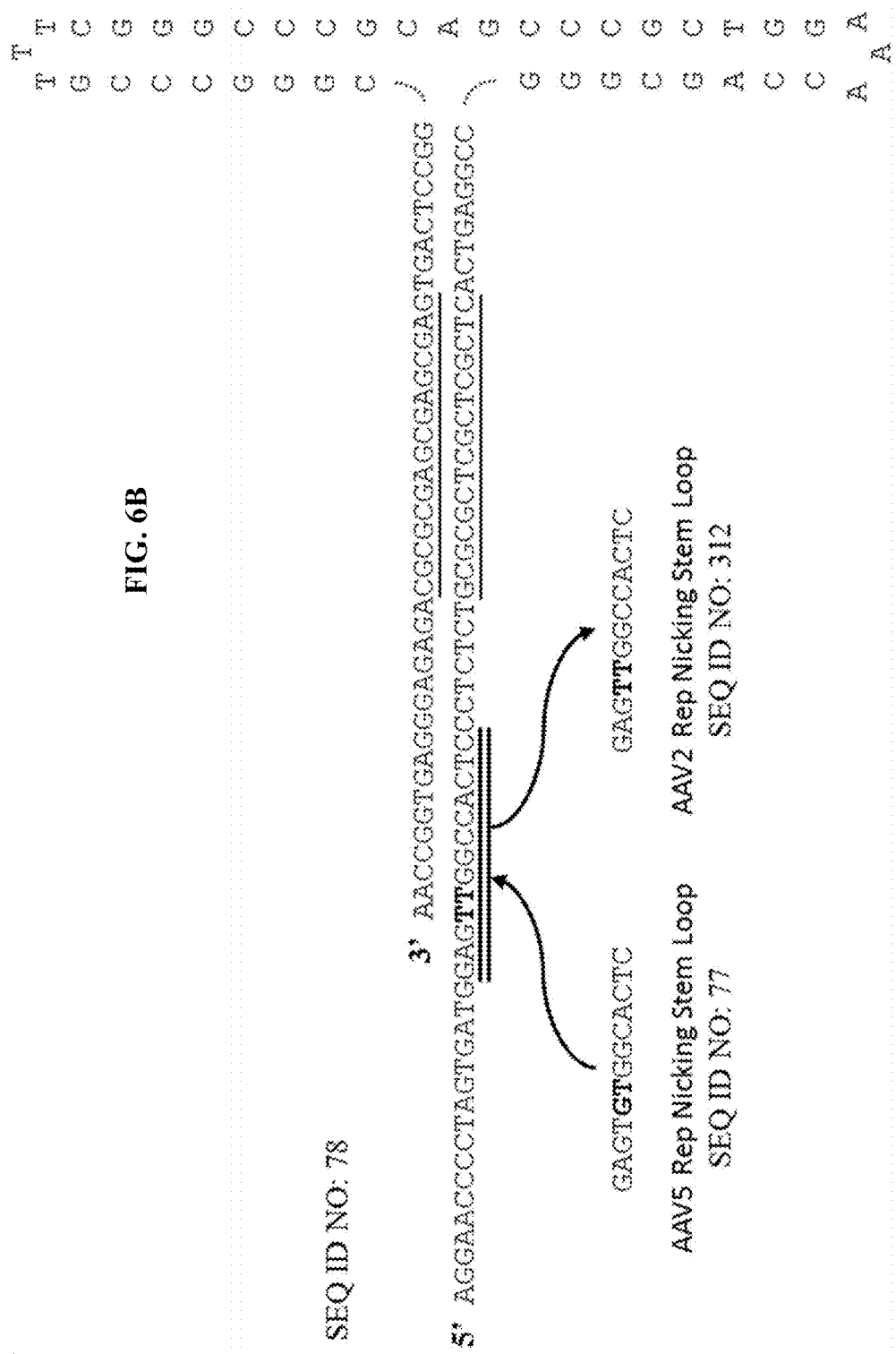
FIG. 6B is a schematic diagram comprising the AAV5 Rep nicking stem loop sequence (SEQ ID NO: 77) and the AAV2 Rep nicking stem loop sequence (SEQ ID NO: 312) inserted into an AAV2 3' ITR sequence (SEQ ID NO: 78)

Replication of ssDNA AAV genomes begins at the 3' end of the genome where the self-complementary portion of the ITR forms a double stranded region that acts as a primer for the initiation of DNA synthesis, Replication continues in the 5' to 3' direction until a double stranded hairpin structure called the replicative form monomer ($RF_M$) has been formed with a loop at one end (FIG. 5). Rep protein binds to the Rep binding sequence region near the end of the hairpin comprising the loop, and nicks the DNA, allowing the polymerase to replicate the loop and form a linear double stranded DNA molecule. The complementary strands are then separated by Rep protein to allow reformation of the ITR complementary loop and the replication cycle continues on both resultant strands of ssDNA.

In the event that the $RF_M$ species is not nicked by Rep protein, an alternative replication process is used. The 3' end of the molecule reforms the ITR complementary loop and replication continues along the length of the molecule, forming the replicative form dimer duplex ($RF_D$). The $RF_D$ species may be resolved by two different pathways. In the first pathway, productive nicking of the $RF_D$ species on both strands results in two copies of the $RF_M$ species. In the second pathway, the $RF_D$ species reforms the ITR complementary loop allowing replication and formation of a 2× $RF_D$ species. Productive nicking of the 2× $RF_D$ species results in two copies of the $RF_D$ species.

An AAV genome comprising one engineered Rep binding sequence region with decreased affinity for Rep protein and one wild-type Rep binding sequence region prevents productive nicking. A lack of binding to the engineered Rep binding sequence region reduces nicking and promotes replication of the $RF_M$ species by the alternative pathway. In the resultant $RF_D$ species, the position of the engineered Rep binding sequence region reduces Rep binding and promotes productive replicative cycling of the $RF_D$ species. In the second cycle of $RF_D$ species replication a wild-type Rep binding sequence region is positioned to promote nicking and results in two copies of the $RF_D$ species.

Viral particles. e.g., AAV particles, produced from viral genomes comprising wild-type ITR regions are observed to contain both single stranded and self-complementary viral genomes. Self-complementary AAV genomes are derived from unprocessed replicative intermediates. The nucleic acid content of recombinant AAV analyzed by analytical ultracentrifugation has shown that although the Raleigh interference curves for DNA species with sedimentation coefficients of 84S and 106S indicate similar particle numbers, the 106S absorbance at 260 nm is 1.6 times greater than the 84S peak. The difference in absorbance peak area indicates greater nucleic acid content in the 106S peak. Thus, approximately half of the viral particles contain a self-complementary genome that is 1.6 times as large as the single stranded genome.

Intermediate replicative species are successfully packaged in virus particles. AAV viral particles produced in vitro are collected by ultracentrifugation and the DNA genomes isolated by standard molecular biology techniques known in the art. The genomes are separated by denaturing (alkaline) gel electrophoresis. Analysis of the DNA content banding pattern has shown multiple sizes of viral genomes including scAAV, scAAV intermediate species, ssAAV monomer, and an ssAAV repaired from scAAV.

In accordance with the present disclosure, a parvoviral particle comprising a duplexed genome is provided. In one embodiment, the parvoviral particle comprises a parvoviral capsid and a viral genome comprising: a first parvoviral inverted terminal repeat sequence, a first heterologous sequence, a parvoviral inverted terminal repeat nucleotide sequence comprising an engineered Rep binding sequence region, a second heterologous sequence, wherein the second heterologous sequence is complementary to the first heterologous sequence, and a second parvoviral inverted terminal repeat sequence. The viral genome is capable of intra-strand base-pairing between the heterologous nucleotide sequences upon release from the parvoviral capsid. The parvoviral particle can optionally further comprise a sequence encoding an engineered Rep protein which binds to the Rep binding sequence region and/or engineered Rep binding sequence region with decreased affinity.

In another embodiment, the parvoviral particle comprises a parvoviral capsid and a parvoviral genome comprising: a first parvoviral inverted terminal repeat sequence, a first heterologous sequence, a parvoviral inverted terminal repeat nucleotide sequence comprising a chimeric nicking stem loop, a second heterologous sequence, wherein the second heterologous sequence is complementary to the first heterologous sequence, and a second parvoviral inverted terminal repeat sequence. The parvoviral particle can further comprise a sequence encoding an engineered Rep protein which binds to the Rep binding sequence region and/or engineered Rep binding sequence region with decreased affinity.

The present disclosure additionally provides compositions and methods for improving the transduction efficiency and heterologous gene expression of viral particles having parvoviral polynucleotide sequences by altering one or more of several Rep binding activities to effect the production of viral particles having a self-complementary or duplexed genome, for example, by altering the Rep binding sequence region, and/or by altering one or more Rep proteins, and/or by altering the Rep nicking sequence found in parvoviral ITR sequences. Thus, the present disclosure provides, among other things, a parvoviral polynucleotide, such as an adeno-associated viral (AAV) polynucleotide, comprising an engineered Rep binding sequence region and/or an altered Rep nicking sequence. In addition, the present disclosure provides an engineered Rep protein, and a polynucleotide sequence encoding the engineered Rep protein, which can be used independently in the production of a viral particle having a self-complementary or duplexed genome (i.e., with wild-type Rep binding sequence region and wild-type Rep nicking stem loop) or can be used in conjunction with an engineered Rep binding sequence region and/or an altered Rep nicking sequence in the production of a viral particle having a self-complementary or duplexed genome.

II. ENGINEERED REP BINDING SEQUENCE REGION (ERBSR) AND POLYNUCLEOTIDES

One way to promote the generation of self-complementary parvoviral genome sequences is to alter or modify the Rep binding sequence region such that Rep binding is decreased, thus affecting the nicking activity of the Rep protein and consequently promoting the generation of self-complementary parvoviral genome sequences. Accordingly, the present disclosure provides a nucleic acid comprising an eRBSR in which one or more of the nucleotides in the engineered Rep binding sequence region are altered or modified as compared to the native or wild-type Rep binding sequence region.

As used herein, the term "altered nucleotide" or the term "altered" as it is used to describe a nucleotide, refers to a nucleotide that differs from the native nucleotide found at the same sequence position in a nucleic acid or polynucleotide sequence, including an eRBSR or polynucleotide comprising an eRBSR. The altered nucleotide can contain any naturally or non-naturally occurring nucleoside selected from adenosine, guanosine, uridine, cytidine, thymidine, as long as it differs from the native nucleoside. Any known method can be used to produce an eRBSR having one or more of the altered nucleotides. In one embodiment, the altered nucleotide is designed in silica and manufactured by methods standard in the art including solid phase synthesis. In one embodiment, the altered nucleotide is designed in silico and manufactured by the phosphoramidite method of solid state synthesis.

As used herein, there term "modified nucleotide" or the term "modified" as it is used to describe a nucleotide, refers to a nucleotide that has been chemically modified. The present disclosure provides for modified nucleosides and nucleotides. As described herein "nucleoside" is defined as a compound containing a sugar molecule (e.g., a pentose or ribose) or a derivative thereof in combination with an organic base (e.g., a purine or pyrimidine) or a derivative thereof (also referred to herein as "nucleobase"). As described herein, "nucleotide" is defined as a nucleoside including a phosphate group. The modified nucleotides may by synthesized by any useful method, as described herein (e.g., chemically, enzymatically, or recombinantly to include one or more modified or non-natural nucleosides). The chemical modification can be on the nucleobase, and/or the sugar, and/or on the backbone of the nucleotide. The chemical modification can be any chemical modification used to modify nucleic acid.

The modified nucleotides can be modified on the sugar of the nucleic acid. In some embodiments, chemical modifications include for example, the 2' hydroxyl group (OH) can be modified or replaced with a number of different substituents. Exemplary substitutions at the 2'-position include, but are not limited to, H, halo, optionally substituted C1-6 alkyl; optionally substituted C1-6 alkoxy; optionally substituted C6-10 aryloxy; optionally substituted C3-8 cycloalkyl; optionally substituted C3-8 cycloalkoxy; optionally substituted C6-10 aryloxy; optionally substituted C6-10 aryl-C1-6 alkoxy, optionally substituted C1-12 (heterocyclyl)oxy, a sugar (e.g., ribose, pentose, or any described herein); a polyethyleneglycol (PEG), —O(CH2CH2O)nCH2CH2OR, where R is H or optionally substituted alkyl, and n is an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20); "locked" nucleic acids (LNA) in which the 2'-hydroxyl is connected by a C1-6 alkylene or C1-6 heteroalkylene bridge to the 4'-carbon of the same ribose sugar, where exemplary bridges included methylene, propylene, ether, or amino bridges; aminoalkyl, aminoalkoxy, amino, and amino acid.

Further examples include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for anhydrohexitol, altritol mannitol, cyclohexanyl, cyclohexenyl, and morpholino that also has a phosphoramidate backbone); multicyclic forms (e.g., tricyclo; and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with α-L-threofuranosyl-(3'→2')), and peptide nucleic acid (PNA, where 2-amino-ethyl-glycine linkages replace the ribose and phosphodiester backbone) The sugar group can also contain one or more carbons that possess the opposite stereochemical configuration than that of the corresponding carbon in ribose.

The modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the modified nucleotide inosine and adenine, cytosine or uracil.

The modified nucleotides can be modified on the nucleobase of the nucleic acid. Examples of nucleobases include, but are not limited to, adenine, guanine, cytosine, thymine, and uracil.

In some embodiments, the modified nucleobase is a modified uracil. Exemplary nucleobases and nucleosides having a modified uracil include pseudouridine (ψ), pyridin-4-one ribonucleoside, 5-aza-uridine, 6-aza-uridine, 2-thio-5-aza-uridine, 2-thio-uridine (s2U), 4-thio-uridine (s4U), 4-thio-pseudouridine, 2-thio-pseudouridine, 5-hydroxy-uridine (ho5U), 5-aminoallyl-uridine, 5-halo-uridine (e.g., 5-iodo-uridine or 5-bromo-uridine), 3-methyl-uridine (m3U), 5-methoxy-uridine (mo5U), uridine 5-oxyacetic acid (cmo5U), uridine 5-oxyacetic acid methyl ester (mcmo5U), 5-carboxymethyl-uridine (cm5U), 1-carboxymethyl-pseudouridine, 5-carboxyhydroxymethyl-uridine (chm5U), 5-carboxyhydroxymethyl-uridine methyl ester (mchm5U), 5-methoxycarbonylmethyl-uridine (mcm5U), 5-methoxycarbonylmethyl-2-thio-uridine (mcm5s2U), 5-aminomethyl-2-thio-uridine (nm5s2U), 5-methylaminomethyl-uridine (mnm5U), 5-methylaminomethyl-2-thio-uridine (mnm5s2U), 5-methylaminomethyl-2-seleno-uridine (mnm5se2U), 5-carbamoylmethyl-uridine (ncm5U), 5-carboxymethylaminomethyl-uridine (cmnm5U), 5-carboxymethylaminomethyl-2-thio-uridine (cmnm5s2U), 5-propynyl-uridine, 1-propynyl-pseudouridine, 5-taurinomethyl-uridine (τm5U), 1-taurinomethyl-pseudouridine, 5-taurinomethyl-2-thio-uridine(τm5s2U), 1-taurinomethyl-4-thio-pseudouridine, 5-methyl-uridine (m5U, i.e., having the nucleobase deoxythymine), 1-methylpseudouridine (m1ψ), 5-methyl-2-thio-uridine (m5s2U), 1-methyl-4-thio-pseudouridine (m1s4ψ), 4-thio-1-methyl-pseudouridine, 3-methyl-pseudouridine m3ψ), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m5D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine (also known as 1-methylpseudouridine (m1ψ)), 3-(3-amino-3-carboxypropypuridine (acp3U), 1-methyl-3-(3-aniino-3-carboxypropyppseudouridine (acp3 ψ), 5-(isopentenylaminomethyl)uridine (inm5U), 5-(isopentenylaminomethyl)-2-thio-uridine (inm5s2U), α-thio-uridine, 2'-O-methyl-uridine (Um), 5,2'-O-dimethyl-uridine (m5Um), 2'-O-methyl-pseudouridine (ψm), 2-thio-2'-O-methyl-uridine (s2Um), 5-methoxycarbonylmethyl-2'-O-methyl-uridine (mcm5Um), 5-carbamoylmethyl-2'-O-methyl-uridine (ncm5Um), 5-carboxymethylaminomethyl-2'-O-methyl-uridine (cmnm5Um), 3,2'-O-dimethyl-uridine (m3Um), 5-(isopentenylaminomethyl)-2'-O-methyl-uridine (inm5Um), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine (m3C), N4-acetyl-cytidine (ac4C), 5-formyl-cytidine (f5C), N4-methyl-cytidine (m4C), 5-methyl-cytidine (m5C), 5-halo-cytidine (e.g., 5-iodo-cytidine), 5-hydroxymethyl-cytidine (hm5C), 1-methyl-pseudoisocytidine, pyrrolo-cytidine, pyrrolo-pseudoisocytidine, 2-thio-cytidine (s2C), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine (k2C), α-thio-cytidine, 2'-O-methyl-cytidine Cm), 5,2'-O-dimethyl-cytidine (m5Cm), N4-acetyl-2'-O-methyl-cytidine ac4Cm), N4,2'-O-dimethyl-cytidine (m4Cm), 5-formyl-2'-O-methyl-cytidine (f5Cm), N4,N4,2'-O-trimethyl-cytidine (m42C), 1-thio-cytidine, 2'-F-ara-cytidine, 2'-F-cytidine, and 2'-OH-ara-cytidine.

In some embodiments, the modified nucleobase is a modified adenine. Exemplary nucleobases and nucleosides having a modified adenine include 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine (m1A), 2-methyl-adenine (m2A), N6-methyl-adenosine (m6A), 2-methylthio-N6-methyl-adenosine (ms2m6A), N6-isopentenyl-adenosine (i6A), 2-methylthio-N6-isopentenyl-adenosine (ms2i6A), N6-(cis-hydroxyisopentenyl)adenosine (io6A), 2-methylthio-N6-(cis-hydroxyisopentenyl) adenosine (ms2io6A), N6-glycinylcarbamoyi-adenosine (g6A), N6-threonylcarbamoyl-adenosine (t6A), N6-methyl-N6-threonylcarbamoyl-adenosine (m6t6A), 2-methylthio-N6-threonylcarbamoyl-adenosine (ms2g6A), N6,N6-dimethyl-adenosine (m62A), N6-hydroxynorvalylcarbamoyladenosine (hn6A), 2-methylthio-N6-hydroxynorvalylcarbamoyl-adenosine (ms2hn6A), N6-acetyl-adenosine (ac6A), 7-methyl-adenine, 2-methyl-thio-adenine, α-thio-adenosine, 2'-O-methyl-adenosine (Am), N6,2'-O-dimethyl-adenosine (m6Am), N6,N6,2'-O-trimethyl-adenosine (m62Am), 1,2'-O-dimethyl-adenosine (m1Am), 2'-O-ribosyladenosine (phosphate) (Ar(p)), 2-amino-N6-methyl-purine, 1-thio-adenosine, 8-azido-adenosine, 2c-F-ara-adenosine, 2'-F-adenosine, 2'-OH-ara-adenosine, and N6-(19-amino-pentaoxanonadecyl)-adenosine.

In some embodiments, the modified nucleobase is a modified guanine. Exemplary nucleobases and nucleosides having a modified guanine include inosine (I), 1-methyl-inosine (m1I), wyosine (imG), methylwyosine (mimG), 4-demethyl-wyosine (imG-14), isowyosine (imG2), wybutosine (yW), peroxywybutosine (o2yW), hydroxywybutosine (OHyW), undermodified hydroxywybutosine (OHyW*), 7-deaza-guanosine, queuosine (Q), epoxyqueuosine (oQ), galactosyl-queuosine (galQ), mannosyl-queuosine (manQ), 7-cyano-7-deaza-guanosine (preQ0), 7-aminomethyl-7-deaza-guanosine (preQ1), archaeosine (G+), 7-deaza-8-aza-guanosine, 6-thio-guanosine, 6-thio-7-deaza-guanosine, 6-thio-7-deaza-8-aza-guanosine, 7-methyl-guanosine (m7G), 6-thio-7-methyl-guanosine, 7-methyl-inosine, 6-methoxy-guanosine, 1-methyl-guanosine (m1G), N2-methyl-guanosine (m2G), N2,N2-dimethyl-guanosine (m22G), N2,7-dimethyl-guanosine (m2,7G), N2, N2,7-dimethyl-guanosine (2,2,7G), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine (m2Gm), N2,N2-dimethyl-2'-O-methyl-guanosine (m22Gm), 1-methyl-2'-O-methyl-guanosine (m1Gm), N2,7-dimethyl-2'-O-methyl-guanosine (m2,7Gm), 2'-O-methyl-inosine (Im), 1,2'-O-dimethyl-inosine (m1Im), and 2'-O-ribosylguanosine (phosphate) (Gr(p)).

The nucleobase of the nucleotide can be independently selected from a purine, a pyrimidine, or a purine or pyrimidine analog. For example, the nucleobase can be independently selected from adenine, cytosine, guanine, uracil, or hypoxanthine. In another embodiment, the nucleobase can also include, for example, naturally-occurring and synthetic derivatives of a base, including pyrazolo[3,4-d]pyrimidines, 5-methylcytosine (5-me-C), 5-hydroxy methyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d] pyrimidines, pyrazin-2-ones, 1,2,4-triazine, pyridazine; and 1,3,5 triazine. When the nucleotides are depicted using the shorthand A, G, C, T or U, each letter refers to the representative base and/or derivatives thereof, e.g., A includes adenine or adenine analogs, e.g., 7-deaza adenine).

The modified nucleotides can be modified on the internucleoside linkage (e.g., phosphate backbone). Herein, in the context of the polynucleotide backbone, the phrases "phosphate" and "phosphodiester" are used interchangeably. Backbone phosphate groups can be modified by replacing one or more of the oxygen atoms with a different substituent. Further, the modified nucleosides and nucleotides can include the wholesale replacement of an unmodified phosphate moiety with another internucleoside linkage as described herein. Examples of modified phosphate groups include, but are not limited to, phosphorothioate, phosphoroselenates, boranophosphates, boranophosphate esters, hydrogen phosphonates, phosphoramidates, phosphorodiamidate, alkyl or aryl phosphonates, and phosphotriesters. Phosphorodithioates have both non-linking oxygens replaced by sulfur. The phosphate linker can also be modified by the replacement of a linking oxygen with nitrogen (bridged phosphoramidates), sulfur (bridged phosphorothioates), and carbon (bridged methylene-phosphonates).

The α-thio substituted phosphate moiety is provided to confer stability to RNA and DNA polymers through the unnatural phosphorothioate backbone linkages, Phosphorothioate DNA and RNA have increased nuclease resistance and subsequently a longer half-life in a cellular environment.

In specific embodiments, a modified nucleoside includes an alpha-thio-nucleoside (e.g., 5'-O-(1-thiophosphate)-adenosine, 5'-O-(1-thiophosphate)-cytidine (α-thio-cytidine), 5'-O-(1-thiophosphate)-guanosine, 5'-O-(1-thiophosphate)-uridine, or 5'-O-(1-thiophosphate)-pseudouridine).

In some embodiments, a combination of modifications to the sugar, the nucleobase, and/or the internucleoside linkage may be used.

Methods for chemically modifying nucleic acids are known in the all and include, for example, any available technique including, but not limited to, chemical synthesis, enzymatic synthesis, and enzymatic or chemical cleavage of a longer precursor. Methods of synthesizing nucleotides are known in the art (see, e.g., Gait, M. J. (ed.) Oligonucleotide synthesis: a practical approach, Oxford [Oxfordshire], Washington, D.C.: IRL. Press, 1984; and Herdewijn, P. (ed.) Oligonucleotide synthesis: methods and applications, Methods in Molecular Biology, v. 288 (Clifton, N.J.) Totowa, N.J.: Humana Press, 2005; both of which are incorporated herein by reference in their entirety).

In one embodiment, the engineered Rep binding sequence region or eRBSR has a single altered or modified nucleotide as compared to the native Rep binding sequence region. In another embodiment, the eRBSR has two or more altered or modified nucleotides as compared to the native Rep binding sequence region. In certain embodiments, the eRBSR has two to twelve altered or modified nucleotides, including, for example, 2, 3, 4, 5, 6, 7, 8, 9, 10, 11, or 12 altered or modified nucleotides as compared to the native Rep binding sequence region. In one embodiment, all of the nucleotides of the eRBSR are altered, e.g., such as in a swapped sequence (discussed below), as long as the eRBSR retains some minimal binding with the Rep protein.

In another embodiment, the eRBSR has one or more nucleotide insertions, deletions, substitutions, or any combination thereof as compared to the corresponding native Rep binding sequence region. For example, the engineered Rep binding sequence region can comprise a sequence having one or more nucleotides that differ from the Rep binding sequence region of an adeno-associated virus (AAV), including the Rep binding sequence region of AAV1, AAV2, AAV3, AAV4, AAV5, AAV6, AAV7, AAV 8, AAV9, AAV10, AAV11, AAV12, AAV rh8, AAVrh10, AAV-DJ, and AAV-DJ8.

In another embodiment, the present disclosure provides a nucleic acid comprising an eRBSR in which the Rep binding sequence region is not native to the parvoviral genome. The eRBSR can comprise a Rep binding sequence region that is found in a different parvoviral serotype or species genome. In one embodiment, the eRBSR is a Rep binding sequence region from a parvoviral serotype or species that differs from the serotype or species of the native parvoviral ITR sequence. In one embodiment, the eRBSR is a Rep binding sequence region from a parvoviral serotype or species that differs from the serotype or species of the native Rep protein or sequence encoding the Rep protein. Thus, in certain embodiments, the eRBSR is created by swapping the native Rep binding sequence region with all or most of the Rep binding sequence region of a different serotype or species. In one embodiment, the entire Rep binding sequence region is swapped. In another embodiment, a portion or partial sequence of the Rep binding sequence region is swapped. In one embodiment, the engineered Rep binding sequence region can comprise a non-native or swapped Rep binding sequence region from an AAV viral particle, including the Rep binding sequence region of AAV1, AAV2, AAV3, AAV4, AAV5, AAV6, AAV7, AAV8, AAV9, AAV10, AAV11, AAV12, AAVrh8, AAVrh10, AAV-DJ, and AAV-DJ8. In one embodiment, the eRBSR for an AAV2 polynucleotide, genome, or viral particle (i.e., comprising an AAV2 ITR and/or AAV2 Rep protein coding sequence) is the Rep binding sequence region found in AAV-5 (Table 1; SEQ ID NO: 3, SEQ ID NO: 4).

In other embodiments, the engineered Rep binding sequence region can comprise a sequence having both alterations and chemical modifications. Thus, in one embodiment, the eRBSR comprises one or more nucleotides that are altered and one or more nucleotides that are chemically modified. Examples of suitable chemical modifications are provided above.

The engineered Rep binding sequence region must have minimal length sufficient to bind a Rep protein and is only constrained in its maximal length by the length of any ITR packaged in the viral particle. In one embodiment, the eRBSR can approximate the length of a typical parvoviral ITR sequence. In one embodiment, the eRBSR is from about four to about 145 nucleotides in length. In one embodiment, the engineered Rep binding sequence region is from four to 145 nucleotides in length. In another embodiment, the engineered Rep binding sequence region is from about four to about sixty-four nucleotides in length, including any length within that size range, for example 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 19, 40, 41, 42, 43, 44, 45, 46, 47, 48, 49, 50 51, 52, 53, 54, 55, 56, 57, 58, 59, 60, 61, 62, 63, and 64 nucleotides in length. In other embodiments, the engineered Rep binding sequence region is from about four to about forty-eight, about four to about thirty-six, about four to about twenty-four, about four to about twenty, about four to about sixteen, and about four to about eight nucleotides in length. In another embodiment, the engineered Rep binding sequence region is from about eight to about twenty, about eight to about sixteen, and about eight to twelve nucleotides in length. In another embodiment, the engineered Rep binding sequence region is four, eight, twelve, sixteen, or twenty nucleotides in length. In one embodiment, the eRBSR is sixteen nucleotides in length.

In one embodiment, the eRBSR is a nucleic acid comprising one or more consensus motifs having the sequence GCTC. In one embodiment, the eRBSR comprises one to three GCTC consensus motifs. In one embodiment, the eRBSR comprises one GCTC consensus motif. In one embodiment, the eRBSR comprises two GCTC consensus motifs. In one embodiment, the eRBSR comprises three GCTC consensus motifs. In any of these embodiments, the one to three GCTC consensus motifs can function as an eRBSR when the consensus motif(s) sequence is substituted for (swapped with) the native Rep binding sequence region. Thus, the eRBSR is created by swapping the native Rep binding sequence region with one, two, or three GCTC consensus motif(s). In one embodiment, the entire native Rep binding sequence region is swapped. In another embodiment, a portion or partial sequence of the native Rep binding sequence region is swapped. In any of these embodiments, the eRBSR is about 4-20 nucleotides in length. In one embodiment, the eRBSR has a length of about 4-20 nucleotides and comprises one GCTC motif. In another embodiment, the eRBSR has a length of 4-20 nucleotides and comprises one GCTC motif. In another embodiment, the eRBSR has a length of 4-16 nucleotides and comprises one GCTC motif. In any of these variations, the eRBSR can have a sequence selected from: [GCTC]-(N)x (SEQ ID NO: 292) or (N)x-[GCTC] (SEQ ID NO: 293), wherein x=0-16 and N is any naturally or non-naturally occurring nucleoside selected from adenosine, guanosine, uridine, cytidine, thymidine. In one variation, x=0-12. In another embodiment, the eRBSR has a length of about 8-20 nucleotides and comprises two GCTC motifs. In another embodiment, the eRBSR has a length of 8-20 nucleotides and comprises two GCTC motifs. In another embodiment, the eRBSR has a length of 8-16 nucleotides and comprises two GCTC motifs. In any of these variations, the eRBSR can have a sequence selected from: (1) [GCTC]2-(N)x (SEQ ID NO: 294) or (N)x-[GCTC]2 (SEQ ID NO: 295), wherein x is 0-12 and N is any naturally or non-naturally occurring nucleoside selected from adenosine, guanosine, uridine, cytidine, thymidine; (2) [GCTC]N)x-[GCTC]-(N)y (SEQ ID NO: 296) or (N)x-[GCTC]-(N)y-[GCTC] (SEQ ID NO: 297), wherein x and y are independently 0-12, with the proviso that x+y<12 and N is any naturally or non-naturally occurring nucleoside selected from adenosine, guanosine, uridine, cytidine, thymidine; and (3) (N)x-[GCTC]2-(N)y (SEQ ID NO: 298) or [GCTC]-(N)x-[GCTC] (SEQ ID NO: 299), wherein x and y are independently 0-12, with the proviso that x+y<12 and N is any naturally or non-naturally occurring nucleoside selected from adenosine, guanosine, uridine, cytidine, thymidine. In one variation, x=0-8 and y=0-8, with the proviso that x+y<8. In another embodiment, the eRBSR has a length of 12-20 nucleotides and comprises three GCTC motifs. In one embodiment, the eRBSR has a length of 12-20 nucleotides and comprises three GCTC motifs. In another embodiment, the eRBSR has a length of 12-16 nucleotides and comprises three GCTC motifs. In any of these variations, the eRBSR can have a sequence selected from: (1) [GCTC]3-(N)x (SEQ ID NO: 300) or (N)x-[GCTC]3 (SEQ ID NO: 301), wherein x is 0-8 and N is any naturally or non-naturally occurring nucleoside selected from adenosine, guanosine, uridine, cytidine, thymidine; (2) [GCTC]-(N)x-[GCTC]2-(N)y (SEQ ID NO: 302) or (N)x-[GCTC]-(N)y-[GCTC]2 (SEQ ID NO: 303), wherein x and y are independently 0-8, with the proviso that x+y<8 and N is any naturally or non-naturally occurring nucleoside selected from adenosine, guanosine, uridine, cytidine, thymidine; (3) [GCTC]2-(N)x-[GCTC]N)y (SEQ ID NO: 304) or Nx-[GCTC]2-Ny-[GCTC] (SEQ ID NO: 305), wherein x and y are independently 0-8, with the proviso that x+y<8 and N is any naturally or non-naturally occurring nucleoside selected from adenosine, guanosine, uridine, cytidine, thymidine; (4)

(N)x-[GCTC]3-(N)y (SEQ ID NO: 306) or [GCTC]-(N)x-[GCTC]-(N)y-[GCTC] (SEQ ID NO: 307), wherein x and y are independently 0-8, with the proviso that x+y<8 and N is any naturally or non-naturally occurring nucleoside selected from adenosine, guanosine, uridine, cytidine, thymidine. In one variation, x and y are independently 0-4, with the proviso that x+y<4. In any of these embodiments, the engineered Rep binding sequence region comprising one, two, or three GCTC consensus motifs can be swapped with a Rep binding sequence region from an AAV viral genome, including the Rep binding sequence region of AAV1, AAV2, AAV3, AAV4, AAV5, AAV6, AAV7, AAV8, AAV9, AAV10, AAV11, AAV12, AAVrh8, AAVrh10, AAV-DJ, and AAV-DJ8. Also, in any of these embodiments, one or more of the nucleotides in at least one of the GCTC consensus motifs is altered or modified.

In one embodiment, the eRBSR is a nucleic acid comprising one or more consensus motifs having the sequence GCTC, in which one or more of the nucleotides in at least one of the GCTC consensus motifs is altered or modified. In one embodiment, one or more of the GCTC consensus motif(s) is altered or modified to a motif sequence selected from the group consisting of (1) NCTC, (2) GNTC, (3) GCNC, (4) GCTN, and (5) in the case of two or more altered or modified motif sequences, any combination of these altered or modified motifs, wherein N is either any naturally or non-naturally occurring nucleoside selected from adenosine, guanosine, uridine, cytidine, thymidine with the proviso that N differs from the consensus nucleotide in that position or N is a chemically modified nucleotide, in which the chemical modification(s) can be on the nucleobase, and/or on the sugar and/or on the backbone. In another embodiment, one or more of the GCTC consensus motif(s) is altered or modified to a motif sequence selected from the group consisting of (1) NNTC, (2) GNNC, (3) GCNN, (4) GNTN, (5) NCNC, (6) NCTN, and (7) in the case of two or more altered or modified GCTC: motif sequences, any combination of these altered or modified motifs, wherein N is any naturally or non-naturally occurring nucleoside selected from adenosine, guanosine, uridine, cytidine, thymidine with the proviso that N differs from the consensus nucleotide in that position or N is a chemically modified nucleotide, in which the chemical modification(s) can be on the nucleobase, and/or on the sugar and/or on the backbone. The individual GCTC consensus motifs can be contiguous with one another or can be separated by intervening sequence, in certain of these embodiments having two or more GCTC consensus motifs, the consensus GCTC motifs are contiguous with one another. In other of these embodiments having one or more GCTC consensus motifs none of the consensus motifs are contiguous with one another. In other individual embodiments, two, three, four, five or more GCTC consensus motifs are contiguous with one another.

In one embodiment, the eRBSR is a nucleic acid comprising one or more consensus motifs having the sequence GCTC, in which one or more of the nucleotides in at least one of the GCTC consensus motifs is altered or modified. In one embodiment, one or more of the GCTC consensus motif(s) is altered to a motif sequence selected from the group consisting of (1) NCTC, (2) GNTC, (3) GCNC, (4) GCTN, and (5) in the case of two or more altered motif sequences, any combination of these modified altered motifs, wherein N is any naturally or non-naturally occurring nucleoside selected from adenosine, guanosine, uridine, cytidine, thymidine. In one embodiment, one or more of the GCTC consensus motifs) contains at least one nucleotide which is chemically modified. The chemical modification(s) can be on the nucleobase, and/or on the sugar and/or on the backbone. The individual GCTC consensus motifs can be contiguous with one another or can be separated by intervening sequence. In certain of these embodiments having two or more GCTC consensus motifs, the consensus GCTC motifs are contiguous with one another. In other of these embodiments having one or more GCTC consensus motifs none of the consensus motifs are contiguous with one another. In other individual embodiments, two, three, four, five or more GCTC consensus motifs are contiguous with one another.

In one embodiment, the eRBSR has the formula (GCTC)x (SEQ ID NO: 308), where x=1-4, in which one or more of the nucleotides in at least one of the GCTC consensus motifs is altered or modified. In one embodiment, one nucleotide in at least one of the GCTC consensus motifs is altered or modified. In one variation of this embodiment, one nucleotide in one of the GCTC consensus motifs is altered or modified. In another variation, one nucleotide in two of the GCTC consensus motifs is altered or modified. In yet another variation, one nucleotide in three of the GCTC consensus motifs is altered or modified. In still another variation, one nucleotide in four of the GCTC consensus motifs is altered or modified. In one embodiment, two nucleotides in at least one of the GCTC consensus motifs is altered or modified. In variations of this embodiment, two nucleotides in one, two, three, or four of the GCTC consensus motifs are altered or modified.

In one embodiment, the eRBSR has the formula $(GCTC)_x$-$N_y$-$(GCTC)_z$ (SEQ ID NO: 309), wherein N is any naturally or non-naturally occurring nucleoside selected from adenosine, guanosine, uridine, cytidine, thymidine; x and z are 0-2 with the proviso that when x=0, z=1 or 2, and when z=0. x=1 or 2; and y=0-8, in which one or more of the nucleotides in at least one of the GCTC consensus motifs is modified. In one embodiment, the eRBSR has the formula $(GCTC)$-$N_y$-$(GCTC)_z$-$N_y$-$(GCTC)_w$ (SEQ ID NO: 310), wherein N is any naturally or non-naturally occurring nucleoside selected from adenosine, guanosine, uridine, cytidine, thymidine; w, x, and z are 0-2 with the proviso that when x=0, z=1 or 2 and w=1 or 2, when z=0, x=1 or 2 and w=1 or 2; when w=0, x=1 or 2 and z=1 or 2, and y=0-8. In any of the embodiments described here, when y=4 the N's can comprise a GCTC consensus motif in which at least one of the nucleotides in the consensus motif is altered or modified. In one variation of this embodiment, one of the nucleotides in the consensus motif is altered or modified. In another variation of this embodiment, two of the nucleotides in the consensus motif is altered or modified. Also, in any of the embodiments described here, when y=8 the N's can comprise two GCTC consensus motif in which at least one of the nucleotides in at least one of the consensus motifs is altered or modified. In one variation of this embodiment, one of the nucleotides in one or both of the consensus motifs is altered or modified. In another variation of this embodiment, two of the nucleotides in one or both of the consensus motifs is altered or modified.

Table 1 provides Rep binding sequence regions found in various AAV serotypes and species which can function as an eRBSR (SEQ ID NOs: 1-20).

TABLE 1

Native or Wild-Type Rep Binding Sequence Regions

| Rep-binding sequence | Sequence | SEQ ID NO |
|---|---|---|
| AAV2 5' | GCGCGCTCGCTCGCTC | 1 |
| AAV2 3' | GAGCGAGCGAGCGCGC | 2 |
| AAV5 5' | GCTCGCTCGCTGGCTC | 3 |
| AAV5 3' | GAGCCAGCGAGCGAGC | 4 |
| AAV1 5' | GCGCGCTCGCTCGCTC | 5 |
| AAV1 3' | GAGCGAGCGAGCGCGC | 6 |
| AAV3 5' | GCGCACTCGCTCGCTC | 7 |
| AAV3 3' | GAGCGAGCGAGTGCGC | 8 |
| AAV4 5' | GCGCGCTCGCTCACTC | 9 |
| AAV4 3' | GAGTGAGCGAGCGCGC | 10 |
| AAV7 5' | GCGCGCTCGCTCGCTC | 11 |
| AAV7 3' | GAGCGAGCGAGCGCGC | 12 |
| Avian AAV Strain DA1 5' | GCTCGCTCGCTC | 13 |
| Avian AAV Strain DA1 3' | GAGCGAGCGAGC | 14 |
| Avian AAV ATCC VR-865 5' | GCTCGCTCGCTC | 15 |
| Avian AAV ATCC VR-865 3' | GAGCGAGCGAGC | 16 |
| Bovine AAV5' | GCTCGTTCGCTGGCTC | 17 |
| Bovine AAV3' | GAGCCAGCGAACGAGC | 18 |
| Snake AAV5' | GCGCGCGCTC | 19 |
| Snake AAV3' | GAGCGCGCGC | 20 |

Table 2 provides engineered Rep binding sequence regions which can function as an eRBSR (SEQ ID NOs: 21-66).

TABLE 2

Engineered Rep Binding Sequence Regions

| Sequence | SEQ ID NO |
|---|---|
| GCTCNNNNNNNNNNNNNNNN | 21 |
| GCTCNNNNNNNNNNNN | 22 |
| GCTCNNNNNNNN | 23 |
| GCTCNNNN | 24 |
| NNNNNNNNNNNNNNNNGCTC | 25 |
| NNNNNNNNNNNNGCTC | 26 |
| NNNNNNNNGCTC | 27 |
| NNNNGCTC | 28 |
| GCTCNNNNNNNNNNNNGCTC | 29 |
| GCTCNNNNNNNNGCTC | 30 |
| GCTCNNNNGCTC | 31 |
| GCTCGCTCNNNNNNNNNNNN | 32 |
| GCTCGCTCNNNNNNNN | 33 |
| GCTCGCTCNNNN | 34 |
| GCTCGCTCGCTCNNNNNNNN | 35 |
| GCTCGCTCGCTCNNNN | 36 |
| NNNNNNNNNNNNGCTCGCTC | 37 |
| NNNNNNNNGCTCGCTC | 38 |
| NNNNGCTCGCTC | 39 |
| NNNNNNNNGCTCGCTCGCTC | 40 |
| NNNNGCTCGCTCGCTC | 41 |
| GCTCGCTCNNNNNNNNGCTC | 42 |
| GCTCGCTCNNNNGCTC | 43 |
| GCTCNNNNNNNNGCTCGCTC | 44 |
| GCTCNNNNGCTCGCTC | 45 |
| NNNNGCTCGCTCGCTCNNNN | 46 |
| NNNNNNGCTCGCTCNNNN | 47 |
| NNNNGCTCGCTCNNNNNNNN | 48 |
| NNNNGCTCGCTCNNNN | 49 |
| NNNNNNNNNNNNGCTCNNNN | 50 |
| NNNNNNNNGCTCNNNNNNNN | 51 |
| NNNNNNNNGCTCNNNN | 52 |
| NNNNGCTCNNNN | 53 |
| NNNNGCTCNNNNNNNNNNNN | 54 |
| NNNNGCTCNNNNNNNN | 55 |
| GCTCNNNNGCTCNNNN | 56 |
| GCTCNNNNNNNNGCTCNNNN | 57 |
| GCTCNNNNGCTCNNNNNNNN | 58 |
| NNNNGCTCNNNNGCTC | 59 |
| NNNNGCTCNNNNNNNNGCTC | 60 |
| NNNNNNNNGCTCNNNNGCTC | 61 |
| GCTCGGGG | 62 |
| GCTCGGGGG | 63 |
| GCTCGGGGGG | 64 |
| GCTCGGGGGGG | 65 |
| GCTCGGGGGGGG | 66 |

Table 3 provides oligonucleotide sequences that comprise Rep protein binding properties which may therefore function as an eRBSR (SEQ NOs: 79-197) (Chiorini et al. 1995 Journal of Virology 69(11) 7334-7338, the contents of which are incorporated herein by reference in their entirety).

TABLE 3

Rep Binding Sequence Region Oligonucleotides

| Sequence | SEQ ID NO |
|---|---|
| ATACGCCGCCTCGCGCTCAG | 79 |
| ATCTGTCGCTCGTCCGGCTA | 80 |
| TCCGCGCTGGCTCATCGTCC | 81 |
| TCCGCGCTGGCTCATCGTCC | 82 |
| TCCCCGCCCCCGCTCATTCT | 83 |
| GTGCCCCCGCTCAGAGTCCA | 84 |
| TTTACCGCCGCTCAGATAGA | 85 |
| GACCCCCAGGCGCTCCTATG | 86 |
| ATCTCGCTCATGCCCCTTAG | 87 |
| TCCCCGGTCAGGGGCTCACT | 88 |
| CCGCCGCTCTATCCACTGGT | 89 |
| TTGCCTCGCTGCTACTGTTC | 90 |
| CATATCTCCGCTTAGTTGCC | 91 |
| TCGTTAAGAACCTTCCTCAT | 92 |
| CCCCCGCATCCTCCGCCTTC | 93 |
| CATATCTCCGCTTAGTTGCC | 94 |
| CACAGTTCTCGCCTACCCGT | 95 |
| CTCTCCTTCAGGGCCTCAGC | 96 |
| GCTGCCCGCGTACTCACCCG | 97 |
| GCTCGAAGGAAGCGGGGAAC | 98 |
| GTCAGTTCGCTGGGTGATTC | 99 |
| ATCGGACGGCTTCGTTGTGC | 100 |
| TCGCTGACCAAGCCGCATGC | 101 |
| CCAGTATTCTGCGCAGCTGG | 102 |
| GGCGTCCCCTTTCCTTTTCG | 103 |
| TAATCGTATGCATCGTCGTG | 104 |
| TGAACGGTCGCGACGCAGCA | 105 |
| ACGTTCAACCCGCCGCGTCG | 106 |
| ATCGGACGGCTTCGTTGTGC | 107 |
| CCATGTGTTGCGCCCGTCGC | 108 |
| GGTCCCCCCATGCACTGCCC | 109 |
| CCCGTATCCACGCCCCACGC | 110 |
| TGCCCCACGCGCGCTCGTAC | 111 |
| ATGCTTTCTCGCTCAGTCC | 112 |
| ACACTTCTCACTCGCTGCCT | 113 |
| CCTTCGCGCTCGTTCGAATA | 114 |
| TGCTTTCTCGCTCAGTCC | 115 |
| GCGATTGCCTCGGTGGCTCA | 116 |
| CTTCACTTACTCGCGCACCC | 117 |
| TGCCCTTGGCTTGCTCAGTG | 118 |
| GTCTCGCTCGGTCAGCTACT | 119 |
| ATCCGTTCACTCGTTCGCCT | 120 |
| ACGCACTCACTCGCCGGCGC | 121 |
| CTCTTGCTCGTCAATTGCT | 122 |
| GGGTGCTCGCCTGGGTTGCG | 123 |
| CCAGTGCTCACTCAGCTCGC | 124 |
| TCGGCGCTCGCTCGGTCCTC | 125 |
| CGCGGGTTGTTTTCACTCAC | 126 |
| TGTCATCTGCTCGCTCACTT | 127 |
| AGATCCTTGTGGCTCACTCG | 128 |
| ACTGGCTGGTTCGCTCAGAC | 129 |
| CCACAGATGTAGCTCACTCA | 130 |
| CTGGTATCGCTCACTTGACC | 131 |
| TCGCGCTCGTTCGCCTCTGC | 132 |
| AGATCCTTGTGGCTCACTCG | 133 |
| CAATCAGTTAACCACTTCAA | 134 |
| CTCGCTTGCAGTCACTCACT | 135 |
| GAGTTTATCTCATGTTCTGC | 136 |
| CAATTCAGCCAACCACTCAA | 137 |
| GCTGACTCGTTGACTCATCT | 138 |
| TCTCCGCTGGTTCACCGTAC | 139 |
| TGTGCGGCCCACTGAGACGT | 140 |
| CCACGTGCTCGCTCAACCTT | 141 |
| TCCTACAGCTTGCTCACTCT | 142 |
| CACAGTTACTGGCTCACTGA | 143 |
| GGGGTTGGTTGGTTCACTCC | 144 |
| GGGTGCTCGCCTGGGTTGCG | 145 |
| GCCACTTAGCGTACTGGTTC | 146 |
| CCCTGTTCGCTTGCTCGTTC | 147 |
| TTAACATGGCGCGTTCACTG | 148 |
| CCATCTTATTGGTTCACTGG | 149 |
| CTCTTCCCGCGCACTGACTC | 150 |
| CTAAGATGCCCGCTCGCTC | 151 |
| GTATGGCACTCGCTCGCTGG | 152 |
| TGCATCTGCCCTTGCTCACT | 153 |
| ACTCACTCACTGAGTTGTCC | 154 |

TABLE 3-continued

Rep Binding Sequence Region Oligonucleotides

| Sequence | SEQ ID NO |
|---|---|
| TTCGTTGGCTCACTCACCCC | 155 |
| GTGCCCGTTTCTACTCACTG | 156 |
| TGGTCGCTCGCCCCAGCCGC | 157 |
| TTGCTTGCTCACTCCGCGCT | 158 |
| CGCCAGCTCCCTCCTCATGC | 159 |
| CCTCCACTCGCTGGGTGAGC | 160 |
| TCGTCGCTCGCTCTGCATCC | 161 |
| TACCGCGATCTCGCTCTCTG | 162 |
| CCCACGCCCTCGCTCACTGC | 163 |
| TCTCTGTCACTCGTCTCCGG | 164 |
| CTCGTGCCCCGGTGCGCTCA | 165 |
| CGTGTACTTCGTGCTCAGCC | 166 |
| CCCGTGTAGGTGCGCTCGCT | 167 |
| TCCACCCTACTCCGTCGGCC | 168 |
| CTCACCGCACTCACTGGCCC | 169 |
| GCCCTCCTTTCGCTCGTTT | 170 |
| CCTCTCCGCGTGCCCACTCG | 171 |
| CCTTCTTTTCCGCTGGCTCA | 172 |
| CTCGTGCCCCGGTGCGCTCA | 173 |
| GGCGATTCACTCATCTGACC | 174 |
| ACTGCCCGGCCGTTTCGCTC | 175 |
| CCTCTCCGCGTGCCCACTCG | 176 |
| GCTTGCTCGACCCAGCCACG | 177 |
| CCTGGTTCGGTCCTTCTCCC | 178 |
| ATCCTCCTATCTCACTCGCT | 179 |
| CCCGGGTACTGACTCGCGCT | 180 |
| TCCATGCCACTTGGTTCACT | 181 |
| CTGCTATCGTTAACTCACCT | 182 |
| TGCACTCATTCGACTGCCTC | 183 |
| CGAGCGAGCTTAGTGAACGT | 184 |
| AGCTGGTCGGTGTTCACTGC | 185 |
| ATTCAGTCGCGGTTGCGCAC | 186 |
| TCTCGCTGGTTCAGTCCTTC | 187 |
| GCATTTCTGGGTAGCTCGCT | 188 |
| TAGCTGAATCGCCAGGCTTG | 189 |
| TGGCTCATTCATTGAGTCCA | 190 |
| CATTGGCTGTTGCTGACT | 191 |
| TCCATGCCACTTGGTTCACT | 192 |

TABLE 3-continued

Rep Binding Sequence Region Oligonucleotides

| Sequence | SEQ ID NO |
|---|---|
| GCCCCTCCTTTCGCTCGTTT | 193 |
| CGGCCCCTTCCCACTGGCTC | 194 |
| CGCCAGCTCCCTCCTCATGC | 195 |
| GTCGCTCCCTCCTTACCGCG | 196 |
| CCAGCGAACGCCCTCCCGCA | 197 |

In some embodiments, the present disclosure provides an eRBSR comprising any of SEQ ID NOs: 1-20, 21-66, and/or 79-197. Any one of the Rep binding sequence regions listed in Table 1 can function as an eRBSR when substituted into a non-native ITR sequence in place of the native Rep binding sequence regions. In one embodiment, SEQ ID NOs: 3-4 (AAV-5) are inserted into an AAV1, AAV2, AAV3, AAV4, AAV6, AAV7, AAV8, AAV9, AAV10, AAV11, AAV12, AAVrh8, AAVrh10, AAV-DJ, and AAV-DJ8 in place of the native AAV5 Rep binding sequence regions. In other embodiments, SEQ ID NOs: 7-8 (AAV3) are inserted into an AAV1, AAV2, AAV4, AAV5, AAV6, AAV7, AAV8, AAV9, AAV10, AAV11, AAV12, AAVrh8, AAVrh10, AAV-DJ, and AAV-DJ8 in place of the native AAV3 Rep binding sequence regions. In other embodiments, SEQ ID NOs: 9-10 (AAV4) are inserted into an AAV 1. AAV2, AAV3, AAV5, AAV6, AAV7, AAV8, AAV9, AAV10, AAV11, AAV12, AAVrh8, AAVrh10, AAV-DJ, and AAV-DJ8 in place of the native AAV4 Rep binding sequence regions. In other embodiments, SEQ ID NOs: 1-2 (AAV2/AAV1/AAV7) are inserted into an AAV3, AAV4, AAV5, AAV6, AAV8, AAV9, AAV10, AAV11, AAV12, AAVrh8, AAVrh10, AAV-DJ, and AAV-DJ8 in place of the native AAV2 Rep binding sequence regions. In other embodiments, SEQ ID NOs: 17-18 (bovine) are inserted into an AAV1, AAV2, AAV3, AAV4, AAV5, AAV6, AAV7, AAV8, AAV9, AAV10, AAV11, AAV12, AAVrh8, AAVrh10, AAV-DJ, and AAV-DJ8 in place of the native Rep binding sequence regions. In other embodiments. SEQ ID NOs: 19-20 (snake) are inserted into an AAV1, AAV2, AAV3, AAV4, AAV5, AAV6, AAV7, AAV8, AAV9, AAV10, AAV11, AAV12, AAVrh8, AAVrh10, AAV-DJ, and AAV-DJ8 in place of the native Rep binding sequence regions. In other embodiments, SEQ ID NOs: 13-14 (avian) are inserted into an AAV1, AAV2, AAV3, AAV4, AAV5, AAV6, AAV7, AAV8, AAV9, AAV10, AAV11, AAV12, AAVrh8, AAVrh10, AAV-DJ, and AAV-DJ8 in place of the native Rep binding sequence regions.

In another embodiment, the present disclosure provides an engineered Rep binding sequence region in which one or more nucleotides in any of SEQ ID NOs: 1-20 listed in Table 1 is altered or modified as discussed elsewhere herein. For example, any of the Rep binding sequence regions listed in Table 1 (SEQ ID NOs: 1-20) can be altered by having one or more nucleotide insertions, deletions, substitutions, or any combination thereof as compared to the corresponding native Rep binding sequence region.

In certain embodiments, the engineered Rep binding sequence region is selected from the sequences of SEQ ID NO: 68 (GCGCCGCATGCGGCTC) (αPal), SEQ ID NO: 71 (GAGCGGGGGCGCGCTC) (5-5/EGR) and SEQ ID NO: 74 (CCGACCACGACGACGG) (JcDNVNS1).

The eRBSRs provided here can be made by methods commonly known and practiced by those skilled in the art.

For example, the eRBSRs provided here can be designed in silico and synthesized using molecular biology techniques well known to those of skill in the art. See, e.g., Sambrook et al, Molecular Cloning: A Laboratory Manual, Cold Spring Harbor Press (Cold Spring Harbor, N.Y.).

In any of SEQ ID NOs: 1-291, one or more nucleotides can be altered or modified as provided in the present disclosure.

As discussed herein, the Rep binding sequence region of the parvoviral genome is altered and/or modified to decrease the binding of the Rep protein so as to promote the production of a parvovirus having a duplexed or self-complementary genome. Thus, the engineered Rep binding sequence regions (eRBSRs) provided herein comprise at least one nucleic acid sequence that has decreased binding with wild-type and/or engineered Rep protein. In one embodiment, the engineered Rep binding sequence region has decreased binding with a wild-type Rep protein as compared to the binding with the corresponding wild-type or native Rep binding sequence region. In another embodiment, the engineered Rep binding sequence region has decreased binding with an engineered Rep protein as compared to the binding with the corresponding wild-type or native Rep binding sequence region. In another embodiment, the engineered Rep binding sequence region has decreased binding with both wild-type and engineered Rep protein as compared to the respective binding with the corresponding wild-type or native Rep binding sequence region. In one embodiment, the binding affinity of an eRBSR with a wild-type and/or engineered Rep protein is decreased 1-10 fold relative to the binding affinity of the corresponding wild-type or native Rep binding sequence region with the same Rep protein. In one embodiment, the binding affinity is decreased by at least 2-fold. In another embodiment, the binding affinity is decreased by at least 5-fold. In a further embodiment, the binding affinity is decreased by at least 10-fold. In one embodiment, the wild-type Rep protein with which the eRBSR has decreased binding affinity is an AAV Rep protein. In another embodiment, the engineered Rep protein with which the eRBSR has decreased affinity is derived from an AAV Rep protein that has been altered or modified, e.g., having one or more altered or modified nucleotides. In certain embodiments, the wild-type AAV Rep protein is selected from Rep22, Rep68, Rep78, Rep4-0, and Rep52. In certain embodiments, the engineered AAV Rep protein is selected from a Rep 22, Rep68, Rep78, Rep40, and Rep52 that has one or more altered or modified nucleotides.

The binding affinity can be measured by several methods well-known in the art, including electro-mobility shift assay and surface plasmon resonance, as described in the Examples section. In one embodiment, the binding affinities of the following polypeptide-polynucleotide pairs are determined using an Octet surface plasmon resonance instrument (ForteBio, Menlo Park, Calif.): wild-type Rep protein and a wild-type Rep binding sequence region, an engineered Rep protein and a wild-type Rep binding sequence region, a wild-type Rep protein and an eRBSR, an engineered Rep protein and an eRBSR. The polynucleotide encoding either a wild-type Rep binding sequence region or an engineered Rep binding sequence region is immobilized on the biosensor layer. A solution is prepared comprising either wild-type Rep protein or engineered Rep protein that is then passed over the biosensor to determine the rate of association ($K_a$). A second solution devoid of wild-type or Rep protein is passed over the saturated biosensor layer to determine the rate of dissociation ($K_d$).

The present disclosure also provides polynucleotides comprising any of the engineered Rep binding sequence regions (eRBSRs) described herein. The polynucleotide can be any deoxyribonucleotide or ribonucleotide polymer or sequence of nucleotide bases, in linear or circular conformation, and in either single- or double-stranded form. The polynucleotide can include natural nucleotides, known maims of natural nucleotides, as well as nucleotides that are modified in the base, sugar, and/or phosphate moieties (e.g., the phosphorothioate backbone). Thus, the polynucleotide can be RNA, DNA or DNA-RNA hybrid sequences that are naturally occurring or non-naturally occurring nucleotides.

The polynucleotide comprising the eRBSR can further comprise one or more heterologous sequences. The heterologous sequence can be any sequence that is not native to the viral genome. Heterologous sequences include regulatory sequences, sequences encoding a nucleic acid, such as but not limited to an siRNA, dsRNA, miRNA, antisense, aptamer, and the like, genome editing sequences, sequence encoding a polypeptide (e.g., such as a transgene), functional domain sequences, marker, tag, stuffer sequences, linker sequences. In one embodiment, the heterologous sequence is operatively linked to one or more regulatory sequence(s) that allows expression of the heterologous sequence.

In one embodiment, the polynucleotide comprises one or more parvoviral inverted terminal repeat (ITR) sequences wherein one of the ITR sequences comprises an eRBSR. Typically, the FIR sequence comprising the eRBSR also contains a reverse complementary sequence of the eRBSR downstream of the eRBSR such that the eRBSR and the reverse complementary sequence are capable of intra-strand base-pairing. Thus, in one embodiment, the polynucleotide comprises a parvoviral ITR nucleotide sequence comprising an eRBSR wherein the parvoviral ITR nucleotide sequence is capable of forming a double-stranded engineered Rep binding sequence region. In one embodiment, the engineered Rep binding sequence region is located between a 5' parvoviral inverted terminal repeat sequence and a 3' parvoviral inverted terminal repeat sequence. In another embodiment, the engineered Rep binding sequence region is located within a parvoviral inverted terminal repeat sequence.

The parvoviral inverted terminal repeat sequences) can be a full-length ITR sequence, a partial ITR sequence, or an ITR with an additional sequence, for example, one or more regulatory sequences, one or more functional domain sequence(s) and/or one or more stuffer or linker sequences. The parvoviral inverted terminal repeat sequence(s) can comprise naturally-occurring or wild-type sequence(s) or variant sequence(s), including natural variants and artificial variants, as well as truncated and elongated ITR sequences. The parvoviral ITR sequence can alternatively be modified to include one or more insertions, deletions and/or substitutions.

In one embodiment, in a polynucleotide comprising an eRBSR which comprises an ITR sequence, the polynucleotide can further comprise a regulatory sequence or other heterologous sequence, such as a payload sequence. In one embodiment, the heterologous sequence is operatively linked to one or more regulatory sequence(s) that allows expression of the heterologous sequence. In one embodiment, the polynucleotide comprises a first ITR sequence comprising an eRBSR and a second ITR sequence, wherein the heterologous sequence is flanked by the first and second ITR sequences. In any of these embodiments, the ITR sequence can be an adeno-associated virus (AAV) ITR or derived from an adeno-associated virus (AAV) ITR. AAV ITR sequences include any of those having an AAV1, AAV2, AAV3, AAV4, AAV5, AAV6, AAV7, AAV8, AAV9, AAV10, AAV11, AAV12, AAVrh8, AAVrh10, AAV-DJ, and AAV-DJ8 ITR sequence or a sequence derived therefrom.

In one embodiment, the parvoviral polynucleotide comprises in the 5' to 3' direction: (a) a 5' parvoviral inverted terminal repeat sequence; (b) a first payload encoding region; (c) an engineered Rep binding sequence region; (d) a second payload encoding region; and (e) a 3' parvoviral inverted terminal repeat sequence. In this embodiment, the first and second payload encoding regions are essentially self-complementary and may form a hairpin structure that comprises the parvoviral polynucleotide. In one embodiment, the parvoviral polynucleotide (e.g., a parvoviral genome) is an AAV polynucleotide, genome or parvoviral particle.

The designations of 5' and 3' with respect to the ITR sequences are also referred to as "left" and "right" ITR. The 5' and 3' wild-type ITR sequences encoded by ssDNA and dsDNA are reverse complements of each other that encode identical secondary structures. The AAV2 ssDNA genome, for example, comprises a TT dimer Rep nicking site within the nicking stem loop sequence of one ITR and a complementary AA dimer within the nicking stem loop sequence of the second ITR. As discussed herein, Rep protein only nicks AAV2 ssDNA at the TT dimer Rep nicking site. As used herein, the term 3' or "right" designates the ITR comprising the Rep nicking site.

In one embodiment, the transgene or payload sequence encodes human aromatic L-amino acid decarboxylase. In another embodiment, the transgene or payload sequence encodes human SOD1. In another embodiment, the transgene or payload sequence encodes human frataxin (FXN).

The present disclosure provides a polynucleotide comprising an eRBSR in which the binding affinity of a Rep protein (wild-type or engineered) to the eRBSR is decreased relative to the binding of a polynucleotide comprising a wild-type or native Rep binding sequence region. In one embodiment, the binding affinity is decreased 1-10 fold relative to a polynucleotide comprising a wild-type Rep binding sequence region. In one embodiment, the binding affinity is decreased at least 2-fold. In another embodiment, the binding affinity is decreased at least 5-fold. In a further embodiment, the binding affinity is decreased at least 10-fold. In one embodiment, the Rep protein is Rep68 or Rep78. In one embodiment, the wild-type AAV Rep protein is selected from Rep 22. Rep68, Rep78, Rep40, and Rep52. In another embodiment, the engineered AAV Rep protein is selected from a Rep 22. Rep68, Rep78, Rep40, and Rep52 that has one or more altered or modified nucleotides.

The present disclosure also provides a polynucleotide comprising an engineered Rep binding sequence region in which the nicking by a Rep protein (wild-type or engineered) decreased relative to the nicking of a polynucleotide comprising a wild-type Rep binding sequence region. In one embodiment, the nicking is decreased 1-10 fold relative to the nicking of a polynucleotide comprising a wild-type Rep binding sequence region. In one embodiment, the nicking is decreased by at least 2-fold. In another embodiment, the nicking is decreased by at least 5-fold. In a further embodiment, the nicking is decreased by at least 10-fold. In one embodiment, the Rep protein is Rep68 or Rep78. In one embodiment, the Rep protein is Rep68 or Rep78. In one embodiment, the wild-type AAV Rep protein is selected from Rep 22. Rep68, Rep78, Rep40, and Rep52. In another embodiment, the engineered AAV Rep protein is selected from a Rep 22, Rep68, Rep78, Rep40, and Rep52 that has one or more altered or modified nucleotides.

The present disclosure also provides polynucleotide comprising an engineered. Rep binding sequence region in which the presence of the engineered Rep binding sequence region results in an increase in the generation of self-complementary AAV genomes during viral genome replication.

In any of the above-described embodiments, the polynucleotide is an AAV polynucleotide or derived from an AAV polynucleotide. AAV polynucleotides include those of AAV1, AAV2, AAV3, AAV4, AAV 5, AAV6, AAV7, AAV8, AAV9, AAV10, AAV11, AAV12, AAVrh8, AAVrh10, AAV-DJ, and AAV-DJ8.

In one embodiment, the serotype which may be useful in the present invention may be AAV-DJ8. The amino acid sequence of AAV-DJ8 may comprise two or more mutations in order to remove the heparin binding domain (HBD). As a non-limiting example, the AAV-DJ sequence described as SEQ ID NO: 1 in U.S. Pat. No. 7,588,772, the contents of which are herein incorporated by reference in their entirety, may comprise two mutations: (1) R587Q where arginine (R; arg) at amino acid 587 is changed to glutamine (Q; gin) and (2) R590T where arginine (R; arg) at amino acid 590 is changed to threonine (T; thr). As another non-limiting example, the AAV-DJ sequence may comprise three mutations: (1) K406R where lysine (K; lys) at amino acid 406 is changed to arginine (R; arg), (2) R587Q where arginine (R; arg) at amino acid 587 is changed to glutamine (Q; gln) and (3) 85901 where arginine (R; arg) at amino acid 590 is changed to threonine (T; thr).

Swapped Nicking Stem Loop

Parvoviral ITR sequences comprise a short self-complementary region that forms a secondary structure loop required for nicking single stranded DNA during the course of replication as discussed previously: The nicking stem loop sequence varies between parvoviral serotypes and may be between about 20-25 nucleotides in length spanning the border between the A and D regions of the parvoviral genome. Complementary sequences of about 6-10 nucleotides form the stem of the secondary structure. The loop at the top of the stem is a non-complementary sequence of about 3-6 nucleotides that further comprises the terminal resolution site where the nicking of the phosphodiester backbone occurs. The terminal resolution site, or nicking site, of the AAV2 genome is a TT dimer that is located at the end of the ITR A region adjacent to the D region. This TT dimer is also present in the AAV1, AAV3, AAV4, and AAV7 genomes. An alternative nicking stem loop and nicking site is exemplified by AAV5, wherein the nicking site is a GT dimer. Nicking of the parvoviral genome only occurs at the nicking site, TT or GT, comprised within the nicking stem loop sequence that spans the A and D regions. Nicking of the parvoviral genome does not occur at the reverse complementary nicking site, AA or AC, comprised within a reverse complementary nicking stem loop sequence that spans the A and D regions.

Parvoviral serotypes with closely related genomes encode Rep proteins that are complementary. For example, An AAV2 Rep protein may productively promote replication of an AAV3 genome by binding to the AAV3 genome Rep binding sequence and cutting the nicking stein loop at the nicking site. However, some parvoviral serotypes encode Rep proteins that recognize heterologous Rep binding sequence regions, nicking stem loops, and nicking sites that are not cross-complementary. In one example, an AAV2 Rep protein may not nick the nicking stem loop of an AAV5 genome due to the lack of the TT dimer.

Accordingly, one way to promote the generation of self-complementary parvoviral genome sequences is to alter or modify the Rep nicking stem loop such that nicking by a heterologous Rep protein is abolished, consequently promoting the generation of self-complementary parvoviral genome sequences as discussed above in the previous section. The present disclosure thus provides a chimeric, altered, or modified Rep nicking stem loop sequence designed to decrease or abolish the nicking activity of the Rep protein.

Typically, the Rep nicking stem loop sequence of a parvoviral genome is from about 20 to about 2.5 nucleotides in length. The present disclosure accordingly provides a chimeric, altered, or modified Rep nicking stem loop sequence that is from about 20 to about 25 nucleotides in length. In one embodiment, the chimeric, altered, or modified Rep nicking sequence is from 20 to 25 nucleotides in length.

The present disclosure provides a nucleic acid comprising a Rep nicking stem loop in which one or more of the nucleotides in the nicking stem loop are altered or modified as compared to the native nicking stem loop. An "altered" nucleotide can be any nucleotide having a naturally or non-naturally occurring nucleoside selected from adenosine, guanosine, uridine, cytidine, thymidine, as long as it differs from the native nucleoside. Methods for producing nucleic acid sequences with altered nucleosides have been discussed herein in the previous section. A modified nucleotide refers to a nucleotide that has been chemically modified, in which the modification can be on the nucleobase, and/or the sugar, and/or on the backbone of the nucleotide. The chemical modification can be any chemical modification used to modify nucleic acids. Examples of suitable chemical modifications have been provided herein in the previous section, along with methods for chemically modifying a nucleic acid.

In one embodiment, the Rep nicking stem loop sequence has a single altered or modified nucleotide as compared to the native Rep nicking stem loop sequence. In another embodiment, the Rep nicking stem loop sequence has two or more altered or modified nucleotides as compared to the native Rep nicking stein loop sequence. In certain embodiments, the Rep nicking stem loop sequence has two to twenty five altered or modified nucleotides, including, for example, 2, 3, 4, 5, 6, 7, 8, 9, 10, 11, 12, 13, 14, 15, 16, 17, 18, 19, 20, 21, 22, 23, 24, or 25 altered or modified nucleotides as compared to the native Rep nicking stem loop sequence. In one embodiment, all of the nucleotides of the Rep nicking stem loop sequence are altered or modified.

In another embodiment, the Rep nicking sequence has one or more nucleotide insertions, deletions, substitutions, or any combination thereof as compared to the corresponding native Rep nicking sequence. In one embodiment, the Rep nicking sequence can comprise a sequence having one or more nucleotides that differ from the Rep nicking sequence of an adeno-associated virus (AAV), including the Rep nicking sequence of AAV 1, AAV2, AAV3, AAV4, AAV5, AAV6, AAV7, AAV8, AAV9, AAV10, AAV11, AAV12, AAVrh8, AAVrh10, AAV-DJ, and AAV-DJ8.

In other embodiments, the Rep nicking stem loop can comprise a sequence having both alterations and chemical modifications. Thus, in one embodiment, the Rep nicking stem loop comprises one or more nucleotides that are altered and one or more nucleotides that are chemically modified.

The present disclosure further provides a chimeric nicking stem loop, in which the Rep nicking stem loop is not native to the parvoviral genome. In one embodiment, the invention provides a chimeric nicking stem loop in which the chimeric nicking stem loop is from a parvoviral serotype or species that differs from the serotype or species of the native parvoviral ITR sequence. In one embodiment, the chimeric nicking stem loop is from a parvoviral serotype or species that differs from the serotype or species of the native Rep protein or sequence encoding the Rep protein. The chimeric nicking stem loop is created by substituting or swapping the native Rep nicking stem loop with the Rep nicking stem loop of a different serotype or species. In one embodiment, the entire Rep nicking stem loop is swapped. In another embodiment, a portion of the Rep nicking stem loop is swapped. In another embodiment, the Rep nicking stein loop comprises a non-native or swapped Rep nicking stein loop from an AAV viral genome, including but not limited to the Rep nicking stem loop of AAV1, AAV2, AAV3, AAV4, AAV5, AAV6, AAV7, AAV8, AAV9, AAV10, AAV11, AAV12, AAVrh8, AAVrh10, AAV-DJ, and AAV-DJ8.

The Rep nicking stein loops found in various AAV serotypes and species are shown in FIG. 3 and FIG. 4 and provided in Table 4. The genome sequences of several different AAV serotypes and species including AAV1, AAV2, AAV3, AAV4, AAV5, AAV7, AAV8, Bat AAV, Bovine AAV, Snake AAV, Avian AAV DA-1, and Avian AAV VR865 (SEQ ID NO: 280-291) were obtained from the NCBI Genome database. The 5' and 3' inverted terminal repeat sequences of selected genomes were aligned with the Clustal Omega multiple sequence alignment program using either AAV2 or AAV5 as the parent sequence, as shown in FIG. 3 and FIG. 4, respectively. Additional Rep nicking stem loops found in the ITR sequences of other parvoviral serotypes and species, including AAV8 5' ITR (SEQ ID NO: 253), AAV8 3' ITR (SEQ ID NO: 254), Bat AAV 5' ITR (SEQ ID NO: 261), Bat AAV 3' ITR (SEQ ID NO: 262) are obtained in the same manner using this alignment program.

TABLE 4

Native or Wild-Type Rep Nicking Stem Loop Sequences

| Name | Sequence | SEQ ID NO |
|---|---|---|
| AAV2 5' | AGAGGGAGTGGCCAACTCCATCA | 198 |
| AAV2 3' | TGATGGAGTTGGCCACTCCCTCT | 199 |
| AAV5 5' | GGGGGAGAGTGCCACACTCTCA | 200 |
| AAV5 3' | TGAGAGTGTGGCACTCTCCCCC | 201 |
| AAV1 5' | AGAGGGAGTGGGCAACTCCATCA | 202 |
| AAV1 3' | TGATGGAGTTGCCCACTCCCTCT | 203 |
| AAV3 5' | AGAGGGAGTGGCCAACTCCATCA | 204 |
| AAV3 3' | TGATGGAGTTGGCCACTCCCTCT | 205 |
| AAV4 5' | AGAGGGAGTGGCCAACTCCATCA | 206 |
| AAV4 3' | TGATGGAGTTGGCCACATTAGCT | 207 |
| AAV7 5' | AGAGGGAGTGGCCAACTCCATCA | 208 |
| AAV7 3' | AATGGAGTTGGCCACTCCCTCT | 209 |

TABLE 4-continued

Native or Wild-Type Rep Nicking Stem Loop Sequences

| Name | Sequence | SEQ ID NO |
|---|---|---|
| Avian AAV Strain DA1 5' | ACTGGCCAGCACTCCGGTGA | 210 |
| Avian AAV Strain DA1 3' | TCACCGGAGTGCTGGCCAGT | 211 |
| Avian AAV ATCC VR-865 5' | ACTGGCCAGCACTCCGGTGA | 212 |
| Avian AAV ATCC VR-865 3' | TCACCGGAGTGCTGGCCAGT | 213 |
| Bovine AAV 5' | GGGGGGGAGTGCCACACTCTCT | 214 |
| Bovine AAV 3' | AGAGAGTGTGGCACTCCCCCCC | 215 |
| Snake AAV 5' | TGGGGCGAGTGCCCTGCTC | 216 |
| Snake AAV 3' | GAGCAGGGCACTCGCCCCA | 217 |

Based on the sequence alignments, several different Rep nicking stem loops were identified (see boxed sequence in FIG. 3 and FIG. 4). The Rep nicking stem loops for AAV2, AAV1, AAV3, and AAV7 share the same nicking stem loop sequence: AGAGGGAGTGGCCAACTCCATCA (SEQ ID NO: 198) on the 5' ITR and its reverse complement TGATGGAGTFGGCCACTCCCTCT (SEQ ID NO:199) on the 3'ITR. AAV-4 has the same nicking sequence on the 5' ITR and a slightly different sequence on the 3' ITR (TGATGGAGTTGGCCACATTAGCT; SEQ ID NO: 207). The Rep nicking stem loop for AAV5 is GGGGGAGAGTGCCACACTCTCA (SEQ IF) NO: 200) on the 5' ITR and its reverse complement TGAGAGTGIGGCACTCTCCCCC (SEQ ID NO: 201) on the 3' ITR. The Rep nicking stein loop for bovine AAV is GGGGGGGAGTGCCACACTCTCT (SEQ ID NO: 214) on the 5' ITR and its reverse complement is AGAGAGTGTGGCACTCCCCCCC (SEQ ID NO: 215) on the 3' ITR. The Rep nicking stem loop for snake AAV is TGGGGCGAGTGCCCTGCTC (SEQ ID NO: 216) on the 5' ITR and its reverse complement is GAGCAGGGCACTCGCCCCA (SEQ ID NO: 217) on the 3' ITR. The Rep nicking stem loop for avian AAV (AAVDA1 and VR865) is ACTGGCCAGCACTCCGGTGA (SEQ ID NO: 210) on the 5' ITR and its reverse complement is TCACCGGAGTGCTGGCCAGT (SEQ ID NO: 211) on the 3' ITR. In one embodiment, the Rep nicking stem loop comprises any of SEQ ID NOs: 21-66. In another embodiment, the Rep nicking stem loop comprises any of SEQ ID NOs: 198-217, in which one or more nucleotides are altered or modified.

The chimeric nicking stem loop is achieved by swapping the nicking stem loop sequence of one parvoviral serotype or species with the native nicking stem loop sequence of a different parvoviral serotype or species. In one embodiment, the nicking stem loop sequence of any of SEQ ID NOs: 198-217 (listed in above paragraph) is swapped with the native nicking stem loop sequence of a different parvoviral serotype or species. In one embodiment, the nicking stem loop for AAV2 (SEQ ID NO: 199) (which is the same nicking stem loop for AAV1, AAV3, and AAV7) is swapped into (replaces all or a portion of) the native nicking stem loop sequence in any of the following ITR sequences: AAV4, AAV5, AAV6, AAV8, AAV9, AAV10, AAV11, AAV12, AAVrh8, AAVrh10, AAV-DJ, and AAV-DJ8 ITR. In another embodiment, the nicking stem loop for AAV4 (SEQ ID NO: 207) is swapped into (replaces all or a portion of) the native nicking stein loop sequence in any of the following ITR sequences: AAV1, AAV2, AAV3, AAV5, AAV6, AAV7, AAV8, AAV9, AAV10, AAV11, AAV12, AAVrh8, AAVrh10, AAV-DJ, and AAV-DJ8 ITR. In another embodiment, the nicking stem loop for AAV5 (SEQ ID NO: 201) is swapped into (replaces all or a portion of) the native nicking stein loop sequence in any of the following ITR sequences: AAV1, AAV2, AAV3, AAV4, AAV6, AAV7, AAV8, AAV9, AAV10, AAV11, AAV12, AAVrh8, AAVrh10, AAV-DJ, and AAV-DJ8 HR. In an additional embodiment, the nicking stem loop for bovine AAV (SEQ ID NO: 215) is swapped into (replaces all or a portion of) the native nicking stem loop sequence in any of the following ITR sequences: AAV1, AAV2, AAV3, AAV4, AAV5, AAV6, AAV7, AAV8, AAV9, AAV10, AAV11, AAV12, AAVrh8, AAVrh10, AAV-DJ, and AAV-DJ8 ITR. In yet another embodiment, the nicking stem loop for snake AAV (SEQ ID NO: 217) is swapped into (replaces all or a portion of) the native nicking stem loop sequence in any of the following ITR sequences: AAV1, AAV2, AAV3, AAV4, AAV5, AAV6, AAV7, AAV8, AAV9, AAV10, AAV11, AAV12, AAVrh8, AAVrh10, AAV-DJ, and AAV-DJ8 ITR. In still another embodiment, the nicking stem loop for avian AAVDA1 or avian AAVVR865 (SEQ ID NO: 211) is swapped into (replaces all or a portion of) the native nicking stem loop sequence in any of the following ITR sequences: AAV1, AAV2, AAV3, AAV4, AAV5, AAV6, AAV7, AAV8, AAV9, AAV10, AAV11, AAV12, AAVrh8, AAVrh10, AAV-DJ, and AAV-DJ8 ITR.

In other embodiments, the polynucleotide comprising the chimeric nicking stein loop comprises any of SEQ ID NOs: 218-240. (Table 5). In one embodiment, the nicking stem loop for AAV2 is swapped with (replaces all of) the native nicking stem loop sequence of the AAV5 ITR sequence (SEQ ID NO: 218). In one embodiment, the nicking stem loop for AAV4 is swapped with (replaces all of) the native nicking stem loop sequence of the AAV5 ITR sequence (SEQ ID NO: 219). In one embodiment, the nicking stem loop for AAV2 is swapped with (replaces all of) the native nicking stem loop sequence of the AAV4 ITR sequence (SEQ ID NO: 220). In one embodiment, the nicking stem loop for AAV5 is swapped with (replaces all of) the native nicking stem loop sequence of the AAV2 ITR sequence (SEQ ID NO: 221). In one embodiment, the nicking stem loop for AAV5 is swapped with (replaces all of) the native nicking stem loop sequence of the AAV1 ITR sequence (SEQ ID NO: 222). In one embodiment, the nicking stem loop for AAV5 is swapped with (replaces all of) the native nicking stem loop sequence of the AAV3 ITR sequence (SEQ ID NO: 223). In one embodiment, the nicking stem loop for AAV5 is swapped with (replaces all of) the native nicking stem loop sequence of the AAV4 ITR sequence (SEQ ID NO: 224). In one embodiment, the nicking stem loop for AAV5 is swapped with (replaces all of) the native nicking stem loop sequence of the AAV7 ITR sequence (SEQ ID NO: 225). In one embodiment, the nicking stem loop for Bovine AAV is swapped with (replaces all of) the native nicking stem loop sequence of the AAV2 ITR sequence (SEQ ID NO: 226). In one embodiment, the nicking stem loop for Bovine AAV is swapped with (replaces all of) the native nicking stem loop sequence of the AAV1 ITR sequence (SEQ ID NO: 227). In one embodiment, the nicking stem loop for Bovine AAV is swapped with (replaces all of) the native nicking stem loop sequence of the AAV3 ITR sequence (SEQ ID NO: 228). In one embodiment, the nicking stem loop for Bovine AAV is swapped with (replaces all of) the native nicking stem loop sequence of the AAV4 ITR sequence (SEQ ID NO: 229). In one embodiment, the nicking stem loop for Bovine AAV is swapped with (replaces all of) the native nicking stem loop sequence of the AAV7 ITR sequence (SEQ ID NO: 230). In one embodiment, the nicking stem loop for Snake AAV is swapped with (replaces all of) the native nicking stem loop sequence of the AAV2 ITR sequence (SEQ ID NO: 231). In one embodiment, the nicking stein loop for Snake AAV is swapped with (replaces all of) the native nicking stem loop sequence of the AAV1 ITR sequence (SEQ ID NO: 232). In one embodiment, the nicking stem loop for Snake AAV is swapped with (replaces all of) the native nicking stem loop sequence of the AAV3 ITR sequence (SEQ ID NO: 233). In one embodiment, the nicking stem loop for Snake AAV is swapped with (replaces all of) the native nicking stem loop sequence of the AAV4 ITR sequence (SEQ NO: 234). In one embodiment, the nicking stem loop for Snake AAV is swapped with (replaces all of) the native nicking stem loop sequence of the AAV7 ITR sequence (SEQ ID NO: 235). In one embodiment, the nicking stem loop for Avian AAV is swapped with (replaces all of) the native nicking stem loop sequence of the AAV2 ITR sequence (SEQ NO: 236). In one embodiment, the nicking stem loop for Avian AAV is swapped with (replaces all of) the native nicking stem loop sequence of the AAV1 ITR sequence (SEQ ID NO: 237). In one embodiment, the nicking stem loop for Avian AAV is swapped with (replaces all of) the native nicking stem loop sequence of the AAV3 ITR sequence (SEQ ID NO: 238). In one embodiment, the nicking stem loop for Avian AAV is swapped with (replaces all of) the native nicking stem loop sequence of the AAV4 ITR sequence (SEQ ID NO: 239). In one embodiment, the nicking stem loop for Avian AAV is swapped with (replaces all of the native nicking stem loop sequence of the AAV7 ITR sequence (SEQ ID NO: 240).

TABLE 5

Chimeric Rep Stem Loop Sequences

| Acceptor ITR | Donor Nicking Stem Loop | Chimeric Sequence | SEQ ID NO |
|---|---|---|---|
| AAV5 | AAV2 | TACAAAACCCCCTTGCTTGATGGAGTTGGCCACTCCCT CTCTGTCGCGTTCGCTCGCTCGCTGGCTCGTTTGGGGGG GCGACGGCCAGAGGGCCGTCGTCTGGCAGCTCTTTGAG CTGCCACCCCCCAAACGAGCCAGCGAGCGAGCGAAC GCGACAGGGGGGAGAG | 218 |
| AAV5 | AAV4 | TACAAAACCCCCTTGCTTGATGGAGTTGGCCACATTACT CTCTGTCGCGTTCGCTCGCTCGCTGGCTCGTTTGGGGGG GCGACGGCCAGAGGGCCGTCGTCTGGCAGCTCTTTGAG CTGCCACCCCCCAAACGAGCCAGCGAGCGAGCGAAC GCGACAGGGGGGAGAG | 219 |
| AAV4 | AAV2 | TGGCAAACCAGATGATGGAGTTGGCCACTCCCTCTATG CGCGCTCGCTCACTCACTCGGCCCTGGAGACCAAAGGT CTCCAGACTGCCGGCCTCTGGCCGGCAGGGCCGAGTGA GTGAGCGAGCGCGCATAGAGGGAGTGGCCAA | 220 |
| AAV2 | AAV5 | AGGAACCCCTAGTGAGAGTGTGGCACTCTCCCCCCTGC GCGCTCGCTCGCTCACTGAGGCCGCCCGGGCAAAGCCC GGGCGTCGGGCGACCTTTGGTCGCCCGGCCTCAGTGAG CGAGCGAGCGCGCAGAGAGGGAGTGGCCAA | 221 |
| AAV1 | AAV5 | TTACCCCTAGTGAGACTTGTGGCACTCTCCCCCCTGCGC GCTCGCTCGCTCGGTGGGGCCGGCAGAGCAGAGCTCTG CCGTCTGCGGACCTTTGGTCCGCAGGCCCCACCGAGCG AGCGAGCGCGCAGAGAGGGAGTGGGCAA | 222 |
| AAV3 | AAV5 | GCCATACCTCTAGTGAGAGTGTGGCACTCTCCCCCATG CGCACTCGCTCGCTCGGTGGGGCCGGACGTGCAAAGCA CGTCCGTCTGGCGACCTTTGGTCGCCAGGCCCCACCGA GCGAGCGAGTGCGCATAGAGGGAGTGGCCAA | 223 |
| AAV4 | AAV5 | TGGCAAACCAGATGAGAGTGTGGCACTCTCCCCCATGC GCGCTCGCTCACTCACTCGGCCCTGGAGACCAAAGGTC TCCAGACTGCCGGCCTCTGGCCGGCAGGGCCGAGTGAG TGAGCGAGCGCGCATAGAGGGAGTGGCCAA | 224 |
| AAV7 | AAV5 | CGCGGTACCCCTAGTGAGAGTGTGGCACTCTCCCCCAT GCGCGCTCGCTCGCTCGGTGGGGCCGGCAGAGCAGAG CTCTGCCGTCTGCGGACCTTTGGTCCGCAGGCCCCACC GAGCGAGCGAGCGCGCATAGAGGGAGTGGCCAA | 225 |
| AAV2 | Bovine | AGGAACCCCTAGAGAGTGTGGCACTCCCCCCCCTGC GCGCTCGCTCGCTCACTGAGGCCGCCCGGGCAAAGCCC GGGCGTCGGGCGACCTTTGGTCGCCCGGCCTCAGTGAG CGAGCGAGCGCGCAGAGAGGGAGTGGCCAA | 226 |

TABLE 5-continued

Chimeric Rep Stem Loop Sequences

| Acceptor ITR | Donor Nicking Stem Loop | Chimeric Sequence | SEQ ID NO |
|---|---|---|---|
| AAV1 | Bovine | TTACCCCTAGAGAGAGTGTGGCACTCCCCCCCTGCGC GCTCGCTCGCTCGGTGGGGCCGGCAGAGCAGAGCTCTG CCGTCTGCGGACCTTTGGTCCGCAGGCCCCACCGAGCG AGCGAGCGCGCAGAGAGGGAGTGGGCAA | 227 |
| AAV3 | Bovine | GCCATACCTCTAGAGAGAGTGTGGCACTCCCCCCCATG CGCACTCGCTCGCTCGGTGGGGCCGGACGTGCAAAGCA CGTCCGTCTGGCGACCTTTGGTCGCCAGGCCCCACCGA GCGAGCGAGTGCGCATAGAGGGAGTGGCCAA | 228 |
| AAV4 | Bovine | TGGCAAACCAGAAGAGAGTGTGGCACTCCCCCCCATGC GCGCTCGCTCACTCACTCGGCCCTGGAGACCAAAGGTC TCCAGACTGCCGGCCTCTGGCCGGCAGGGCCGAGTGAG TGAGCGAGCGCGCATAGAGGGAGTGGCCAA | 229 |
| AAV7 | Bovine | CGCGGTACCCCTAGAGAGAGTGTGGCACTCCCCCCCAT GCGCGCTCGCTCGCTCGGTGGGGCCGGCAGAGCAGAG CTCTGCCGTCTGCGGACCTTTGGTCCGCAGGCCCCACC GAGCGAGCGAGCGCGCATAGAGGGAGTGGCCAA | 230 |
| AAV2 | Snake | AGGAACCCCTAGGAGCAGGGCACTCGCCCCACTGCGC GCTCGCTCGCTCACTGAGGCCGCCCGGGCAAAGCCCGG GCGTCGGGCGACCTTTGGTCGCCCGGCCTCAGTGAGCG AGCGAGCGCGCAGAGAGGGAGTGGCCAA | 231 |
| AAV1 | Snake | TTACCCTTAGAGAGAGTCTGGCACTCCCCCCCCTGCGC GCTCGCTCGCTCGGTGGGGCCGGCAGAGCAGAGCTCTG CCGTCTGCGGACCTTTGGTCCGCAGGCCCCACCGAGCG AGCGAGCGCGCAGAGAGGGAGTGGGCAA | 232 |
| AAV3 | Snake | GCCATACCTCTAGGAGCAGGGCACTCGCCCCAATGCGC ACTCGCTCGCTCGGTGGGGCCGGACGTGCAAAGCACGT CCGTCTGGCGACCTTTGGTCGCCAGGCCCCACCGAGCG AGCGAGTGCGCATAGAGGGAGTGGCCAA | 233 |
| AAV4 | Snake | TGGCAAACCAGAGAGCAGGGCACTCGCCCCAATGCGC GCTCGCTCACTCACTCGGCCCTGGAGACCAAAGGTCTC CAGACTGCCGGCCTCTGGCCGGCAGGGCCGAGTGAGT GAGCGAGCGCGCATAGAGGGAGTGGCCAA | 234 |
| AAV7 | Snake | CGCGGTACCCCTAGGAGCAGGGCACTCGCCCCAATGCG CGCTCGCTCGCTCGGTGGGGCCGGCAGAGCAGAGCTCT GCCGTCTGCGGACCTTTGGTCCGCAGGCCCCACCGAGC GAGCGAGCGCGCATAGAGGGAGTGGCCAA | 235 |
| AAV2 | Avian | AGGAACCCCTAGTCACCGGAGTGCTGGCCAGTCTGCGC GCTCGCTCGCTCACTGAGGCCGCCCGGGCAAAGCCCGG GCGTCGGGCGACCTTTGGTCGCCCGGCCTCAGTGAGCG AGCGAGCGCGCAGAGAGGGAGTGGCCAA | 236 |
| AAV1 | Avian | TTACCCCTAGTCACCGGAGTGCTGGCCAGTCTGCGCGC TCGCTCGCTCGGTGGGGCCGGCAGAGCAGAGCTCTGCC GTCTGCGGACCTTTGGTCCGCAGGCCCCACCGAGCGAG CGAGCGCGCAGAGAGGGAGTGGGCAA | 237 |
| AAV3 | Avian | GCCATACCTCTAGTCACCGGAGTGCTGGCCAGTATGCG CACTCGCTCGCTCGGTGGGGCCGGACGTGCAAAGCACG TCCGTCTGGCGACCTTTGGTCGCCAGGCCCCACCGAGC GAGCGAGTGCGCATAGAGGGAGTGGCCAA | 238 |
| AAV4 | Avian | TGGCAAACCAGATCACCGGAGTGCTGGCCAGTATGCGC GCTCGCTCACTCACTCGGCCCTGGAGACCAAAGGTCTC CAGACTGCCGGCCTCTGGCCGGCAGGGCCGAGTGAGT GAGCGAGCGCGCATAGAGGGAGTGGCCAA | 239 |
| AAV7 | Avian | CGCGGTACCCCTAGTCACCGGAGTGCTGGCCAGTATGC GCGCTCGCTCGCTTGGTGGGGCCGGCAGAGCAGAGCTC TGCCGTCTGCGGACCTTTGGTCCGCAGGCCCCACCGAG CGAGCGAGCGCGCATAGAGGGAGTGGCCAA | 240 |

IV. ENGINEERED REP PROTEIN AND POLYNUCLEOTIDES

The present disclosure also provides a polypeptide comprising an engineered Rep protein and a polynucleotide encoding the polypeptide comprising the engineered. Rep protein. The engineered Rep protein of the present disclosure comprises at least one amino acid that is altered or modified as compared to the corresponding wild-type Rep protein. In one embodiment, the engineered Rep protein comprises one or more amino acids involved with DNA binding that are altered or modified as compared to the corresponding wild-type Rep protein. The engineered Rep protein has decreased binding to its cognate Rep binding sequence region and, as a consequence, promotes the formation of a self-complementary viral genome during replication.

Rep protein is an essential viral protein that catalyzes several reactions during viral replication. The N-terminal domain of Rep protein, consisting of about the first 200 amino acids, has site-specific endonuclease and sequence-specific DNA binding activities. The C-terminal region of Rep protein has ATPase and 3'-5' helicase activities. The Rep protein interacts with the viral ITRs, which serve as viral origins of replication, in the performance of these various functions. Within the ITRs are two sequences required for replication: a Rep binding sequence region consisting of several direct repeats of a 5'-GCTC-3' motif and a terminal resolution site, or nicking site. Viral replication requires Rep binding at the Rep binding sequence region and subsequent cleavage of the ssDNA at the nicking site to generate the 3'-OH group which allows conversion of the viral ends into linear duplex DNA. An additional Rep binding sequence comprising a CTTTG motif, located in the loop region between the B and B' sequences of the ITR hairpin, aids in determining the directionality of parvoviral genome replication. The endonuclease domain of the Rep protein recognizes the nicking site substrate in the context of an ssDNA stem loop secondary structure generated by the Rep helicase activity.

The Rep protein is altered so as to decrease its binding with its cognate Rep binding sequence region by altering or modifying amino acid residues involved in DNA binding. Previous studies analyzing the crystal structure of AAV5 Rep protein bound to the AAV5 Rep binding sequence region indicate which residues play a role in DNA binding. (Hickman et al 2004 The Nuclease Domain of Adeno-Associated Virus Rep Coordinates Replication Initiation Using Two Distinct DNA Recognition Interfaces, Molecular Cell 13:403-414, the contents of which are referenced herein in their entirety). The N-terminal domain of Rep protein has determinants for ITR binding and has been shown to specifically bind ITR sequences (Owens 1993, Yoon, 2001, Hickman). In the Hickman studies, a crystal structure of an AAV5 N-terminal Rep protein fragment (AA 1-197) bound to a 26 bp double-stranded sequence containing the AAV5 Rep binding sequence region was analyzed. Three-dimensional modeling showed that the stable protein-DNA complex contained five Rep protein monomers bound independently to one molecule of the AAV5 Rep binding sequence region, which adopted an overall β-DNA structure. Further examination of the crystal structure showed that the five monomers bind to the Rep binding sequence region and spiral around the DNA axis, off-set from one another by four base pairs. The studies further revealed that the structural elements of the Rep protein integral to recognition and binding of the repeated GCTC consensus motif in the Rep binding sequence region are the surface loop sequence between the β4 and β5 strands (referred to as the β4/β5 loop; residues 135-144) and the α-helix C sequence (residues 101-118), which are located along one edge of the central β sheet.

Figure 7:
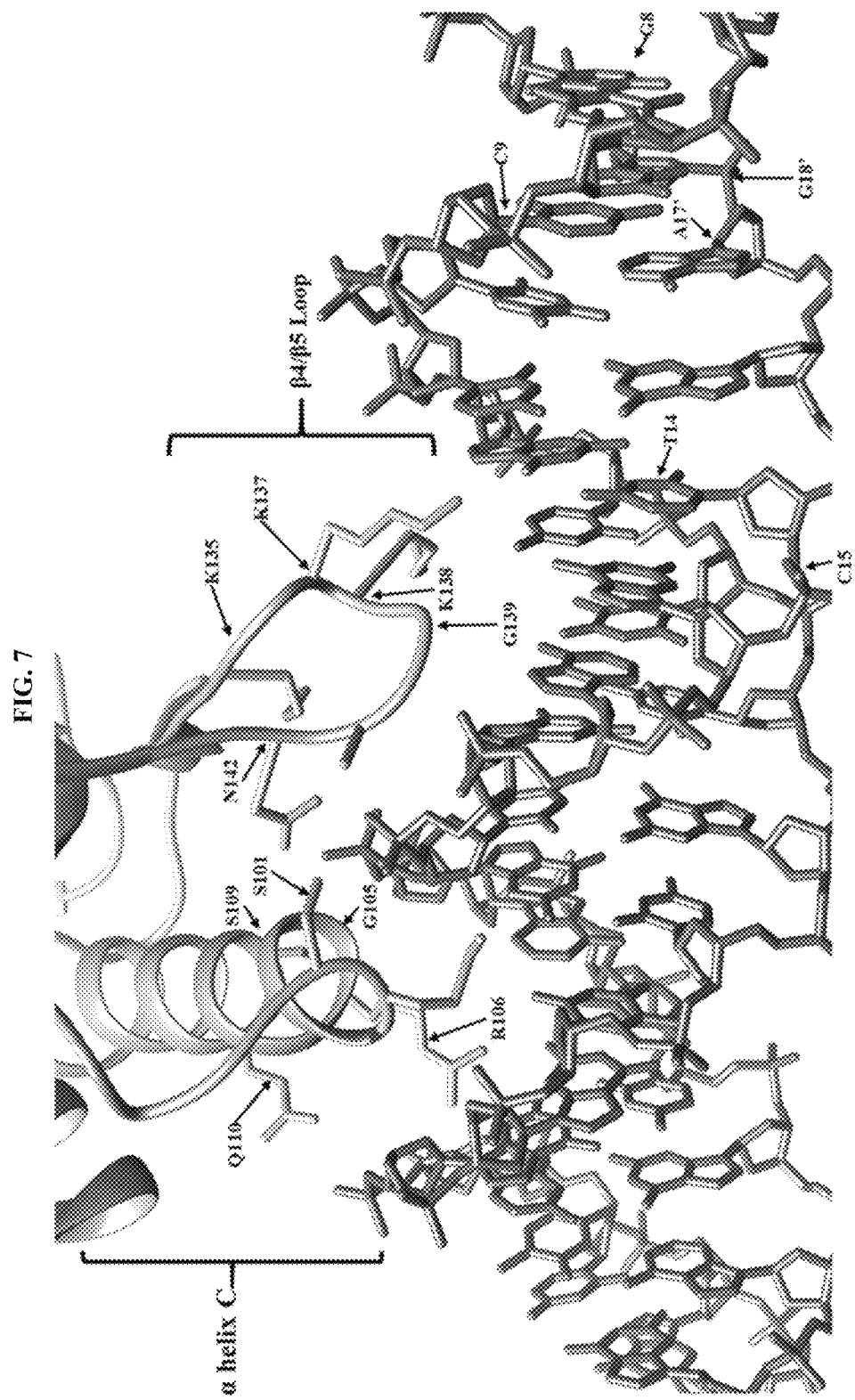
FIG. 7 is a schematic depicting a 3-dimensional model showing Rep protein binding to the Rep binding domain of the AAV5 ITR. Arrows indicate amino acid and nucleic acid residues involved in binding affinity.

FIG. 7 is a schematic depicting a three-dimensional model showing Rep protein binding to the Rep binding domain of the AAV5 ITR. As shown in FIG. 7, several amino acid residues in the β4/β5 loop (amino acid residues K135, K137, and N142) and in the α-helix C (S101, G105, 5109, and Q110) contact the phosphodiester backbone in the major groove structure of the Rep binding sequence region. FIG. 7 also shows the amino acid residues in the α-helix C (R106, K137, and K138) and an amino acid residue in the β4/β5 loop (K137) that contact one or more nucleosides in the Rep binding sequence region. Amino acid residue K137 contacts both the phosphodiester backbone and one or more nucleosides in the Rep binding sequence region. The identified amino acid residues contribute to Rep protein binding to its cognate Rep binding sequence region, with those residues contacting the phosphodiester backbone contributing to stabilization of the protein-DNA interaction and those residues contacting one or more nucleosides contributing to the specificity of the interaction.

An alignment of the polynucleotide sequences encoding Rep protein from different AAV serotypes (AAV5, AAV2Rep68, AAV2Rep78, AAV2Rep40, AAV2Rep52, AAV1, AAV3, AAV4, AAV7, and AAV8) and AAV species (Avian AAVDA-1, Avian AAVVR865, Bat, and Bovine), shown in FIG. 8, shows that the identified amino acids discussed above are conserved across AAV serotypes and AAV species. An analysis of the correlation between structural features of the Rep binding sequence region in the ITR and the degree of conservation of the Rep protein sequence was performed in silico. The combination of sequence and structural analysis of Rep proteins confirms that the identified conserved residues of the α-helix C and β-sheet 4/β-sheet 5 loop are involved in DNA binding and are the appropriate target residues for alteration and/or modification. Table 6 provides a list of target residues within structural elements of the Rep protein that contact the phosphodiester backbone contributing to stabilized protein-DNA interaction as shown in FIG. 7. Table 7 provides a list of target residues in the Rep protein that contact nucleosides of either DNA strand (the complementary strand is noted with a ') contributing to specific protein-DNA interaction as shown in FIG. 7. The residue numbering used here and in Tables 4 and 5 are that of AAV5. Corresponding residues in other AAV serotypes and species can be obtained using the sequence alignment shown in FIG. 8. Of the ten residues that form direct side chain interactions with the Rep binding sequence region, seven are strictly conserved among serotypes AAV2-6. There are three consecutive amino acids in the β4/β5 loop that are highly conserved- Gly-139, Gly-140, and Ala-141 (in AAV5), which correlate to three sequential Glycines in AAV2-6. Other conserved residues in the β4/β5 loop are Asp-142, Lys-135, and Lys-137. Conserved residues in the α-helix C are Ser101, Met-102, Gly105, Arg-106, Ser-109, Gln-110, Lys137, and Lys138. Arg-106 and Lys-137 provide important base contacts and Lys-135 forms a salt bridge to the phosphate backbone.

TABLE 6

Residues Contacting the Phosphodiester Backbone Contributing to Stabilized Protein-DNA Interaction

| Residue | Structural Element |
|---|---|
| S101 | A helix C |
| G105 | A helix C |
| S109 | A helix C |
| Q110 | A helix C |
| K135 | β4/β5 loop |
| K137 | β4/β5 loop |
| N142 | β4/β5 loop |

TABLE 7

Residues Contacting Nucleosides Contributing to Specific Protein-DNA Interaction

| Residue | Nucleoside |
|---|---|
| R106 | T14, C15 |
| K137 | G18', C9, G8 |
| K138 | G8 |
| G139 | A17' |

The engineered Rep protein of the present disclosure comprises one or more amino acids that are altered or modified as compared to the corresponding wild-type Rep protein, in which modification(s) and/or alteration(s) results in decreased binding to the Rep binding sequence region. The engineered Rep protein can be derived from an AAV Rep protein. In one embodiment, the engineered Rep protein is derived from an AAV Rep protein selected from an AAV1, AAV2, AAV3, AAV4, AAV5, AAV7, AAV8, Avian AAVDA-1, Avian AAV VR865, Bat, Snake, and Bovine AAV Rep protein (SEQ ID NO: 265-279). In one embodiment, the engineered Rep protein is derived from an AAV Rep protein selected from art AAV6, AANT9, AAV10, AAV12, AAVrh8, AAVrh10, and AAV-DJ Rep protein. In one embodiment, the AAV Rep protein from which the engineered Rep protein is derived is selected from AAV2 Rep68, AAV2 Rep78, AAV2 Rep40, AAV2 Rep52, AAV1 Rep, AAV3 Rep, AAV4 Rep, AAV7 Rep, AAV 8 Rep, Avian Rep, Bat Rep, or Bovine Rep. In some embodiments, the AAV Rep protein from which the engineered Rep protein is derived is Rep protein 68 or Rep protein 78. AAV Rep78 proteins are described in International Patent Publication No. WO2001032711, WO2007130519, and WO2007148971, the contents of which are herein incorporated by reference in their entirety.

The engineered Rep protein can be derived from a naturally-occurring parvoviral Rep protein or a naturally-occurring variant parvoviral Rep protein. Alternatively, the Rep protein can be derived from a non-naturally Rep protein, including, for example, a synthetic or artificial Rep protein. The Rep protein can be altered by insertions, deletions, and/or substitutions of amino acid residues. In one embodiment, the engineered Rep protein has at least 85% sequence identity with any of the AAV Rep proteins disclosed herewith. In another embodiment, the engineered Rep protein has at least 90% sequence identity with any of the AAV Rep proteins disclosed herewith, including 90% 91%, 92%, 93%, 94%, 95%, 96%, 97% 98%, and 99% identity with the AAV Rep proteins.

In one embodiment, the one or more altered or modified amino acid residues in the engineered Rep protein is an amino acid residue that in its wild-type form (i.e., unaltered or unmodified form) contacts a Rep binding sequence region. In one embodiment, one of the altered or modified amino acid residues in the engineered Rep protein is an amino acid residue that in its wild-type (unaltered or unmodified) form contacts a Rep binding sequence region. In another embodiment two of the altered or modified amino acid residues are amino acid residues that in their wild-type form contact a Rep binding sequence region. In another embodiment, three of the altered or modified amino acid residues are amino acid residues that in their wild-type form contact a Rep binding sequence region. In another embodiment, four of the modified amino acid residues are amino acid residues that in their wild-type form contact a Rep binding sequence region. In another embodiment, about 10% to about 50% of the amino acid residues that in their wild-type form (unaltered or unmodified form) contact a Rep binding sequence region are altered or modified in the engineered Rep protein. In one embodiment, at least 10% of the amino acid residues that in their wild-type form contact a Rep binding sequence region are altered or modified. In one embodiment, at least 20%, 30%, 40% or 50% of the amino acid residues that in their wild-type form contact a Rep binding sequence region are altered or modified.

In one embodiment, the one or more altered or modified amino acid residue(s) of the engineered Rep protein is an amino acid residue(s) that in its wild-type form (i.e., unaltered or unmodified) contacts the phosphodiester backbone of a nucleotide sequence comprising the Rep binding sequence region. In another embodiment, the one or more altered or modified amino acid residue(s) of the engineered Rep protein is an amino acid residue(s) that in its wild-type form contacts at least one nucleoside of a nucleotide sequence comprising a Rep binding sequence region. In another embodiment, the one or more altered or modified amino acid residue(s) of the engineered Rep protein is an amino acid residue(s) that in its wild-type form contacts the phosphodiester backbone and at least one nucleoside of a nucleotide sequence comprising a Rep binding sequence region. In one embodiment, the one or more altered or modified amino acid residue(s) of the engineered Rep protein is an amino acid residue that in its wild-type form stabilizes the binding of Rep protein to a Rep binding sequence region. In one embodiment, the one or more altered or modified amino acid residue(s) in the engineered. Rep protein is an amino acid residue(s) that in its wild-type form is located in the α-helix C of the Rep protein. In one variation of this embodiment, the altered or modified amino acid residue(s) further contacts the phosphodiester backbone and/or at least one nucleoside of a nucleotide sequence comprising a Rep binding sequence region. In another embodiment, the one or more altered or modified amino acid residue(s) in the engineered Rep protein is an amino acid residue(s) that in its wild-type form is located in the β4/β5 loop of the Rep protein. In one variation of this embodiment, the altered or modified amino acid residue(s) further contacts the phosphodiester backbone and/or at least one nucleoside of a nucleotide sequence comprising a Rep binding sequence region. In another embodiment, the one or more altered or modified amino acid residue(s) is selected from the amino acid residue that is or corresponds with: (1) Serine-101; (2) Glycine-105; (3) Arginine-106; (4) Serine-109; (5) Glutamine-110; (6) Lysine-135; (7) Lysine-137; (8) Lysine-138; (9) Glycine-139; and (10) Asparagine-142. In another embodiment, the one or more altered or modified amino acid residue(s) is selected from the amino acid residue that is or corresponds with: (1) Glycine-140; (2) Alanine-141; and (3) Met-102.

In one embodiment, the one or more altered or modified amino acid residue(s) of the engineered Rep protein is modified by conservative substitution with a different amino acid having similar biochemical properties as the wild-type residue. For example, acidic amino acid residues, e.g., Aspartic acid and Glutamic acid can be substituted with one another. Basic amino acids, such as Lysine, Arginine, and Histidine, can be substituted with one another. Hydrophobic aliphatic amino acids, such as Valine, Isoleucine, Leucine, and Alanine, can be substituted with one another. Hydrophobic aromatic amino acids, such as Phenylalanine, Tyrosine, and Tryptophan, can be substituted with one another. Neutral polar amino acids, such as Asparagine, Cysteine, Glutamine, Methionine, Serine, and Threonine, can be substituted with one another, Hydrophilic amino acids, such as Alanine, Proline, Glycine, Glutamic acid, Aspartic acid, Glutamine, Asparagine, Serine, and Threonine, can be substituted with one another. These are non-limiting examples of conservative amino acid substitution and are not meant to exclude other combinations of amino acid substitutions.

In one embodiment, the engineered Rep protein comprises one or more alterations in amino acid residue(s) corresponding to the following amino acid residues in wild-type AAV5 Rep protein sequence selected from: (1) amino acid corresponding to Glycine-139 substituted with a Proline, Alanine, or Serine residue; (2) amino acid corresponding to Glycine-140 substituted with a Proline, Alanine, or Serine residue; (3) amino acid corresponding to Alanine-141 substituted with a Serine, Glycine, Threonine, Cysteine, or Valine residue; (4) amino acid corresponding to Lysine-138 substituted with a Arginine, Glutamine, Glutamic acid, Asparagine, or Serine residue; (5) amino acid corresponding to Methionine-102 substituted with a Leucine, Isoleucine, Glutamine, Valine, or Phenylalanine residue; (6) amino acid corresponding to Serine-109 substituted with a Threonine, Alanine, Asparagine, Aspartic acid, Glutamine, Glutamic acid, Glycine, Lysine, or Threonine residue; (7) amino acid corresponding to Glutamine-110 substituted with an Arginine, Asparagine, Aspartic acid, Histidine, Lysine, or Serine residue; (8) amino acid corresponding with Asparagine-142 substituted with an Aspartic acid, Serine, Glutamine, or Glutamic acid residue; (9) amino acid corresponding to Lysine-137 substituted with a Arginine, Glutamine, Glutamic acid, Asparagine, or Serine residue; (10) amino acid corresponding to Lysine-135 substituted with a Arginine, Glutamine, Glutamic acid, Asparagine, or Serine residue; (11) amino acid corresponding to Ser-101 substituted with a Threonine, Alanine, Asparagine, Aspartic acid, Glutamine, Glutamic acid, Glycine, Lysine, or Threonine residue; (12) amino acid corresponding to Glycine-105 substituted with a Proline, Alanine, or Serine residue; (13) amino acid corresponding to Arginine 106 substituted with a Lysine or Histidine residue; and (14) any combination of these alterations. In one embodiment, the engineered Rep protein comprises one or more alterations in amino acid residue(s) corresponding to the following amino acid residues in wild-type AAV5 Rep protein sequence selected from: (1) amino acid corresponding to Lycine-135 substituted with Glycine; (2)) amino acid corresponding to Lycine-135 substituted with Threonine. (3) amino acid corresponding to Asparagine 142 substituted with Glycine, (4) amino acid corresponding to Asparagine 142 substituted with Threonine, (5) amino acid corresponding to Lycine-135 substituted with Glycine and amino acid corresponding to Asparagine 142 substituted with Glycine; (6) amino acid corresponding to Lycine-135 substituted with Glycine and amino acid corresponding to Asparagine 142 substituted with Threonine; (7) amino acid corresponding to Lycine-135 substituted with Threonine and amino acid corresponding to Asparagine 142 substituted with Glycine; and (8) amino acid corresponding to Lycine-135 substituted with Threonine and amino acid corresponding to Asparagine 142 substituted with Threonine. The amino acid residue position numbering in the listed substitutions corresponds with the position numbering found in the wild-type AAV5 Rep protein (SEQ ID NO: 269). Corresponding amino acid residues at these positions for other AAV serotypes and species of Rep proteins can be found in the sequence alignments provided in FIG. 8. Corresponding amino acid residues at these positions for additional parvoviral serotypes and species of Rep proteins can be determined by sequence alignment analysis using the methods described herein or otherwise known in the art.

In any of the above-described embodiments, the altered or modified amino acid residue(s) of the engineered Rep protein has decreased contact with a wild-type Rep binding sequence region relative to the amount of contact a wild-type Rep protein has with the wild-type Rep binding sequence region. In another embodiment, the modified amino acid residue(s) of the engineered Rep protein has decreased contact with an engineered Rep binding sequence region relative to the amount of contact a wild-type Rep protein has with the engineered Rep binding sequence region. In another embodiment, the modified amino acid residue(s) of the engineered Rep protein has decreased contact with an engineered Rep binding sequence region relative to the amount of contact it has with a wild-type Rep binding sequence region. In any of these embodiments, the engineered Rep binding sequence region can be an engineered Rep binding sequence region provided in the present disclosure.

In another embodiment, the one or more altered or modified amino acid residue(s) of the engineered Rep protein is modified by non-conservative substitution with a different amino acid residue.

In any of these embodiments in which the altered or modified amino acid residue of the engineered Rep protein is an amino acid residue that in its wild-type form contacts a Rep binding sequence region, the Rep binding sequence region can be a wild-type Rep binding sequence region or an engineered Rep binding sequence region. Thus, in one embodiment in which the altered or modified amino acid residue of the engineered Rep protein is an amino acid residue that in its wild-type form contacts a Rep binding sequence region, the Rep binding sequence region is a wild-type Rep binding sequence region. The wild-type Rep binding sequence region can be an AAV Rep binding sequence region. In certain specific embodiments, the AAV is selected from any of the AAV serotypes and species provided herein. In one embodiment wherein the altered or modified amino acid residue of the engineered Rep protein is an amino acid residue that in its wild-type form contacts a Rep binding sequence region, the Rep binding sequence region is selected from any of SEQ ID NOs: 1-20, 21-66, and/or 79-197. Also, in any of these embodiments in which the altered or modified amino acid residue of the engineered Rep protein is an amino acid residue that in its wild-type form contacts a Rep binding sequence region, the Rep binding sequence region can be an engineered Rep binding sequence region. The engineered Rep binding sequence region can be derived from art AAV Rep binding sequence region. In certain specific embodiments, the AAV is selected from any of the AAV serotypes and species provided herein. In another embodiment wherein the altered or modified amino acid residue of the engineered Rep protein is an amino acid residue that in its wild-type form contacts an engineered. Rep binding sequence region, the engineered Rep binding sequence region is selected from any of the engineered Rep binding sequence regions provided in the present disclosure. In some embodiments the engineered Rep binding sequence region is selected from any of SEQ ID NOs: 1-20, 21-66, and/or 79-197.

In one embodiment, the modified amino acid residue of the engineered Rep protein is modified by chemical, enzymatic, or other post-translational modification.

The engineered Rep protein has decreased binding affinity with a Rep binding sequence region as a result of the one or more alterations and/or modifications. In one embodiment, the engineered Rep protein has decreased binding affinity with a wild-type Rep binding sequence region relative to the binding affinity of a wild-type Rep protein with the wild-type Rep binding sequence region as a result of the one or more alterations and/or modifications. In another embodiment, the engineered Rep protein has decreased binding affinity with an engineered Rep binding sequence region relative to the binding affinity of a wild-type Rep protein with the engineered Rep binding sequence region. In another embodiment, the engineered Rep protein has decreased binding affinity with an engineered Rep binding sequence region relative to the binding affinity it has with a wild-type Rep binding sequence region. In any of these embodiments, the binding affinity is decreased about 2-fold to about 20-fold. In another embodiment, the binding affinity is decreased at least 2-fold, at least 5-fold, at least 10-fold, or at least 20-fold. In any of these embodiments, the Rep binding sequence region is a wild-type Rep binding sequence region, for example, an AAV Rep binding sequence region, such as an AAV Rep binding sequence region selected from any of the AAV serotypes and species provided herein. In any of these embodiments, the Rep binding sequence region is an engineered Rep binding sequence region, for example, an engineered Rep binding sequence region derived from aft AAV Rep binding sequence region, such as AAV Rep binding sequence region selected from any of the AAV serotypes and species provided herein.

V. PAYLOAD: TRANSGENES, POLYPEPTIDE-ENCODING POLYNUCLEOTIDES AND/OR MODULATORY NUCLEIC ACIDS

The payload construct vector of the present invention comprises a nucleic acid sequence encoding at least one "payload molecule." As used herein, a "payload molecule" refers to a transgene, a polynucleotide encoding a polypeptide or a modulatory nucleic acid. The payload molecule may comprise any nucleic acid encoded in the viral genome produced in accordance with the present invention for expression in a target cell transduced or contacted with the viral particle.

According to the present invention, the payload construct vector encodes a "payload construct." As used herein, a "payload construct" is a polynucleotide sequence encoding at least a payload molecule and sufficient ITR sequence to allow for expression of the payload molecule in a cell transduced with the viral particle.

The payload molecule may comprise a polypeptide, an RNA molecule, or any other gene product that is desired for expression in the target cell. The payload construct may comprise a combination of coding and non-coding nucleic acid sequences.

In one embodiment, the payload construct vector comprises more than one nucleic acid sequences encoding more than one payload molecule of interest. In such an embodiment, a payload construct vector encoding more than one payload molecule may be replicated and packaged into a viral particle. A target cell transduced with a viral particle comprising more than one payload molecule may express each of the payload molecules in a single cell.

In some embodiments, the payload construct vector sequence may encode a coding or non-coding RNA.

Where the payload construct vector sequence encodes a polypeptide, the polypeptide may be a peptide or protein. A protein encoded by the payload construct vector sequence may comprise a secreted protein, an intracellular protein, an extracellular protein, and/or a membrane protein. The encoded proteins may be structural or functional. Proteins encoded by the payload construct vector or payload construct include, but are not limited to, mammalian proteins. The viral vectors encoding polypeptides (e.g., mRNA) of the invention may be used in the fields of human disease, antibodies, viruses, veterinary applications and a variety of in vivo and in vitro settings.

In some embodiments, the viral particles are useful in the field of medicine for the treatment, palliation or amelioration of conditions or diseases such as, but not limited to, blood, cardiovascular, CNS, dermatology, endocrinology, genetic, genitourinary, gastrointestinal, musculoskeletal, oncology, and immunology, respiratory, sensory and anti-infective.

In some embodiments, viral particles in accordance with the present invention may be used for the treatment of disorders, and/or conditions, including but not limited to one or more of the following: autoimmune disorders (e.g. diabetes, lupus, multiple sclerosis, psoriasis, rheumatoid arthritis); inflammatory disorders (e.g. arthritis, pelvic inflammatory disease); neurological disorders (e.g. Alzheimer's disease, Huntington's disease; autism; Parkinson's disease); cardiovascular disorders (e.g. atherosclerosis, hypercholesterolemia, thrombosis, clotting disorders, angiogenic disorders such as macular degeneration); proliferative disorders (e.g. cancer, benign neoplasms); respiratory disorders (e.g. chronic obstructive pulmonary disease); digestive disorders (e.g. inflammatory bowel disease, ulcers); musculoskeletal disorders (e.g. fibromyalgia, arthritis); endocrine, metabolic, and nutritional disorders (e.g. diabetes, osteoporosis); urological disorders (e.g. renal disease); psychological disorders (e.g. depression, schizophrenia); skin disorders (e.g. wounds, eczema); blood and lymphatic disorders (e.g. anemia, hemophilia); etc.

In some embodiments, the payload construct encodes a messenger RNA (mRNA). As used herein, the term "messenger RNA" (mRNA) refers to any polynucleotide which encodes a polypeptide of interest and which is capable of being translated to produce the encoded polypeptide of interest in vitro, in vivo, in situ or ex vivo.

Traditionally, the basic components of an mRNA molecule include at least a coding region, a 5'UTR, a 3'UTR, a 5' cap and a poly-A tail. According to the present invention, payload constructs encoding mRNA may comprise a coding region only. They may also comprise a coding region and at least one UTR. They may also comprise a coding region, 3'UTR and a poly-A tail.

In one embodiment the polypeptide encoded by the payload construct is between 50-5000 amino acids in length. In some embodiments the protein encoded is between 50-2000 amino acids in length. In some embodiments the protein encoded is between 50-1500 amino acids in length. In some embodiments the protein encoded is between 50-1000 amino acids in length. In some embodiments the protein encoded is between 50-800 amino acids in length. In some embodiments the protein encoded is between 50-600 amino acids in length. In some embodiments the protein encoded is between 50-400 amino acids in length. In some embodiments the protein encoded is between 50-200 amino acids in length. In some embodiments the protein encoded is between 50-100 amino acids in length.

In some embodiments the peptide encoded by the payload construct is between 4-50 amino acids in length. In one embodiment, the shortest length of a region of the payload molecule of the present invention encoding a peptide can be the length that is sufficient to encode for a tetrapeptide, a pentapeptide, a hexapeptide, a heptapeptide, an octapeptide, a nonapeptide, or a decapeptide. In another embodiment, the length may be sufficient to encode a peptide of 2-30 amino acids, e.g. 5-30, 10-30, 2-25, 5-25, 10-25, or 10-20 amino acids. The length may be sufficient to encode for a peptide of at least 11, 12, 13, 14, 15, 17, 20, 25 or 30 amino acids, or a peptide that is no longer than 50 amino acids, e.g. no longer than 35, 30, 25, 20, 17, 15, 14, 13, 12, 11 or 10 amino acids.

An RNA encoded by the payload construct may comprise an mRNA, tRNA, rRNA, tmRNA, miRNA, RNAi, siRNA, piRNA, shRNA antisense RNA, double stranded RNA, snRNA, snoRNA, and long non-coding RNA (lncRNA). Examples of such lncRNA molecules and RNAi constructs designed to target such lncRNA any of which may be encoded in the payload constructs are taught in International Publication, WO2012/018881 A2, the contents of which are incorporated herein by reference in their entirety.

In one embodiment, the payload construct encodes a microRNA or miRNA as the payload molecule. These payload molecules are also referred to as modulatory nucleic acid payloads.

microRNAs (or miRNA) are 19-25 nucleotide long non-coding RNAs that bind to the 3'UTR of nucleic acid molecules and down-regulate gene expression either by reducing nucleic acid molecule stability or by inhibiting translation. The payload constructs of the invention may comprise one or more microRNA target sequences, microRNA sequences, or microRNA seeds. Such sequences may correspond to any known microRNA such as those taught in US Publication US200510261218 and US Publication US2005/0059005, the contents of which are incorporated herein by reference in their entirety.

A microRNA sequence comprises a "seed" region, i.e., a sequence in the region of positions 2-8 of the mature microRNA, which has perfect Watson-Crick complementarily to the miRNA target sequence. A microRNA seed may comprise positions 2-8 or 2-7 of the mature microRNA. In some embodiments, a microRNA seed may comprise 7 nucleotides (e.g., nucleotides 2-8 of the mature microRNA), wherein the seed-complementary site in the corresponding miRNA target is flanked by an adenine (A) opposed to microRNA position 1. In some embodiments, a microRNA seed may comprise 6 nucleotides (e.g., nucleotides 2-7 of the mature microRNA), wherein the seed-complementary site in the corresponding miRNA target is flanked by an adenine (A) opposed to microRNA position 1. See, for example, Grimson A, Farh K K, Johnston W K, Garrett-Engele P. Lim L P, Bartel D P; Mol Cell. 2007 Jul. 6; 27(1):91-105; each of which is herein incorporated by reference in their entirety.

The bases of the microRNA seed have complete complementarily with the target sequence:

A payload molecule may comprise polypeptides that serve as marker proteins to assess cell transformation and expression, fusion proteins, polypeptides having a desired biological activity, gene products that can complement a genetic defect, RNA molecules, transcription factors, and other gene products that are of interest in regulation and/or expression. A payload molecule may comprise nucleotide sequences that provide a desired effect or regulatory function (e.g., transposons, transcription factors). A payload molecule may comprise, but is not limited to: hormone receptors (e.g., mineral corticosteroid, glucocorticoid, and thyroid hormone receptors); intramembrane proteins (e.g., TM-1 and TM-7); intracellular receptors (e.g., orphans, retinoids, vitamin D3 and vitamin A receptors); signaling molecules (e.g., kinases, transcription factors, or molecules such signal transducers and activators of transcription receptors of the cytokine superfamily (e.g, erythropoietin, growth hormone, interferons, and interleukins, and colony-stimulating factors; G-protein coupled receptors, e.g., hormones, calcitonin, epinephrine, gastrin, and paracrine or autocrine mediators, such as somatostatin or prostaglandins); neurotransmitter receptors (norepinephrine, dopamine, serotonin or acetylcholine); pathogenic antigens, which can be of viral, bacterial, allergenic, or cancerous origin; and tyrosine kinase receptors (such as insulin growth factor, and nerve growth factor).

A payload molecule may comprise a gene therapy product. A gene therapy product may comprise a polypeptide, an RNA molecule, or other gene product that, when expressed in a target cell, provides a desired therapeutic effect. In some embodiments, a gene therapy product may comprise a substitute for a non-functional gene that is absent or mutated. In some embodiments, a gene therapy product may comprise a method for elimination of a gene that is overactive or dysregulated. Goldsmith et al., WO 90/07936, the contents of which are incorporated herein by reference in their entirety.

A payload construct vector encoding a payload molecule may comprise a selectable marker. A selectable marker may comprise a gene sequence or a protein encoded by that gene sequence expressed in a host cell that allows for the identification, selection, and/or purification of the host cell from a population of cells that may or may not express the selectable marker. In one embodiment the selectable marker provides resistance to survive a selection process that would otherwise kill the host cell, such as treatment with an antibiotic. In some embodiments an antibiotic selectable marker may comprise one or more antibiotic resistance factors, including but not limited to neomycin resistance (e.g., neo), hygromycin resistance, kanamycin resistance, and/or puromycin resistance.

In some embodiments a selectable marker may comprise a cell-surface marker, such as any protein expressed on the surface of the cell including, but not limited to receptors, CD markers, lectins, integrins, or truncated versions thereof. In some embodiments, cells that comprise a cell-surface marker may be selected using an antibody targeted to the cell-surface marker. In some embodiments an antibody targeted to the cell-surface marker may be directly conjugated with a selection agent including, but not limited to a fluorophore, sepharose, or magnetic bead. In some embodiments an antibody targeted to the cell-surface marker may be detected using a secondary labeled antibody or substrate which binds to the antibody targeted to the cell-surface marker. In some embodiments, a selectable marker may comprise negative selection by using an enzyme, including but not limited to Herpes simplex virus thymidine kinase (HSVTX) that converts a pro-toxin (ganciclovir) into a toxin or bacterial Cytosine Deaminase (CD) which converts the pro-toxin 5'-fluorocytosine (5'-FC) into the toxin 5'-fluorouracil (5'-FU). In some embodiments, any nucleic acid sequence encoding a polypeptide can be used as a selectable marker comprising recognition by a specific antibody.

In some embodiments, a payload construct vector encoding a payload molecule may comprise a selectable marker including, but not limited to, β-lactamase, luciferase, β-galactosidase, or any other reporter gene as that term is understood in the art, including cell-surface markers, such as CD4 or the truncated nerve growth factor (NGFR) (for GFP, see WO 96/23810; Heim et al., Current Biology 2:178-182 (1996); Heim et al., Proc. Natl. Acad. Sci. USA (1995); or Heim et al., Science 373:663-664 (1995); for β-lactamase, see WO 96/30540). In some embodiments, a nucleic acid encoding a selectable marker may comprise a fluorescent protein. A fluorescent protein as herein described may comprise any fluorescent marker including but not limited to green, yellow, and/or red fluorescent protein (GFP, YFP, and RFP).

In accordance with the invention, a payload molecule comprising a nucleic acid for expression in a target cell will be incorporated into the viral particle produced in the viral replication cell if the payload molecule is located between two ITR sequences, or is located on either side of an asymmetrical ITR engineered with two D regions.

A payload construct vector sequence encoding one or more payload molecules for expression in a target cell may comprise one or more nucleotide sequences operably linked to at least one target cell-compatible promoter. A person skilled in the art may recognize that a target cell may require a specific promoter including but not limited to a promoter that is species specific, inducible, tissue-specific, or cell cycle-specific Parr et al., Nat Med. 3:1145-9 (1997).

VI. VIRAL PRODUCTION

The present disclosure provides a method for increasing the generation of self-complementary (SC) AAV during AAV genome replication in a viral replication cell comprising contacting the viral replication cell or tissue with an AAV polynucleotide or AAV genome or AAV particle comprising a chimeric Rep binding sequence region, or contacting the cell or tissue with a vector comprising the AAV polynucleotide or AAV genome, or contacting the cell or tissue with any of the described compositions, including pharmaceutical compositions.

Figure 9:
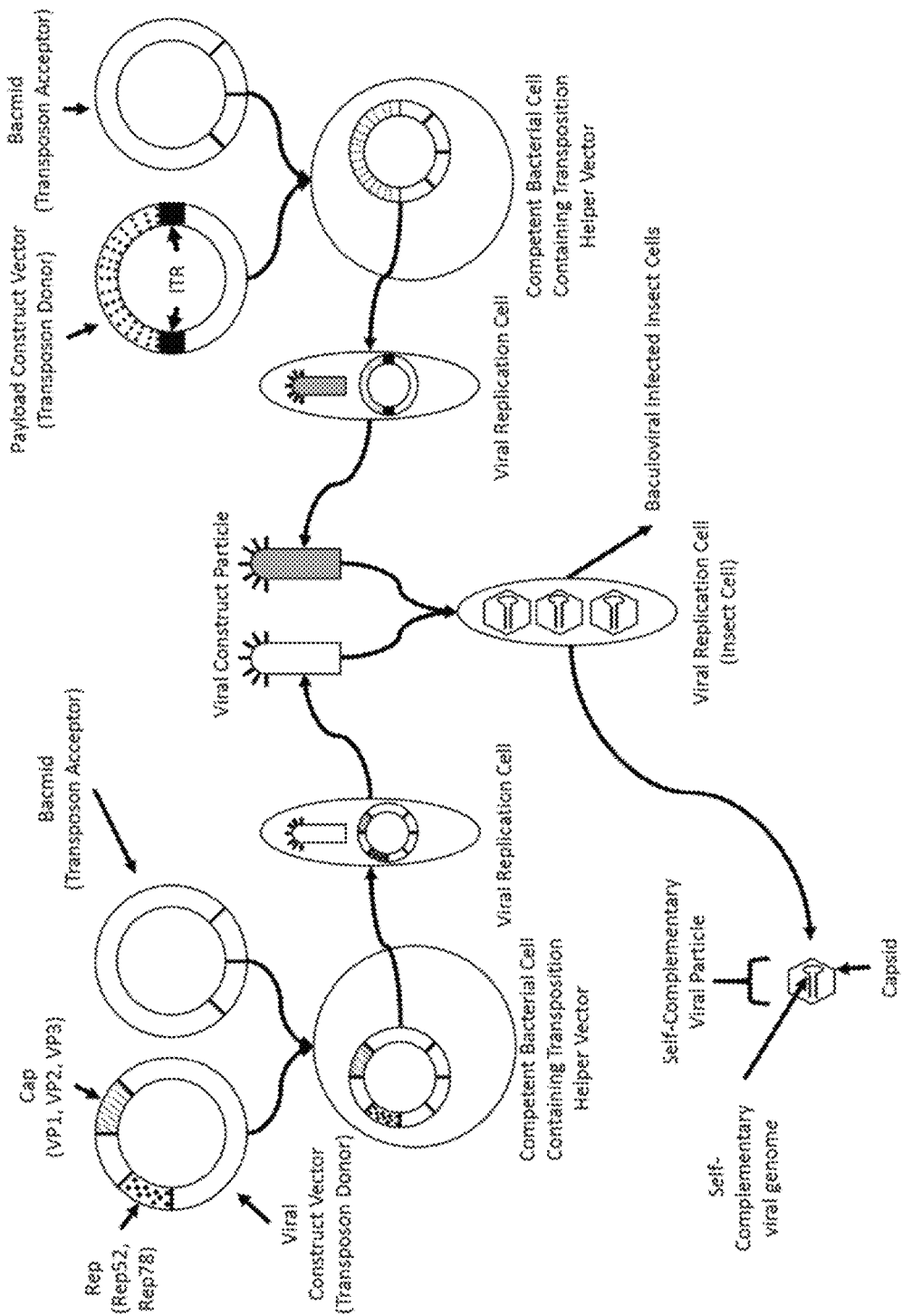
FIG. 9 is a diagram depicting the steps involved in scAAV viral particle production.
Figure 10:
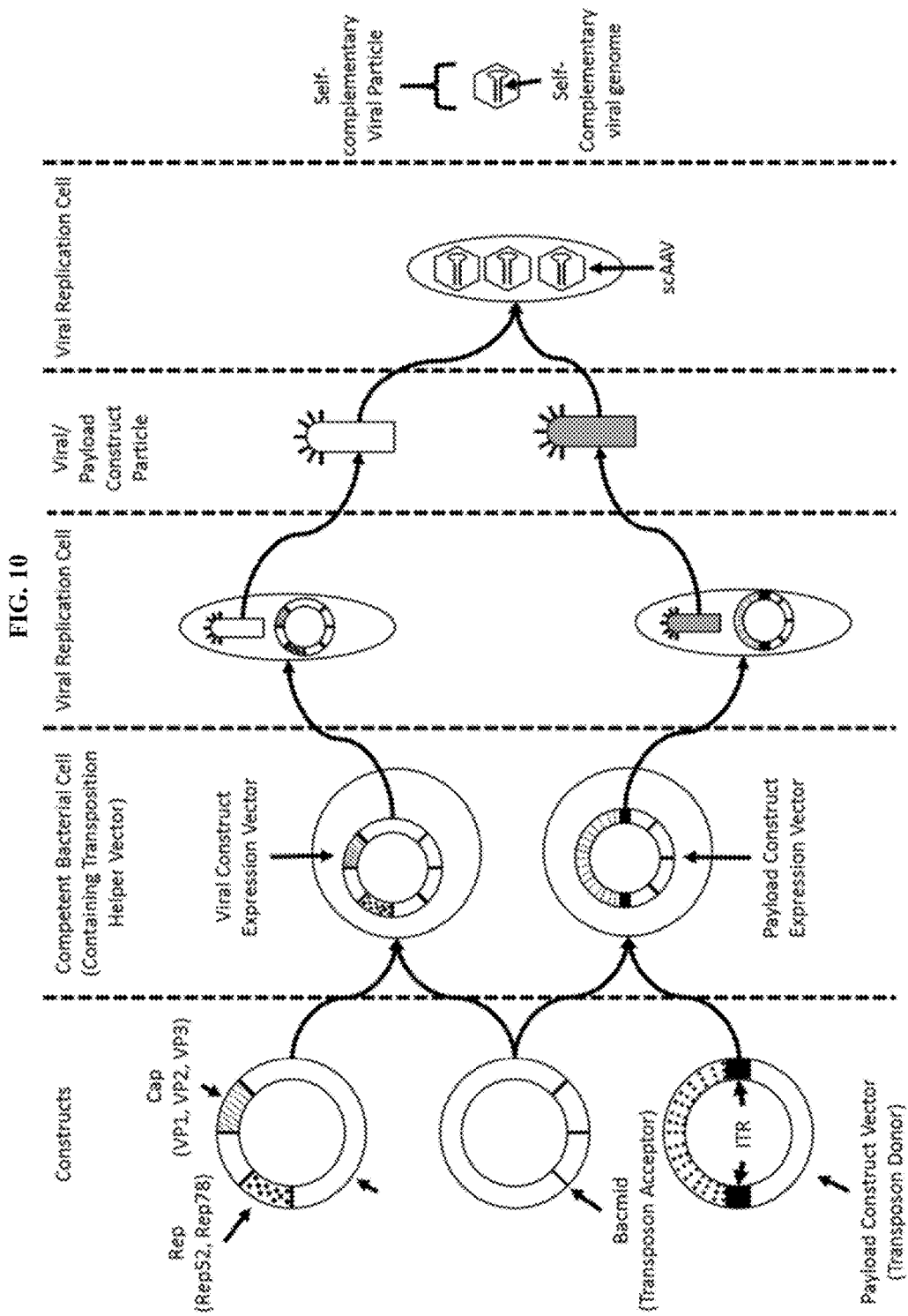
FIG. 10 is a diagram depicting the steps involved in scAAV viral particle production divided by the stages of production.

The present disclosure provides a method for producing an AAV particle having enhanced (increased, improved) transduction efficiency comprising the steps of: 1) co-transfecting competent bacterial cells with a bacmid vector and either a viral construct vector or payload construct vector, 2) isolating the resultant viral construct expression vector and payload construct expression vector and separately transfecting viral replication cells, 3) isolating and purifying resultant payload and viral construct particles comprising viral construct expression vector or payload construct expression vector, 4) co-infecting a viral replication cell with both the payload and viral construct particles comprising viral construct expression vector or payload construct expression vector, 5) harvesting and purifying the viral particle comprising a self-complementary parvoviral genome (FIG. 9 and FIG. 10).

Vectors

The invention also provides nucleic acids encoding the mutated or modified virus capsids and capsid proteins of the invention. Further provided are vectors comprising the nucleic acids, and cells (in vivo or in culture) comprising the nucleic acids and/or vectors of the invention. Suitable vectors include without limitation viral vectors (e.g., adenovirus, AAV, herpesvirus, vaccinia, poxviruses, baculoviruses, and the like), plasmids, phage, YACs, BACs, and the like as are well known in the art. Such nucleic acids, vectors and cells can be used, for example, as reagents (e.g., helper packaging constructs or packaging cells) for the production of modified virus capsids or virus vectors as described herein.

The molecules of the invention which contain AAV sequences include any genetic element (vector) which may be delivered to a host cell, e.g., naked DNA, a plasmid, phage, transposon, cosmid, episome, a protein in a non-viral delivery vehicle (e.g., a lipid-based carrier), virus, etc., which transfers the sequences carried thereon. The selected vector may be delivered by any suitable method, including transfection, electroporation, liposome delivery, membrane fusion techniques, high velocity DNA-coated pellets, viral infection and protoplast fusion. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y.

The transgene can be carried on any suitable vector, e.g., a plasmid, which is delivered to a host cell. The plasmids useful in this invention may be engineered such that they are suitable for replication and, optionally, integration in prokaryotic cells, mammalian cells, or both. These plasmids contain sequences permitting replication of the transgene in eukaryotes and/or prokaryotes and selection markers for these systems. Selectable markers or reporter genes may include sequences encoding geneticin, hygromnicin or purimycin resistance, among others. The plasmids may also contain certain selectable reporters or marker genes that can be used to signal the presence of the vector in bacterial cells, such as ampicillin resistance. Other components of the plasmid may include an origin of replication and an amplicon, such as the amplicon system employing the Epstein Barr virus nuclear antigen. This amplicon system, or other similar amplicon components permit high copy episomal replication in the cells. Preferably, the molecule carrying the transgene is transfected into the cell, where it may exist transiently. Alternatively, the transgene may be stably integrated into the genome of the host cell, either chromosomally or as an episome. In certain embodiments, the transgene may be present in multiple copies, optionally in head-to-head, head-to-tail, or tail-to-tail concatamers. Suitable transfection techniques are known and may readily be utilized to deliver the transgene to the host cell.

Cells

The present disclosure provides a cell comprising an engineered Rep protein or an AAV polynucleotide, AAV genome, or AAV comprising an engineered Rep protein, a cell comprising a viral vector comprising the AAV polynucleotide or AAV genome, and a cell comprising a composition comprising the AAV polynucleotide or AAV genome or the AAV or a composition comprising the viral vector.

Viral production of the invention disclosed herein describes processes and methods for producing viral vector that contacts a target cell to deliver a payload construct, e.g.

a recombinant viral construct, which comprises a nucleotide encoding a payload molecule.

In one embodiment, the viral vector of the invention may be produced in a viral replication cell that comprises an insect cell.

Growing conditions for insect cells in culture, and production of heterologous products in insect cells in culture are well-known in the art, see U.S. Pat. No. 6,204,059, the contents of which are herein incorporated by reference in their entirety.

Any insect cell which allows for replication of parvovirus and which can be maintained in culture can be used in accordance with the present invention. Cell lines may be used from *Spodoptera frugiperda*, including, but not limited to the Sf9 or Sf21 cell lines, *drosophila* cell lines, or mosquito cell lines, such as, *Aedes albopictus* derived cell lines. Use of insect cells for expression of heterologous proteins is well documented, as are methods of introducing nucleic acids, such as vectors, e.g., insect-cell compatible vectors, into such cells and methods of maintaining such cells in culture. See, for example, METHODS IN MOLECULAR BIOLOGY, ed. Richard, Humana Press, NJ (1995); O'Reilly et al., BACULOVIRUS EXPRESSION VECTORS, A LABORATORY MANUAL, Oxford Univ. Press (1994); Samulski et al., *J. Vir.* 63:3822-8 (1989); Kajigaya et al., *Proc. Nat'l Acad. Sci. USA* 88: 4646-50 (1991); Ruffing et al., *J. Vir.* 66:6922-30 (1992); Kimbauer et al., *Vir.* 219:37-44 (1996); Zhao et al., *Vir.* 272:382-93 (2000); and Samulski et al., U.S. Pat. No. 6,204,059, the contents of each of which are herein incorporated by reference in their entirety.

The viral replication cell may be selected from any biological organism, including prokaryotic (e.g., bacterial) cells, and eukaryotic cells, including, insect cells, yeast cells and mammalian cells. Viral replication cells may comprise mammalian cells such as A549, WEH1, 3T3, 10T1/2, BHK, MDCK, COS 1, COS 7, BSC 1, BSC 40, BMT 10, VERO. W138, HeLa, 293, Saos, C2C12, L cells, HT1080, HepG2 and primary fibroblast, hepatocyte and myoblast cells derived from mammals. Viral replication cells of the invention comprise cells derived from mammalian species including, but not limited to, human, monkey, mouse, rat, rabbit, and hamster or cell types, including but not limited to fibroblast, hepatocyte, tumor cell, cell line transformed cell, etc.

Small Scale Production of the Self-Complementary Viral Particle

Viral production of the invention disclosed herein describes processes and methods for producing viral vector that contacts a target cell to deliver a payload construct, e.g. a recombinant viral construct, which comprises a nucleotide encoding a payload molecule.

In one embodiment, the viral vector of the invention may be produced in a viral replication cell that comprises a mammalian cell.

Viral replication cells commonly used for production of recombinant AAV viral vector include, but are not limited to 293 cells, COS cells, Heta cells, KB cells, and other mammalian cell lines as described in U.S. Pat. Nos. 6,156,303, 5,387,484, 5,741,683, 5,691,176, and 5,688,676; U.S. patent application 2002/0081721, and International Patent Applications WO 00/47757, WO 00/24916, and WO 96/17947, the contents of each of which are herein incorporated by reference in their entireties.

In one embodiment, viral vector produced in mammalian-cells wherein all three VP proteins are expressed at a stoichiometry approaching 1:1:10 (VP1:VP2:VP3), The regulatory mechanisms that allow this controlled level of expression include the production of two mRNAs, one for VP1, and the other for VP2 and VP3, produced by differential splicing.

In another embodiment, viral vector is produced in mammalian cells using a triple transfection method wherein a payload construct, parvoviral Rep, and Cap and helper virus are comprised within three different constructs. The triple transfection method of the three components of AAV viral vector production may be utilized to produce small lots of virus for assays including transduction efficiency, target tissue (tropism) evaluation, and stability.

Large Scale Production of the Self Complementary Viral Particle Baculovirus

Self-complementary viral particle production of the invention disclosed herein describes processes and methods for producing scAAV that contacts a target cell to deliver a payload construct which comprises a nucleotide encoding a payload molecule.

In one embodiment, the process comprises production of viral particles in a baculoviral system using a viral construct vector and a payload construct vector as depicted in FIG. 9 and FIG. 10. Briefly, the viral construct vector and the payload construct vector of the invention are each incorporated by a transposon donor/acceptor system into a bacmid, also known as a baculovirus plasmid, by standard molecular biology techniques known and performed by a person skilled in the art. Transfection of separate viral replication cell populations produces two baculoviruses, one that comprises the viral construct expression vector, and another that comprises the payload construct expression vector. The two baculoviruses depicted in FIG. 9 and FIG. 10 may be used to infect a single viral replication cell population for production of scAAV.

Baculovirus expression vectors for producing viral particles in insect cells, including but not limited to *Spodoptera frugiperda* (SP)) cells, provide high titers of viral particle product. Recombinant baculovirus encoding the viral construct expression vector and payload construct expression vector initiates a productive infection of viral replicating cells. Infectious baculovirus particles released from the primary infection secondarily infect additional cells in the culture, exponentially infecting the entire cell culture population in a number of infection cycles that is a function of the initial multiplicity of infection, see Urabe, M. et al. J Virol. 2006 February; 80(4):1874-85, the contents of which are herein incorporated by reference in their entirety.

Production of viral particles with baculovirus in an insect cell system may address known baculovirus genetic and physical instability. In one embodiment, the production system of the invention addresses baculovirus instability over multiple passages by utilizing a titerless infected-cells preservation and scale-up system. Small scale seed cultures of viral producing cells are transfected with viral expression constructs encoding the structural, non-structural, components of the viral particle. Baculovirus-infected viral producing cells are harvested into aliquots that may be cryopreserved in liquid nitrogen; the aliquots retain viability and infectivity for infection of large scale viral producing cell culture Wasilko D J et al. Protein Expr Purif. 2009 June; 65(2):122-32, the contents of which are herein incorporated by reference in their entirety.

A genetically stable baculovirus may be used to produce the source of one or more of the components for producing viral particles in invertebrate cells. In one embodiment, defective baculovirus expression vectors may be maintained episomally in insect cells. In such an embodiment the bacmid vector is engineered with replication control elements, including but not limited to promoters, enhancers, and/or cell-cycle regulated replication elements.

In one embodiment, baculoviruses may be engineered with a (non-) selectable marker for recombination into the chitinase/cathepsin locus. The chia/v-cath locus is non-essential for propagating baculovirus in tissue culture, and the V-cath (EC 3.4.22.50) is a cysteine endoprotease that is most active on Arg-Arg dipeptide containing substrates. The Arg-Arg dipeptide is present in densovirus and parvovirus capsid structural proteins but infrequently occurs in dependovirus VP1.

In one embodiment, stable viral replication cells permissive for baculovirus infection are engineered with at least one stable integrated copy of any of the elements necessary for AAV replication and viral particle production including, but not limited to, the entire AAV genome, Rep and Cap genes, Rep genes, Cap genes, each Rep protein as a separate transcription cassette, each VP protein as a separate transcription cassette, the AAP (assembly activation protein), or at least one of the baculovirus helper genes with native or non-native promoters.

Large-Scale Production Methods

In some embodiments, viral particle production may be modified to increase the scale of production. Large scale viral production methods according to the present invention may include any of those taught in U.S. Pat. Nos. 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498 and 7,491,508 or International Publication Nos, WO1996039530, WO1998010088, WO1999014354, WO1999015685, WO1999047691, WO2000055342, WO2000075353 and WO2001023597, the contents of each of Which are herein incorporated by reference by reference in their entirety. Methods of increasing viral particle production scale typically comprise increasing the number of viral replication cells. In some embodiments, viral replication cells comprise adherent cells. To increase the scale of viral particle production by adherent viral replication cells, larger cell culture surfaces are required. In some cases, large-scale production methods comprise the use of roller bottles to increase cell culture surfaces. Other cell culture substrates with increased surface areas are know) in the art. Examples of additional adherent cell culture products with increased surface areas include, but are not limited to CELLSTACK®, CELLCUBE® (Corning Corp., Corning, N.Y.) and NUNC™ CELL FACTORY™ (Thermo Scientific. Waltham, Mass.) In some cases, large-scale adherent cell surfaces may comprise from about 1,000 $cm^2$ to about 100,000 $cm^2$. In some cases, large-scale adherent cell cultures may comprise from about $10^7$ to about $10^9$ cells, from about $10^8$ to about $10^{10}$ cells, from about $10^9$ to about $10^{12}$ cells or at least $10^{12}$ cells. In some cases, large-scale adherent cultures may produce from about $10^9$ to about $10^{12}$, from about $10^{10}$ to about $10^{13}$, from about $10^{11}$ to about $10^{14}$, from about $10^{12}$ to about $10^{15}$ or at least $10^{15}$ viral particles.

In some embodiments, large-scale viral production methods of the present invention may comprise the use of suspension cell cultures. Suspension cell culture allows for significantly increased numbers of cells. Typically, the number of adherent cells that can be grown on about 10-50 $cm^2$ of surface area can be grown in about 1 $cm^3$ volume in suspension.

Transfection of replication cells in large-scale culture formats may be carried out according to any methods known in the art. For large-scale adherent cell cultures, transfection methods may include, but are not limited to the use of inorganic compounds (e.g. calcium phosphate) organic compounds [e.g. polyethyleneimine (PEI)] or the use of non-chemical methods (e.g. electroporation). With cells grown in suspension, transfection methods may include, but are not limited to the use of calcium phosphate and the use of PEI. In some cases, transfection of large scale suspension cultures may be carried out according to the section entitled "Transfection Procedure" described in Feng, L. et al., 2008. Biotechnol Appl Biochem. 50:121-32, the contents of which are herein incorporated by reference in their entirety. According to such embodiments, PEI-DNA complexes may be formed for introduction of plasmids to be transfected. In some cases, cells being transfected with PEI-DNA complexes may be 'shocked' prior to transfection. This comprises lowering cell culture temperatures to 4° C. for a period of about 1 hour. In some cases, cell cultures may be shocked for a period of from about 10 minutes to about 5 hours. In some cases, cell cultures may be shocked at a temperature of from about 0° C. to about 20° C.

In some cases, transfections may include one or more vectors for expression of an RNA effector molecule to reduce expression of nucleic acids from one or more payload construct. Such methods may enhance the production of viral particles by reducing cellular resources wasted on expressing payload constructs. In some cases, such methods may be carried according to those taught in US Publication No. US2014/0099666, the contents of which are herein incorporated by reference in their entirety.

Bioreactors

In some embodiments, cell culture bioreactors may be used for large scale viral production. In some cases, bioreactors comprise stirred tank reactors. Such reactors generally comprise a vessel, typically cylindrical in shape, with a stirrer (e.g. impeller). In some embodiments, such bioreactor vessels may be placed within a water jacket to control vessel temperature and/or to minimize effects from ambient temperature changes. Bioreactor vessel volume may range in size from about 500 nil to about 2 L, from about 1 L to about 5 L, from about 2.5 L to about 20 L, from about 10 L to about 50 L, from about 25 L to about 100 L, from about 75 L to about 500 L, from about 250 L to about 2,000 L, from about 1,000 L to about 10,000 L, from about 5,000 L to about 50,000 L or at least 50,000 L. Vessel bottoms may be rounded or flat. In some cases, animal cell cultures may be maintained in bioreactors with rounded vessel bottoms.

In some cases, bioreactor vessels may be warmed through the use of a thermocirculator. Thermocirculators pump heated water around water jackets. In some cases, heated water may be pumped through pipes (e.g, coiled pipes) that are present within bioreactor vessels. In some cases, warm air may be circulated around bioreactors, including, but not limited to air space directly above culture medium. Additionally, pH and $CO_2$ levels may be maintained to optimize cell viability.

In some cases, bioreactors may comprise hollow-fiber reactors. Hollow-fiber bioreactors may support the culture of both anchorage dependent and anchorage independent cells. Further bioreactors may include, but are not limited to packed-bed or fixed-bed bioreactors. Such bioreactors may comprise vessels with glass beads for adherent cell attachment. Further packed-bed reactors may comprise ceramic beads.

In some cases, viral particles are produced through the use of a disposable bioreactor. In some embodiments, such bioreactors may include WAVE™ disposable bioreactors.

In some embodiments, viral particle production in animal cell bioreactor cultures may be carried out according to the methods taught in U.S. Pat. Nos. 5,064,764, 6,194,191, 6,566,118, 8,137,948 or US Patent Application No. US2011/0229971, the contents of each of which are herein incorporated by reference in their entirety.

Cell Lysis

Cells of the invention, including, but not limited to viral production cells, may be subjected to cell lysis according to any methods known in the art. Cell lysis may be carried out to obtain one or more agents (e.g. viral particles) present within any cells of the invention. In some embodiments, cell lysis may be carried out according to any of the methods listed in U.S. Pat. Nos. 7,326,555, 7,579,181, 7,048,920, 6,410,300, 6,436,394, 7,732,129, 7,510,875, 7,445,930, 6,726,907, 6,194,191, 7,125,706, 6,995,006, 6,676,935, 7,968,333, 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498 and 7,491,508 or International Publication Nos. WO1996039530, WO1998010088, 101999014354, WO1999015685, WO1999047691, WO2000055342, WO2000075353 and WO2001023597, the contents of each of which are herein incorporated by reference in their entirety. Cell lysis methods may be chemical or mechanical. Chemical cell lysis typically comprises contacting one or more cells with one or more lysis agents. Mechanical lysis typically comprises subjecting one or more cells to one or more lysis conditions and/or one or more lysis forces.

In some embodiments, chemical lysis may be used to lyse cells. As used herein, the term "lysis agent" refers to any agent that may aid in the disruption of a cell. In some cases, lysis agents are introduced in solutions, termed lysis solutions or lysis buffers. As used herein, the term "lysis solution" refers to a solution (typically aqueous) comprising one or more lysis agents. In addition to lysis agents, lysis solutions may include one or more buffering agents, solubilizing agents, surfactants, preservatives, cryoprotectants, enzymes, enzyme inhibitors and/or chelators. Lysis buffers are lysis solutions comprising one or more buffering agents. Additional components of lysis solutions may include one or more solubilizing agents. As used herein, the term "solubilizing agent" refers to a compound that enhances the solubility of one or more components of a solution and/or the solubility of one or more entities to which solutions are applied. In some cases, solubilizing agents enhance protein solubility. In some cases, solubilizing agents are selected based on their ability to enhance protein solubility while maintaining protein conformation and/or activity.

Exemplary lysis agents may include any of those described in U.S. Pat. Nos. 8,685,734, 7,901,921, 7,732,129, 7,223,585, 7,125,706, 8,236,495, 8,110,351, 7,419,956, 7,300,797, 6,699,706 and 6,143,567, the contents of each of which are herein incorporated by reference in their entirety. In some cases, lysis agents may be selected from lysis salts, amphoteric agents, cationic agents, ionic detergents and non-ionic detergents. Lysis salts may include, but are not limited to sodium chloride (NaCl) and potassium chloride (KCl). Further lysis salts may include any of those described in U.S. Pat. Nos. 8,614,101, 7,326,555, 7,579,181, 7,048,920, 6,410,300, 6,436,394, 7,732,129, 7,510,875, 7,445,930, 6,726,907, 6,194,191, 7,125,706, 6,995,006, 6,676,935 and 7,968,333, the contents of each of which are herein incorporated by reference in their entirety. Concentrations of salts may be increased or decreased to obtain an effective concentration for rupture of cell membranes. Amphoteric agents, as referred to herein, are compounds capable of reacting as an acid or a base. Amphoteric agents may include, but are not limited to lysophosphatidylcholine, 3-((3-Cholamidopropyl)dimethylammonium)-1-propane-sulfonate (CHAPS), ZWITTERGENT® and the like. Cationic agents may include, but are not limited to cetyltrimethylammonium bromide (C(16)TAB) and Benzalkonium chloride. Lysis agents comprising detergents may include ionic detergents or non-ionic detergents. Detergents may function to break apart or dissolve cell structures including, but not limited to cell membranes, cell walls, lipids, carbohydrates, lipoproteins and glycoproteins. Exemplary ionic detergents include any of those taught in U.S. Pat. Nos. 7,625,570 and 6,593,123 or US Publication No. US2014/0087361, the contents of each of which are herein incorporated by reference in their entirety. Some ionic detergents may include, but are not limited to sodium dodecyl sulfate (SDS), cholate and deoxycholate. In some cases, ionic detergents may be included in lysis solutions as a solubilizing agent. Non-ionic detergents may include, but are not limited to octylglucoside, digitonin, lubrol, C12E8, TWEEN®-20, TWEEN®-80, Triton X-100 and Noniodet P-40. Non-ionic detergents are typically weaker lysis agents, but may be included as solubilizing agents for solubilizing cellular and/or viral proteins. Further lysis agents may include enzymes and urea. In some cases, one or more lysis agents may be combined in a lysis solution in order to enhance one or more of cell lysis and protein solubility. In some cases, enzyme inhibitors may be included in lysis solutions in order to prevent proteolysis that may be triggered by cell membrane disruption.

In some embodiments, mechanical cell lysis is carried out. Mechanical cell lysis methods may include the use of one or more lysis conditions and/or one or more lysis forces. As used herein, the term "lysis condition" refers to a state or circumstance that promotes cellular disruption. Lysis conditions may comprise certain temperatures, pressures, osmotic purity, salinity and the like. In some cases, lysis conditions comprise increased or decreased temperatures. According to some embodiments, lysis conditions comprise changes in temperature to promote cellular disruption. Cell lysis carried out according to such embodiments may include freeze-thaw lysis. As used herein, the term "freeze-thaw lysis" refers to cellular lysis in which a cell solution is subjected to one or more freeze-thaw cycles. According to freeze-thaw lysis methods, cells in solution are frozen to induce a mechanical disruption of cellular membranes caused by the formation and expansion of ice crystals. Cell solutions used according to freeze-thaw lysis methods, may further comprise one or more lysis agents, solubilizing agents, buffering agents, cryoprotectants, surfactants, preservatives, enzymes, enzyme inhibitors and/or chelators. Once cell solutions subjected to freezing are thawed, such components may enhance the recovery of desired cellular products. In some cases, one or more cyroprotectants are included in cell solutions undergoing freeze-thaw lysis. As used herein, the term "cryoprotectant" refers to an agent used to protect one or more substances from damage due to freezing. Cryoprotectants of the invention may include any of those taught in US Publication No. US2013/0323302 or U.S. Pat. Nos. 6,503,888, 6,180,613, 7,888,096, 7,091,030, the contents of each of which are herein incorporated by reference in their entirety. In some cases, cryoprotectants may include, but are not limited to dimethyl sulfoxide, 1,2-propanediol, 2,3-butanediol, formamide, glycerol, ethylene glycol, 1,3-propanediol and n-dimethyl formamide, polyvinylpyrrolidone, hydroxy ethyl starch, agarose, dextrans, inositol, glucose, hydroxyethylstarch, lactose, sorbitol, methyl glucose, sucrose and urea. In some embodiments, freeze-thaw lysis may be carried out according to any of the methods described in U.S. Pat. No. 7,704,721, the contents of which are herein incorporated by reference in their entirety.

As used herein, the term "lysis force" refers to a physical activity used to disrupt a cell. Lysis forces may include, but are not limited to mechanical forces, some forces, gravitational forces, optical forces, electrical forces and the like. Cell lysis carried out by mechanical force is referred to herein as "mechanical lysis." Mechanical forces that may be used according to mechanical lysis may include high shear fluid forces. According to such methods of mechanical lysis, a microfluidizer may be used. Microfluidizers typically comprise an inlet reservoirs where cell solutions may be applied. Cell solutions may then be pumped into an interaction chamber via a pump (e.g. high-pressure pump) at high speed and/or pressure to produce shear fluid forces. Resulting lysates may then be collected in one or more output reservoir. Pump speed and/or pressure may be adjusted to modulate cell lysis and enhance recovery of products (e.g. viral particles). Other mechanical lysis methods may include physical disruption of cells by scraping.

Cell lysis methods may be selected based on the cell culture format of cells to be lysed. For example, with adherent cell cultures, some chemical and mechanical lysis methods may be used. Such mechanical lysis methods may include freeze-thaw lysis or scraping. In another example, chemical lysis of adherent cell cultures may be carried out through incubation with lysis solutions comprising surfactant, such as Triton-X-100. In some cases, cell lysates generated from adherent cell cultures may be treated with one more nucleases to lower the viscosity of the lysates caused by liberated DNA.

In one embodiment, a method for harvesting AAV without lysis may be used for efficient and scalable AAV production. In a non-limiting example, viral particles may be produced by culturing an AAV lacking a heparin binding site, thereby allowing the AAV to pass into the supernatant, in a cell culture, collecting supernatant from the culture; and isolating the AAV from the supernatant, as described in US Patent Application 20090275107, the contents of which are incorporated herein by reference in their entirety.

Clarification

Cell lysates comprising viral particles may be subjected to clarification. Clarification refers to initial steps taken in purification of viral particles from cell lysates. Clarification serves to prepare lysates for further purification by removing larger, insoluble debris. Clarification steps may include, but are not limited to centrifugation and filtration. During clarification, centrifugation may be carried out at low speeds to remove larger debris, only. Similarly, filtration may be carried out using filters with larger pore sizes so that only larger debris is removed. In some cases, tangential flow filtration may be used during clarification. Objectives of viral clarification include high throughput processing of cell lysates and to optimize ultimate viral recovery. Advantages of including a clarification step include scalability for processing of larger volumes of lysate. In some embodiments, clarification may be carried out according to any of the methods presented in U.S. Pat. Nos. 8,524,446, 5,756,283, 6,258,595, 6,261,551, 6,270,996, 6,281,010, 6,365,394, 6,475,769, 6,482,634, 6,485,966, 6,943,019, 6,953,690, 7,022,519; 7,238,526, 7,291,498; 7,491,508, US Publication Nos. US2013/0045186, US2011/0263027, US2011/ 0151434, US2003/0138772, and International Publication Nos. WO2002012455, WO1996039530, WO1998010088, WO1999014354, WO1999015685, WO1999047691, WO2000055342, WO2000075353 and WO2001023597; the contents of each of which are herein incorporated by reference in their entirety.

Methods of cell lysate clarification by filtration are well understood in the art and may be carried out according to a variety of available methods including, but not limited to passive filtration and flow filtration. Filters used may comprise a variety of materials and pore sizes. For example, cell lysate filters may comprise pore sizes of from about 1 µM to about 5 µM, from about 0.5 µM to about 2 µM, from about 0.1 µM to about 1 µM, from about 0.05 µM to about 0.5 µM and from about 0.001 µM to about 0.1 µM. Exemplary pore sizes for cell lysate filters may include, but are not limited to, 2.0, 1.9, 1.8, 1.7, 1.6, 1.5, 1.4, 1.3, 1.2, 1.1, 1, 0.9, 0.8, 0.7, 0.6, 0.5, 0.4, 0.3, 0.2, 0.1, 0.95, 0.9, 0.85, 0.8, 0.75, 0.7, 0.65, 0.6, 0.55, 0.5, 0.45, 0.4, 0.35, 0.3, 0.25, 0.2, 0.15, 0.1, 0.05, 0.22, 0.21, 0.20, 0.19, 0.18, 0.17, 0.16, 0.15, 0.14, 0.13, 0.12, 0.11, 0.1, 0.09, 0.08, 0.07, 0.06, 0.05, 0.04, 0.03, 0.02, 0.01, 0.02, 0.019, 0.018, 0.017, 0.016, 0.015, 0.014, 0.013, 0.012, 0.011, 0.01, 0.009, 0.008, 0.007, 0.006, 0.005, 0.004, 0.003, 0.002, 0.001 and 0.001 µM. In one embodiment, clarification may comprise filtration through a filter with 2.0 µM pore size to remove large debris, followed by passage through a filter with 0.45 µM pore size to remove intact cells.

Filter materials may be composed of a variety of materials. Such materials may include, but are not limited to polymeric materials and metal materials (e.g. sintered metal and pored aluminum). Exemplary materials may include, but are not limited to nylon, cellulose materials (e.g. cellulose acetate), polyvinylidene fluoride (PVDF), polyethersulfone, polyamide, polysulfone, polypropylene and polyethylene terephthalate. In some cases, filters useful for clarification of cell lysates may include, but are not limited to ULTIPLEAT PROFILE™ filters (Pall Corporation, Port Washington N.Y.), SUPOR™ membrane filters (Pall Corporation Port Washington, N.Y.)

In some cases, flow filtration may be carried out to increase filtration speed and/or effectiveness. In some cases, flow filtration may comprise vacuum filtration. According to such methods, a vacuum is created on the side of the filter opposite that of cell lysate to be filtered. In some cases, cell lysates may be passed through filters by centrifugal forces. In some cases, a pump is used to force cell lysate through clarification filters. Flow rate of cell lysate through one or more filters may be modulated by adjusting one of channel size and/or fluid pressure.

According to some embodiments, cell lysates may be clarified by centrifugation. Centrifugation may be used to pellet insoluble particles in the lysate. During clarification, centrifugation strength [expressed in terms of gravitational units (g), which represents multiples of standard gravitational force] may be lower than in subsequent purification steps. In some cases, centrifugation may be carried out on cell lysates at from about 200 g to about 800 g, from about 500 g to about 1500 g, from about 1000 g to about 5000 g, from about 1200 g to about 10000 g or from about 8000 g to about 15000 g. In some embodiments, cell lysate centrifugation is carried out at 8000 g for 15 minutes. In some cases, density gradient centrifugation may be carried out in order to partition particulates in the cell lysate by sedimentation rate. Gradients used according to methods of the present invention may include, but are not limited to cesium chloride gradients and iodixanol step gradients.

Purification Chromatography

In some cases, viral particles may be purified from clarified cell lysates by one or more methods of chromatography. Chromatography refers to any number of methods known in the art for separating out one or more elements from a mixture. Such methods may include, but are not limited to ion exchange chromatography (e.g. cation exchange chromatography and anion exchange chromatography,) immunoaffinity chromatography and size-exclusion chromatography. In some embodiments, methods of viral chromatography may include any of those taught in U.S. Pat. Nos. 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498 and 7,491,508 or international Publication Nos. WO1996039530, WO199801.0088, WO1999014354, WO1999015685, WO1999047691, WO2000055342, WO2000075353 and WO2001023597, the contents of each of which are herein incorporated by reference by reference in their entirety.

In some embodiments, ion exchange chromatography may be used to isolate viral particles. Ion exchange chromatography is used to bind viral particles based on charge-charge interactions between capsid proteins and charged sites present on a stationary phase, typically a column through which viral preparations (e.g, clarified lysates) are passed. After application of viral preparations, bound viral particles may then be eluted by applying an elution solution to disrupt the charge-charge interactions. Elution solutions may be optimized by adjusting salt concentration and/or to enhance recovery of bound viral particles. Depending on the charge of viral capsids being isolated, cation or anion exchange chromatography methods may be selected. Methods of ion exchange chromatography may include, but are not limited to any of those taught in U.S. Pat. Nos. 7,419,817, 6,143,548, 7,094,604, 6,593,123, 7,015,026 and 8,137,948, the contents of each of which are herein incorporated by reference in their entirety.

In some embodiments, immunoaffinity chromatography may be used. Immunoaffinity chromatography is a form of chromatography that utilizes one or more immune compounds (e.g. antibodies or antibody-related structures) to retain viral particles. Immune compounds may bind specifically to one or more structures on viral particle surfaces, including, but not limited to one or more viral coat proteins. In some cases, immune compounds may be specific for a particular viral variant. In some cases, immune compounds may bind to multiple viral variants. In some embodiments, immune compounds may include recombinant single-chain antibodies. Such recombinant single chain antibodies may include those described in Smith, R. H. et al., 2009. Mol Ther. 17(11):1888-96, the contents of which are herein incorporated by reference in their entirety. Such immune compounds are capable of binding to several AAV capsid variants, including, but not limited to AAV1, AAV2, AAV6 and AAV8.

In some embodiments, size-exclusion chromatography (SEC) may be used. SEC may comprise the use of a gel to separate particles according to size. In viral particle purification, SEC filtration is sometimes referred to as "polishing." In some cases, SEC may be carried out to generate a final product that is near-homogenous. Such final products may in some cases be used in pre-clinical studies and/or clinical studies (Kotin, R. M. 2011. Human Molecular Genetics. 20(1):R2-R6, the contents of which are herein incorporated by reference in their entirety). In some cases, SEC may be carried out according to any of the methods taught in U.S. Pat. Nos. 6,143,548, 7,015,026, 8,476,418, 6,410,300, 8,476,418, 7,419,817, 7,094,604, 6,593,123, and 8,137,948, the contents of each of which are herein incorporated by reference in their entirety.

In one embodiment, the compositions comprising at least one viral particle may be isolated or purified using the methods described in U.S. Pat. No. 6,146,874, the contents of which are herein incorporated by reference in their entirety.

In one embodiment, the compositions comprising at least one viral particle may be isolated or purified using the methods described in U.S. Pat. No. 6,660,514, the contents of which are herein incorporated by reference in their entirety.

In one embodiment, the compositions comprising at least one viral particle may be isolated or purified using the methods described in U.S. Pat. No. 8,283,151, the contents of which are herein incorporated by reference in their entirety.

In one embodiment, the compositions comprising at least one viral particle may be isolated or purified using the methods described in U.S. Pat. No. 8,524,446, the contents of which are herein incorporated by reference in their entirety.

VII. TREATMENT AND PHARMACEUTICAL COMPOSITIONS

The present disclosure additionally provides a method for treating a disease, disorder and/or condition in a mammalian subject, including a human subject, comprising administering to the subject any of the above-described AAV polynucleotides or AAV genomes or AAV comprising a chimeric Rep binding sequence region or administering to the subject a vector comprising the AAV polynucleotide or AAV genome, or administering to the subject any of the described compositions, including pharmaceutical compositions. In one embodiment, the disease, disorder and/or condition is a neurological disease, disorder and/or condition. In one embodiment, the neurological disease, disorder and/or condition is Parkinson's disease. In another embodiment, the neurological disease, disorder and/or condition is Friedreich's Ataxia. In another embodiment, the neurological disease, disorder and/or condition is Amyotrophic lateral sclerosis (ALS). In another embodiment, the disease, disorder and/or condition is a muscular or cardiac disease, disorder and/or condition. In another embodiment, the disease, disorder and/or condition is an immune system disease, disorder and/or condition.

The present disclosure provides a composition comprising an AAV polynucleotide or AAV genome or AAV particle comprising an engineered Rep binding sequence region and at least one excipient.

The present disclosure also provides a pharmaceutical composition comprising an adeno-associated virus (AAV) comprising any of the above-described AAV polynucleotides or AAV genomes and one or more pharmaceutically acceptable excipients.

Although the descriptions of pharmaceutical compositions, e.g., those viral vectors comprising a payload to be delivered, provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

In some embodiments, compositions are administered to humans, human patients or subjects. For the purposes of the present disclosure, the phrase "active ingredient" generally refers either to the viral particle carrying the payload or to the payload molecule delivered by the viral particle as described herein.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered.

Formulation

The viral particles of the invention can be formulated using one or more excipients to: (1) increase stability; (2) increase cell transfection or transduction; (3) permit the sustained or delayed release; (4) alter the biodistribution (e.g., target the viral particle to specific tissues or cell types); (5) increase the translation of encoded protein in vivo; and/or (6) alter the release profile of encoded protein in vivo.

Formulations of the present invention can include, without limitation, saline, lipidoids, liposomes, lipid nanoparticles, polymers, lipoplexes, core-shell nanoparticles, peptides, proteins, cells transfected with viral vectors (e.g., for transplantation into a subject), nanoparticle mimics and combinations thereof. Further, the viral vectors of the present invention may be formulated using self-assembled nucleic acid nanoparticles.

Formulations of the pharmaceutical compositions described herein may be prepared by any method known or hereafter developed in the art of pharmacology. In general, such preparatory methods include the step of associating the active ingredient with an excipient and/or one or more other accessory ingredients.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient (e.g, scAAV), the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

In some embodiments, the formulations described herein may contain at least one payload molecule. As a non-limiting example, the formulations may contain 1, 2, 3, 4 or 5 payload molecules. In one embodiment the formulation may contain a payload construct encoding proteins selected from categories such as, but not limited to, human proteins, veterinary proteins, bacterial proteins, biological proteins, antibodies, immunogenic proteins, therapeutic peptides and proteins, secreted proteins, plasma membrane proteins, cytoplasmic and cytoskeletal proteins, intracellular membrane bound proteins, nuclear proteins, proteins associated with human disease and/or proteins associated with non-human diseases. In one embodiment, the formulation contains at least three payload construct encoding proteins.

The formulations of the invention can include one or more excipients, each in an amount that together increases the stability of the viral particle, increases cell transfection or transduction by the viral particle, increases the expression of viral particle encoded protein, and/or alters the release profile of viral particle encoded proteins. In some embodiments, a pharmaceutically acceptable excipient may be at least 95%, at least 96%, at least 97%, at least 98%, at least 99%, or 100% pure. In some embodiments, an excipient is approved for use for humans and for veterinary use. In some embodiments, an excipient may be approved by United States Food and Drug Administration. In some embodiments, an excipient may be of pharmaceutical grade. In some embodiments, an excipient may meet the standards of the United States Pharmacopoeia (USP), the European Pharmacopoeia (EP), the British Pharmacopoeia, and/or the International Pharmacopoeia.

Excipients, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21$^{st}$ Edition, A. R., Gennaro, Lippincott, Williams & Wilkins, Baltimore, Md., 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Diluents may include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Additives include physiologically biocompatible buffers (e.g., trimethylamine hydrochloride), addition of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). In addition, antioxidants and suspending agents can be used.

Cryoprotectants

In some embodiments, viral particle formulations may comprise cyroprotectants. As used herein, the term "cryoprotectant" refers to one or more agents that when combined with a given substance, helps to reduce or eliminate damage to that substance that occurs upon freezing. In some embodiments, cryoprotectants are combined with viral particles in order to stabilize them during freezing. Frozen storage between −20° C. and −80° C. may be advantageous for long term (e.g. 36 months) stability of viral particles. In some embodiments, cryoprotectants are included in viral particle formulations to stabilize them through freeze/thaw cycles and under frozen storage conditions. Cryoprotectants of the present invention may include, but are not limited to sucrose, trehalose, lactose, glycerol, dextrose, raffinose and/or mannitol. Trehalose is listed by the Food and Drug Administration as being generally regarded as safe (GRAS) and is commonly used in commercial pharmaceutical formulations.

Bulking Agents

In some embodiments, viral particle formulations may comprise bulking agents. As used herein, the term "bulking agent" refers to one or more agents included in formulations to impart a desired consistency to the formulation and/or stabilization of formulation components. In some embodiments, bulking agents are included in lyophilized viral particle formulations to yield a "pharmaceutically elegant" cake, stabilizing the lyophilized viral particles during long term (e.g. 36 month) storage. Bulking agents of the present invention may include, but are not limited to sucrose, trehalose, mannitol, glycine, lactose and/or raffinose. In some embodiments, combinations of cryoprotectants and bulking agents (for example, sucrose/glycine or trehalose/mannitol) may be included to both stabilize viral particles during freezing and provide a bulking agent for lyophilization.

Inactive Ingredients

In some embodiments, formulations may comprise at least one excipient which is an inactive ingredient. As used herein, the term "inactive ingredient" refers to one or more inactive agents included in formulations. In some embodiments, all, none or some of the inactive ingredients which may be used in the formulations of the present invention may be approved by the US Food and Drug Administration (FDA).

Formulations of viral particles disclosed herein may include cations or anions. In one embodiment, the formulations include metal cations such as, but not limited to, Zn2+, Ca2+, Cu2+, Mg+ and combinations thereof.

Administration

The viral particles of the present invention may be administered by any route which results in a therapeutically effective outcome. These include, but are not limited to enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intraconal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration which is then covered by a dressing which occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal. In specific embodiments, compositions may be administered in a way which allows them cross the blood-brain barrier, vascular barrier, or other epithelial barrier. In one embodiment, a formulation for a route of administration may include at least one inactive ingredient.

Dosing

The present invention provides methods comprising administering viral particles and their payload or complexes in accordance with the invention to a subject in need thereof. Viral particle pharmaceutical, imaging, diagnostic, or prophylactic compositions thereof, may be administered to a subject using any amount and any route of administration effective for preventing, treating, diagnosing, or imaging a disease, disorder, and/or condition (e.g., a disease, disorder, and/or condition relating to working memory deficits). The exact amount required will vary from subject to subject, depending on the species, age, and general condition of the subject, the severity of the disease, the particular composition, its mode of administration, its mode of activity, and the like. Compositions in accordance with the invention are typically formulated in unit dosage form for ease of administration and uniformity of dosage. It will be understood, however, that the total daily usage of the compositions of the present invention may be decided by the attending physician within the scope of sound medical judgment. The specific therapeutically effective, prophylactically effective, or appropriate imaging dose level for any particular patient will depend upon a variety of factors including the disorder being treated and the severity of the disorder: the activity of the specific compound employed; the specific composition employed; the age, body weight, general health, sex and diet of the patient; the time of administration, route of administration, and rate of excretion of the specific payload employed; the duration of the treatment; drugs used in combination or coincidental with the specific compound employed; and like factors well known in the medical arts.

In certain embodiments, viral particle pharmaceutical compositions in accordance with the present invention may be administered at dosage levels sufficient to deliver from about 00001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg, from about 0.01 rag/kg to about 50 mg/kg, from about 0.1 mg/kg to about 40 mg/kg, from about 0.5 ma/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect.

The desired dosage may be delivered three tithes a day, two tithes a day, once a day, every other day, every third day, every week, every two weeks, every three weeks, or every four weeks. In certain embodiments, the desired dosage may be delivered using multiple administrations (e.g, two, three, four, five, six, seven, eight, nine, ten, eleven, twelve, thirteen, fourteen, or more administrations). When multiple administrations are employed, split dosing regimens such as those described herein may be used. As used herein, a "split dose" is the division of single unit dose or total daily dose into two or more doses, e.g., two or more administrations of the single unit dose. As used herein, a "single unit dose" is a dose of any therapeutic administered in one dose/at one time/single route/single point of contact, i.e., single administration event. As used herein, a "total daily dose" is an amount given or prescribed in 24 hour period. It may be administered as a single unit dose. In one embodiment, the viral particles of the present invention are administered to a subject in split doses. The viral particles may be formulated in buffer only or in a formulation described herein.

A pharmaceutical composition described herein can be formulated into a dosage form described herein, such as a topical, intranasal, pulmonary, intratracheal, or injectable (e.g., intravenous, intraocular, intravitreal, intramuscular, intracardiac, intraperitoneal, and subcutaneous).

Combinations

The viral particles may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, diagnostic, or imaging compositions in combination with agents that may improve their bioavailability, reduce and/or modify their metabolism, inhibit their excretion, and/or modify their distribution within the body.

Delivery

Delivery to Cells

The present disclosure provides a method of delivering to a cell or tissue any of the above-described engineered Rep proteins or AAV polynucleotides, AAV genomes, or AAV comprising an engineered Rep protein comprising contacting the cell or tissue with the Rep protein or AAV polynucleotide or AAV genome or AAV, or contacting the cell or tissue with a particle comprising the AAV polynucleotide or AAV genome, or contacting the cell or tissue with any of the described compositions, including pharmaceutical compositions. The method of delivering the AAV polynucleotide or AAV genome or AAV to a cell or tissue can be accomplished in vitro, ex vivo, or in vivo.

Delivery to Subjects

The present disclosure additionally provides a method of delivering to a subject, including a mammalian subject, any of the above-described AAV polynucleotides or AAV genomes or AAV comprising an engineered Rep binding sequence region comprising administering to the subject the AAV polynucleotide or AAV genome or AAV, or administering to the subject a particle comprising the AAV polynucleotide or AAV genome, or administering to the subject any of the described compositions, including pharmaceutical compositions.

The pharmaceutical compositions of viral particles described herein may be characterized by one or more of bioavailability, therapeutic window and/or volume of distribution.

Bioavailability

Viral particles of the present invention, when formulated into compositions with delivery/formulation agents or vehicles as described herein, may exhibit increased bioavailability as compared to compositions lacking delivery agents as described herein. As used herein, the term "bioavailability" refers to the systemic availability of a given amount of a particular agent administered to a subject. Bioavailability may be assessed by measuring the area under the curve (AUC) or the maximum serum or plasma concentration ($C_{max}$) of the unchanged form of a compound following administration of the compound to a mammal. AUC is a determination of the area under the curve plotting the serum or plasma concentration of a compound along the ordinate (Y-axis) against time along the abscissa (X-axis). Generally, the AUC for a particular compound (e.g., scAAV) may be calculated using methods known to those of ordinary skill in the art and as described in G. S. Banker, Modern Pharmaceutics, Drugs and the Pharmaceutical Sciences, v. 72, Marcel Dekker, New York, Inc., 1996, the contents of which are herein incorporated by reference in their entirety.

$C_{max}$ values are maximum concentrations of compounds achieved in serum or plasma of a subject following administration of compounds to the subject. $C_{max}$ values of particular compounds may be measured using methods known to those of ordinary skill in the art. As used herein, the phrases "increasing bioavailability" or "improving the pharmacokinetics," refer to actions that may increase the systemic availability of a viral particle of the present invention (as measured by AUC, $C_{max}$, or $C_{min}$) in a subject. In some embodiments, such actions may comprise co-administration with one or more delivery agents as described herein. In some embodiments, the bioavailability of viral particles (e.g., scAAV) may increase by at least about 2%, at least about 5%, at least about 10%, at least about 15%, at least about 20%, at least about 25%, at least about 30%, at least about 35%, at least about 40%, at least about 45?, at least about 50%, at least about 55%, at least about 60%, at least about 65%, at least about 70%, at least about 75%, at least about 80%, at least about 85f/h, at least about 90%, at least about 95% or about 100%.

Therapeutic Window

Viral particles of the present invention, when formulated with one or more delivery agents as described herein, may exhibit increases in the therapeutic window of compound and/or composition administration as compared to the therapeutic window of viral particles administered without one or more delivery agents as described herein. As used herein, the term "therapeutic window" refers to the range of plasma concentrations, or the range of levels of therapeutically active substance at the site of action, with a high probability of eliciting a therapeutic effect. In some embodiments, therapeutic windows of viral particles when administered in a formulation may increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% or about 100%.

Volume of Distribution

Viral particles e.g., scAAV) of the present invention, when formulated with one or more delivery agents as described herein, may exhibit an improved volume of distribution ($V_{dist}$), e.g., reduced or targeted, relative to formulations lacking one or more delivery agents as described herein. $V_{dist}$ relates the amount of an agent in the body to the concentration of the same agent in the blood or plasma. As used herein, the term "volume of distribution" refers to the fluid volume that would be required to contain the total amount of an agent in the body at the same concentration as in the blood or plasma: $V_{dist}$ equals the amount of an agent in the body/concentration of the agent in blood or plasma. For example, for a 10 mg dose of a given agent and a plasma concentration of 10 mg/L, the volume of distribution would be 1 liter. The volume of distribution reflects the extent to which an agent is present in the extravascular tissue. Large volumes of distribution reflect the tendency of agents to bind to the tissue components as compared with plasma proteins. In clinical settings, $V_{dist}$ may be used to determine loading doses to achieve steady state concentrations. In some embodiments, volumes of distribution of viral particle compositions of the present invention when co-administered with one or more delivery agents as described herein may decrease at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%.

Kits and Devices

The invention provides a variety of kits for conveniently and/or effectively carrying out methods of the present invention. Typically kits will comprise sufficient amounts and/or numbers of components to allow a user to perform multiple treatments of a subject(s) and/or to perform multiple experiments.

In one aspect, the present invention provides kits comprising the molecules (viral particles) of the invention. In one embodiment, the kit comprises one or more functional antibodies or function fragments thereof.

Said kits can be for viral particle production. The kit may further comprise packaging and instructions and/or a delivery agent to form a formulation composition. The delivery agent may comprise a saline, a buffered solution, or any delivery agent disclosed herein.

In one embodiment, the buffer solution may include sodium chloride, calcium chloride, phosphate and/or EDTA. In another embodiment, the buffer solution may include, but is not limited to, saline, saline with 2 mM calcium, 50 sucrose, 5% sucrose with 2 mM calcium, 5% Mannitol, 5% Mannitol with 2 mM calcium, Ringer's lactate, sodium chloride, sodium chloride with 2 mM calcium and mannose (See e.g., U.S. Pub. No, 20120258046; herein incorporated by reference in its entirety). In a further embodiment, the buffer solutions may be precipitated or may be lyophilized. The amount of each component may be varied to enable consistent, reproducible higher concentration saline or simple buffer formulations. The components may also be varied in order to increase the stability of the viral particle or any expression construct taught herein in the buffer solution over a period of time and/or under a variety of conditions.

In one aspect, the present invention provides kits for viral particle production, comprising: an expression particle and a payload construct particle provided in an amount effective to produce a desired amount of a viral particle when introduced into a target cell and packaging and instructions.

Any of the particles, constructs, polynucleotides or polypeptides of the present invention may be comprised in a kit. In some embodiments, kits may further include reagents and/or instructions for creating and/or synthesizing compounds and/or compositions of the present invention. In some embodiments, kits may also include one or more buffers. In some embodiments, kits of the invention may include components for making protein or nucleic acid arrays or libraries and thus, may include, for example, solid supports.

In some embodiments, kit components may be packaged either in aqueous media or in lyophilized form. The container means of the kits will generally include at least one vial, test tube, flask, bottle, syringe or other container means, into which a component may be placed, and preferably, suitably aliquoted. Where there are more than one kit component, (labeling reagent and label may be packaged together), kits may also generally contain second, third or other additional containers into which additional components may be separately placed. In some embodiments, kits may also comprise second container means for containing sterile, pharmaceutically acceptable buffers and/or other diluents. In some embodiments, various combinations of components may be comprised in one or more vial. Kits of the present invention may also typically include means for containing compounds and/or compositions of the present invention, e.g., proteins, nucleic acids, and any other reagent containers in close confinement for commercial sale. Such containers may include injection or blow-molded plastic containers into which desired vials are retained.

In some embodiments, kit components are provided in one and/or more liquid solutions. In some embodiments, liquid solutions are aqueous solutions, with sterile aqueous solutions being particularly preferred. In some embodiments, kit components may be provided as dried powder(s). When reagents and/or components are provided as dry powders, such powders may be reconstituted by the addition of suitable volumes of solvent. In some embodiments, it is envisioned that solvents may also be provided in another container means. In some embodiments, labeling dyes are provided as dried powders. In some embodiments, it is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 micrograms or at least or at most those amounts of dried dye are provided in kits of the invention. In such embodiments, dye may then be resuspended in any suitable solvent, such as DMSO.

In some embodiments, kits may include instructions for employing kit components as well the use of any other reagent not included in the kit. Instructions may include variations that may be implemented.

Devices

In some embodiments, compounds and/or compositions of the present invention may be combined with, coated onto or embedded in a device. Devices may include, but are not limited to, dental implants, stents, bone replacements, artificial joints, valves, pacemakers and/or other implantable therapeutic devices.

The present invention provides for devices which may incorporate viral particles that encode one or more payload molecules. These devices contain in a stable formulation the viral particles which may be immediately delivered to a subject in need thereof, such as a human patient.

Devices for administration may be employed to deliver the viral particles of the present invention according to single, multi- or split-dosing regimens taught herein.

Method and devices known in the art for multi-administration to cells, organs and tissues are contemplated for use in conjunction with the methods and compositions disclosed herein as embodiments of the present invention. These include, for example, those methods and devices having multiple needles, hybrid devices employing for example lumens or catheters as well as devices utilizing heat, electric current or radiation driven mechanisms.

In one embodiment, the chimeric polynucleotide is administered subcutaneously or intramuscularly via at least 3 needles to three different, optionally adjacent, sites simultaneously, or within a 60 minutes period (e.g., administration to 4, 5, 6, 7, 8, 9, or 10 sites simultaneously or within a 60 minute period).

VIII. DEFINITIONS

At various places in the present specification, substituents of compounds of the present disclosure are disclosed in groups or in ranges. It is specifically intended that the present disclosure include each and every individual subcombination of the members of such groups and ranges. The following is a non-limiting list of term definitions.

Activity: As used herein, the term "activity" refers to the condition in which things are happening or being done. Compositions of the invention may have activity and this activity may involve one or more biological events.

Administered in combination: As used herein, the term "administered in combination" or "combined administration" refers to simultaneous exposure to two or more agents (e.g., scAAV) administered at the same time or within an interval such that the subject is at some point in time simultaneously exposed to both and/or such that there may be an overlap in the effect of each agent on the patient. In some embodiments, at least one dose of one or more agents is administered within about 24 hours, 12 hours, 6 hours, 3 hours, 1 hour, 30 minutes, 15 minutes, 10 minutes, 5 minutes, or 1 minute of at least one dose of one or more other agents. In some embodiments, administration occurs in overlapping dosage regimens. As used herein, the term "dosage regimen" refers to a plurality of doses spaced apart in time. Such doses may occur at regular intervals or may include one or more hiatus in administration. In some embodiments, the administration of individual doses of one or more compounds and/or compositions of the present invention, as described herein, are spaced sufficiently closely together such that a combinatorial (e.g., a synergistic) effect is achieved.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, mean that the moieties are physically associated or connected with one another, either directly or via one or more additional moieties that serve as linking agents, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Biomolecule: As used herein, the term "biomolecule" is any natural molecule which is amino acid-based, nucleic acid-based, carbohydrate-based or lipid-based, and the like.

Biologically active: As used herein, the phrase "biologically active" refers to a characteristic of any substance (e.g., an scAAV) that has activity in or on a biological system and/or organism. For instance, a substance that, when administered to an organism, has a biological effect on that organism, is considered to be biologically active. In particular embodiments, a compounds and/or compositions of the present invention may be considered biologically active if even a portion of is biologically active or mimics an activity considered to biologically relevant.

Biological system: As used herein, the term "biological system" refers to a group of organs, tissues, cells, intracellular components, proteins, nucleic acids, molecules (including, but not limited to biomolecules) that function together to perform a certain biological task within cellular membranes, cellular compartments, cells, tissues, organs, organ systems, multicellular organisms, or any biological entity. In some embodiments, biological systems are cell signaling pathways comprising intracellular and/or extracellular cell signaling biomolecules. In some embodiments, biological systems comprise growth factor signaling events within the extracellular/cellular matrix and/or cellular niches.

Compound: As used herein, the term "compound," refers to a distinct chemical entity. In some embodiments, a particular compound may exist in one or more isomeric or isotopic forms (including, but not limited to stereoisomers, geometric isomers and isotopes). In some embodiments, a compound is provided or utilized in only a single such form. In some embodiments, a compound is provided or utilized as a mixture of two or more such forms (including, but not limited to a racemic mixture of stereoisomers). Those of skill in the art appreciate that some compounds exist in different such forms, show different properties and/or activities (including, but not limited to biological activities). In such cases it is within the ordinary skill of those in the art to select or avoid particular forms of the compound for use in accordance with the present invention. For example, compounds that contain asymmetrically substituted carbon atoms can be isolated in optically active or racemic forms. Methods on how to prepare optically active forms from optically active starting materials are known in the art, such as by resolution of racemic Mixtures or by stereoselective synthesis.

Conserved: As used herein, the term "conserved" refers to nucleotides or amino acid residues of polynucleotide or polypeptide sequences, respectively, that are those that occur unaltered in the same position of two or more sequences being compared. Nucleotides or amino acids that are relatively conserved are those that are conserved among more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of an oligonucleotide or polypeptide or may apply to a portion, region or feature thereof.

In one embodiment, conserved sequences are not contiguous. Those skilled in the art are able to appreciate how to achieve alignment when gaps in contiguous alignment are present between sequences, and to align corresponding residues not withstanding insertions or deletions present.

Delivery: As used herein, "delivery" refers to the act or manner of delivering a compound, substance, entity, moiety, cargo or payload to a target. Such target may be a cell, tissue, organ, organism, or system (whether biological or production).

Delivery Agent: As used herein, "delivery agent" refers to any agent which facilitates, at least in part, the in vivo delivery of one or more substances (including, but not limited to a compounds and/or compositions of the present invention, e.g., viral particles or expression vectors) to targeted cells.

Destabilized: As used herein, the term "destable," "destabilize," or "destabilizing region" means a region or molecule that is less stable than a starting, reference, wild-type or native form of the same region or molecule.

Detectable label: As used herein, "detectable label" refers to one or more markers, signals, or moieties which are attached, incorporated or associated with another entity, which markers, signals or moieties are readily detected by methods known in the art including radiography, fluorescence, chemiluminescence, enzymatic activity, absorbance, immunological detection and the like. Detectable labels may include radioisotopes, fluorophores, chromophores, enzymes, dyes, metal ions, ligands, biotin, avidin, streptavidin and haptens, quantum dots, polyhistidine tags, myc tags, flag tags, human influenza hemagglutinin (HA) tags and the like. Detectable labels may be located at any position in the entity with which they are attached, incorporated or associated. For example, when attached, incorporated in or associated with a peptide or protein, they may be within the amino acids, the peptides, or proteins, or located at the N- or C-termini.

Engineered: used herein, embodiments of the invention are "engineered" when they are designed to have a feature or property, whether structural or chemical, that varies from a starting point, wild-type or native molecule. Thus, engineered agents or entities are those whose design and/or production include an act of the hand of man.

Epitope: As used herein, an "epitope" refers to a surface or region on a molecule that is capable of interacting with a biomolecule. For example a protein may contain one or more amino acids, e.g., an epitope, which interacts with an antibody, e.g., a biomolecule. In some embodiments, when referring to a protein or protein module, an epitope may comprise a linear stretch of amino acids or a three dimensional structure formed by folded amino acid chains.

eRBSR: As used herein, an "eRBSR" is an engineered Rep binding sequence region. eRBSRs may range in size from 4-160 nucleotides. When making reference to any of Rep binding sequence, Rep binding sequence region, or eRBSR, it is understood that these sequences and or regions may be substantially double stranded and therefor the recited lengths or sizes may be greater.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; (4) folding of a polypeptide or protein; and (5) post-translational modification of a polypeptide or protein.

Feature: As used herein, a "feature" refers to a characteristic, a property, or a distinctive element.

Formulation: As used herein, a "formulation" includes at least a compound and/or composition of the present invention (e.g., a vector, scAAV particle, etc.) and a delivery agent.

Fragment: A "fragment," as used herein, refers to a contiguous portion of a whole. For example, fragments of proteins may comprise polypeptides obtained by digesting full-length protein isolated from cultured cells. In some embodiments, a fragment of a protein includes at least 3, 4, 5, 6, 7, 8, 9, 10, 11, 12, 13, 14, 15, 16, 17, 18, 19, 20, 2.5, 30, 35, 40, 45, 50, 55, 60, 65, 70, 75, 80, 85, 90, 95, 100, 150, 200, 250 or more amino acids. In some embodiments, fragments of an antibody include portions of an antibody subjected to enzymatic digestion or synthesized as such.

Functional: As used herein, a "functional" biological molecule is a biological entity with a structure and in a form in which it exhibits a property and/or activity by which it is characterized.

Homology: As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99f/6 identical or similar. The term "homologous" necessarily refers to a comparison between at least two sequences (polynucleotide or polypeptide sequences). In accordance with the invention, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is typically determined by the ability to encode a stretch of at least 4-5 uniquely specified amino acids. In accordance with the invention, two protein sequences are considered to be homologous if the proteins are at least about 50%, 60%, 70%, 80%, or 90% identical for at least one stretch of at least about 20 amino acids. In many embodiments, homologous protein may show a large overall degree of homology and a high degree of homology over at least one short stretch of at least 3.4, 5, 6, 7, 8, 9, 10, 11, 12, 13, 14, 15, 16, 17, 18, 19, 20, 25, 30, 35, 40, 45, 50 or more amino acids. In many embodiments, homologous proteins share one or more characteristic sequence elements. As used herein, the term "characteristic sequence element" refers to a motif present in related proteins. In some embodiments, the presence of such motifs correlates with a particular activity (such as biological activity).

Identity: As used herein, the term "identity" refers to the overall relatedness between polymeric molecules, e.g., between oligonucleotide molecules (e.g. DNA molecules and/or RNA molecules) nd/or between polypeptide molecules. Calculation of the percent identity of two polynucleotide sequences, for example, may be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I. Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined, for example using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Computer software to determine homology between two sequences include, but are not limited to, GCG program package, Devereux, J., et al., *Nucleic Acids Research*, 12(1), 387 (1984)), BLASTP, BLASTN, and FASTA Altschul, S. F. et al. *J. Molec. Biol.*, 215, 403 (1990)).

Inhibit expression of a gene: As used herein, the phrase "inhibit expression of a gene" means to cause a reduction in the amount of an expression product of the gene. The expression product may be RNA transcribed from the gene (e.g. mRNA) or a polypeptide translated from snRNA transcribed from the gene. Typically a reduction in the level of mRNA results in a reduction in the level of a polypeptide translated therefrom. The level of expression may be determined using standard techniques for measuring mRNA or protein.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" is synonymous with "separated," but carries with it the inference separation was carried out by the hand of man. In one embodiment, an isolated substance or entity is one that has been separated from at least some of the components with which it was previously associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 950, about 96%, about 97%, about 98%, about 99%, or more than about 99° pure. As used herein, a substance is "pure" if it is substantially free of other components.

Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art. In some embodiments, isolation of a substance or entity includes disruption of chemical associations and/or bonds. In some embodiments, isolation includes only the separation from components with which the isolated substance or entity was previously combined and does not include such disruption.

Linker: As used herein, a linker refers to a moiety that connects two or more domains, moieties or entities. In one embodiment, a linker may comprise 10 or more atoms. In a further embodiment, a linker may comprise a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. In some embodiments, a linker may comprise one or more nucleic acids comprising one or more nucleotides. In some embodiments, the linker may comprise an amino acid, peptide, polypeptide or protein. In some embodiments, a moiety bound by a linker may include, but is not limited to an atom, a chemical group, a nucleoside, a nucleotide, a nucleobase, a sugar, a nucleic acid, an amino acid, a peptide, a polypeptide, a protein, a protein complex, a payload (e.g., a therapeutic agent marker (including, but not limited to a chemical, fluorescent, radioactive or bioluminescent marker). The linker can be used for any useful purpose, such as to form multimers or conjugates, as well as to administer a payload, as described herein. Examples of chemical groups that can be incorporated into the linker include, but are not limited to, alkyl, alkenyl, alkynyl, amino, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers. Other examples include, but are not limited to, cleavable moieties within the linker, such as, for example, a disulfide bond (—S—S—) or an azo bond (—N=N—), which can be cleaved using a reducing agent or photolysis. Non-limiting examples of a selectively cleavable bonds include an amido bond which may be cleaved for example by the use of tris(2-carboxyethyl)phosphine (TCEP), or other reducing agents, and/or photolysis, as well as an ester bond which may be cleaved for example by acidic or basic hydrolysis.

Modified: As used herein, the term "modified" refers to a changed state or structure of a molecule or entity as compared with a parent or reference molecule or entity. Molecules may be modified in many ways including chemically, structurally, and functionally. In some embodiments, compounds and/or compositions of the present invention are modified by the introduction of non-natural amino acids, or non-natural nucleotides.

Mutation: As used herein, the term "mutation" refers to a change and/or alteration. In some embodiments, mutations may be changes and/or alterations to proteins (including peptides and polypeptides) and/or nucleic acids (including polynucleic acids). In some embodiments, mutations comprise changes and/or alterations to a protein and/or nucleic acid sequence. Such changes and/or alterations may comprise the addition, substitution and or deletion of one or more amino acids (in the case of proteins and/or peptides) and/or nucleotides (in the case of nucleic acids and or polynucleic acids). In embodiments wherein mutations comprise the addition and/or substitution of amino acids and/or nucleotides, such additions and/or substitutions may comprise 1 or more amino acid and/or nucleotide residues and may include modified amino acids and/or nucleotides.

Naturally occurring: As used herein, "naturally occurring" means existing in nature without artificial aid, or involvement of the hand of man.

Non-human vertebrate: As used herein, a "non-human vertebrate" includes all vertebrates except Homo sapiens, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Off-target: As used herein, "off target" refers to any unintended effect on any one or more target, gene and/or cellular transcript.

Operably linked: As used herein, the phrase "operably linked" refers to a functional connection between two or more molecules, constructs, transcripts, entities, moieties or the like.

Particle: As used herein, a "particle" is a virus comprised of at least two components, a protein capsid and a polynucleotide sequence enclosed within the capsid.

Patient: As used herein, "patient" refers to a subject who may seek or be in need of treatment, requires treatment, is receiving treatment, will receive treatment, or a subject who is under care by a trained (e.g., licensed) professional for a particular disease or condition.

Payload construct: As used herein, "payload construct" is one or more polynucleotide regions encoding or comprising a payload molecule of interest, e.g., a transgene, a polynucleotide encoding a polypeptide or multi-polypeptide or a modulatory or regulatory nucleic acid, that that is flanked on one or both sides by an inverted terminal repeat (ITR) sequence. A vector which comprises a payload construct is a "payload construct vector."

Payload construct expression vector: As used herein, a "payload construct expression vector" is a vector which comprises a payload construct and which further comprises one or more polynucleotide regions encoding or comprising components for viral expression in a viral replication cell.

Peptide: As used herein, the term "peptide" refers to a chain of amino acids that is less than or equal to about 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: As used herein, the term "pharmaceutically acceptable excipient," as used herein, refers to any ingredient other than active agents (e.g., as described herein) present in pharmaceutical compositions and having the properties of being substantially nontoxic and non-inflammatory in subjects. In some embodiments, pharmaceutically acceptable excipients are vehicles capable of suspending and/or dissolving active agents. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: Pharmaceutically acceptable salts of the compounds described herein are forms of the disclosed compounds wherein the acid or base moiety is in its salt form (e.g., as generated by reacting a free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Pharmaceutically acceptable salts include the conventional non-toxic salts, for example, from non-toxic inorganic or organic acids. In some embodiments a pharmaceutically acceptable salt is prepared from a parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science*, 66, 1-19 (1977), each of which is incorporated herein by reference in its entirety. Pharmaceutically acceptable solvate: The term "pharmaceutically acceptable solvate," as used herein, refers to a crystalline form of a compound wherein molecules of a suitable solvent are incorporated in the crystal lattice. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate." in some embodiments, the solvent incorporated into a solvate is of a type or at a level that is physiologically tolerable to an organism to which the solvate is administered (e.g., in a unit dosage form of a pharmaceutical composition).

Pharmacokinetic: As used herein, "pharmacokinetic" refers to any one or more properties of a molecule or compound as it relates to the determination of the fate of substances administered to living organisms. Pharmacokinetics are divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Proliferate: As used herein, the term "proliferate" means to grow, expand, replicate or increase or cause to grow, expand, replicate or increase. "Proliferative" means having the ability to proliferate. "Anti-proliferative" means having properties counter to or in opposition to proliferative properties.

Protein of interest: As used herein, the terms "proteins of interest" or "desired proteins" include those provided herein and fragments, mutants, variants, and alterations thereof.

Purified: As used herein, the term "purify" means to make substantially pure or clear from unwanted components, material defilement, admixture or imperfection. "Purified" refers to the state of being pure. "Purification" refers to the process of making pure.

Region: As used herein, the term "region" refers to a zone or general area. In some embodiments, when referring to a protein or protein module, a region may comprise a linear sequence of amino acids along the protein or protein module or may comprise a three dimensional area, an epitope and/or a cluster of epitopes. In some embodiments, regions comprise terminal regions. As used herein, the term "terminal region" refers to regions located at the ends or termini of a given agent. When referring to proteins, terminal regions may comprise N- and/or C-termini. N-termini refer to the end of a protein comprising an amino acid with a free amino group. C-termini refer to the end of a protein comprising an amino acid with a free carboxyl group. N- and/or C-terminal regions may there for comprise the N- and/or C-termini as well as surrounding amino acids. In some embodiments, N- and/or C-terminal regions comprise from about 3 amino acid to about 30 amino acids, from about 5 amino acids to about 40 amino acids, from about 10 amino acids to about 50 amino acids, from about 20 amino acids to about 100 amino acids and/or at least 100 amino acids. In some embodiments, N-terminal regions may comprise any length of amino acids that includes the N-terminus, but does not include the C-terminus. In some embodiments, C-terminal regions may comprise any length of amino acids, which include the C-terminus, but do not comprise the N-terminus.

In some embodiments, when referring to a polynucleotide, a region may comprise a linear sequence of nucleic acids along the polynucleotide or may comprise a three dimensional area, secondary structure, or tertiary structure. In some embodiments, regions comprise terminal regions. As used herein, the term "terminal region" refers to regions located, at the ends or termini of a given agent. When referring to polynucleotides, terminal regions may comprise 5' and 3' termini. 5' termini refer to the end of a polynucleotide comprising a nucleic acid with a free phosphate group. 3' termini refer to the end of a polynucleotide comprising a nucleic acid with a free hydroxyl group, 5' and 3' regions may there for comprise the 5' and 3' termini as well as surrounding nucleic acids. In some embodiments, 5' and 3' terminal regions comprise from about 9 nucleic acids to about 90 nucleic acids, from about 15 nucleic acids to about 120 nucleic acids, from about 30 nucleic acids to about 150 nucleic acids, from about 60 nucleic acids to about 300 nucleic acids and/or at least 300 nucleic acids. In some embodiments, 5' regions may comprise any length of nucleic acids that includes the 5' terminus, but does not include the 3' terminus. In some embodiments, 3' regions may comprise any length of nucleic acids, which include the 3' terminus, but does not comprise the 5' terminus, Rep binding sequence: As used herein, a "Rep binding sequence" is a series of linked nucleosides which interact with one or more Rep proteins. Rep binding sequences may range from 4-160 nucleotides.

Rep binding sequence region: As used herein, a "Rep binding sequence region" is a nucleotide sequence which interacts with one or more Rep proteins. A Rep binding sequence region may range from 4-160 nucleotides. In one embodiment, the Rep binding region is a nucleotide sequence located within an inverted terminal repeat (ITR).

Sample: As used herein, the term "sample" refers to an aliquot or portion taken from a source and/or provided for analysis or processing. In some embodiments, a sample is from a biological source such as a tissue, cell or component part (e.g. a body fluid, including but not limited to blood, mucus, lymphatic fluid, synovial fluid, cerebrospinal fluid, saliva, amniotic fluid, amniotic cord blood, urine, vaginal fluid and semen). In some embodiments, a sample may be or comprise a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. In some embodiments, a sample is or comprises a medium, such as a nutrient broth or gel, which may contain cellular components, such as proteins or nucleic acid molecule. In some embodiments, a "primary" sample is an aliquot of the source. In some embodiments, a primary sample is subjected to one or more processing (e.g., separation, purification, etc) steps to prepare a sample for analysis or other use.

Self-complementary genome: As used herein, a "self-complementary genome" is a polynucleotide comprising, in the 5' to 3' direction, a first parvoviral inverted terminal repeat sequence, a first heterologous sequence, a parvoviral inverted terminal repeat (ITR) nucleotide sequence comprising an engineered Rep binding sequence region, a second heterologous sequence, wherein the second heterologous sequence is complementary to the first heterologous sequence, and a second parvoviral inverted terminal repeat sequence.

Self-complementary viral particle: As used herein, a "self-complementary viral particle" is a particle comprised of at least two components, a protein capsid and a polynucleotide sequence encoding a self-complementary genome enclosed within the capsid.

Signal Sequences: As used herein, the phrase "signal sequences" refers to a sequence which can direct the transport or localization.

Single unit dose: As used herein, a "single unit dose" is a dose of any therapeutic administered in one dose/at one time/single route/single point of contact, i.e., single administration event. In some embodiments, a single unit dose is provided as a discrete dosage form (e.g., a tablet, capsule, patch, loaded syringe, vial, etc.).

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Split dose: As used herein, a "split dose" is the division of single unit dose or total daily dose into two or more doses.

Stable: As used herein "stable" refers to a compound or entity that is sufficiently robust to survive isolation to a useful degree of purity from a reaction mixture, and preferably capable of formulation into an efficacious therapeutic agent.

Stabilized: As used herein, the term "stabilize," "stabilized," "stabilized region" means to make or become stable. In some embodiments, stability is measured relative to an absolute value. In some embodiments, stability is measured relative to a reference compound or entity.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially equal: As used herein as it relates to time differences between doses, the term means plus/minus 2%.

Substantially simultaneously: As used herein and as it relates to plurality of doses, the term typically means within about 2 seconds.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Synthetic: The term "synthetic" means produced, prepared, and/or manufactured by the hand of man. Synthesis of polynucleotides or polypeptides or other molecules of the present invention may be chemical or enzymatic.

Targeted Cells: As used herein, "targeted cells" refers to any one or more cells of interest. The cells may be found in vitro, in vivo, in situ or in the tissue or organ of an organism. The organism may be an animal, preferably a mammal, more preferably a human and most preferably a patient.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition. In some embodiments, a therapeutically effective amount is provided in a single dose. In some embodiments, a therapeutically effective amount is administered in a dosage regimen comprising a plurality of doses. Those skilled in the an will appreciate that in some embodiments, a unit dosage form may be considered to comprise a therapeutically effective amount of a particular agent or entity if it comprises an amount that is effective when administered as part of such a dosage regimen.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in a 24 hour period. It may be administered as a single unit dose.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition anchor to a subject who exhibits only early signs of a disease, disorder, and/or condition for the purpose of decreasing the risk of developing pathology associated with the disease, disorder, and/or condition.

Unmodified: As used herein, "unmodified" refers to any substance, compound or molecule prior to being changed in any way. Unmodified may, but does not always, refer to the wild-type or native form of a biomolecule or entity. Molecules or entities may undergo a series of modifications whereby each modified product may serve as the "unmodified" starting molecule or entity for a subsequent modification.

Vector: As used herein, a "vector" is any molecule or moiety which transports, transduces or otherwise acts as a carrier of a heterologous molecule.

Viral construct expression vector: As used herein, a "viral construct expression vector" is a vector which comprises one or more polynucleotide regions encoding or comprising Rep and or Cap that further comprises one or more polynucleotide regions encoding or comprising components for viral expression in a viral replication cell. Viral vectors of the present invention may be produced recombinantly and may be based on and/or may comprise adeno-associated virus (AAV) parent or reference sequence. Such parent or reference AAV sequences may serve as an original, second, third or subsequent sequence for engineering viral vectors. In non-limiting examples, such parent or reference AAV sequences may comprise any one or more of the following sequences: a polynucleotide sequence encoding a polypeptide or multi-polypeptide, which may be wild-type or modified from wild-type and which may encode full-length or partial sequence of a protein, protein domain, or one or more subunits of a protein; a polynucleotide comprising a modulatory or regulatory nucleic acid which may be wild-type or modified from wild-type; and a transgene that may or may not be modified from wild-type sequence. These AAV sequences may serve as either the "donor" sequence of one or more codons (at the nucleic acid level) or amino acids (at the polypeptide level) or "acceptor" sequences of one or more codons (at the nucleic acid level) or amino acids (at the polypeptide level).

Viral construct vector: As used herein, a "viral construct vector" is a vector which comprises one or more polynucleotide regions encoding or comprising Rep and or Cap.

Viral genome: As used herein, a "viral genome" is a payload construct that has been rescued from a payload construct expression vector and is packaged within a viral particle.

Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

IX. EXAMPLES

Example 1. eRBSR Design

To identify the Rep binding sequence regions at the genomic sequence level, the genome sequences of several different AAV serotypes and species including AAV1, AAV2, AAV4, AAV5, AAV7, AAV8, Bat AAV, Bovine AAV, Snake AAV, Avian AAV DA-1, and Avian AAV VR865 (SEQ ID NO: 280-291) were obtained from the NCBI Genome database. The 5' and 3' inverted terminal repeat sequences of selected genomes were aligned with the Clustal Omega multiple sequence alignment program using either AAV2 or AAV5 as the parent sequence, as shown in FIG. 3 and FIG. 4, respectively. Additional Rep binding sequence regions found in the ITR sequences of other parvoviral serotypes and species, including AAV8 5' ITR (SEQ ID NO: 253), AAV8 3' ITR (SEQ ID NO: 254), Bat AAV 5' ITR (SEQ ID NO: 261). Bat AAV 3' ITR (SEQ ID NO: 262) are obtained in the same manner using this alignment program.

Based on the genomic sequence alignments, two groups of Rep binding sequence regions, "AAV2-like" and "AAV5-like," were identified as regions of interest with FIG. 3 showing the sequences having the AAV2-like Rep binding sequence region and FIG. 4 showing the sequences having the AAV5-like Rep binding sequence region, in which the underlined regions represent the complementary Rep binding sequence region in the 5' and 3' ITR regions. The Rep binding sequence regions share a consensus GCTC motif that is repeated four to five times. In total, the identified consensus Rep binding sequence regions are about 16-20 nucleotides in length.

In some embodiments, eRBSRs comprise one, two, or three GCTC consensus motif(s). In other embodiments, eRBSRs comprise four or five GCTC consensus motifs in which at least one nucleotide in one or more of the consensus motif(s) is altered to a motif sequence selected from the group consisting of (1) NCTC, (2) GNTC, (3) GCNC, (4) GCTN, and (5) in the case of two or more altered motif sequences, any combination of these modified altered motifs, wherein N is any naturally or non-naturally occurring nucleoside selected from adenosine, guanosine, uridine, cytidine, thymidine. In a further embodiment, eRBSRs comprise four or five GCTC: consensus motifs in which at least one nucleotide in one or more of the GCTC consensus motif(s) contains at least one nucleotide which is chemically modified.

Table 1 provides the Rep binding sequence regions of these different AAV serotypes and species (SEQ ID NOs: 1-20). Table 2 provides engineered Rep binding sequence regions which can function as an eRBSR (SEQ ID NOs: 21-66). Table 3 provides oligonucleotide sequences that comprise Rep protein binding properties which may therefore function as an eRBSR (SEQ ID NOs: 79-197) (Chiorini et al. 1995 Journal of Virology 69(11) 7334-7338). Any of SEQ ID NOs: 1-20, 21-66, and/or 79-197 can be used as an eRBSR, for example, by replacing a native or wild-type Rep binding sequence region with any heterologous sequence of SEQ ID NOs: 1-20, 21-66, and/or 79-197. For example, any of the native Rep binding sequence regions found in AAV1, AAV2, AAV3, AAV4, AAV5, AAV6, AAV7, AAV8, AAV9, AAV10, AAV11, AAV12, AAVrh8, AAVrh10, AAV-DJ, and AAV-DJ8 can be replaced with any of SEQ ID NOs: 1-20, 21-66, and/or 79-197 as long as the eRBSR is derived from a different AAV serotype or species than that of the AAV ITR. Alternatively, any of SEQ ID NOs: 1-20, 21-66, and/or 79-197 can be used as an eRBSR by altering or modifying one or more nucleotides in any of the sequences.

Example 2. eRBSR with Reduced Binding Affinity for Rep Protein

Any of the eRBSRs provided in Example 1 or elsewhere herein can be tested to confirm its reduced binding to Rep protein by determining the dissociation constant or Kd. The Kd of wild-type Rep78 protein for its cognate Rep binding sequence region in AAV2 is approximately 1 nM as measured by electro-mobility shift assay (EMSA) (Chiorini et al. 1994, Sequence Requirements for Stable Binding and Function of Rep68 on the Adeno-Associated Virus Type 2 Inverted Terminal Repeats, Journal of Virology 68:11; 7448-7457). Decreased binding is measured as an increase in the dissociation constant, Kd, over wild-type, i.e., a Kd greater than 1 nM.

Figure 11A:
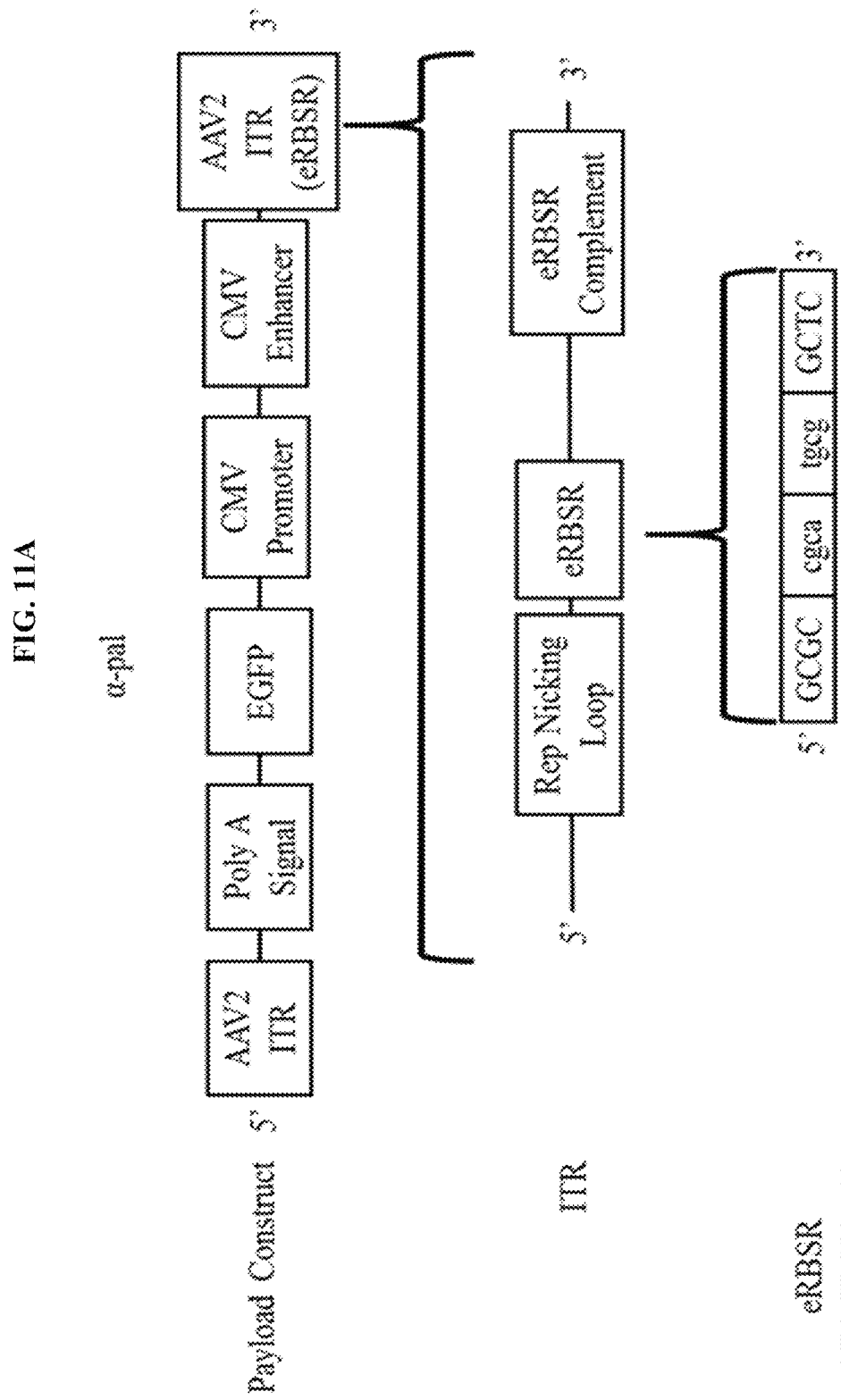
Figure 11C:
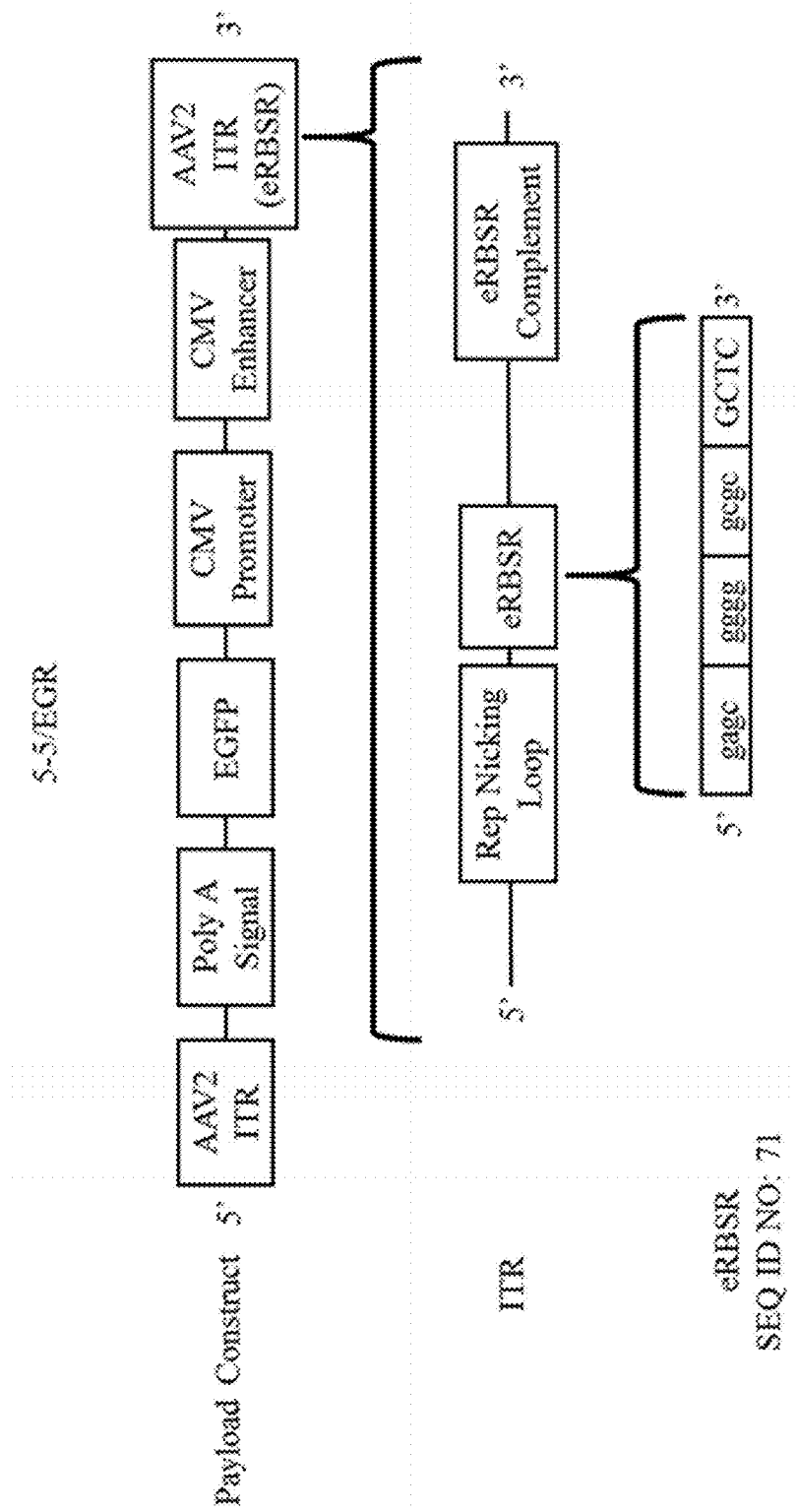
Figure 11E:
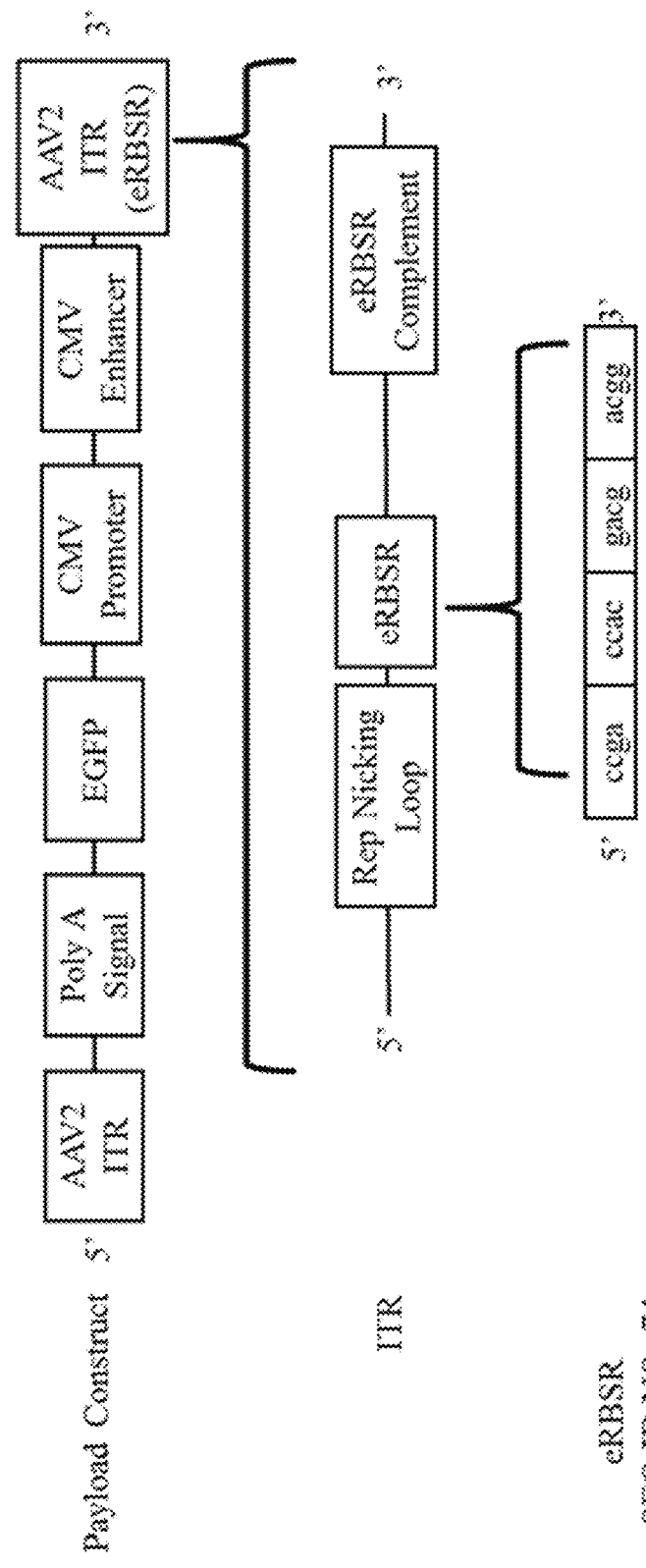

In previous experiments, the 5-5/EGR oligonucleotide (SEQ ID NO:71) shown in FIG. 11C exhibits stable, but weaker binding affinity for Rep78, the wild-type Rep found in AAV2, (5-10-fold less binding) than wild-type AAV2 Rep binding sequence region (Chiorini et al. Journal of Virology 1995, 7334-7338). In the same experiments it was found that alpha-PAL (SEQ ID NO: 68) and JcDNV NS1 (SEQ ID NO: 74) sequences, shown in FIGS. 11A and 11E respectively, were determined to exhibit weak, non-specific binding to Rep78 in EMSA experiments The binding affinity of three different eRBSRs are tested in comparison with the binding of the known AAV2 Rep binding sequence region, JcDNV (SEQ ID NO: 74), ∞PAL (SEQ ID NO: 68), and 5-5/EGR (SEQ ID NO: 71) oligonucleotides are individually inserted into AAV2 ITR sequence by swapping them into (replacing) the native Rep binding sequence region of the AAV2 ITR, which has the formula [GCGC]-[GCTC]$_3$ (SEQ ID NO: 311), FIG. 11F, FIG. 11B, and FIG. 11D, respectively. The wild-type AAV2 ITR having the native AAV2 Rep binding sequence region is used as a positive control. All of the sequences are first designed in silico and then synthesized using standard molecular biology techniques well known to those of skill in the art See, e.g., Sambrook et al, Molecular Cloning: A Laboratory Manual, Cold Spring Harbor Press (Cold Spring Harbor, N.Y.). Rep protein utilized in binding assays as described herein are expressed from polynucleotides transfected into E. coli cells and purified by methods known to those of skill in the art. Polypeptides can also be synthesized by well-known solid phase peptide synthesis methods (Merrifield, J. Am. Chem. Soc., 85:2149 (1962); Stewart and Young, Solid Phase Peptide Synthesis (Freeman, San Francisco, 1969) pp. 27-62). These and other suitable production methods are within the knowledge of those of skill in the art and are not a limitation of the present invention.

To determine initial binding, the modified AAV2 ITRs having the various described sequences are chemically synthesized and purified according to standard procedures. Double-stranded DNA probes are individually generated by annealing primers to the modified AAV2 ITRs comprising the ∞PAL eRBSR, 5-5/EGR eRBSR, and JcDNV eRBSR sequences, as well as the wild-type AAV2 ITR, and extending the sequence with the Klenow fragment of DNA polymerase and radiolabeled nucleotides.

An in vitro binding assay is performed in which the radio-labeled double-stranded AAV2 ITRs comprising ∞PAL eRBSR, 5-5/EGR eRBSR, and JcDNV eRBSR sequences, as well as wild-type AAV2 ITR having the native AAV2 Rep binding sequence region, are combined with varying concentrations of wild-type Rep protein (Rep78) under conditions which favor Rep protein binding to the AAV2 Rep binding sequence region substrate. Chiorini et al. Journal of Virology 1995, 7334-7338 describes a Rep78 protein available for use in various experiments (see also, Chiorini et al., 1994, J. Virol., 68:797-804; Chiorini et al., J. Virol., 68: 7448-7457). The resultant protein-DNA complexes formed in the binding experiments are separated on a non-denaturing polyacrylamide gel under conditions known for electro-mobility shift assay. The concentrations of bound and free radiolabeled eRBSR are determined using a PhosphoImager (Molecular Dynamics). A plot of the ratio of bound eRBSR versus Rep protein concentration is used to determine the Kd of each eRBSR.

To determine the binding affinities (Kd) of ∞PAL eRBSR, 5-5/EGR eRBSR, and JcDNV eRBSR binding, competition binding EMSA experiments are performed, in which radio-labeled double-stranded wild-type AAV2 ITR is incubated with Rep78 in the presence of 5-, 10-, or 15-fold excess of the following unlabeled competitor sequences: (1) AAV2 ITR having the native AAV2 Rep binding sequence region (positive control), (2) modified AAV2 ITR having the ∞PAL sequence, (3) modified AAV2 FIR having the 5-5/EGR sequence (eRBSR), and (4) modified AAV2 ITR having the JcDNV eRBSR sequence. The resultant protein-DNA complexes formed in the competition binding experiments are determined by EMSA. The concentrations of bound radio-labeled wild-type AAV2 ITR in the presence of various concentrations of unlabeled competitor DNA (eRBSRs) is determined using a PhosphoImager (Molecular Dynamics). A plot of the ratio of bound AAV2 ITR probe in the presence or absence of various concentrations of unlabeled competitor eRBSR DNA is used to determine the Kd of each eRBSR. eRBSR sequences having a Kd greater than that of the wild-type AAV2 ITR (with native Rep binding sequence region) bind with less affinity to Rep protein than the native Rep binding sequence region and are candidates for use in generating self-complementary viral particles. EMSA methods are provided in Chiorini et al. 1995 Determination of Adeno-Associated Virus Rep68 and Rep78 Binding Sites by Random Sequence Oligonucleotide Selection, Journal of Virology 69:11, 7334-7338, the contents of which are incorporated herein in their entirety.

Example 3. eRBSR with Reduced Banding Affinity for Rep Protein

Another technique used to test the binding of an eRBSR is surface plasmon resonance, which is a label free technique used to determine the binding affinity (Kd) between molecules. Briefly, a first molecule is immobilized on a biosensor adjacent to an internal reference surface. White light reflected from the two surfaces creates an interference pattern that is shifted when a second molecule is bound to the first. The second molecule in a first solution is passed over the biosensor in a constant flow to determine the rate of association with the first molecule until the signal is saturated to determine the $K_a$ value of the binding interaction. A second solution devoid of the second molecule is then passed over the biosensor to determine the $K_d$ value of the binding interaction.

The binding affinities of the following polypeptide-polynucleotide pairs are determined using an Octet surface plasmon resonance instrument (ForteBio, Menlo Park, Calif.): (1) AAV2 wild-type Rep protein (Rep78) and AAV2 wild-type ITR containing the native Rep binding sequence region; (2) AAV2 wild-type Rep protein (Rep78) and modified AAV2 ITR having the ∞PAL eRBSR sequence, (3) AAV2 wild-type Rep protein (Rep78) and modified AAV2 ITR having the 5-5/EGR, eRBSR sequence, and (4) AAV2 wild-type Rep protein (Rep78) and modified AAV2 ITR having the JcDNV eRBSR sequence. The wild-type Rep protein (Rep78) is immobilized on the biosensor layer. A solution containing either (1) AAV2 wild-type ITR containing the native Rep binding sequence region; (2) modified AAV2 ITR having the ∞PAL eRBSR sequence; (3) modified AAV2 ITR having the 5-5/EGR eRBSR sequence; or (4) modified AAV2 ITR having the JcDNV eRBSR sequence is passed over the biosensor having immobilized Rep78 protein to determine the rate of association for each of the polynucleotides. A second solution devoid of the polynucleotide is passed over the saturated biosensor layer to determine the rate of dissociation.

Example 4. Chimeric Nicking Stem Loop Design

To identify the Rep nicking stem loop at the genomic sequence level, the genome sequences of several different AAV serotypes and species including AAV1, AAV2, AAV3, AAV4, AAV5, AAV7, AAV8, Bat AAV, Bovine AAV, Snake AAV, Avian AAV DA-1, and Avian AAV VR865 (SEQ ID NO: 280-291) were obtained from the NCBI Genome database. The 5' and 3' inverted terminal repeat sequences of selected genomes were aligned with the Clustal Omega multiple sequence alignment program using either AAV2 or AAV5 as the parent sequence, as shown in FIG. 3 and FIG. 4, respectively. Additional Rep nicking stem loops found in the ITR sequences of other parvoviral serotypes and species, including AAV8 5' ITR (SEQ ID NO: 253). AAV8 3' ITR (SEQ ID NO: 254), Bat AAV 5' ITR (SEQ ID NO: 261), Bat AAV 3' ITR (SEQ ID NO: 262) are obtained in the same manner using this alignment program.

Based on the genomic sequence alignments, several different Rep nicking stein loops were identified (see boxed sequence in FIG. 3 and FIG. 4), The Rep nicking stem loops for AAV2, AAV1, AAV3, and AAV7 share the same nicking stem loop: AGAGGGAGTGGCCAACTCCATCA (SEQ ID NO:198) on the 5' ITR and its reverse complement TGATGGAGTTGGCCACTCCCTCT (SEQ ID NO:199) on the 3'ITR. AAV-4 has the same nicking sequence on the 5' ITR and a slightly different sequence on the 3' ITR, (TGATGGAGTTGGCCACATTAGCT; SEQ ID NO: 207). The Rep nicking stem loop for AAV5 is GGGGGAGAGTGCCACACTCTCA (SEQ ID NO: 200) on the 5' ITR and its reverse complement is TGAGAGTGTGGCACTCTCCCCC (SEQ ID NO: 201) on the 3' ITR. The Rep nicking stem loop for bovine AAV is GGGGGGGAGTGCCACACTCTCT (SEQ ID NO: 214) on the 5' ITR and its reverse complement is AGAGAGTGTGGCACTCCCCCC (SEQ ID NO: 215) on the 3' ITR. The Rep nicking stem loop for snake AAV is TGGGGCGAGTGCCCTGCTC (SEQ ID NO: 216) on the 5' ITR and its reverse complement is GAGCAGGGCACTCGCCCCA (SEQ ID NO: 217) on the 3' ITR. The Rep nicking stem loop for avian AAV (AAVDA1 and VR865) is ACTGGCCAGCACTCCGGTGA (SEQ ID NO: 210) on the 5' ITR and its reverse complement is TCACCGGAGTGCTGGCCAGT (SEQ ID NO: 211) on the 3' ITR.

A chimeric nicking stem loop is achieved by swapping the nicking stem loop sequence of one parvoviral serotype or species with the native nicking stem loop sequence of a different parvoviral serotype or species. For example, the chimeric nicking stem loop for AAV5 (SEQ ID NO: 201) is swapped into (replaces) the native nicking stem loop sequence in any of the following ITR sequences: AAV4, AAV5, AAV6, AAV8, AAV9, AAV10, AAV11, AAV12, AAVrh8. AAVrh10, AAV-DJ, and AAV-DJ8 ITR. In one embodiment, the chimeric nicking stem loop for AAV5 (SEQ ID NO: 201) is swapped into (replaces) the native nicking stem loop sequence in AAV2 (SEQ ID NO: 199). Additional nicking stem loop sequences are shown in Table 4. The sequences for certain chimeric nicking stem loop ITR sequences are provided in Table 5.

Example 5. Design of Engineered Rep Protein

The Rep protein is altered so as to decrease its binding with its cognate Rep binding sequence region. Residues in the Rep protein that contact the phosphate backbone, one or more nucleosides, or both the phosphate backbone and one or more nucleosides are altered.

Modified Rep protein design was performed in silico utilizing structural and sequence analysis of the Rep protein interaction with the AAV Rep binding sequence region. FIG. 7 is a schematic depicting a 3-dimensional model showing Rep protein binding to the Rep binding domain of the AAV5 ITR. A crystal structure showing the binding interaction between AAV5 Rep protein residues 1-197 and a double stranded oligonucleotide sequence encoding the AAV5 Rep binding sequence region (SEQ ID NOs: 3-4) was previously analyzed (Hickman et al 2004 The Nuclease Domain of Adeno-Associated Virus Rep Coordinates Replication Initiation Using Two Distinct DNA Recognition interfaces, *Molecular Cell* 13:403-414, the contents of which are referenced herein in their entirety). According to these studies, five Rep protein monomers bind independently to the Rep binding sequence region on the ITR and spiral around the DNA axis, off-set by four base pairs. As discussed elsewhere herein a repeated GCTC tetranucleotide sequence is necessary for recognition by Rep protein. The two structural elements of Rep protein that are important for binding are the surface loop between the β4 and β5 (referred to as the β4/β5 loop; residues 135-144) and the α-helix C (residues 101-118), which are located along one edge of the central β sheet. The β4/β5 loop interacts with four bases from the major groove side. Of the eight residues that form direct side chain interactions with the Rep binding sequence region, seven are strictly conserved among serotypes AAV2-6. There are three consecutive amino acids in the β4/β5 loop that are highly conserved- Gly-139, Gly-140, and Ala-141 (in AAV5), which correlate with three sequential Glycines in AAV2-6. Other conserved residues in the β4/β5 loop are Asp-142, Lys-135, Lys-137, and Lys-138. Conserved residues in the α-helix C are Met-102, Arg-106, Ser-109, and Glu-110. Arg-106 and Lys-137 provide important base contacts and Lys-135 forms a salt bridge to the phosphate backbone. Mutations of three residues: Arg-106, Lys-135, and Lys-137 results in complete loss of Rep binding (Hickman et al, 2004 Molecular Cell 13:403-414).

An alignment of the polynucleotide sequences encoding Rep protein from different AAV serotypes (AAV5, AAV2Rep68, AAV2Rep78, AAV2Rep40, AAV2Rep52, AAV1, AAV3, AAV4, AAV7, and AAV8) and AAV species (Avian AAVDA-1, Avian AAVVR865, Bat, and Bovine) was constructed to identify those amino acids having conserved specificity and conserved affinity in areas of Rep protein secondary structure (α-helix and β sheet) at the sequence level. FIG. 8 shows the sequence alignment. Amino acids having conserved specificity and conserved affinity in Rep proteins found in the genomes of other parvoviral serotypes and species, including snake AAV (SEQ ID NO: 279), are obtained in the same manner using this alignment program. An analysis of the correlation between structural features of the Rep binding sequence region in the ITR and the degree of conservation of the Rep protein sequence was performed in silico. The combination of sequence and structural analysis of Rep proteins identified nine conserved residues of the α-helix C and β-sheet 4/β-sheet 5 loop, which were identified as targets for modification (see Table 6 and Table 7).

Residues in the Rep protein identified for alteration or modification are listed here. The residue numbering is that of AAV5, and which corresponding residues in other AAV serotypes and species can be obtained using the sequence alignment in FIG. 8. (1) the amino acid corresponding to Gly-139 can be substituted with a Proline, Alanine, or Serine residue; (2) the amino acid corresponding to Gly-140 can be substituted with a Proline, Alanine, or Serine residue; (3) the amino acid corresponding to Ala-141 can be substituted with a Serine, Glycine, Threonine, Cysteine, or Valine residue; (4) the amino acid corresponding to Lys-138 can be substituted with Arginine, Glutamine, Glutamic acid, Asparagine, and Serine; (5) the amino acid corresponding to Met-102 can be substituted with Leucine, Isoleucine, Glutamine, Valine, or Phenylalanine; (6) the amino acid corresponding to Ser-109 can be substituted with Threonine, Alanine, Asparagine, Aspartic acid, Glutamine, Glutamic acid, Glycine, Lysine, or Threonine; (7) the amino acid corresponding to Glu-110 can be substituted with Arginine, Asparagine, Aspartic acid, Histidine, Lysine, or Serine; (8) the amino acid corresponding with Asp 142 can be substituted with Asparagine, Aspartic acid, Serine, Glutamine, or Glutamic acid.

Example 6. Engineered Rep Protein with Reduced Binding Affinity for Native Rep Binding Sequence Region Rep protein affinity for a Rep binding sequence region is reduced by modification of one or more highly conserved residues that have been shown to contact the DNA and are highly conserved across all Rep proteins. The identified residues contact either the phosphodiester backbone and/or the nucleosides, contributing to stabilized protein-DNA interaction of a Rep protein binding site.

Residues K135 and N142 of the AAV5 Rep 22 protein β4/β5 loop, are identified as contributing to DNA binding affinity. K135 and N142 are altered to either Glycine or Threonine. The following modifications are tested to determine the effect on DNA binding: (1) K135G, (2) K135T, (3) N142G, (4) N142T, (5) K135G-N142G, (6) K135G-N142T, (7) K135T-N142G, and/or (8) K135T-N142T. Engineered Rep protein polynucleotide sequences comprising modified residues are designed in vitro and synthesized by standard techniques as described herein. The modified Rep proteins are expressed in E. coli and purified according to standard procedures. An in vitro binding assay is performed with one or more of the listed engineered Rep proteins and a radiolabeled AAV5 Rep binding sequence region oligonucleotide probe (SEQ ID NO: 3-4) at varying concentrations. The resultant protein-DNA complexes are separated on a non-denaturing polyacrylamide gel. The concentrations of bound and free probe is determined using a PhosphoImager (Molecular Dynamics). A plot of the ratio of bound-free probe versus protein concentration is used to determine the Kd of each modified Rep protein.

The DNA binding affinity of the engineered Rep proteins can also be measured using surface plasmon resonance (ForteBio, Menlo Park, Calif.) using the following engineered Rep protein and DNA species: (1) AAV5 wild-type Rep protein and AAV5 wild-type ITR containing the native Rep binding sequence region (SEQ ID NO: 3-4) and (2) any of the engineered Rep proteins listed above and AAV5 wild-type ITR containing the native Rep binding sequence region (SEQ ID NO: 3-4). The polynucleotide encoding the wild-type AAV5 Rep binding sequence region is immobilized on the biosensor layer. A solution is prepared comprising AAV5 wild-type Rep protein or any of the engineered Rep proteins listed above, which is then passed over the biosensor to determine the rate of association. A second solution devoid of the engineered Rep protein or wild-type Rep protein is passed over the saturated biosensor layer to determine the rate of dissociation.

Example 7. Engineered Rep Protein with Reduced Binding Affinity for eRBSR

Rep protein affinity for a Rep binding sequence region is reduced by modification of one or more highly conserved residues that have been shown to contact the DNA and are highly conserved across all Rep proteins. The identified residues contact either the phosphodiester backbone and/or the nucleosides, contributing to stabilized protein-DNA interaction of a. Rep protein binding site.

Residues K135 and N142 of the AAV5 Rep 22 protein β4/β5 loop, are identified as contributing to DNA binding affinity. K135 and N142 are altered to either Glycine or Threonine. The following modifications are tested to determine the effect on DNA binding: (1) K135G, (2) K135T, (3) N142G, (4) N142T, (5) K135G-N142G, (6) K135G-N142T, (7) K135T-N142G, and/or (8) K135T-N142T. Engineered Rep protein polynucleotide sequences comprising modified residues are designed in vitro and synthesized by standard techniques as described herein. The modified. Rep proteins are expressed in E. coli and purified according to standard procedures. An in vitro binding assay is performed with one or more of the listed engineered Rep proteins and a radiolabeled oligonucleotide probe comprising an eRBSR at varying concentrations. The resultant protein-DNA complexes are separated on a non-denaturing polyacrylamide gel. The concentrations of bound and free probe is determined using a. PhosphoImager (Molecular Dynamics). A plot of the ratio of bound-free probe versus protein concentration is used to determine the Kd of each modified Rep protein.

The DNA binding affinity of the engineered Rep proteins can also be measured using surface plasmon resonance (ForteBio, Menlo Park, Calif.) using the following engineered Rep DNA species: (1) AAV2 ITR having the native AAV2 Rep binding sequence region (SEQ ID NOs: 1-2), (2) modified AAV2 ITR having the ∞PAL sequence (eRBSR) (SEQ ID NO: 68), (3) modified AAV2 ITR having the 5-5/EGR sequence (eRBSR) (SEQ ID NO: 71), (4) modified AAV2 ITR having the JcDNV NS1 sequence (eRBSR) (SEQ ID NO: 74). The polynucleotide encoding either the wild-type or engineered Rep binding sequence region is immobilized on the biosensor layer. A solution is prepared comprising AAV5 wild-type Rep protein or any of the engineered Rep proteins listed above, which is then passed over the biosensor to determine the rate of association. A second solution devoid of the engineered Rep protein or wild-type Rep protein is passed over the saturated biosensor layer to determine the rate of dissociation.

Example 8. Determination of Production of Recombinant scAAV scAAV is produced utilizing vectors comprising eRBSRs, engineered Rep protein, or chimeric nicking stem loops and combinations thereof. The relative production of scAAV using any of the disclosed sequences of the invention alone or in combination is quantified in the following manner.

A culture of 293 cells engineered to produce helper components required for AAV production is co-transfected with the viral construct expression vector, comprising any engineered Rep protein, and payload construct expression vector, comprising any eRBSR, chimeric nicking stem loop, or combination thereof. The culture is maintained for 48 hours while scAAV is produced and released into the medium.

The viral replication cells are lysed using the Microfluidizer™ (Microfluidics International Corp., Newton, Mass.), high shear force fluid processor. The resultant cell lysate is clarified by low speed centrifugation followed by tangential flow filtration. The resultant clarified lysate is then processed by ethanol precipitation to isolate the scAAV genomes.

The titer of AAV particles produced and purified by the methods described herein is determined by real-time quantitative polymerase chain reaction (qPCR) on a thermal cycler equipped with an excitation source filters, and detector for quantification of the reaction such as, but not limited to, the 7500 FAST Real-Time PCR system (Applied Biosystems, Foster City Calif.). AAV particles produced and purified by the methods described herein is treated with proteinase K, serially diluted, and PCR-amplified using a fluor such as, but not limited to, SYBR green (Applied Biosystems, Foster City, Calif.) with primers specific to the NAV genome ITR sequences. Linearized AAV vector genome is used as a copy number standard. The cycling conditions are: 95° C. for 3 min, followed by 35 cycles of 95° C. for 30 sec, 60° C. for 30 sec, and 72° C. for 30 sec.

The production of scAAV genomes is assessed by gel electrophoresis. The genomes isolated as described above are separated by denaturing (alkaline) gel electrophoresis. Analysis of the DNA content banding pattern has shown multiple sizes of viral genomes including scAAV, scAAV intermediate species, ssAAV monomer, and an ssAAV repaired from scAAV. Quantitation of the relative amounts of intermediate species is determined by densitometry and the efficiency of scAAV production quantified as a ratio of scAAV produced by wild-type versus eRBSR, engineered Rep protein, chimeric nicking stem loop constructs, and combinations thereof.

Example 9. Gene Expression

The level of transgene expression by AAV particles produced and purified by the methods described herein is determined by real-time quantitative polymerase chain reaction (qPCR). A culture of 293 cells engineered to produce helper components required for AAV production is infected by scAAV particles produced as described herein.

The target 293 cells are harvested at a series of time points, lysed and the mRNA is purified. The level of transgene expressed is determined by reverse transcription (qPCR) on a thermal cycler equipped with an excitation source filters, and detector for quantification of the reaction such as, but not limited to, the 7500 FAST Real-Time PCR system (Applied Biosystems, Foster City Calif.). AAV particles produced and purified by the methods described herein is treated with proteinase K, serially diluted, and PCR-amplified using a fluor such as, but not limited to, SYBR green (Applied Biosystems, Foster City, Calif.) with primers specific to the transgene sequence. A reference transgene oligonucleotide is used as a copy number standard. The cycling conditions are: 95° C. for 3 min, followed by 35 cycles of 95° C. for 30 sec, 60° C. for 30 sec, and 72° C. for 30 sec.

Example 10. Recombinant scAAV Production in Invertebrate Cells

The AAV viral construct vector encodes the three structural cap proteins, VP1, VP2, and VP3, in a single open reading frame regulated by utilization of both alternative splice acceptor and non-canonical translational initiation codon(s). In-frame and out-of-frame ATG triplets preventing translation initiation at a position between the VP1 and VP2 start codons are eliminated. Both Rep78 and Rep52 are translated from a single transcript: Rep78 translation initiates at a non-AUG codon and Rep52 translation initiates at the first AUG in the transcript.

The nucleotides that encode the structural VP1, VP2, and VP3 capsid proteins and non-structural Rep78 and Rep52 proteins are contained on one viral expression construct under control of the baculovirus major late promoter.

The payload construct vector encodes two ITR sequences flanking a transgene polynucleotide encoding a polypeptide or modulatory nucleic acid. The ITR sequences allow for replication of a polynucleotide encoding the transgene and ITR sequences alone that will be packaged within the capsid of the viral vector. The replicated polynucleotide encodes ITR sequences on the 5' and 3' ends of the molecule. The 3' ITR encodes an eRBSR that exhibits a ten-fold reduction in binding affinity as compared to a wild-type Rep binding sequence region. The reduced binding affinity of Rep protein for the eRBSR results in reduced nicking of the terminal resolution site located in the nicking stem loop. A failure to resolve the intermediate replication structure by nicking of the stem loop results in an alternative replication pathway and generation of the self-complementary AAV genome species of the polynucleotide encoding the payload and ITR sequences.

The payload construct vector and viral construct vector each comprise a Tn7 transposon element that transposes the ITR-payload sequences or the Rep and Cap sequences respectively to a bacmid that comprises the attTn7 attachment site. Competent bacterial DH10 cells are transfected with either the payload construct vector or viral construct vector. The resultant viral construct expression vector and payload construct expression vector produced in the competent cell are then purified by detergent lysis and purification on DNA columns.

Separate seed cultures of Sf9 cells in serum free suspension culture are transfected with the viral construct expression vector or payload construct expression vector. The cultures are maintained for 48 hours while baculovirus is produced and released into the medium. The baculovirus released into the media continue to infect Sf9 cells in an exponential manner until all of the Sf9 cells in the culture are infected at least once. The baculoviral infected insect cells (BIIC) and media of the seed culture is harvested and divided into aliquots before being frozen in liquid nitrogen.

A naïve population of un-transfected Sf9 cells is expanded in serum free suspension cell culture conditions. Once the culture growth has reached peak log phase in 1 L of media as measured by optical density the culture is added to a large volume 20 L bioreactor. The bioreactor culture is co-inoculated with a frozen viral construct expression vector and payload construct expression vector BIIC aliquot. The conditions of the Sf9 cell suspension culture is monitored by instruments that measure and/or control external variables that support the growth and activity of viral replication cells such as mass, temperature, CO2, O2, pH, and/or optical density (OD) The Sf9 culture is maintained at optimal conditions until cell population growth has reached peak log phase and before cell growth has plateaued, as measured by optical density.

In each viral replication cell that has been infected with both baculoviruses the payload flanked on one end with an ITR sequence containing an eRBSR is replicated by an alternative pathway producing a self-complementary AAV genome and packaged in a capsid assembled from the proteins VP1, VP2, and VP3.

The viral replication cells are lysed using the Microfluidizer™ (Microfluidics International Corp., Newton, Mass.), high shear force fluid processor. The resultant cell lysate is clarified by low speed centrifugation followed by tangential flow filtration. The resultant clarified lysate is filtered by a size exclusion column to remove any remaining baculoviral particles from solution. The final steps utilize ultracentrifugation and sterile filtration to produce viral particles suitable for use as described herein.

The titer of AAV particles produced and purified by the methods described herein is determined by real-time quantitative polymerase chain reaction (qPCR) on a thermal cycler equipped with an excitation source filters, and detector for quantification of the reaction such as, but not limited to, the 7500 FAST Real-Time PCR system (Applied Biosystems, Foster City Calif.). AAV particles produced and purified by the methods described herein is treated with proteinase K, serially diluted, and PCR-amplified using a fluor such as, but not limited to, SYBR green (Applied Biosystems, Foster City, Calif.) with primers specific to the AAV genome ITR sequences. Linearized AAV vector genome is used as a copy number standard. The cycling conditions are: 95° C. for 3 min, followed by 35 cycles of 95° C. for 30 sec, 60° C. for 30 sec, and 72° C. for 30 sec.

Example 11. Recombinant AAV Production in Mammalian Cells

The AAV viral construct vector encodes the three structural cap proteins, VP1, VP2, and VP3, in a single open reading frame regulated by utilization of both alternative splice acceptor and non-canonical translational initiation codon(s). In-frame and out-of-frame ATG triplets preventing translation initiation at a position between the VP1 and VP2 start codons are eliminated. Both Rep78 and Rep52 are translated from a single transcript: Rep78 translation initiates at a non-AUG codon and Rep52 translation initiates at the first AUG in the transcript.

The nucleotides that encode the structural VP1, VP2, and VP3 capsid proteins and non-structural Rep78 and Rep52 proteins are contained on one viral expression construct under control of the CMV promoter.

The payload construct vector encodes two ITR sequences flanking a transgene polynucleotide encoding a polypeptide or modulatory nucleic acid. The ITR sequences allow for replication of a polynucleotide encoding the transgene and ITR sequences alone that will be packaged within the capsid of the viral vector. The replicated polynucleotide encodes ITR sequences on the 5' and 3' ends of the molecule. The 3' ITR encodes an eRBSR that exhibits a ten-fold reduction in binding affinity as compared to a wild-type Rep binding sequence region. The reduced binding affinity of Rep protein for the eRBSR results in reduced nicking of the terminal resolution site located in the nicking stem loop. A failure to resolve the intermediate replication structure by nicking of the stem loop results in an alternative replication pathway and generation of the self-complementary AAV genome species of the polynucleotide encoding the payload and ITR sequences.

The payload construct vector and viral construct vector each comprise a Tn7 transposon element that transposes the ITR-payload sequences or the Rep and Cap sequences respectively to a bacmid that comprises the attTn7 attachment site. Competent bacterial DH10 cells are transfected with either the payload construct vector or viral construct vector. The resultant viral construct expression vector and payload construct expression vector produced in the competent cell are then purified by detergent lysis and purification on DNA columns.

A seed culture of Chinese Hamster Ovary (CHO) cells adapted for growth in serum free suspension culture is co-transfected with the viral construct expression vector and payload construct expression vector. The culture is maintained for 48 hours while two baculoviruses are produced and released into the medium, one containing the payload construct vector and a second containing the viral expression construct. The baculovirus released into the media continue to infect CHO cells in an exponential manner until all of the CHO cells in the culture are infected at least once with both baculoviruses. In each viral replication cell that has been infected with both baculoviruses the payload flanked on either end with an ITR sequence is replicated and packaged in a capsid assembled from the proteins VP1, VP2, and VP3. The cells and media of the seed culture is harvested and divided into aliquots before being frozen in, for example, liquid nitrogen.

A naïve population of un-transfected CHO cells is expanded in serum free suspension cell culture conditions. Once the culture growth has reached peak log phase in 1 L of media as measured by optical density the culture is added to a large volume 20 L bioreactor. The bioreactor culture is inoculated with a frozen aliquot from the baculovirus seed culture. The conditions of the CHO cell suspension culture is monitored by instruments that measure and/or control external variables that support the growth and activity of viral replication cells such as mass, temperature, CO2, O2, pH, and/or optical density (OD). The CHO culture is maintained at optimal conditions until cell population growth has reached peak log phase and before cell growth has plateaued, as measured by optical density.

The viral replication cells are lysed using the Microfluidizer™ (Microfluidics International Corp., Newton, Mass.), high shear force fluid processor. The resultant cell lysate is clarified by low speed centrifugation followed by tangential flow filtration. The resultant clarified lysate is filtered by a size exclusion column to remove any remaining baculoviral particles from solution. The final steps utilize ultracentrifugation and sterile filtration to produce viral particles suitable for uses described herein.

Example 12. Large Scale PEI Transfection

Polyethyleneimine (PEI) is used to form PEI-DNA complexes. Plasmids being transfected are combined with PEI in PBS and allowed to incubate at room temperature for 10 minutes. HEK 293 cell cultures being transfected are 'shocked' at 4° C. for 1 hour before being returned to the 37° C. incubator for a period of 6-24 hours (to arrest cell cycle at the junction between G2 phase and M phase). PEI-DNA transfection complexes are then added to the cells under shaking conditions and allowed to incubate 6 hours. After incubation, an equal volume of fresh medium is added and cells are incubated for 24-96 hours.

Example 13. Central Nervous System AAV Delivery

Viral particles are produced as taught herein and prepared for delivery to the central nervous system. In one aspect, preparation for CNS delivery is according to the method of Foust et al (Foust, K. D, et al., 2009, Nat Biotechnol 27:59-65, the contents of which are herein incorporated by reference in their entirety).

According to the Foust method, AAV9 viral particles delivered by venous injection are transported across the blood brain barrier (BBB) and carry out astrocyte transduction. Viruses are produced and purified by cesium chloride gradient purification, followed by dialysis against phosphate buffered saline (PBS), Resulting preparations are formulated with 0.001% Pluronic-F68 to discourage viral aggregation, Viral preparations are titrated following quantitative-PCR analysis of viral levels. Purity of viral preparations is further assessed by gel electrophoresis and subsequent silver staining (Invitrogen, Carlsbad, Calif.) Viral preparations are then delivered to subjects by intravenous injection. Viral payloads are delivered to cells of the CNS.

The invention claimed is:

1. A parvoviral ITR nucleotide sequence comprising an engineered parvovirus Rep binding sequence region (eRBSR), wherein the eRBSR comprises one or more GCTC consensus motifs, wherein the eRBSR and parvoviral ITR are from the same parvoviral serotype, wherein, outside the eRBSR, the parvoviral ITR comprises a wild-type parvoviral ITR nucleotide sequence, wherein the eRBSR is not a wild-type JcDNV NS1 region, wherein the parvoviral ITR nucleotide sequence is capable of forming a double-stranded Rep binding sequence region, wherein the binding affinity between a Rep protein and the eRBSR is decreased relative to the binding affinity between the Rep protein and the wild-type parvoviral Rep binding sequence region, and wherein the Rep protein is selected from the group consisting of Rep DA-1, V8-865, AAV1 Rep, AAV3 Rep, AAV4 Rep, AAV6 Rep, AAV7 Rep, AAV8 Rep, AAV9 Rep, AAV10 Rep, or AAV12 Rep.

2. The parvoviral ITR nucleotide sequence of claim 1, wherein the parvoviral ITR nucleotide sequence is an adeno-associated virus (AAV) ITR nucleotide sequence.

3. The parvoviral ITR nucleotide sequence of claim 1, wherein the eRBSR is from about 4 nucleotides to about 64 nucleotides in length.

4. The parvoviral ITR of claim 3, wherein the eRBSR comprises one or more GCTC consensus motif sequences selected from the group consisting of NCTC, GNTC, GCNC, and GCTN, wherein N is a nucleoside selected from adenosine, guanosine, uridine, cytidine, thymidine.

5. The parvoviral ITR of claim 3, wherein the eRBSR sequence is SEQ ID NO: 68 or SEQ ID NO: 71.

6. The parvoviral ITR of claim 1, wherein the eRBSR comprises 2-5 GCTC consensus motif sequences in the one or more GCTC consensus motifs, and wherein two or more of the GCTC consensus motif sequences are contiguous with one another.

7. The parvoviral ITR of claim 1, wherein the eRBSR comprises 2-5 GCTC consensus motif sequences in the one or more GCTC consensus motifs, and wherein none of the GCTC consensus motif sequences are contiguous with one another.

8. The parvoviral ITR of claim 1, wherein at least one of the one or more GCTC consensus motifs comprises the formula $(GCTC)_x\text{-}N_y\text{-}(GCTC)_z$ (SEQ ID NO: 309), wherein N is a nucleoside selected from adenosine, guanosine, uridine, cytidine, thymidine; wherein
x and z are independently 0-5, with the proviso that when x=0, z=1-5, and when z=0,
x=1-5; and
y=0-16.

9. The parvoviral ITR nucleotide sequence of claim 1, wherein the Rep protein is from a different AAV serotype than that of the eRBSR.

10. The parvoviral ITR nucleotide sequence of claim 1, wherein the Rep protein is selected from the group consisting of Rep DA-1, V8-865, AAV1 Rep, AAV3 Rep, AAV4 Rep, AAV7 Rep, and AAV8 Rep.

11. An AAV particle comprising the nucleotide sequence of claim 1.

12. A pharmaceutical composition comprising the AAV particle of claim 11 and one or more pharmaceutically acceptable excipients.

13. A parvoviral ITR nucleotide sequence comprising a Rep nicking sequence and an eRBSR; wherein the eRBSR is from 4 nucleotides to 20 nucleotides in length; wherein the eRBSR comprises one to four altered GCTC motif nucleotide sequences selected from the group consisting of $N_1CTC$, N1NTC, $N_1CNC$, $N_1CTN$, $GN_2TC$, $GN_2NC$, $GN_2TN$, $GCN_3C$, $GCN_3N$, and $GCTN_2$, with N being an adenine, guanine, cytosine, thymine, or uracil, with Ni being an adenine, cytosine, thymine, or uracil, with N2 being an adenine, guanine, thymine, or uracil, and with N3 being an adenine, guanine or cytosine, wherein the parvoviral ITR and eRBSR are of the same parvoviral serotype, wherein, outside the eRBSR, the parvoviral ITR comprises a wild-type parvoviral ITR nucleotide sequence, wherein the eRBSR has decreased binding to a Rep protein compared to the wild-type parvoviral Rep binding sequence region, and wherein the Rep protein is selected from the group consisting of Rep DA-1, V8-865, AAV1 Rep, AAV3 Rep, AAV4 Rep, AAV6 Rep, AAV7 Rep, AAV8 Rep, AAV9 Rep, AAV10 Rep, or AAV12 Rep.

14. The parvoviral ITR nucleotide sequence of claim 13, wherein the eRBSR comprises a sequence selected from the group consisting of SEQ ID NO: 68 and SEQ ID NO: 71.

15. The parvoviral ITR nucleotide sequence of claim 13, wherein the Rep protein is from a different AAV serotype than that of the eRBSR.

16. The parvoviral ITR nucleotide sequence of claim 13, wherein the eRBSR comprises at least one $N_1CTC$ sequence.

17. The parvoviral ITR nucleotide sequence of claim 13, wherein the eRBSR comprises at least one $N_1NTC$ sequence.

18. The parvoviral ITR nucleotide sequence of claim 13, wherein the eRBSR comprises at least one $N_1CNC$ sequence.

19. The parvoviral ITR nucleotide sequence of claim 13, wherein the eRBSR comprises at least one $N_1CTN$ sequence.

20. The parvoviral ITR nucleotide sequence of claim 13, wherein the eRBSR comprises at least one $GN_2TC$ sequence.

21. The parvoviral ITR nucleotide sequence of claim 13, wherein the eRBSR comprises at least one $GN_2NC$ sequence.

22. The parvoviral ITR nucleotide sequence of claim 13, wherein the eRBSR comprises at least one $GN_2TN$ sequence.

23. The parvoviral ITR nucleotide sequence of claim 13, wherein the eRBSR comprises at least one $GCN_3C$ sequence.

24. The parvoviral ITR nucleotide sequence of claim 13, wherein the eRBSR comprises at least one $GCN_3N$ sequence.

25. The parvoviral ITR nucleotide sequence of claim 13, wherein the eRBSR comprises at least one $GCTN_2$ sequence.

26. A parvoviral ITR nucleotide sequence comprising an eRBSR, wherein the eRBSR comprises an altered position of at least one GCTC motif present in the eRBSR compared to a wild-type parvoviral Rep binding sequence region, wherein the eRBSR differs from the wild-type parvoviral Rep binding sequence region by at least one nucleotide, wherein the eRBSR and parvoviral ITR are from the same parvoviral serotype, and wherein the eRBSR has decreased binding to a Rep protein compared to the wild-type parvoviral Rep binding sequence region, and wherein the Rep protein is selected from the group consisting of Rep DA-1, V8-865, AAV1 Rep, AAV3 Rep, AAV4 Rep, AAV6 Rep, AAV7 Rep, AAV8 Rep, AAV9 Rep, AAV10 Rep, or AAV12 Rep.

27. The parvoviral ITR nucleotide sequence of claim 26, wherein the Rep protein is from a different AAV serotype than that of the eRBSR.

28. A parvoviral ITR nucleotide sequence comprising a Rep nicking sequence and an eRBSR; wherein the eRBSR comprises one to five GCTC motif nucleotide sequences; wherein the eRBSR comprises one to four altered GCTC motif nucleotide sequences selected from the group consisting of $N_1CTC$, $N_1NTC$, $N_1CNC$, $N_5CTN$, $GN_2TC$, $GN_4NC$, $GN_2TN$, $GCN_3C$, $GCN_3N$, and $GCTN_2$, with N being an adenine, guanine, cytosine, thymine, or uracil, with Ni being an adenine, cytosine, thymine, or uracil, with $N_2$ being an adenine, guanine, thymine, or uracil, with $N_3$ being an adenine, guanine or cytosine, with $N_4$ being guanine, thymine, or uracil, and with $N_5$ being adenine, cytosine, or uracil; wherein the eRBSR differs from a reference wild-type parvoviral Rep binding sequence region by at least one nucleotide; wherein the eRBSR and parvoviral ITR are from the same parvoviral serotype; wherein the eRBSR has decreased binding to a Rep protein compared to the wild-type parvoviral Rep binding sequence region, and wherein the Rep protein is selected from the group consisting of Rep DA-1, V8-865, AAV1 Rep, AAV3 Rep, AAV4 Rep, AAV6 Rep, AAV7 Rep, AAV8 Rep, AAV9 Rep, AAV10 Rep, or AAV12 Rep.

29. The parvoviral ITR nucleotide sequence of claim 28, wherein the eRBSR, parvoviral ITR, and wild-type parvoviral Rep binding sequence region are from the same parvoviral serotype.

30. The parvoviral ITR nucleotide sequence of claim 28, wherein the eRBSR comprises at least one $N_1CTC$ sequence.

31. The parvoviral ITR nucleotide sequence of claim 28, wherein the eRBSR comprises at least one $N_1NTC$ sequence.

32. The parvoviral ITR nucleotide sequence of claim 28, wherein the eRBSR comprises at least one $N_1CNC$ sequence.

33. The parvoviral ITR nucleotide sequence of claim 28, wherein the eRBSR comprises at least one $N_5CTN$ sequence.

34. The parvoviral ITR nucleotide sequence of claim 28, wherein the eRBSR comprises at least one $GN_2TC$ sequence.

35. The parvoviral ITR nucleotide sequence of claim 28, wherein the eRBSR comprises at least one $GN_4NC$ sequence.

36. The parvoviral ITR nucleotide sequence of claim 28, wherein the eRBSR comprises at least one $GN_2TN$ sequence.

37. The parvoviral ITR nucleotide sequence of claim 28, wherein the eRBSR comprises at least one $GCN_3C$ sequence.

38. The parvoviral ITR nucleotide sequence of claim 28, wherein the eRBSR comprises at least one $GCN_3N$ sequence.

39. The parvoviral ITR nucleotide sequence of claim 28, wherein the eRBSR comprises at least one $GCTN_2$ sequence.

40. The parvoviral ITR nucleotide sequence of claim 28, wherein the parvoviral ITR nucleotide sequence is an AAV ITR nucleotide sequence.

41. The parvoviral ITR nucleotide sequence of claim 28, wherein the eRBSR is from about 4 nucleotides to about 16 nucleotides in length.

42. The parvoviral ITR nucleotide sequence of claim 28, wherein the Rep protein is from a different AAV serotype than that of the eRBSR.

* * * * *

UNITED STATES PATENT AND TRADEMARK OFFICE
CERTIFICATE OF CORRECTION

PATENT NO. : 11,697,825 B2
APPLICATION NO. : 15/535389
DATED : July 11, 2023
INVENTOR(S) : James McLaughlin et al.

It is certified that error appears in the above-identified patent and that said Letters Patent is hereby corrected as shown below:

In the Claims

At Column 305, Claim number 1, Line number 43, delete "AAV10 Rep, or AAV12 Rep." and insert --AAV10 Rep, and AAV12 Rep.--

At Column 306, Claim number 13, Line number 53, delete "$N_1$CTC, N1NTC, $N_1$CNC, $N_1$CTN, $GN_2$TC, $GN_2$NC," and insert --$N_1$CTC, $N_1$NTC, $N_1$CNC, $N_1$CTN, $GN_2$TC, $GN_2$NC,--

At Column 306, Claim number 13, Line number 55, delete "adenine, guanine, cytosine, thymine, or uracil, with Ni being" and insert --adenine, guanine, cytosine, thymine, or uracil, with $N_1$ being--

At Column 306, Claim number 13, Line number 56, delete "an adenine, cytosine, thymine, or uracil, with N2 being an" and insert --an adenine, cytosine, thymine, or uracil, with $N_2$ being an--

At Column 306, Claim number 13, Line number 57, delete "adenine, guanine, thymine, or uracil, and with N3 being an" and insert --adenine, guanine, thymine, or uracil, and with $N_3$ being an--

At Column 306, Claim number 13, Line number 67, delete "AAV10 Rep, or AAV12 Rep." and insert --AAV10 Rep, and AAV12 Rep.--

At Column 307, Claim number 26, Line number 44, delete "parvoviral serotype, and wherein the eRBSR has decreased" and insert --parvoviral serotype, wherein the eRBSR has decreased--

At Column 307, Claim number 26, Line number 49, delete "AAV7 Rep, AAV8 Rep, AAV9 Rep, AAV10 Rep, or AAV12" and insert --AAV7 Rep, AAV8 Rep, AAV9 Rep, AAV10 Rep, and AAV12--

At Column 308, Claim number 28, Line number 1, delete "adenine, guanine, cytosine, thymine, or uracil, with Ni being" and insert --adenine, guanine, cytosine, thymine, or uracil, with $N_1$ being--

Signed and Sealed this
Nineteenth Day of September, 2023

*Katherine Kelly Vidal*
Katherine Kelly Vidal
*Director of the United States Patent and Trademark Office*

At Column 308, Claim number 28, Line number 14, delete "Rep, AAV7 Rep, AAV8 Rep, AAV9 Rep, AAV10 Rep, or" and insert --Rep, AAV7 Rep, AAV8 Rep, AAV9 Rep, AAV10 Rep, and--